(12) United States Patent
Gambacorti Passerini et al.

(10) Patent No.: US 8,895,744 B2
(45) Date of Patent: Nov. 25, 2014

(54) ALFA-CARBOLINE INHIBITORS OF NPM-ALK, RET, AND BCR-ABL

(75) Inventors: Carlo Gambacorti Passerini, Monza (IT); Luca Mologni, Vedano al Lambro (IT); Leonardo Scapozza, Grens (CH); Shaheen Ahmed, Zurich (CH); Peter G. Goekjian, Lyons (FR); David Gueyrard, Montluel (FR); Florence Popowycz, Villeurbanne (FR); Benoit Joseph, Villeurbanne (FR); Cedric Schneider, Val-de-Bride (FR); Pierre Garcia, Juillan (FR)

(73) Assignees: Universita' Degli Studi di Milano-Bicocca, Milan (IT); Universite' de Geneve, Geneva (CH); Universite' Claude Bernard de Lyon 1, Villeurbanne (FR)

( * ) Notice: Subject to any disclaimer, the term of this patent is extended or adjusted under 35 U.S.C. 154(b) by 497 days.

(21) Appl. No.: 13/062,665

(22) PCT Filed: Aug. 27, 2009

(86) PCT No.: PCT/EP2009/006206
§ 371 (c)(1),
(2), (4) Date: Jun. 9, 2011

(87) PCT Pub. No.: WO2010/025872
PCT Pub. Date: Mar. 11, 2010

(65) Prior Publication Data
US 2011/0281862 A1 Nov. 17, 2011

(30) Foreign Application Priority Data
Sep. 8, 2008 (EP) .................................. 08015802

(51) Int. Cl.
A61K 31/44 (2006.01)
C07D 221/22 (2006.01)
C07D 471/04 (2006.01)

(52) U.S. Cl.
CPC .................................. C07D 471/04 (2013.01)
USPC ............................................ 546/79; 514/300

(58) Field of Classification Search
None
See application file for complete search history.

(56) References Cited

U.S. PATENT DOCUMENTS

| 2,690,441 | A | 9/1954 | Burtner et al. |
| 5,532,261 | A * | 7/1996 | DiNinno et al. ......... 514/210.14 |
| 2005/0049265 | A1 | 3/2005 | Adams |

FOREIGN PATENT DOCUMENTS

| EP | 1 367 058 A1 | 12/2003 |
| FR | 2 876 377 A1 | 4/2006 |
| GB | 1 268 772 | 3/1972 |
| GB | 1 268 773 | 3/1972 |
| WO | WO 2006/131552 A1 | 12/2006 |
| WO | WO 2007/097981 A2 | 8/2007 |

OTHER PUBLICATIONS

Silva, A. Mini-Rev. Med. Chem. 2005 vol. 5 pp. 893-891.*
Schneider, C. et al Tetrahedron 2009 vol. 65, pp. 5427-5437.*
J. Wieczorek, et al.: "Antineoplastic Activity of Azacarbazoles I. Synthesis and Antitumor Properties of Alpha-Carboline and Its Selected Derivative", Jan. 1, 1986, Archivum Immunologiae et Therapiae Experimentalis, Polish Academy of Sciences, Wroclaw, PL, pp. 315-321 (XP009048570).
EPO Communication issued Jul. 29, 2014; Application No. 08 015 802.5.

* cited by examiner

Primary Examiner — Heidi Reese
(74) Attorney, Agent, or Firm — Arent Fox LLP

(57) ABSTRACT

The present invention relates to compounds of formula (I)

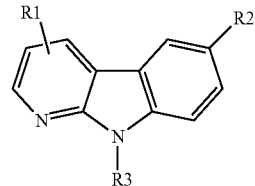

wherein R1, R2 and R3 are as defined in the description, to their pharmaceutical compositions and use thereof for the treatment of cancer expressing oncogenic ALK protein, particularly anaplastic large cell lymphoma (ALCL), diffuse large B cell lymphoma (DLBCL), inflammatory myofibroblastic tumors (IMT) and non-small cell lung cancer (NSCLC).

11 Claims, No Drawings

ALFA-CARBOLINE INHIBITORS OF NPM-ALK, RET, AND BCR-ABL

CROSS-REFERENCE TO RELATED APPLICATION

This application is a National Stage entry of International Application No. PCT/EP2009/006206, having an international filing date of Aug. 27, 2009, which claims priority to European Application No. 08015802.5, filed Sep. 8, 2008, the disclosure of each of which is hereby incorporated in its entirety by reference.

SEQUENCE LISTING

The instant application contains a Sequence Listing which has been submitted in ASCII format via EFS-Web and is hereby incorporated by reference in its entirety. Said ASCII copy, created on Jul. 12, 2011, is named 10050600.txt and is 888 bytes in size.

FIELD OF INVENTION

The present invention relates to compounds that are able to inhibit the activity of the oncogenic protein kinases, including tyrosine kinases such as Anaplastic Lymphoma Kinase (ALK), which is aberrantly expressed and activated in different types of cancers, such as anaplastic large cell lymphoma (ALCL), RET (Rearranged during Transfection), which is involved in the onset of hereditary and sporadic thyroid cancer, and Bcr-Abl an oncogenic fusion protein frequently observed in chronic myeloid leukaemia (CML) patients, and the use of such compounds for the preparation of a pharmaceutical composition.

BACKGROUND OF THE INVENTION

The present invention relates to inhibitors of the oncogenic protein kinases, including ALK, RET and Bcr-Abl. The formula of the inhibitors is disclosed below (Formula I). Such inhibitors can be used for the treatment of hyper-proliferative diseases such as cancer, in particular for the treatment of ALK fusion protein positive cancers, such as anaplastic large cell lymphoma (ALCL), diffuse large B cell lymphoma (DL-BCL), inflammatory myofibroblastic tumours (IMT) and non-small cell lung cancer (NSCLC), as well as T315I Bcr-Abl positive cancers such as Chronic Myeloid Leukemia (CML) and Ph+ Acute lymphoblastic leukemia (ALL), and thyroid cancer linked to RET, such as papillary thyroid carcinoma (PTC) and multiple endocrine neoplasia type 2 (MEN2).

Cancer results from the subversion of processes that control the normal growth, location and mortality of cells. This loss of normal control mechanisms arises from the acquisition of mutations that lead to the oncogenic activation of proteins that are involved in the normal regulation of such processes.

Protein kinases are enzymes that catalyse the transfer of phosphate from adenosine-5'-triphosphate (ATP) to specific amino acid residues in many proteins. Generally, the phosphorylation of a protein changes its functionality, from inactive to active in some cases, and from active to inactive in others. Protein kinases are thus involved in the regulation of many aspects of cell function, as most of the signal transduction pathways controlling cell growth, survival, differentiation and motility are mediated by phosphorylation. Abnormal activity of protein kinases has been implicated in many cancers as well as in other diseases. The human genome encodes at least 518 kinases, of which approximately 90 specifically phosphorylate the phenolic hydroxyl of tyrosine residues. Tyrosine kinases are particularly involved in cell proliferation and survival processes, and their aberrant activation most often leads to oncogenic transformation.

For example, structural alterations in ALK produced by the chromosomal rearrangement t(2q23;5q35) generates the NPM/ALK oncogenic fusion protein associated with ALCL.[1]

[1] Rabbitts, T. H. *Nature*, 1994, 372, 143

Large cell lymphomas represent about 25% of all non-Hodgkin's lymphomas; about one-third of these tumors are anaplastic large cell lymphoma (ALCL). In turn, more than half the patients with ALCL possess a chromosomal translocation that leads to the in-frame juxtaposition of the 5' portion of the nucleophosmin (NPM) gene with the sequence encoding for the catalytic domain of ALK kinase. The resulting chimaeric gene, under the control of the strong NPM promoter, drives the expression of the NPM/ALK oncogenic fusion protein. An additional 10% of ALCL patients carry other ALK fusion proteins. To date, 11 ALK fusions have been described. In all cases, the ALK kinase domain sequence is fused to an aminoterminal protein-protein interaction domain of a protein that is highly expressed in the target cell. Thus, the fusion partner provides constitutive expression (through its promoter) and activation (via oligomerisation). In addition, ALK fusion proteins show anomalous cellular localisation. For example, NPM/ALK is mainly found in the cytoplasm and the nucleus. By contrast, wild-type ALK is a tightly regulated, integral membrane protein that is only activated in the presence of a specific extracellular ligand. ALK is normally expressed in the nervous system during embryonic development and is strongly down-regulated at birth, resulting in barely detectable levels in adult tissues. It has been extensively demonstrated that constitutively active NPM/ALK is a potent oncogene with transforming and tumourigenic properties.[2] Moreover, rearrangement of ALK kinase is a very early event in tumour formation and is necessary for survival of transformed cells. The high level of expression of NPM/ALK and other ALK fusion protein variants in lymphoma cells and their direct role in lymphomagenesis, combined with the fact that normal ALK is expressed at low levels in the human body, suggests that ALK could potentially be an ideal target for therapy.

[2] Morris, S. W; Kirstein, M. N.; Valentine, M. B.; Dittmer, K. G.; Shapiro, D. N.; Saltman, D. L.; Look; A. T. *Science*, 1994, 263, 1281-1284

Chronic Myeloid Leukemia (CML) is a myeloproliferative disease, characterized by the presence of a modified chromosome, named Ph-chromosome. In the eighties, the molecular defect associated with this cytogenetic abnormality was identified and it was established that the Ph-chromosome results from the chromosomal rearrangement t(9q34;22q11) and leads to the formation of the hybrid gene BCR-ABL coding for the oncogenic Bcr-Abl fusion tyrosine kinase associated with CML and ALL[3]. In the late 1980s, the data accumulated on the role of BCR-ABL in onset and progression of CML indicated BCR-ABL as the most attractive target for molecularly targeted therapy approaches. Therefore attempts to inhibit the TK activity of the oncoprotein were initiated and this process finally led to the discovery and the development of imatinib mesylate. Imatinib has been under clinical investigation for almost 8 years (50.000 patients) with remarkable results in terms of durable remissions. During the successful clinical trials, resistance to imatinib emerged particularly in patients with acute leukemias, but it is a potential issue also in patients in chronic phase. The molecular mechanism of resistance has been identified in Bcr-Abl gene amplification and mutations in the catalytic kinase domain of the gene[3]. Mutations render the target kinase insensitive to the drug, either by altering the conformational equilibrium of the catalytic domain, or by changing the drug binding site. This has prompted intense research to find new compounds able to overcome the resistance problem, such as Dasatinib[4], Bosutinib[5] and Nilotinib.[6] These second generation inhibitors show increased potency compared to imatinib and are able to target most of imatinib-resistant clones. However, none of them is able to inhibit efficiently the imatinib-resistant Bcr-Abl T315I mutant. Thus, under the selective pressure of molecularly targeted therapies, the mutation of the gate-keeper amino acid threonine into an isoleucine (T315I) has evolved as the predominant one in patients[3] and has proved to be critical for the resistance of the tumour towards Bcr-Abl kinase selective therapies'. These facts indicate that the T315I mutant is a crucial target for the development of new selective therapies aimed at eradicating the disease.

[3] Ben-Neriah, Y., Daley, G. Q., Mes-Masson, A. M., Witte, O. N. & Baltimore, D. *Science.* 1986, 233, 212
[4] Shah, N. P., Tran, C., Lee, F. Y., Chen, P., Norris, D. & Sawyers, C. L. *Science* 2004 305, 399-401
[5] Puttini, M.; Coluccia, A. M.; Boschelli, F.; Cleris, L.; Marchesi, E.; Donella-Deana, A.; Ahmed, S.; Redaelli, S.; Piazza, R.; Magistroni, V.; Andreoni, F.; Scapozza, L.; Formelli, F. & Gambacorti-Passerini, C. *Cancer Res.* 2006, 66, 11314-11322
[6] Weisberg, E., Manley, P. W., Breitenstein, W., Bruggen, J., Cowan-Jacob, S. W., Ray, A., Huntly, B., Fabbro, D., Fendrich, G., Hall-Meyers, E., Kung, A. L., et al. *Cancer Cell.* 2005 7, 129-141
[7] Gambacorti-Passerini, C. B., Gunby, R. H., Piazza, R., Galietta, A., Rostagno, R. & Scapozza, L. *Lancet Oncol.* 2003, 4, 75-85.

RET (Rearranged during Transfection) proto-oncogene is involved in the onset of hereditary and sporadic thyroid cancer.[8] Activating mutations have been described both in the extracellular and the catalytic domain. In addition, rearranged forms of RET have been identified, in which the kinase domain is fused to an activating gene. In all cases, RET kinase activity is switched on independently of ligand binding and induces malignant transformation of thyroid cells. RET uncontrolled activity is both sufficient and necessary to cause neoplastic phenotype. Therefore, it represents an ideal target for molecular therapy of thyroid neoplasias.

[8] Jhiang S M. *Oncogene* 2000, 19:5590-7.

Several small molecule compounds have been described as RET inhibitors during the last few years.[9] However, all these compounds were developed against other targets and indeed hit a number of other kinases. This fact is likely to cause significant toxicity in clinical practice. Therefore, RET-selective inhibitors are needed for the management of this group of malignancies.

[9] Gunby et al. *Anti-Cancer Agents in Medicinal Chemistry* 2007, 7, 594.

The disclosed inhibition of ALK, RET, and Bcr-Abl mutant T315I has been demonstrated using an ELISA-based in vitro kinase assay that has been previously developed (EP1454992). Furthermore cellular activity of the compounds on NPM/ALK transformed cells has been demonstrated by tritiated thymidine based cell proliferation inhibition assay.

The inhibitors of the present invention have the following formula or pharmaceutical acceptable salts thereof.

DESCRIPTION

In a first aspect, the invention provides a compound of formula (I):

wherein either $R^1$ or $R^2$ is a structure consisting of a linker, spacer, and functional group L-S—X, and the other is chosen from a halogen, alkyl, substituted alkyl, heteroalkyl, substituted heteroalkyl, arylvinyl, substituted arylvinyl, vinyl, substituted vinyl, alkynyl, substituted alkynyl, aryl, substituted aryl, heteroaryl, substituted heteroaryl, acyl, substituted acyl, substituted oxalyl, nitro, nitrovinyl, amino, substituted amino, formyl, carboxyl, or carboxyl derivative. $R^3$ is either H, methyl, ethoxymethyl, or $SO_2Ph$ wherein when $R^1$ is a structure L-S—X:

L is a linker consisting of —CH=CH—, —C($CH_3$)=CH—, or —$CH_2$—$CH_2$ and

S is an aryl, heteroaryl, alkyl, heteroalkyl, substituted alkyl, substituted aryl, substituted heteroaryl, or substituted heteroalkyl, where a heteroalkyl group is defined as —[$(CH_2)_n$Y]$_m$($CH_2)_p$— with Y=O, S, or NH, n, m=1 to 3, and p=0 to 4, with the proviso that when m is 2 or 3, n is not 1 and

X is a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, halogen, or none or L is an aryl group and S is either —O—$(CH_2)_n$— attached at the 4-position (para) of the aryl group through the oxygen atom, where n=1 to 4, or the following structure attached at the 3-position (meta) of the aryl group through the amidic nitrogen:

and

X is a dialkylamine, a heterocyclic amine, or a substituted heterocyclic amine or L is NH or O and S is an aryl group and X is a functional group or a spacer (defined here as an aryl, heteroaryl, alkyl, heteroalkyl, substituted alkyl, substituted aryl, substituted heteroaryl, or substituted heteroalkyl, where a heteroalkyl group is defined as —[$(CH_2)_n$Y]$_m$($CH_2)_p$— with Y=O, S, or NH, n, m=1 to 3, and p=0 to 4, with the proviso that when m is 2 or 3, n is not 1) bearing a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, halogen, or the following structure at the 3-position (meta) of the aryl group:

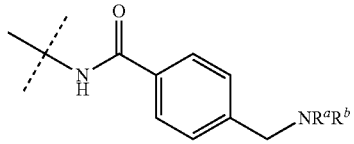

where $R_a$ and or $R_b$ are independently a hydrogen or a group chosen from a C1-C10 alkyl group, a C3-C7 cycloalkyl group, an aryl group, a C3-C12 heterocycle, or $R_a$ and $R_b$ are linked to form with the nitrogen a heterocycle such as an optionally substituted piperidine, piperazine, or morpholine
or
L is an aryl group
and
S is NH attached at the 3-position (meta) of the aryl group
and
X is an arenesulfonyl or alkanesulfonyl group —SO$_2$R$_c$, where $R_c$ is an aryl, alkyl, or trifluoroalkyl group
wherein when R$^2$ is a structure L-S—X:
L is a linker consisting of aryl, substituted aryl, heteroaryl, substituted heteroaryl, —CH$_2$CH$_2$—, —C(CH$_3$)=CH—, —NH—, —O—, —C(O)CH$_2$CH$_2$C(O)—, or —C(O)CH$_2$Y—, where Y=S, O, NH, or none
S is a spacer consisting of an aryl, heteroaryl, heteroalkyl, alkyl, substituted alkyl, substituted aryl, substituted heteroaryl, substituted heteroalkyl, or none, wherein heteroalkyl is as above defined
X is a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, or halogen As used herein, the terms "alkyl", "alkenyl", "alkynyl", "acyl" refer to linear or branched aliphatic chains containing from 1 to 4 carbon atoms, whereas the terms "(hetero)aryl" preferably indicates a 5- to 10-membered (hetero)aromatic ring.

In a first preferred embodiment, the invention provides a compound of formula (Ia):

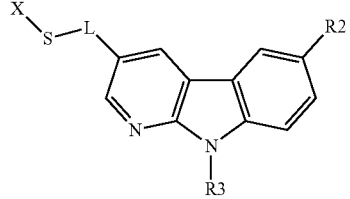

STRUCTURE (Ia)

wherein
L is a linker consisting of —C≡C—, —CH=CH—, —C(CH$_3$)=CH—, or —CH$_2$—CH$_2$—
and
S is an aryl, heteroaryl, alkyl, heteroalkyl, substituted alkyl, substituted aryl, substituted heteroaryl, or substituted heteroalkyl, where a heteroalkyl group is defined as —[(CH$_2$)$_n$Y]$_m$(CH$_2$)$_p$— with Y = O, S, or NH and n, m, and p = 1 to 3, with the proviso that when m is 2 or 3, n is not 1
and

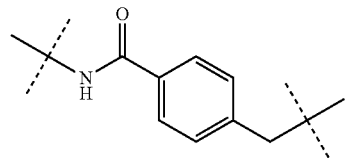

STRUCTURE (Ia)

X is a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, halogen, or none
or
L is an aryl group
and
S is either —O—(CH$_2$)$_n$— attached at the 4-position (para) of the aryl group through the oxygen atom, where n = 1 to 4, or the following structure attached at the 3-position (meta) of the aryl group through the amidic nitrogen:

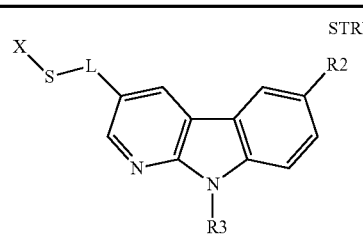

and
X is a dialkylamine NR$_a$R$_b$, where $R_a$ and or $R_b$ are independently hydrogen or a group chosen from a C1-C10 alkyl group, a C3-C7 cycloalkyl group, an aryl group, a C3-C12 heterocycle, or $R_a$ and $R_b$ are linked to form with the nitrogen a heterocycle such as an optionally substituted piperidine, piperazine, or morpholine
or
L is an aryl group
and
S is NH attached at the 3-position (meta) of the aryl group
and
X is an arenesulfonyl or alkanesulfonyl group —SO$_2$R$_c$, where $R_c$ is an aryl, alkyl, or trifluoroalkyl group
or
L is NH
and
S is an aryl or heteroaryl group
and
X is a functional group or a spacer selected from aryl, heteroaryl, alkyl, heteroalkyl, substituted alkyl, substituted aryl, substituted heteroaryl, or substituted heteroalkyl, where a heteroalkyl group is defined as —[(CH$_2$)$_n$Y]$_m$(CH$_2$)$_p$— with Y = O, S, or NH, n, m =1 to 3, and p = 0 to 4, with the proviso that when m is 2 or 3, n is not 1, such spacer bearing a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, halogen, or none
R$^2$ is a halogen, alkyl, substituted alkyl, arylvinyl, substituted arylvinyl, vinyl, substituted vinyl, aryl, substituted aryl, heteroaryl, substituted heteroaryl, acyl, substituted acyl, substituted oxalyl, nitro, nitrovinyl, amino, substituted amino, formyl, or carboxyl, or carboxyl derivative
R$^3$ = H, Me, SO$_2$Ph, or ethoxymethyl In a further preferred embodiment, the invention provides a compound of formula (Ib):

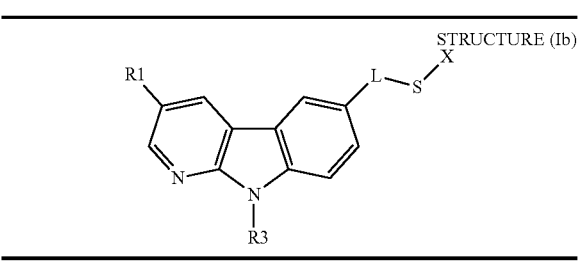

STRUCTURE (Ib)

wherein
L is a linker consisting of aryl, substituted aryl,
heteroaryl, substituted heteroaryl, —CH₂CH₂—,
—C≡C—, —CH=CH—, —C(CH₃)=CH—, —NH—, —O—,
—C(O)CH₂CH₂C(O)—, or —C(O)CH₂Y—, where Y = S,
O, NH, or none
S is a spacer consisting of an aryl, heteroaryl,
heteroalkyl, or alkyl, substituted alkyl, substituted
aryl, substituted heteroaryl, substituted heteroalkyl,
or none, wherein heteroalkyl is as above defined
X is a functional group, comprising an ether,
amine, alcohol, sulfoxide, sulfone, sulfonamide,
tetrazole, carboxylic acid, amide, nitro, aryl,
substituted aryl, alkyl, cycloalkyl, heterocycle,
substituted heterocycle, heteroaryl, substituted
heteroaryl, or halogen
$R^1$ is a halogen, alkyl, substituted alkyl, substituted
alkene, substituted alkynyl, aryl, substituted aryl,
heteroaryl, substituted heteroaryl, heteroalkyl,
substituted heteroalkyl, wherein heteroalkyl is as
above defined, or a group —L—S—X as defined in I(a)
$R^3$ = H, Me, SO₂Ph, or ethoxymethyl In a further preferred embodiment, the invention provides a compound of formula (IIa):

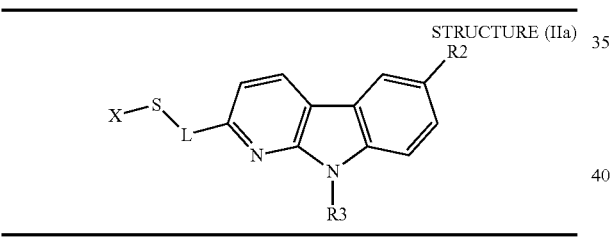

STRUCTURE (IIa)

wherein
L is NH or O
and
S is an aryl or heteroaryl group
and
X is a functional group or a spacer selected from
aryl, heteroaryl, alkyl, heteroalkyl, substituted alkyl,
substituted aryl, substituted heteroaryl, or
substituted heteroalkyl, where a heteroalkyl group is
defined as —[(CH₂)ₙY]ₘ(CH₂)ₚ— with Y = O, S, or
NH, n, m = 1 to 3, and p = 0 to 4, with the proviso
that when m is 2 or 3, n is not 1, such spacer bearing
a functional group, comprising an ether, amine,
alcohol, sulfoxide, sulfone, sulfonamide, tetrazole,
carboxylic acid, amide, nitro, aryl, substituted aryl,
alkyl, cycloalkyl, heterocycle, substituted
heterocycle, heteroaryl, substituted heteroaryl,
halogen, or the following structure at the 3-position
(meta) of the aryl group:

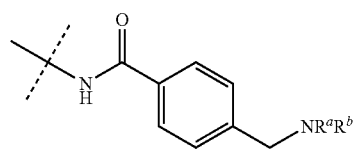

where $R_a$ and or $R_b$ are independently a hydrogen or
a group chosen from a C1-C10 alkyl group, a
C3-C7 cycloalkyl group, an aryl group, a C3-C12
heterocycle, or $R_a$ and $R_b$ are linked to form with
the nitrogen a heterocycle such as an optionally
substituted piperidine, piperazine, or morpholine
or
L is a linker consisting of an —C≡C—, —CH=CH—,
—C(CH₃)=CH—, or —CH₂—CH₂—
and
S is an aryl, heteroaryl, alkyl, heteroalkyl,
substituted alkyl, substituted aryl, substituted
heteroaryl, or substituted heteroalkyl, where a
heteroalkyl group is defined as —[(CH₂)ₙY]ₘ(CH₂)ₚ—
with Y = O, S, or NH and n, m, and p = 1 to 3 with
the proviso that when m is 2 or 3, n is not 1
and
X is a functional group, comprising an ether,
amine, alcohol, sulfoxide, sulfone, sulfonamide,
tetrazole, carboxylic acid, amide, nitro, aryl,
substituted aryl, alkyl, cycloalkyl, heterocycle,
substituted heterocycle, heteroaryl, substituted
heteroaryl, halogen, or none
or
L is an aryl group
and
S is either —O—(CH₂)ₙ— attached at the 4-position
(para) of the aryl group, where n = 1 to 4, or the
following structure attached at the 3-position (meta)
of the aryl group through the amidic nitrogen:

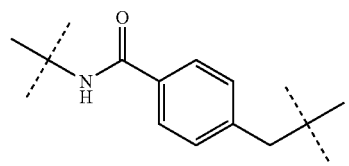

and
X is a dialkylamine NR_aR_b, where $R_a$ and or $R_b$ are
independently a hydrogen or a group chosen from a
C1-C10 alkyl group, a C3-C7 cycloalkyl group, an
aryl group, a C3-C12 heterocycle, or $R_a$ and $R_b$ are
linked to form with the nitrogen a heterocycle such
as an optionally substituted piperidine, piperazine,
or morpholine
or
L is an aryl group
and
S is NH attached at the 3-position (meta) of the
aryl group
and
X is an arenesulfonyl or alkanesulfonyl group
—SO₂R_c, where $R_c$ is an aryl, alkyl, or trifluoroalkyl
group
$R^2$ is a halogen, alkyl, substituted alkyl, arylvinyl,
substituted arylvinyl, vinyl, substituted vinyl,
alkynyl, substituted alkynyl, aryl, substituted aryl,
heteroaryl, substituted heteroaryl, acyl, substituted
acyl, substituted oxalyl, nitro, nitrovinyl, amino,
substituted amino, formyl, or carboxyl, or carboxyl
derivative
$R^3$ = H, Me, SO₂Ph, or ethoxymethyl In a further preferred embodiment, the invention provides a compound of formula (IIb):

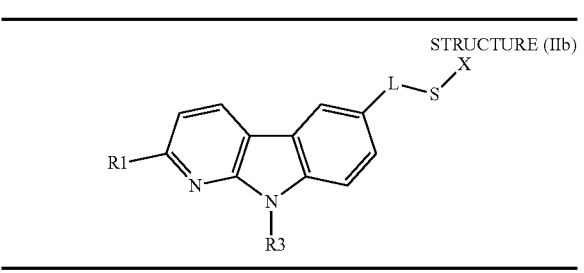

STRUCTURE (IIb)

where
L is a linker consisting of aryl, substituted aryl, heteroaryl, substituted heteroaryl, —CH₂—CH₂—, —C≡C—, —CH=CH—, —C(CH₃)=CH—, —C(O)CH₂CH₂C(O)—, or —C(O)CH2Y—, where Y = S, O, NH, or none
S is a spacer consisting of an aryl, heteroaryl, heteroalkyl, or alkyl, substituted alkyl, substituted aryl, substituted heteroaryl substituted heteroalkyl, or none, wherein heteroalkyl is as above defined
X is a functional group, comprising an ether, amine, alcohol, sulfoxide, sulfone, sulfonamide, tetrazole, carboxylic acid, amide, nitro, aryl, substituted aryl, cycloalkyl, heterocycle, substituted heterocycle, heteroaryl, substituted heteroaryl, or halogen
R¹ is a halogen, alkyl, substituted alkyl, E or Z substituted alkene, substituted alkynyl, aryl, substituted aryl, heteroaryl, substituted heteroaryl, heteroalkyl, substituted heteroalkyl, wherein heteroalkyl is as above defined,
arylamine, substituted arylamine, or a group —L—S—X as defined in II(a)
R³ = H, Me, SO₂Ph, or ethoxymethyl In a further preferred embodiment, the invention provides a compound of formula (IIIa):

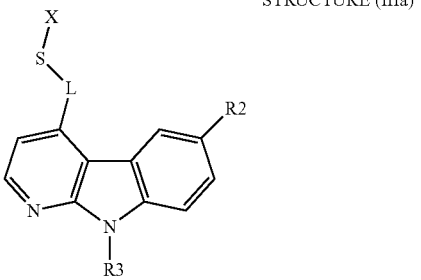

STRUCTURE (IIIa)

wherein
L is NH or O
and
S is an aryl or heteroaryl group
and
X is a functional group or a spacer selected from an aryl, heteroaryl, alkyl, heteroalkyl, substituted alkyl, substituted aryl, substituted heteroaryl, or substituted heteroalkyl, where a heteroalkyl group is defined as —[(CH₂)ₙY]ₘ(CH₂)ₚ— with Y = O, S, or NH, n, m = 1 to 3, and p = 0 to 4, with the proviso that when m is 2 or 3, n is not 1, such spacer bearing a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, halogen, or the following structure at the 3-position (meta) of the aryl group:

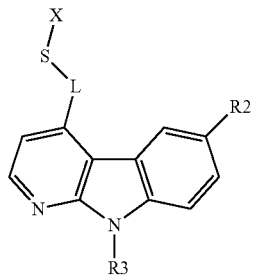

STRUCTURE (IIIa)

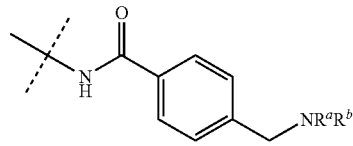

where $R_a$ and or $R_b$ are independently a hydrogen or a group chosen from a C1-C10 alkyl group, a C3-C7 cycloalkyl group, an aryl group, a C3-C12 heterocycle, or $R_a$ and $R_b$ are linked to form with the nitrogen a heterocycle such as an optionally substituted piperidine, piperazine, or morpholine
or
L is a linker consisting of an —C≡C—, —CH=CH—, —C(CH₃)=CH—, or —CH₂—CH₂—
and
S is an aryl, heteroaryl, alkyl, heteroalkyl, substituted alkyl, substituted aryl, substituted heteroaryl, or substituted heteroalkyl, where a heteroalkyl group is defined as —[(CH₂)ₙY]ₘ(CH₂)ₚ— with Y = O, S, or NH and n, m, and p = 1 to 3 with the proviso that when m is 2 or 3, n is not 1
and
X is a functional group, comprising an ether, amine, alcohol, sulfoxide, sulfone, sulfonamide, tetrazole, carboxylic acid, amide, nitro, aryl, substituted aryl, alkyl, cycloalkyl, heterocycle, substituted heterocycle, heteroaryl, substituted heteroaryl, halogen, or none
or
L is an aryl group
and
S is either —O—(CH₂)ₙ— attached at the 4-position (para) of the aryl group, where n = 1 to 4, or the following structure attached at the 3-position (meta) of the aryl group through the amidic nitrogen:

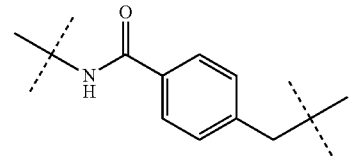

and
X is a dialkylamine $NR_aR_b$, where $R_a$ and or $R_b$ are independently a hydrogen or a group chosen from a C1-C10 alkyl group, a C3-C7 cycloalkyl group, an aryl group, a C3-C12 heterocycle, or $R_a$ and $R_b$ are linked to form with the nitrogen a heterocycle such as an optionally substituted piperidine, piperazine, or morpholine
or
L is an aryl group
and
S is NH attached at the 3-position (meta) of the aryl group
and
X is an arenesulfonyl or alkanesulfonyl group —SO₂$R_c$, where $R_c$ is an aryl, alkyl, or trifluoroalkyl group
R² is a halogen, alkyl, substituted alkyl, arylvinyl, substituted arylvinyl, vinyl, substituted vinyl, alkynyl, substituted alkynyl, aryl, substituted aryl, heteroaryl, substituted heteroaryl, acyl, substituted acyl, substituted

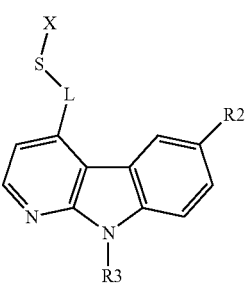

STRUCTURE (IIIa)

oxalyl, nitro, nitrovinyl, amino, substituted amino, formyl, carboxyl, or carboxyl derivative
$R^3$ = H, Me, $SO_2Ph$, or ethoxymethyl In a further preferred embodiment, the invention provides a compound of formula (IIIb):

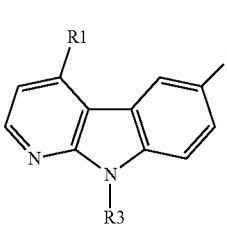

STRUCTURE (IIIb)

where
L is a linker consisting of aryl, substituted aryl, heteroaryl, substituted heteroaryl, —CH₂—CH₂—, —C≡C—, —CH=CH—, —C(CH₃)=CH—, —C(O)CH₂CH₂C(O)—, or —C(O)CH2Y, where Y = S, O, NH, or none
S is a spacer consisting of an aryl, heteroaryl, heteroalkyl, or alkyl, substituted alkyl, substituted aryl, substituted heteroaryl, or substituted heteroalkyl, being heteroalkyl as above defined.
X is a functional group, comprising an ether, amine, alcohol, sulfoxide, sulfone, sulfonamide, tetrazole, carboxylic acid, amide, nitro, aryl, substituted aryl, cycloalkyl, heterocycle, substituted heterocycle, heteroaryl, substituted heteroaryl, or halogen
$R^1$ is a halogen, alkyl, substituted alkyl, aryl, substituted aryl, heteroaryl, substituted heteroaryl, heteroalkyl, substituted heteroalkyl, wherein heteroalkyl is as above defined, arylamine, substituted arylamine, or alkoxy group, or a group —L—S—X as defined in structure III(a)
$R^3$ = H, Me, $SO_2Ph$, or ethoxymethyl The compounds of the invention can be in the form of free bases or as acid addition salts, preferably salts with pharmaceutically acceptable acids. The invention also includes separated isomers and diastereomers of the compounds, or mixtures thereof (e.g. racemic mixtures).

In a further embodiment, the invention provides a pharmaceutical composition containing a compound as above described in association with physiologically acceptable carriers and excipients. The compositions can be in the form of solid, semi-solid or liquid preparations, preferably in form of solutions, suspensions, powders, granules, tablets, capsules, syrups, suppositories, aerosols or controlled delivery systems. The compositions can be administered by a variety of routes, including oral, transdermal, subcutaneous, intravenous, intramuscular, rectal and intranasal, and are preferably formulated in unit dosage form, each dosage containing from about 1 to about 1000 mg, preferably from 1 to 500 mg of active ingredient. The principles and methods for the preparation of pharmaceutical compositions are described for example in Remington's Pharmaceutical Science, Mack Publishing Company, Easton (PA).

In a yet further embodiment, the invention relates to a compound or a pharmaceutical composition as herein provided, for use in the treatment of tumors, especially of ALK-associated, RET-associated or Bcr-Abl-associated tumors. In a preferred embodiment, the compounds or compositions according to the invention are used in the treatment of anaplastic large cell lymphoma, diffuse large B cell lymphoma, inflammatory myofibroblastic tumors, chronic myeloid leukemia or Ph+ acute lymphoblastic leukemia. In a further preferred embodiment, the compounds or compositions are used for the treatment of chronic myeloid leukaemia (CML) resistant to Imatinib or Dasatinib or Nilotinib or Bosutinib.

General Synthesis Strategies

The compounds were prepared by selective sequential derivatization of the α-carboline core. α-Carbolines bearing halo or simple alkyl substituents on the pyridine ring ($R^1$ in structure I) can readily be prepared by Graebe-Ullman reactions from disubstituted pyridine precursors. Electrophilic aromatic substitution provides selective access to disubstituted α-carbolines bearing halo, acyl, carboxyl, carboxamido, oxalyl, nitro, methyl-oxo acetate, or amine at the 6-position ($R^2$ in structure I)

Further elaboration was achieved by palladium catalyzed or nucleophilic substitution of the chloro group on the 2-, 3-, or 4-position of the pyridine ring or the bromo group at the 6-position, using a Buchwald amination (case where L=—NH— or —O—), Suzuki coupling (case where $R^1$, $R^2$, or L=aryl, alkyl, or vinyl), Sonogoshira coupling (case where L=alkynyl), or by nucleophilic aromatic substitution (case where L=—NH— or —O—). Unsymmetrical α-carbolines bearing complex groups on both rings can be prepared by sequential selective palladium catalyzed coupling reactions.

Further functionalisation of the substitutents on the α-carboline core can be achieved either by the use of highly functionalized boronic acids or ester, arylamines, acetylenes, or phenols, or by late-stage derivatization of the linker already on the α-carboline structure. Thus nucleophilic substitution of 6-bromoacetyl-α-carbolines or demethylation of methoxyphenyl-α-carbolines followed by nucleophilic substitution of substituted alkyl halides or substituted alcohols by Mitsunobu reaction, provide access to a wide variety of compounds bearing substituents of the structure L-S—X.

Deprotection of arylsulfonyl groups ($R^3$ on structure 1) was achieved with tetrabutylammonium fluoride or sodium methoxide in methanol. Deprotection of the ethoxymethyl group can be performed under acidic conditions.

Molecules of the following structures have been prepared

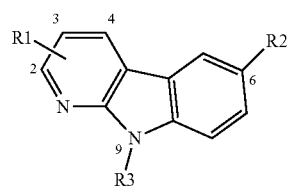

wherein:
when $R^1$ is attached in the 2 position of the α-carboline ring it is selected from:

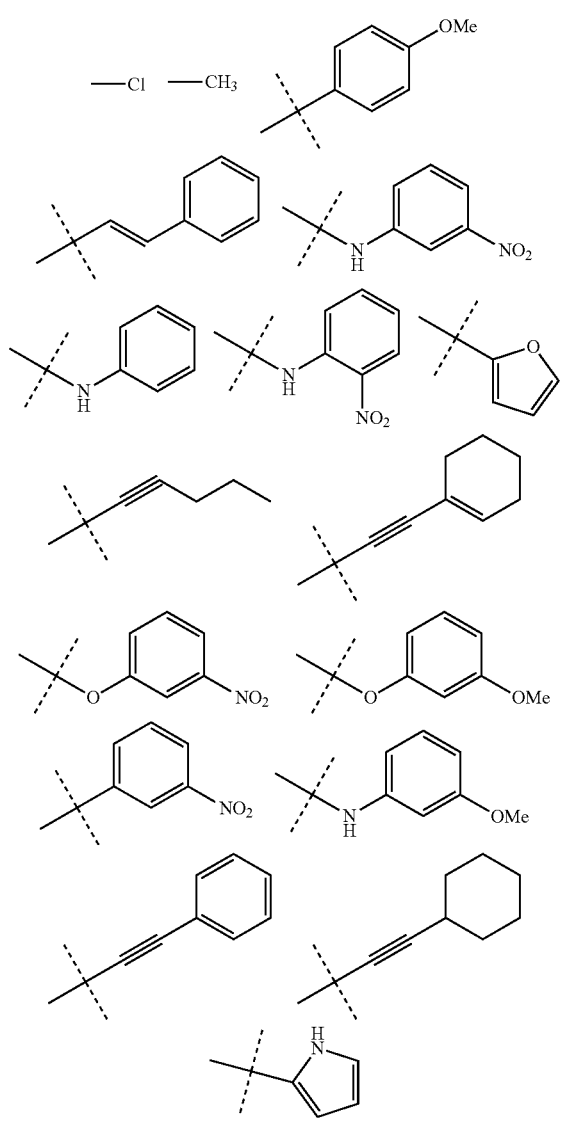
When R[1] is attached in the 3 position of the α-carboline ring it is selected from:
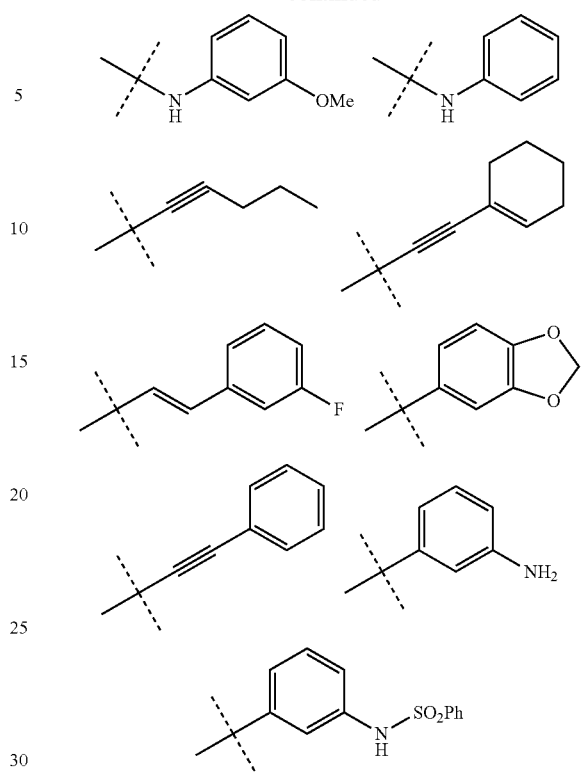
When R[1] is attached in the 4 position of the α-carboline ring it is selected from:
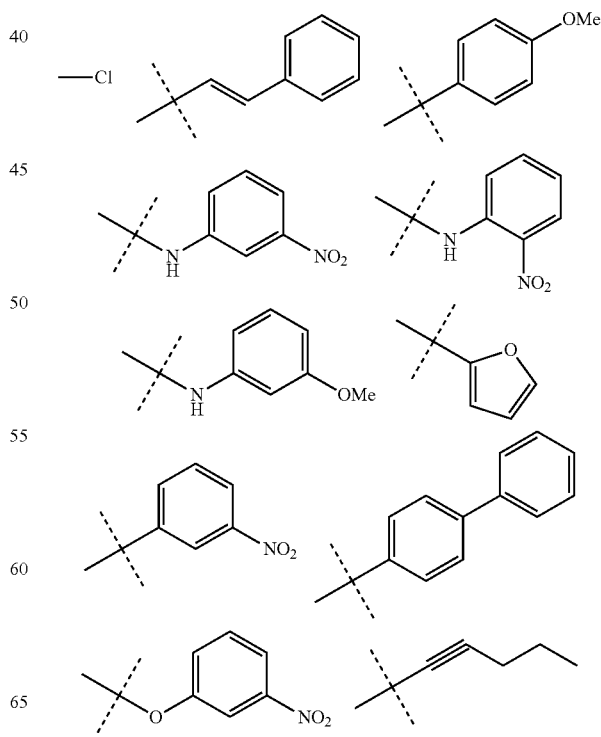
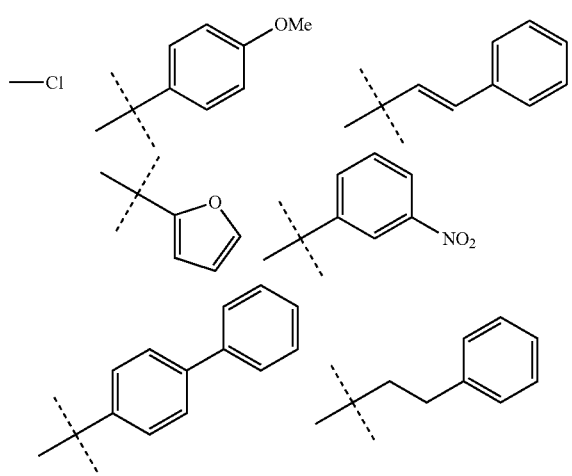

15
-continued
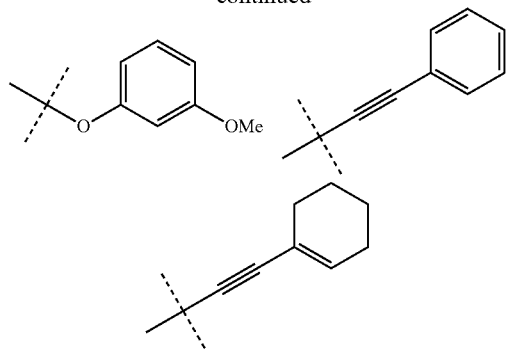
R² is selected from:
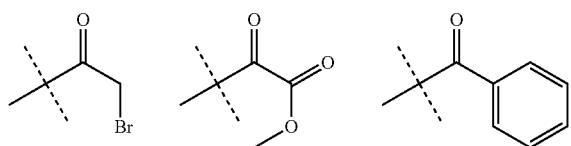
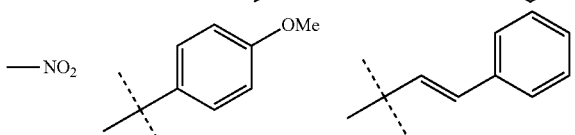
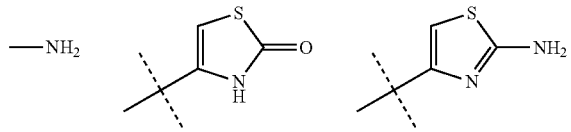
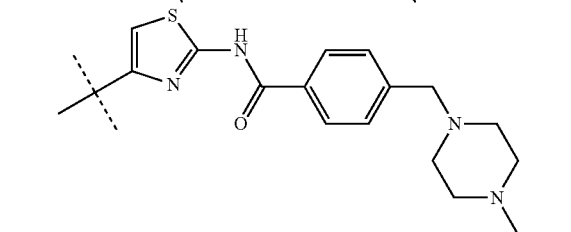
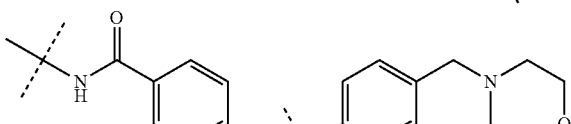
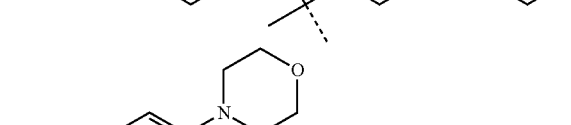
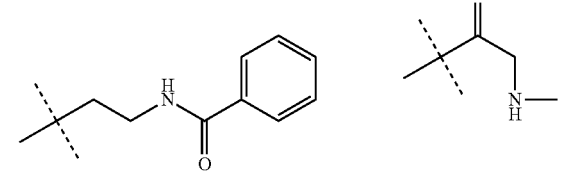
16
-continued
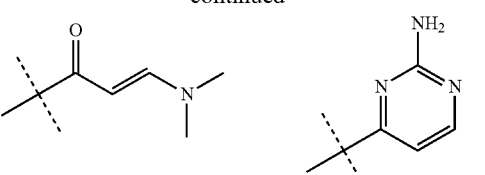
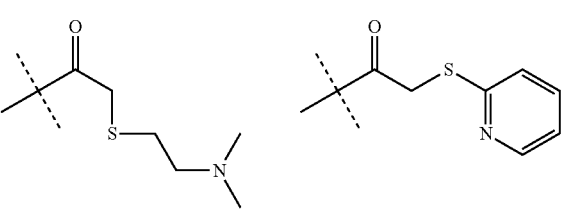
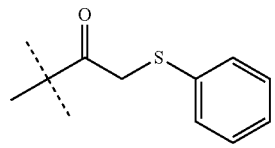
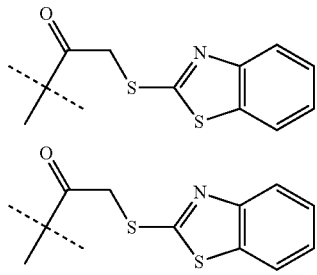
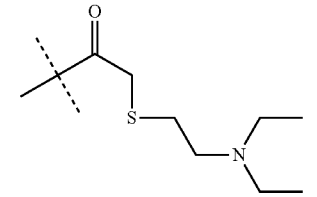
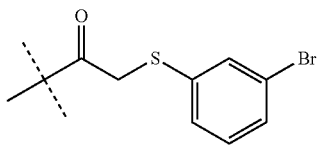
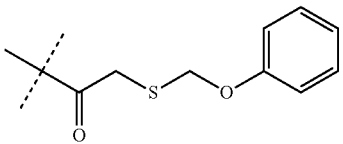
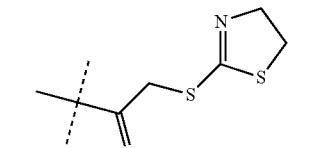
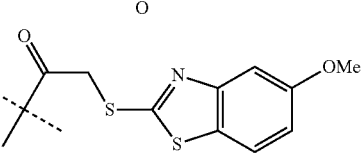

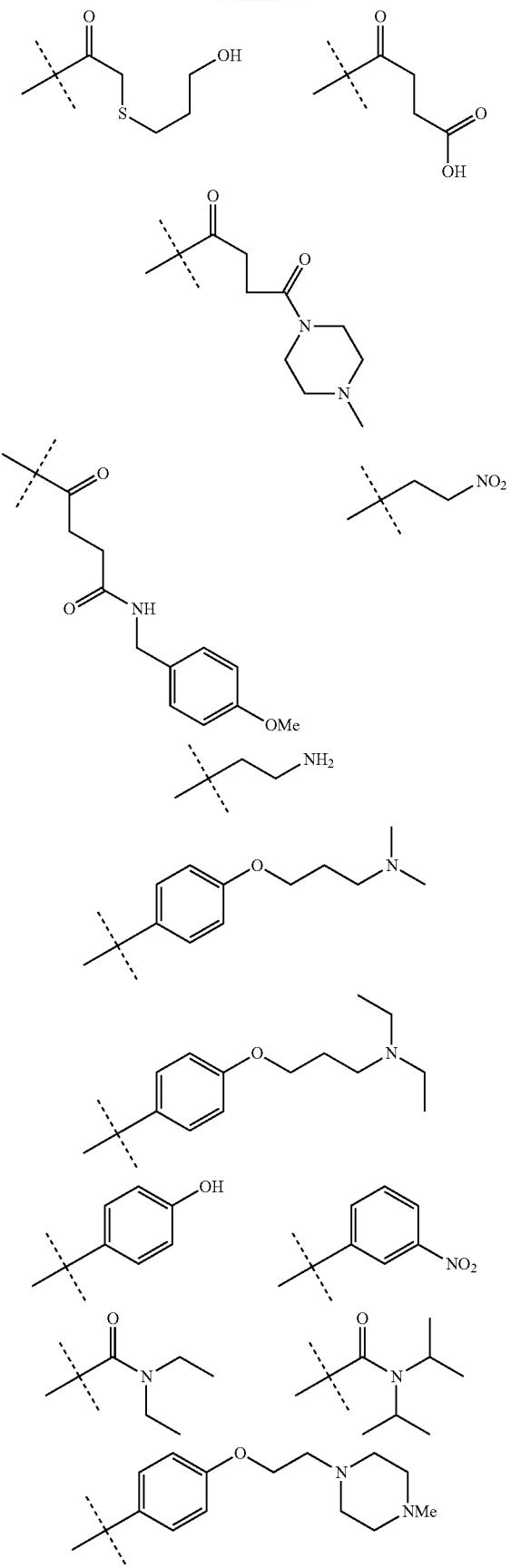

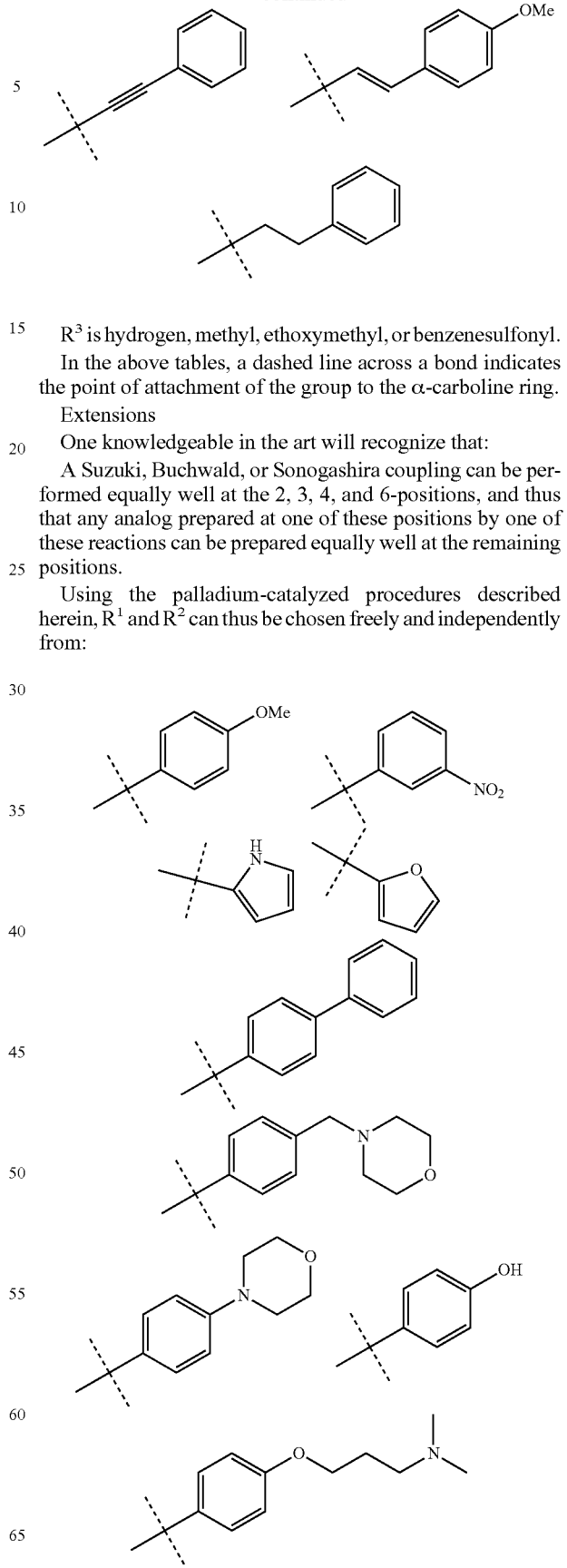

R³ is hydrogen, methyl, ethoxymethyl, or benzenesulfonyl.

In the above tables, a dashed line across a bond indicates the point of attachment of the group to the α-carboline ring.

Extensions

One knowledgeable in the art will recognize that:

A Suzuki, Buchwald, or Sonogashira coupling can be performed equally well at the 2, 3, 4, and 6-positions, and thus that any analog prepared at one of these positions by one of these reactions can be prepared equally well at the remaining positions.

Using the palladium-catalyzed procedures described herein, $R^1$ and $R^2$ can thus be chosen freely and independently from:

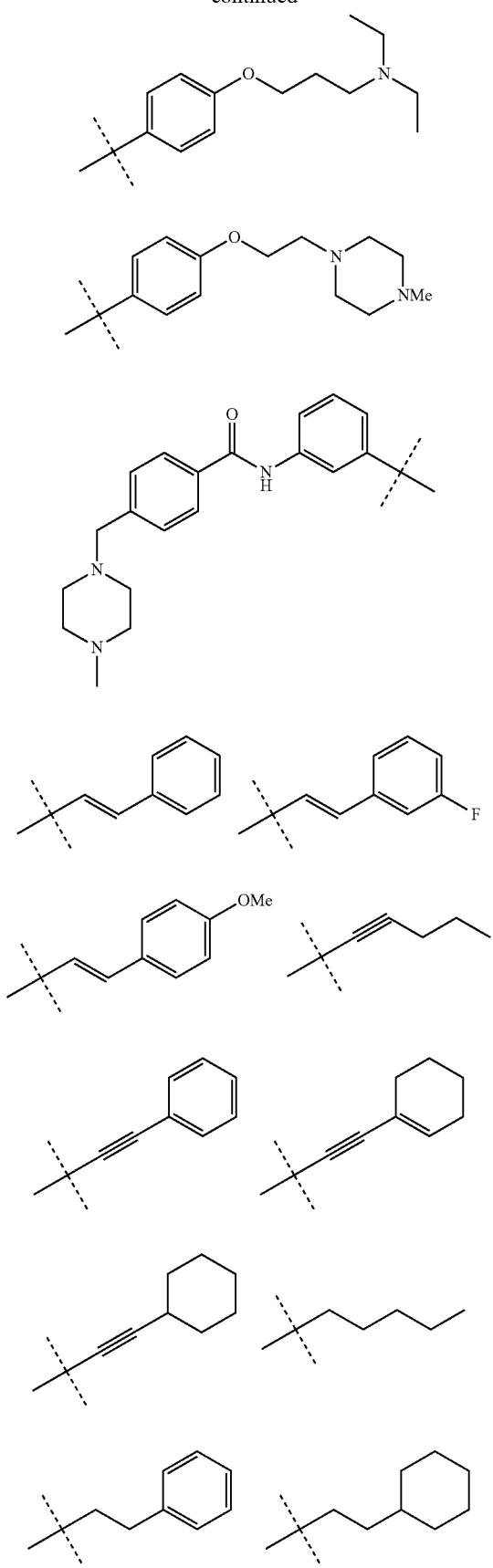
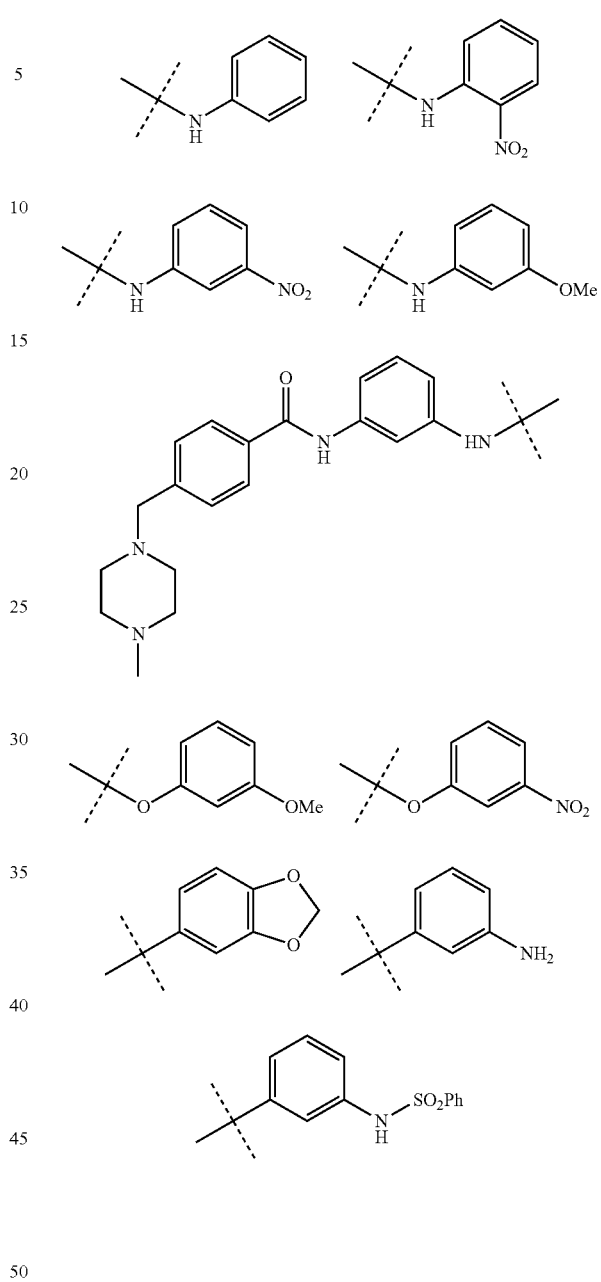

A Suzuki, Buchwald, or Sonogashira coupling can be performed equally well with any other boronic acid or boronic ester, phenol, arylamine, or acetylene, respectively, and that any substitution pattern achieved with one of these compounds can be done with any other one. These include any commercial boronic acids or esters, phenols, arylamines, or acetylenes. Furthermore, one knowledgeable in the art will recognize that more highly functionalized vinyl boronic acids or esters and acetylenes can readily be prepared from substituted benzaldehydes. Compounds where L is a substituted vinyl group and 3 is an aryl or heteroaryl group can be prepared in a regiocontrolled and stereospecific fashion by hydroboration of a substituted arylacetylene.

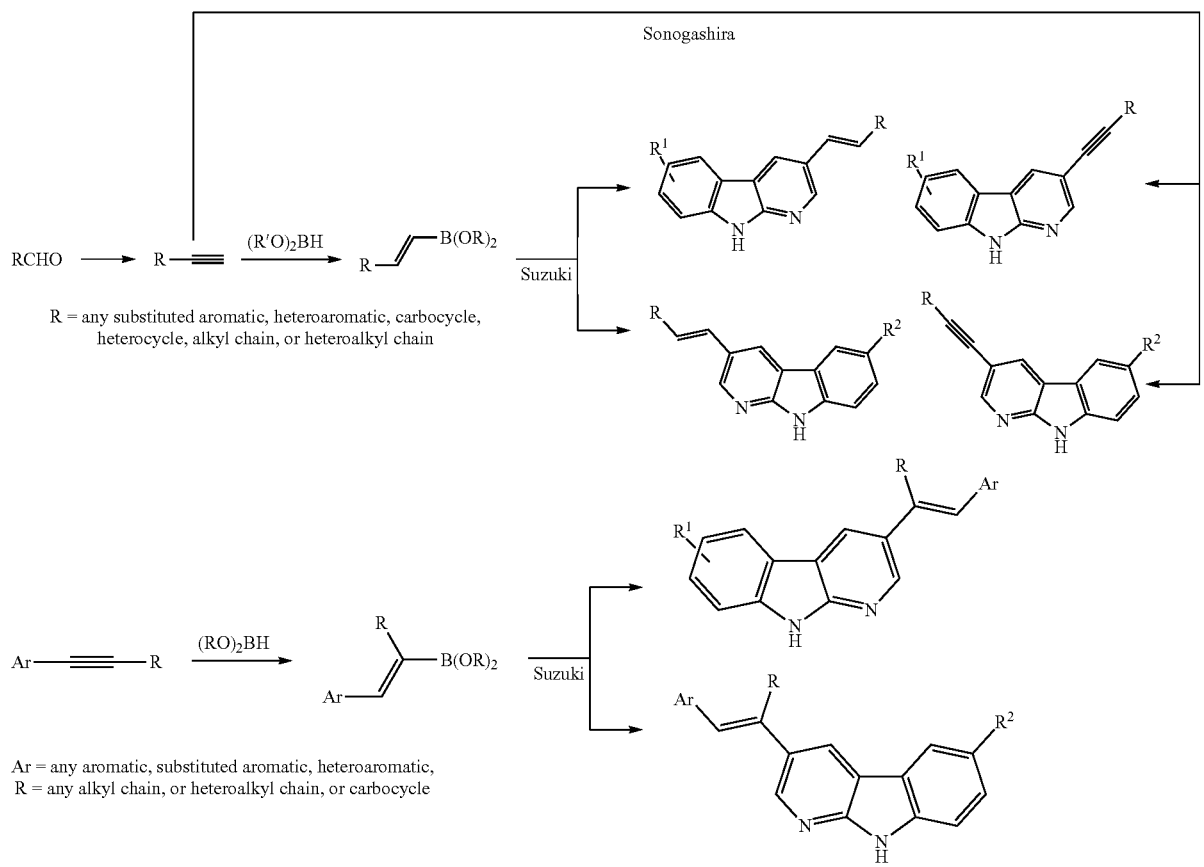

Where a compound having a sidechain of the type L-S—X, where S is an alkyl chain and X is an amine, S can be an alkyl chain of any length from 1 to 10, or a heteroalkyl chain, defined as —$[CH_2]_nY]_m(CH_2)_p$— with Y=O, S, or NH, n, m=1 to 3, and p=2 to 4, with the proviso that when m is 2 or 3 n is not 1, and X can be any polar functional group. For example,

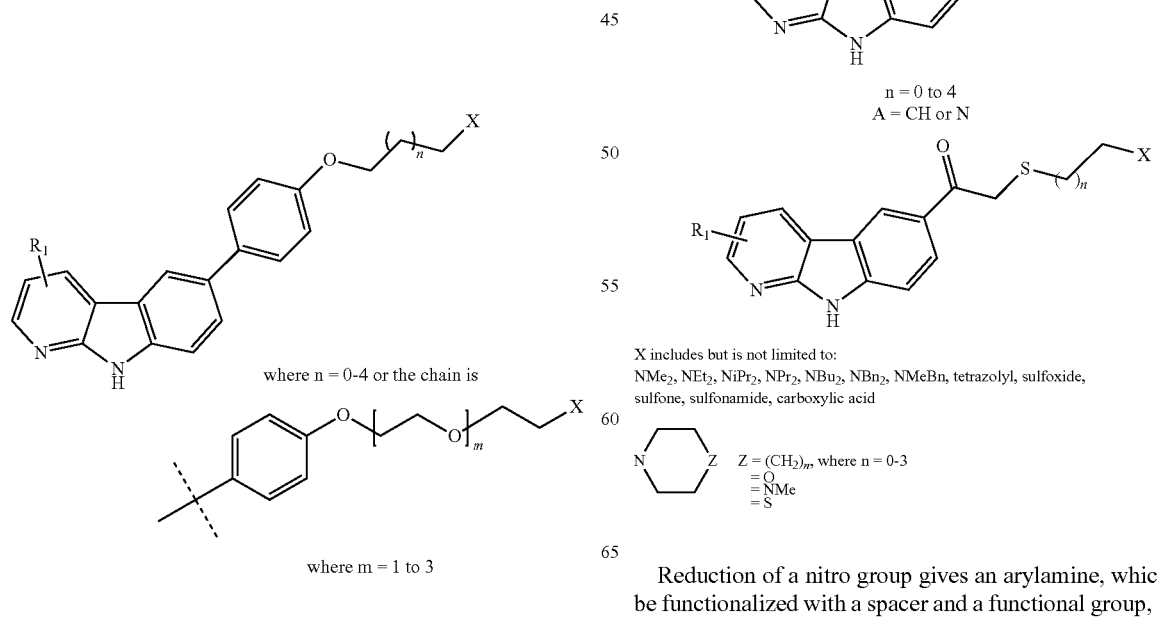

X includes but is not limited to:
$NMe_2$, $NEt_2$, $NiPr_2$, $NPr_2$, $NBu_2$, $NBn_2$, NMeBn, tetrazolyl, sulfoxide, sulfone, sulfonamide, carboxylic acid Reduction of a nitro group gives an arylamine, which can be functionalized with a spacer and a functional group, using for example the sidechain and conditions used with the aminothiazole described in section 5.

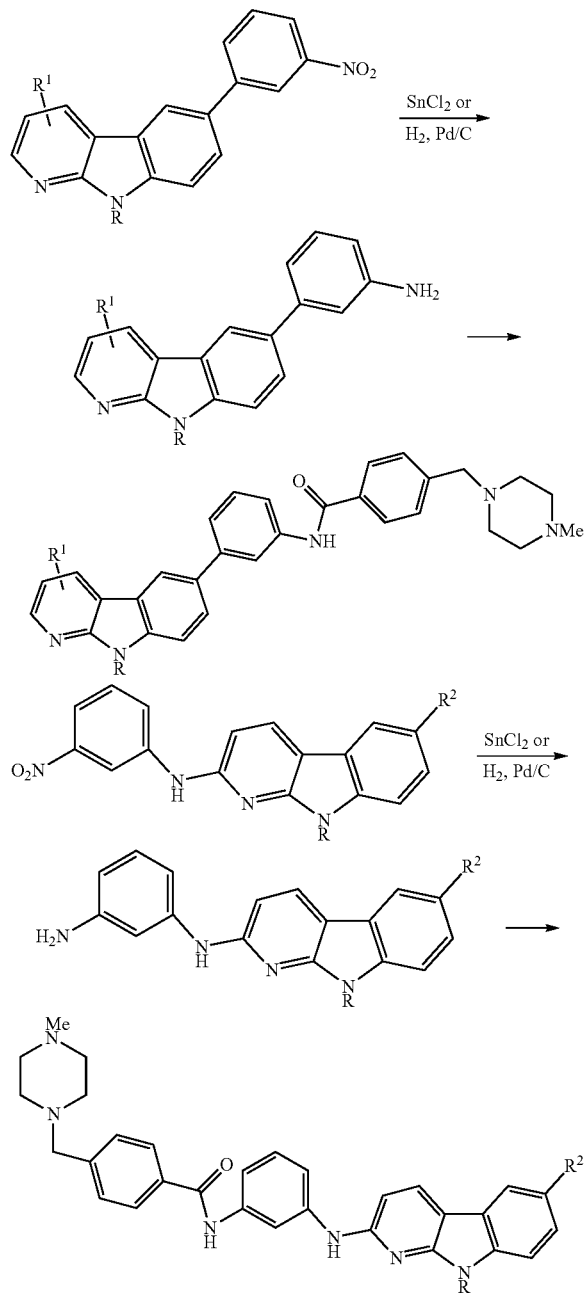

Synthetic Schemes

Synthesis of α-carbolines Substituted on the Pyridine Ring

α-Carbolines substituted on the pyridine ring with alkyl or halogen were prepared from substituted pyridines and benzotriazole by a modified Graebe-Ullman reaction. 4-Chloro-α-carbolines were prepared by N-oxidation followed by a MsCl-induced substitution/rearrangement.

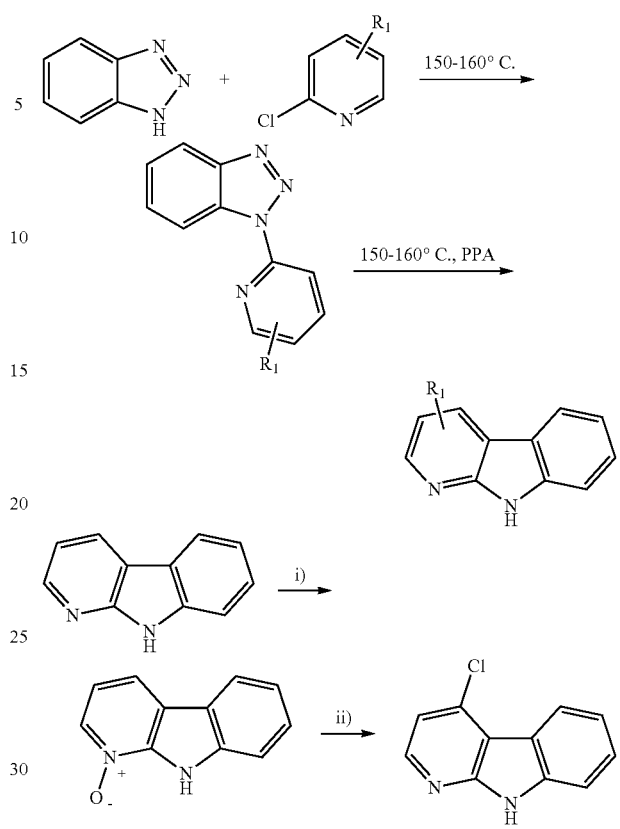

Reagents and conditions: i) mCPBA 70%, acetone, rt, 12 h; ii) DMF, POCl$_3$, 100° C., 6 h.

Synthesis of Disubstituted α-carbolines by Electrophilic Aromatic Substitution

Compounds of structure (Ia or Ib) where $R^2$ is halogen, acyl, nitro, amino, formyl, carboxyl, or carboxyamide were prepared from 3-chloro-α-carboline by electrophilic aromatic substitution.

Further functionalisation was achieved by reduction, Henry condensation, Suzuki coupling (case where $R^2$ or L=heteroaryl, aryl, alkyl, or vinyl), Sonogashira coupling (case where L=acetylene), Buchwald coupling (case where L=NH or O), nucleophilic substitution (case where L=C(O)CH$_2$S), or by amide formation (case where L-X=C(O)CH$_2$CH$_2$C(O)NR$_a$R$_b$).

Compounds of structure (IIa) or (IIb) where $R^2$ is halogen, acyl, nitro, amino, formyl, carboxyl were prepared from 2-chloro-α-carboline or 2-methyl-α-carboline by electrophilic aromatic substitution. Further functionalisation at $R^1$ and $R^2$ was achieved by Suzuki coupling (case where R or L=heteroaryl, aryl, alkyl, or vinyl), by Sonogashira coupling (case where L acetylene), by nucleophilic substitution (case where L=C(O)CH$_2$S), by amide formation (case where L-X=C(O)CH$_2$CH$_2$C(O)NR$_a$R$_b$), or by a Buchwald substitution (case where L=—NH— or —O—).

Compounds of structure (IIIa) or (IIIb) where $R^2$ is halogen, acyl, nitro, amino, formyl, carboxyl were prepared from 4-chloro-α-carboline by electrophilic aromatic substitution. Further functionalisation at $R^1$ and $R^2$ was achieved by Suzuki coupling (case where R or L=heteroaryl, aryl, alkyl, or vinyl), by Sonogashira coupling (L=acetylene), by nucleophilic substitution (case where L=C(O)CH$_2$S), by amide formation (case where L-X=C(O)CH$_2$CH$_2$C(O)NR$_a$R$_b$), or by a Buchwald substitution (case where L=—NH— or —O—).

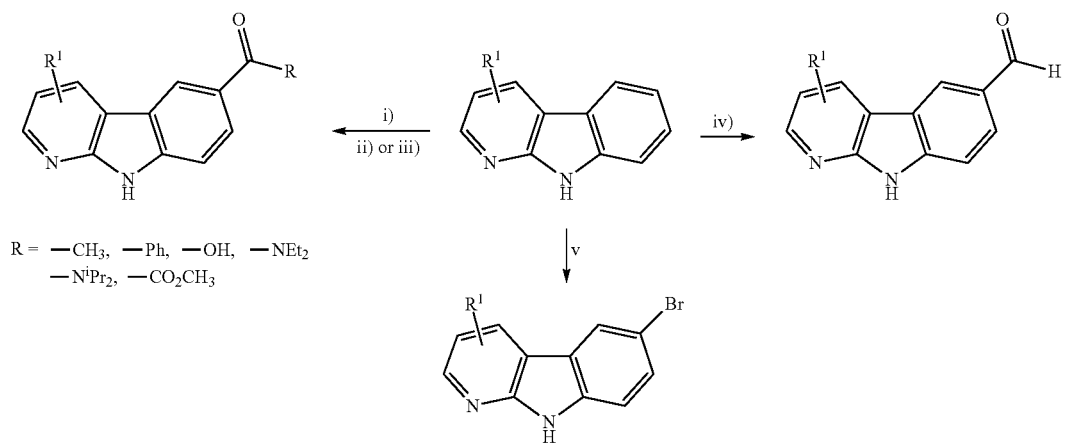

Reagents and conditions: i) {R = —CH₃, —Ph, —CO₂CH₃} AlCl₃ (4.5 equiv.), RCOCl (2 equiv.), CH₂Cl₂, room temperature or reflux, 2-4 h;
ii) {R = —OH} a) AlCl₃ (4.5 equiv.), (COCl)₂ (2 equiv.), CH₂Cl₂, room temperature, 2-4 h, b) H₂O; iii) {R = —NEt₂, —NⁱPr₂} a) AlCl₃ (4.5 equiv.), (COCl)₂ (2 equiv.), CH₂Cl₂, room temperature, 2-4 h, b) HNEt₂, HNⁱPr₂; iv) a) AlCl₃ (7 equiv.), CH₃OCHCl₂ (3 equiv.), CH₂Cl₂, -78° C. to room temperature, 12 h, b) H₂O, v) Br₂ (1.1 equiv.), CH₂Cl₂, room temperature, 1 h.

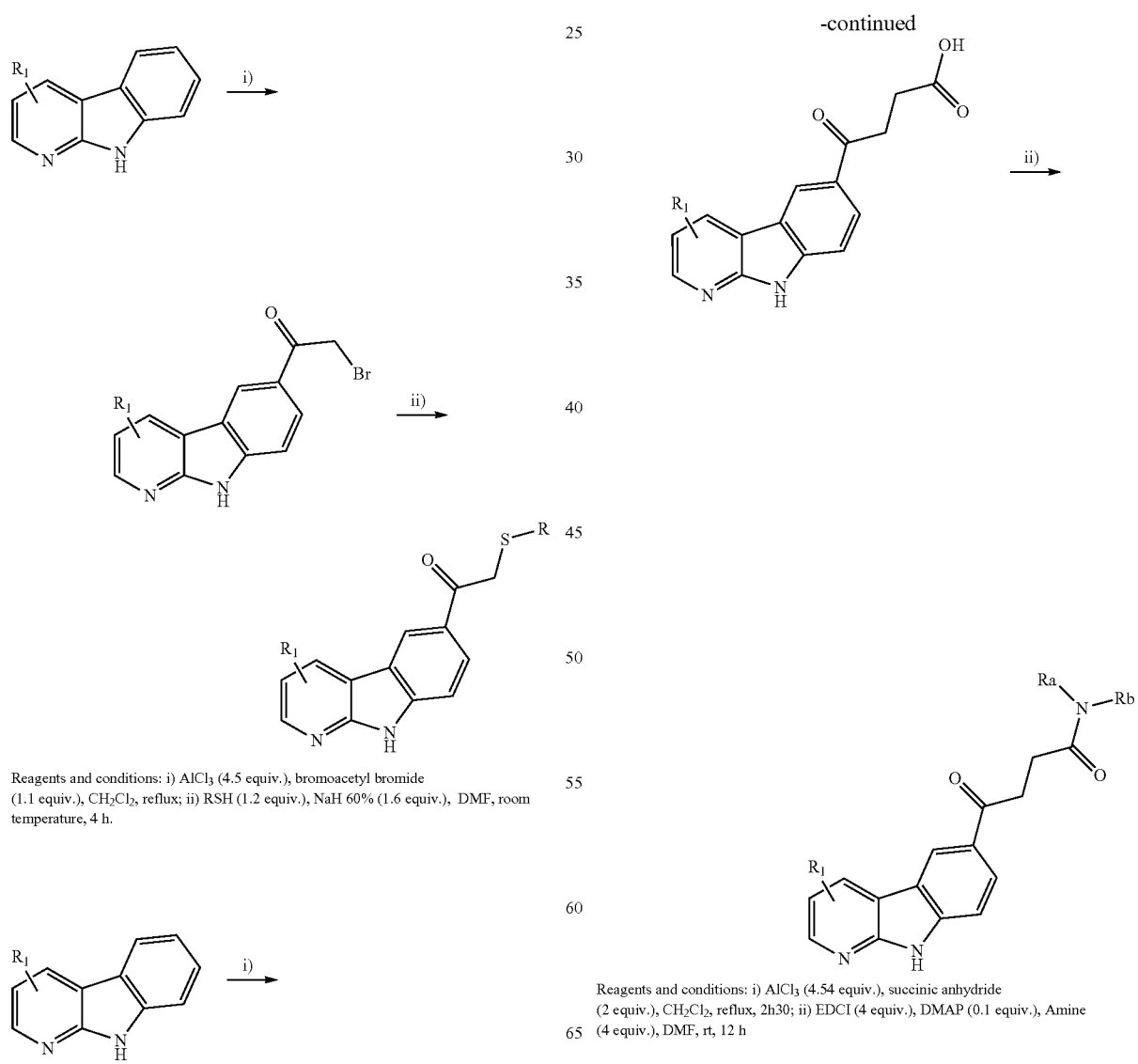

Reagents and conditions: i) AlCl₃ (4.5 equiv.), bromoacetyl bromide (1.1 equiv.), CH₂Cl₂, reflux; ii) RSH (1.2 equiv.), NaH 60% (1.6 equiv.), DMF, room temperature, 4 h.

Reagents and conditions: i) AlCl₃ (4.54 equiv.), succinic anhydride (2 equiv.), CH₂Cl₂, reflux, 2h30; ii) EDCI (4 equiv.), DMAP (0.1 equiv.), Amine (4 equiv.), DMF, rt, 12 h

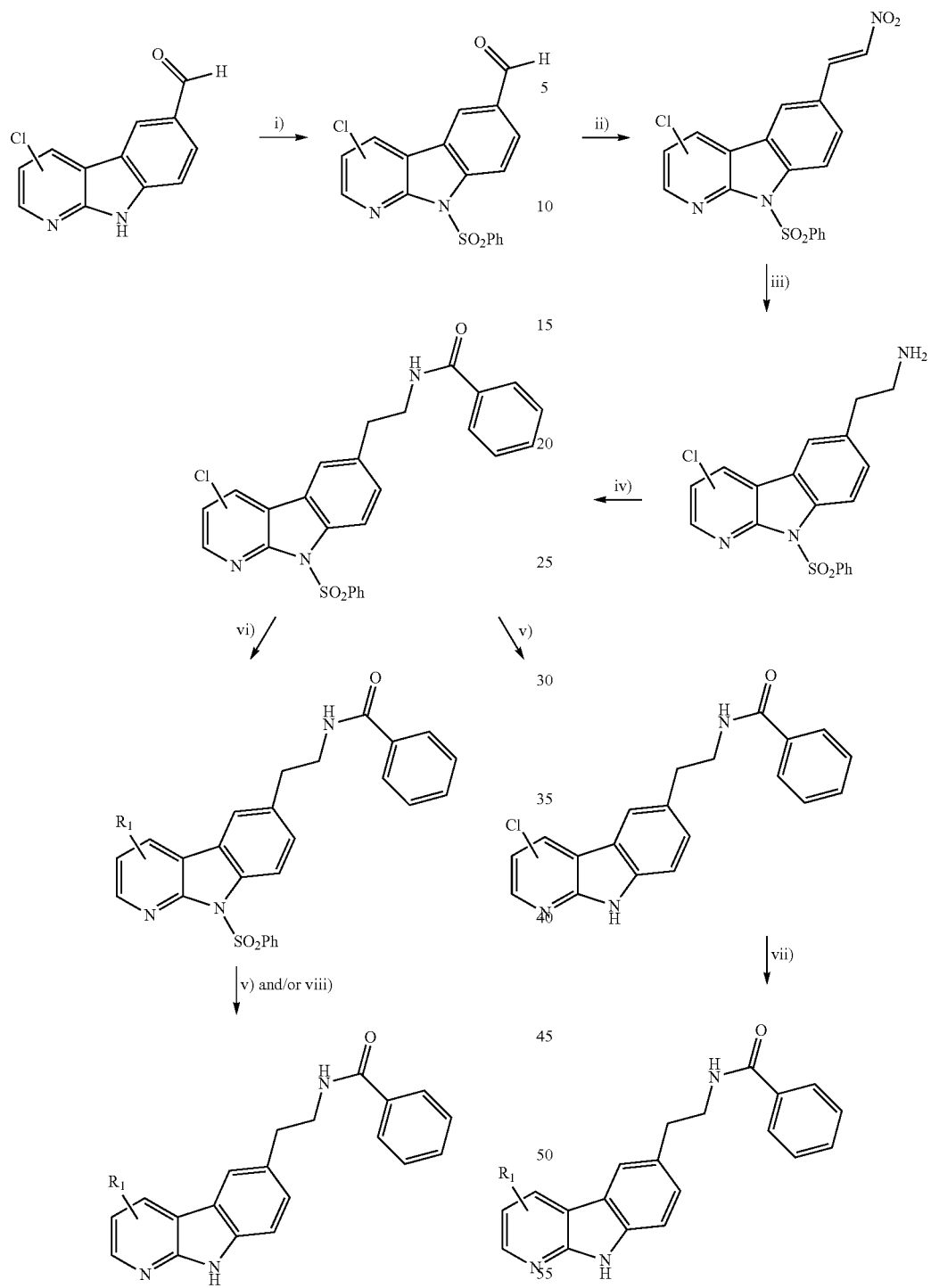

$R^1$ = ArNH or Ar
vi) for Cl at C2 and C4
vii) for Cl at C3

Reagents and conditions: i) NaH 60% (1.1 equiv.), PhSO₂Cl (1.2 equiv.), THF, 0° C. to room temperature, 12 h; ii) AcONH₄ (1.1 equiv.), CH₃NO₂, 100° C., 2 h; iii) NaBH₄ (2.5 equiv.), MeOH, isopropanol, SiO₂, room temperature, 1 h 30; then Ni Raney (cat), MeOH, 50° C., H₂ atm., 12 h;. iv) PhCOCl (1.5 equiv.), Et₃N (4.2 equiv.), CH₂Cl₂, room temperature, 12 h; v) 1.0 M TBAF (5 equiv.), THF, reflux, 4 h. vi) Pd(PPh₃)₄ (0.08 equiv.), K₂CO₃ (3 equiv.), ArB(OH)₂ (1.1 equiv.), H₂O, 1,4-dioxane, 100° C.; vii) Pd(OAc)₂ (0.08 equiv.), S-Phos (0.16 equiv.), K₃PO₄

(2 equiv.) (2.5 mL/mmol) 1,4-dioxane, ArB(OH)$_2$ (1.1 equiv.), 100° C., 12 h; or Pd$_2$(dba)$_3$ (0.08 equiv.), X-Phos (0.16 equiv.), t-BuONa (3 equiv.), t-BuOH, ArNH$_2$ (1.1 equiv.), 100° C., 12 h; viii) Pd$_2$(dba)$_3$ (0.08 equiv.), X-Phos (0.16 equiv.), K$_2$CO$_3$ (3 equiv.), t-BuOH, ArNH$_2$ (1.1 equiv.), 100° C.

Compounds of structure (Ib) where L=heteroaryl, S=carboxyaryl, and X=a heterocyclic amine were prepared according to the following route:

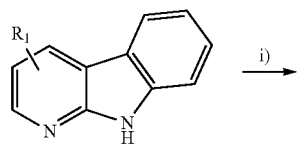

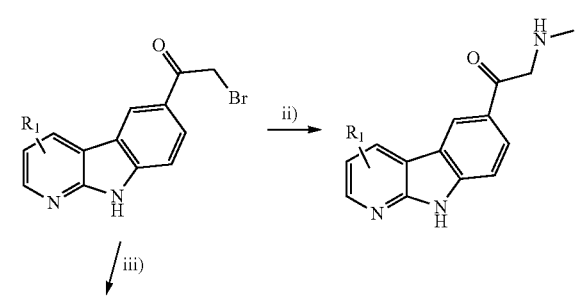

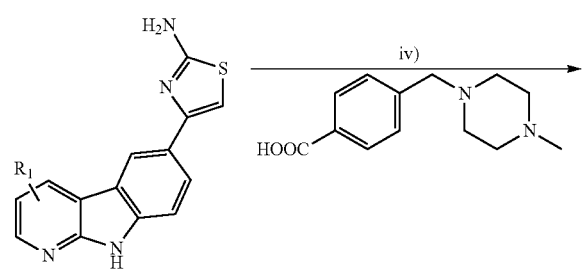

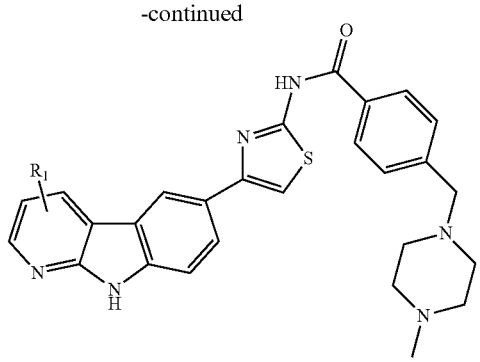

Reagents and conditions: i) AlCl$_3$ (4.5 equiv.), bromoacetyl bromide (1.1 equiv.), CH$_2$Cl$_2$, reflux; ii) MeNH$_2$, EtOH, r.t.; iii) Thiourea, abs EtOH, 50-60° C., 3 h; iv) EDCl (4 equiv.), DMAP (0.15 equiv.), DMF, r.t., 12h Synthesis of Disubstituted α-carbolines by a Regioselective Double Palladium Coupling Sequence Compounds of structure (Ia) where the group X—S-L- represents is heteroaryl, aryl, or and R$^2$ is heteroaryl, aryl, alkyl, alkynyl, arylamino, or vinyl, were prepared by a regioselective double palladium coupling sequence on the 3-chloro-6-bromo-α-carboline, in which the first palladium catalyzed reaction is a Suzuki, Buchwald, or Sonogashira coupling, and the second palladium catalyzed reaction is a Suzuki coupling. Further functionalisation was achieved by demethylation, of the methoxy group or reduction of the nitro group on the newly added aryl group, followed by Mitsunobu substitution, sulfonamide, or amide formation, prior to the second palladium-catalyzed coupling.

Compounds of structure (IIa) where R$^1$ is heteroaryl, aryl, or vinyl and R$^2$ is heteroaryl, aryl, alkyl, acetylene, arylamino, or vinyl, were prepared by a regioselective double palladium coupling sequence on the 2-chloro-6-bromo-α-carboline, in which the first palladium catalyzed reaction is a Suzuki, Buchwald, or Sonogashira coupling, and the second palladium catalyzed reaction is a Suzuki coupling. Further functionalisation can be achieved by demethylation, of the methoxy group or reduction of the nitro group on the newly added aryl group, followed by Mitsunobu substitution, sulfonamide, or amide formation, prior to the second palladium-catalyzed coupling.

Compounds of structure (IIIa) where R is heteroaryl, aryl, or vinyl and R$^2$ is heteroaryl, aryl, alkyl, acetylene, arylamino, or vinyl, were prepared by a regioselective double palladium coupling sequence on the 4-chloro-6-bromo-α-carboline, in which the first palladium catalyzed reaction is a Suzuki, Buchwald, or Sonogashira coupling, and the second palladium catalyzed reaction is a Suzuki coupling. Further functionalisation can be achieved by demethylation, of the methoxy group or reduction of the nitro group on the newly added aryl group, followed by Mitsunobu substitution, sulfonamide, or amide formation, prior to the second palladium-catalyzed coupling.

Compounds of structure (Ib, IIb, and IIIb) where R$^1$ is heteroaryl, aryl, alkyl, acetylene, arylamino, or vinyl, and R$^2$ is heteroaryl, aryl, or vinyl were prepared by a regioselective double palladium coupling sequence on the 2,3, or 4-chloro-6-bromo-□-carboline, in which the first palladium catalyzed reaction is a Suzuki coupling, and the second palladium catalyzed reaction is a Suzuki, Buchwald, or Sonogashira coupling. Further functionalisation can be achieved by demethylation of the methoxy group or reduction of the nitro group on the newly added aryl group, followed by Mitsunobu substitution, sulfonamide, or amide formation.

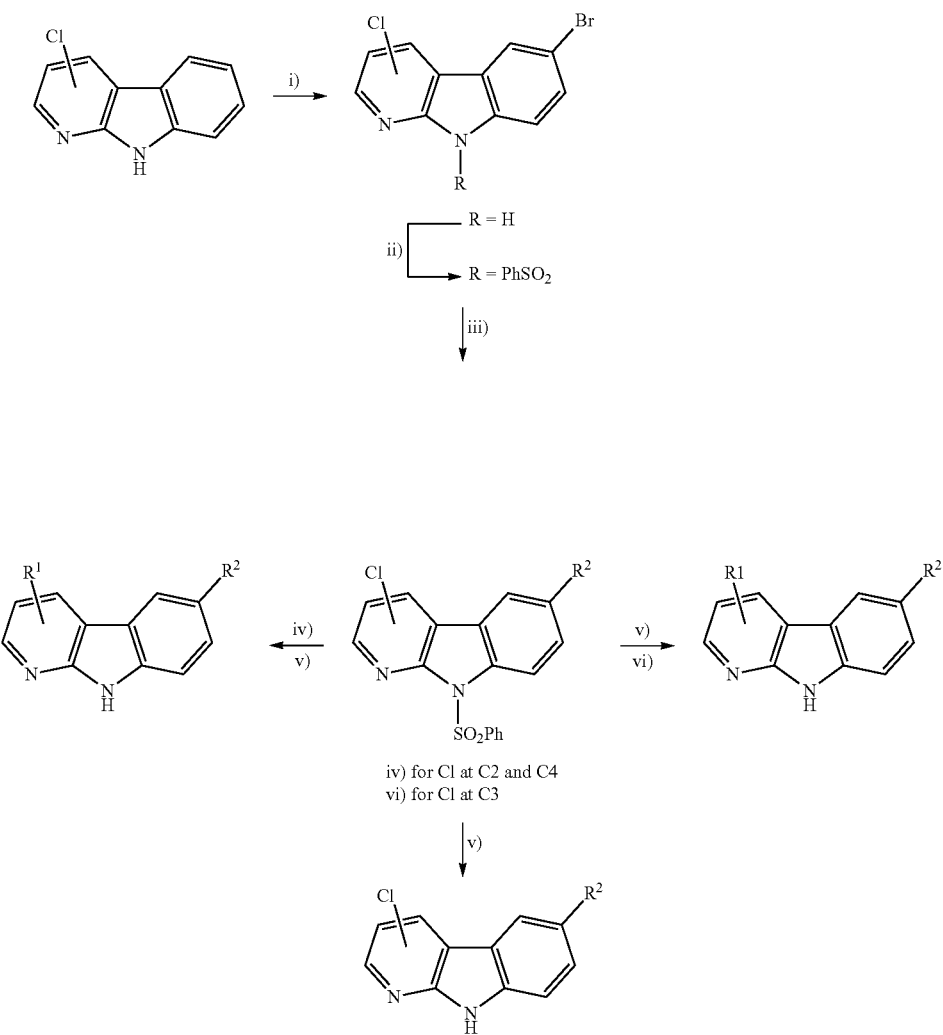

Reagents and conditions: i) Br₂ (1.1 equiv.), CH₂Cl₂, room temperature, 1 h;
ii) NaH 60% (1.1 equiv.) PhSO₂Cl (1.2 equiv.), THF, 0° C. to room temperature, 12
h; iii) Pd(PPh₃)₄ (0.08 equiv.), K₂CO₃ (3 equiv.), ArB(OH)₂ (1.1 equiv.), H₂O,
1,4-dioxane, 70° C. or 100° C.; iv) Pd(PPh₃)₄ (0.08 equiv.), K₂CO₃ (3 equiv.),
ArB(OH)₂ (1.1 equiv.), H₂O, 1,4-dioxane, 100° C.; v) 1.0 M TBAF (5 equiv.), THF,
reflux, 4 h; vi) Pd(OAc)₂ (0.08 equiv.), S-Phos (0.16 equiv.), K₃PO₄ (2 equiv.)
(2.5 mL/mmol) 1,4-dioxane, ArB(OH)₂ (1.1 equiv.), 100° C., 12 h.

Compounds of structure (Ia) where X—S-L- represents arylamino or aryloxy and $R^2$ is heteroaryl, aryl, alkyl, alkynyl, arylamino, or vinyl, were prepared by a regioselective double palladium coupling sequence on the 3-chloro-6-bromo-α-carboline in which the second palladium coupling reaction is a Buchwald reaction.

Compounds of structure (IIa) where X—S-L- represents arylamino or aryloxy and $R^2$ is heteroaryl, aryl, alkyl, alkynyl, arylamino, or vinyl, were prepared by a regioselective double palladium coupling sequence on the 2-chloro-6-bromo-α-carboline in which the second palladium coupling reaction is a Buchwald reaction.

Compounds of structure (IIIa) where X—S-L- represents arylamino or aryloxy and $R^2$ is heteroaryl, aryl, alkyl, alkynyl, arylamino, or vinyl, were prepared by a regioselective double palladium coupling sequence on the 4-chloro-6-bromo-α-carboline in which the second palladium coupling reaction is a Buchwald reaction.

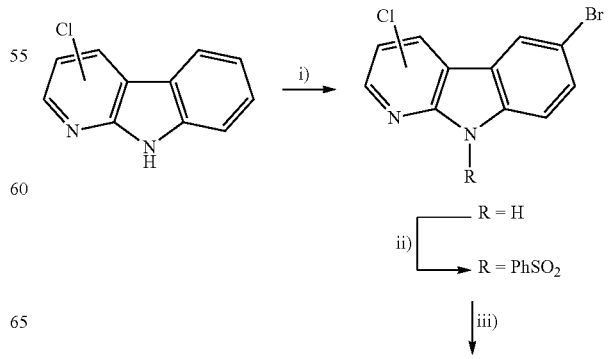

-continued

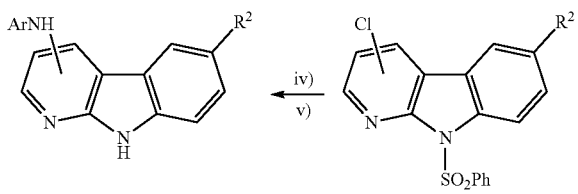

Reagents and conditions: i) Br$_2$ (1.1 equiv.), CH$_2$Cl$_2$, room temperature, 1 h;
ii) NaH 60% (1.1 equiv.) PhSO$_2$Cl (1.2 equiv.), THF, 0° C. to room temperature,
12 h; iii) Pd(PPh$_3$)$_4$ (0.08 equiv.), K$_2$CO$_3$ (3 equiv.), ArB(OH)$_2$ (1.1 equiv.), H$_2$O,
1,4-dioxane, 70° C. or 100° C.; iv) 1.0 M TBAF (5 equiv.), THF, reflux, 4 h; v)
Pd$_2$(dba)$_3$ (0.08 equiv.), X-Phos (0.16 equiv.), K$_2$CO$_3$ or t-BuONa (3 equiv.),
t-BuOH, ArNH$_2$ (1.1 equiv.), 100° C., 12 h.

Compounds of structure (Ia) where X—S-L represents alkynyl or alkyl and R$^2$ is heteroaryl, aryl, alkyl, alkynyl, arylamino or vinyl, were prepared by a regioselective double palladium coupling sequence on the 3-chloro-6-bromo-α-carboline, in which the first palladium catalyzed reaction is a Suzuki, Buchwald, or Sonogashira coupling, and the second palladium catalyzed reaction is a Sonogashira coupling. The resulting acetylenes can be reduced by hydrogenation.

Compounds of structure (IIa) where X—S-L represents alkynyl or alkyl and R$^2$ is heteroaryl, aryl, alkyl, alkynyl arylamino, or vinyl, were prepared by a regioselective double palladium coupling sequence on the 2-chloro-6-bromo-α-carboline, in which the first palladium catalyzed reaction is a Suzuki, Buchwald, or Sonogashira coupling, and the second palladium catalyzed reaction is a Sonogashira coupling. The resulting acetylenes can be reduced by hydrogenation.

Compounds of structure (IIIa) where X—S-L represents alkynyl or alkyl and R$^2$ is heteroaryl, aryl, alkyl, alkynyl, arylamino, or vinyl, were prepared by a regioselective double palladium coupling sequence on the 4-chloro-6-bromo-α-carboline, in which the first palladium catalyzed reaction is a Suzuki, Buchwald, or Sonogashira coupling, and the second palladium catalyzed reaction is a Sonogashira coupling. The resulting acetylenes can be reduced by hydrogenation.

Compounds of structure (Ib, IIb, and IIIb) where R$^1$ is heteroaryl, aryl, alkyl, alkynyl, arylamino, or vinyl, and X—S-L represents alkyl were prepared by a regioselective double palladium coupling sequence on the 2-, 3-, or 4-chloro-6-bromo-α-carboline, in which the first palladium catalyzed reaction is a Sonogashira coupling, and after hydrogenation of the resulting acetylenes, the second palladium catalyzed reaction is a Suzuki, Buchwald, or Sonogashira coupling.

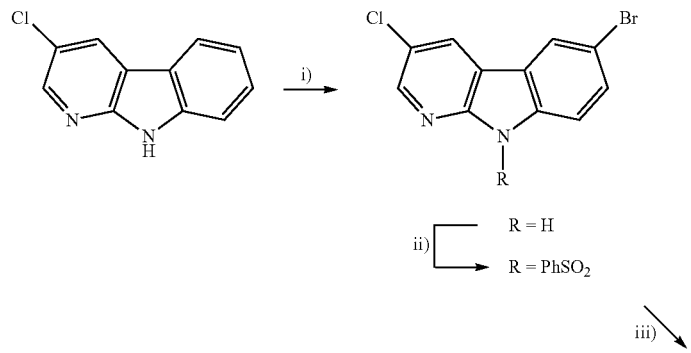

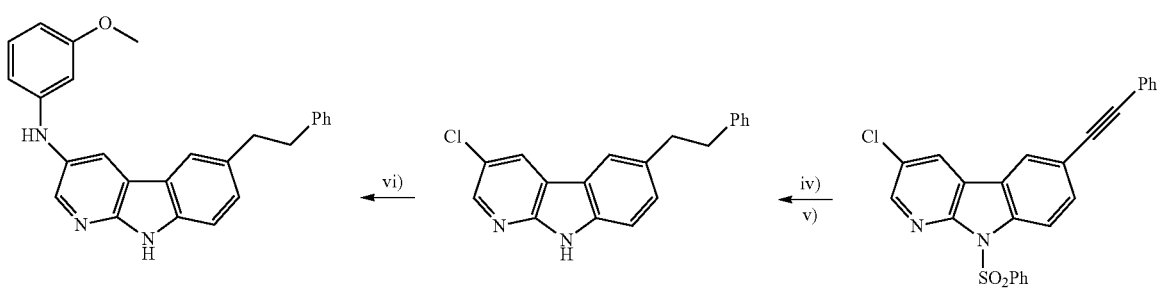

Reagents and conditions: i) Br$_2$ (1.1equiv.), CH$_2$Cl$_2$, room temprature, 1 h; ii) NaH 60% (1.1 equiv.) PhSO$_2$Cl (1.2 equiv.), THF, 0° C. to room
temperature, 12 h; iii) PdCl$_2$(PPh$_3$)$_2$ (0.1 equiv.), CuI (0.2 equiv.), PPh3 (0.1 equiv.), alkyne (3 equiv.), Et$_3$N—DMF (2:1, 80° C.; iv) H$_2$, Pd/C,
MeOH; v) 1.0 M TBAF (5 equiv.), THF, reflux, 4 h; vi) Pd$_2$(dba)$_3$ (0.08 equiv.), X-Phos (0.16 equiv.), K$_2$CO$_3$ or t-BuONa (3 equiv.),
t-BuOH, ArNH$_2$, (1.1 equiv.) 100° C., 12 h.

Compounds of structure Ib in which L is aryl, S is —O(CH$_2$)$_n$— and X is a dialkylamine were prepared by deprotection of the aryl methoxy group and a Mitsunobu substitution, followed after deprotection by a palladium catalyzed Suzuki, Buchwald, or Sonogashira coupling.

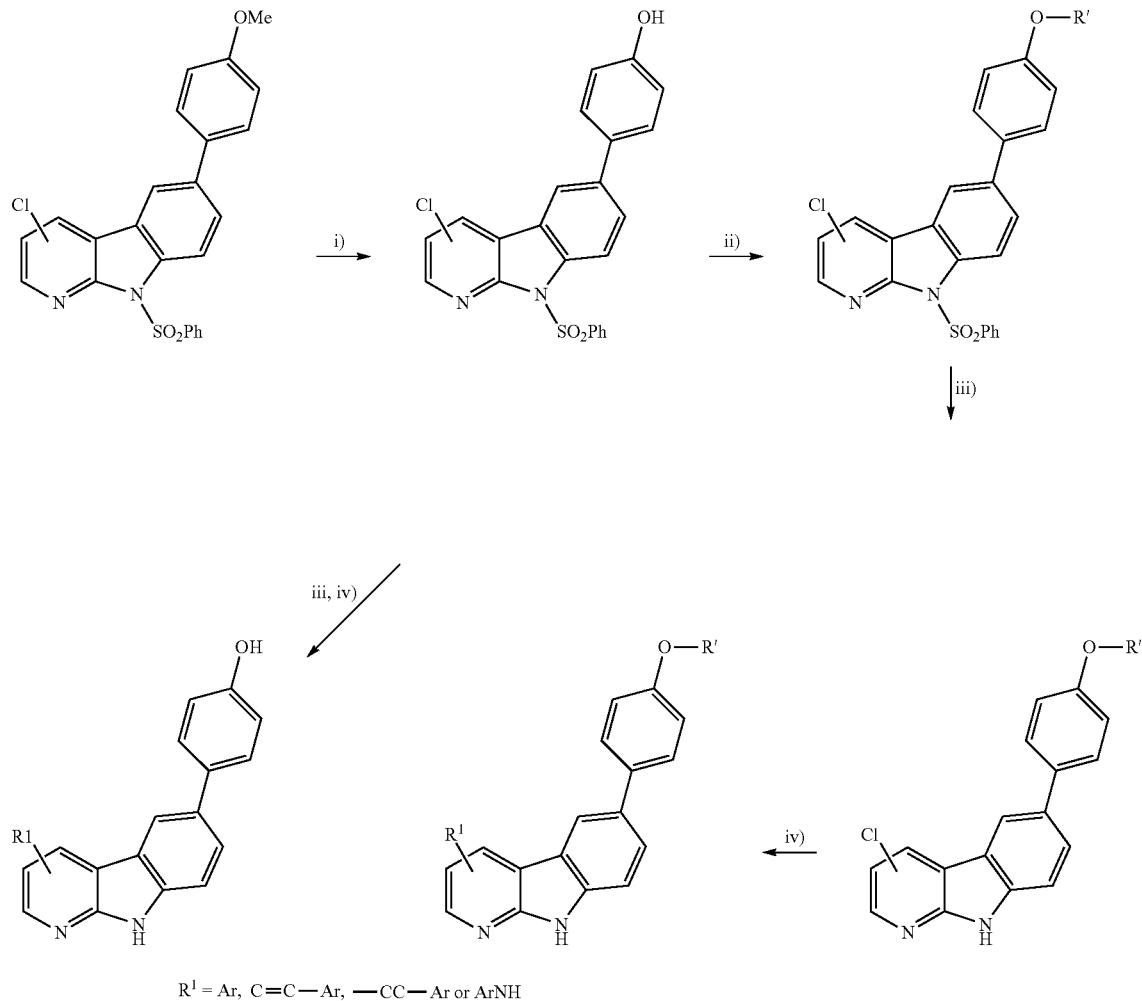

R':

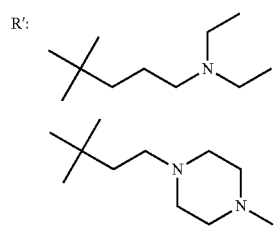

Reagents and conditions: i) BBr$_3$ (4.4 equiv.) in 1M CH$_2$Cl$_2$, r.t. 3 h; ii) DIAD (4 equiv.), PPh$_3$ (3 equiv.), alcohol (5 equiv.), THF, rt, 12 h; iii) Na (10 equiv.), MeOH, reflux, 5 h; iv) Pd(OAc)$_2$ (0.08 equiv.), S-Phos (0.16 equiv.), K$_3$PO$_4$ (2 equiv.) (2.5 mL/mmol) 1,4-dioxane, ArCH═CH—B(OH)$_2$ or ArB(OH)$_2$ (1.1 equiv.), 100° C., 12 h; or PdCl$_2$(CH$_3$CN)$_2$ (0.08 equiv.), X-Phos (0.16 equiv.), Cs$_2$CO$_3$ (4.5 equiv.), or RCCH (1.3 equiv.), CH$_3$CN, 80° C., 12 h; or vi) H$_2$, Pd/C, MeOH; or Pd$_2$(dba)$_3$ (0.08 equiv.), X-Phos (0.16 equiv.), K$_2$CO$_3$ (3 equiv.) t-BuOH, ArNH$_2$ (1.1 equiv.), 100° C., 12 h.

Compounds of structure Ia in which L is aryl, S is NH, and X is SO₂Ph were prepared by reduction of the aryl nitro group followed by sulfonylation.

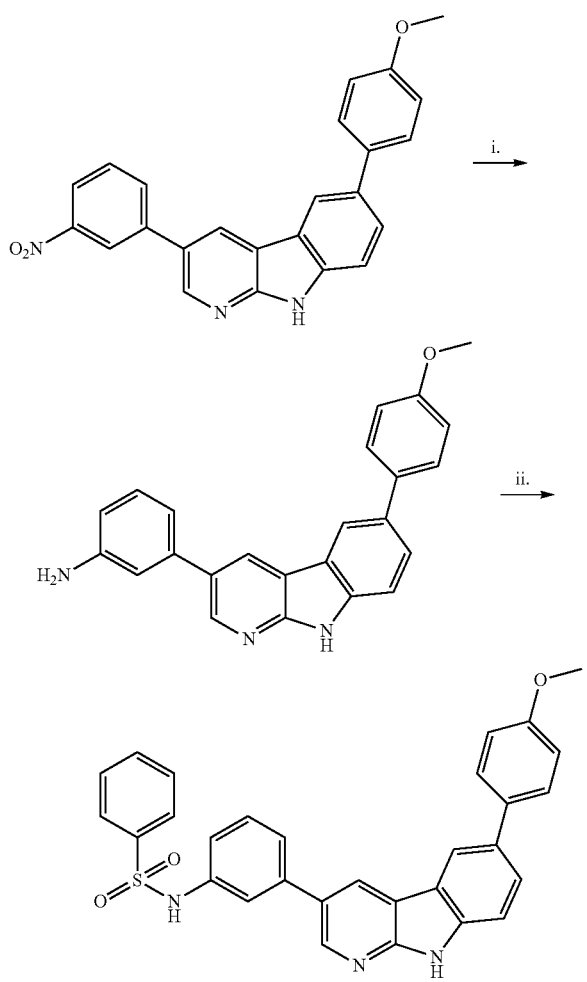

Reagents and conditions: i) H₂, Pd/C, MeOH:THF 8:1, 10 bar, 16 h, room temperature; ii) PhSO₂Cl, pyridine, room temperature, 3 h.

Synthesis of Disubstituted α-Carbolines by a Palladium Coupling Reaction followed by an Electrophilic Substitution Compounds of structure (IIb) where R[1] is a substituted arylamine and X—S-L is acyl, were prepared from 2-chloro-α-carboline by Buchwald coupling, followed by electrophilic aromatic substitution. Further functionalisation at the X—S-L- group can be achieved by nucleophilic substitution (case where L=C(O)CH₂S), or by amide formation (case where L-X=C(O)CH₂CH₂C(O)N R$^a$R$^b$).

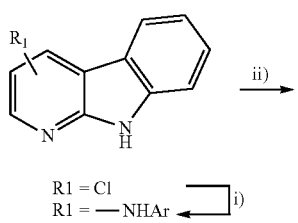

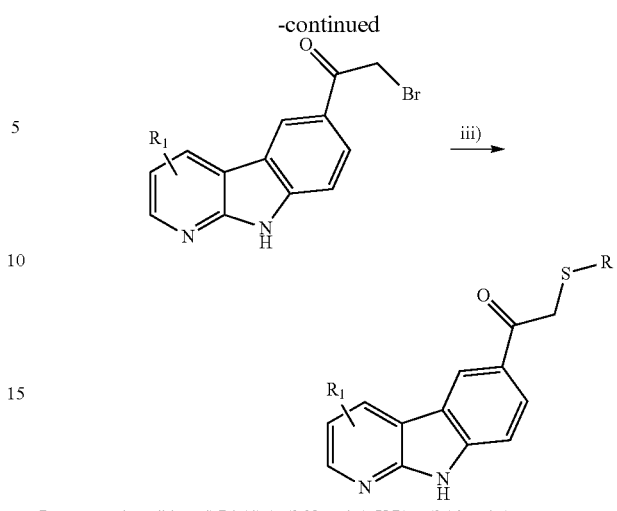

Reagents and conditions: i) Pd₂(dba)₃ (0.08 equiv.), X-Phos (0.16 equiv.), K₂CO₃ or t-BuONa, (3 equiv.) t-BuOH, ArNH₂ (1.1 equiv.), 100° C., 12 h. ii) AlCl₃ (4.5 equiv.), bromoacetyl bromide (1.1 equiv.), CH₂Cl₂, reflux; iii) RSH (1.2 equiv.), NaH 60% (1.6 equiv.), DMF, room temperature, 4 h.

Using these methods the following compounds have been synthesized:
6-acetyl-2-methyl-9H-pyrido[2,3-b]indole (R242),
6-acetyl-3-chloro-9H-pyrido[2,3-b]indole (R253),
2-bromo-I-(3-chloro-9H-pyrido[2,3-b]indol-6-yl)ethanone (R251),
2-bromo-I-(2-chloro-9H-pyrido[2,3-b]indol-6-yl)ethanone (1),
6-benzoyl-2-methyl-9H-pyrido[2,3-b]indole (R243),
methyl 2-oxo-2-[2-methyl-9H-pyrido[2,3-b]indol-6-yl]acetate (R241),
methyl 2-oxo-2-[3-chloro-9H-pyrido[2,3-b]indol-6-yl]acetate (2),
3-chloro-9H-pyrido[2,3-b]indole-6-carbaldehyde (R267),
6-formyl-2-methyl-9H-pyrido[2,3-b]indole-9-carboxylic acid tert-butyl ester (3),
2-methyl-9H-pyrido[2,3-b]indole-6-carbaldehyde (4),
3-chloro-9H-pyrido[2,3-b]indol-6-carboxylic acid (5),
2-methyl-9H-pyrido[2,3-b]indol-6-carboxylic acid (6),
N,N-diethyl-9-methyl-9H-pyrido[2,3-b]indole-6-carboxamide (7),
N,N-diisopropyl-9-methyl-9H-pyrido[2,3-b]indole-6-carboxamide (8),
6-bromo-2-chloro-9H-pyrido[2,3-b]indole (9),
6-bromo-3-chloro-9H-pyrido[2,3-b]indole (R252),
6-bromo-4-chloro-9H-pyrido[2,3-b]indole (10),
4-(3-chloro-9H-pyrido[2,3-b]indol-6-yl)-4-oxo-butyric acid (11),
4-(2-chloro-9H-pyrido[2,3-b]indol-6-yl)-4-oxo-butyric acid (12),
1-(3-chloro-9H-pyrido[2,3-b]indol-6-yl)-2-phenylsulfanylethanone (R275),
1-(3-chloro-9H-pyrido[2,3-b]indol-6-yl)-2-(pyridin-2-ylsulfanyl)ethanone (R272),
2-(benzothiazol-2-ylsulfanyl)-1-(3-chloro-9H-pyrido[2,3-b]indol-6-yl)ethanone (R273),
2-(1H-benzoimidazol-2-ylsulfanyl)-1-(3-chloro-9H-pyrido[2,3-b]indol-6-yl)ethanone (R274),
1-(3-chloro-9H-pyrido[2,3-b]indol-6-yl)-2-(2,2-dimethylaminoethylsulfanyl)ethanone (R284),
1-(3-chloro-9H-pyrido[2,3-b]indol-6-yl)-2-(N,N-diethylaminoethylsulfanyl)ethanone (R283), 2-(3-bromophenyisulfanyl)-1-(3-chloro-9H-pyrido[2,3-b]indol-6-yl)ethanone (R279),
1-(3-chloro-9H-pyrido[2,3-b]indo 1-6-yl)-2-(2-phenoxyethylsulfanyl)ethanone (R280),
1-(3-chloro-9H-pyrido[2,3-b]indol-6-yl)-2-(4,5-dihydrothiazol-2-ylsulfanyl)ethanone (R282),
1-(3-chloro-9H-pyrido[2,3-b]indol-6-yl)-2-(5-methoxybenzothiazol-2-ylsulfanyl)ethanone (R301),
1-(3-chloro-9H-pyrido[2,3-b]indol-6-yl)-2-(3-hydroxypropylsulfanyl)ethan-1-one (R312),
I-(2-chloro-9H-pyrido[2,3-b]indol-6-yl)-2-(N,N-diethylaminoethylsulfanyl)ethan-1-one (R305),
1-(2-chloro-9H-pyrido[2,3-b]indol-6-yl)-2-phenylsulfanylethanone (R306),
4-(9H-pyrido[2,3-b]indo-1-6-yl)thiazol-2(3H)-one (R221),
4-(9H-pyrido[2,3-b]indol-6-yl)thiazol-2-amine (13),
4-(9H-pyrido[2,3-b]indol-6-yl)-4-((4-methylpiperazine-1-yl)methyl)benzamide (R222),
1-(3-chloro-9H-pyrido[2,3-b]indol-6-yl)-4-(4-methylpiperazin-1-yl)butane-1,4-d lone (R303),
1-(2-chloro-9H-pyrido[2,3-b]indol-6-yl)-4-(4-methylpiperazin-1-yl)butane-1,4-dione (R302),
4-(3-chloro-9H-pyrido[2,3-b]indol-6-yl)-N-(4-methoxybenzyl)-4-oxobutyramide (R304),
3-chloro-6-(2'-nitrovinyl)-9H-pyrido[2,3-b]indole (R267),
9-benzenesulfonyl-3-chloro-6-(2'-nitrovinyl)-9H-pyrido[2,3-b]indole (14),
9-benzenesulfonyl-3-chloro-6-(2'-nitroethyl)-9H-pyrido[2,3-b]indole (15),
9-benzenesulfonyl-3-chloro-6-(2'-aminoethyl)-9H-pyrido[2,3-b]indole (16),
N-(2-(9-(benzenesulfonyl)-3-chloro-9H-pyrido[2,3-b]indol-6-yl)ethyl)benzamide (17),
N-(2-(3-chloro-9H-pyrido[2,3-b]indol-6-yl)ethyl)benzamide (R265),
9-benzenesulfonyl-6-bromo-2-chloro-9H-pyrido[2,3-b]indole (19),
9-benzenesulfonyl-6-bromo-3-chloro-9H-pyrido[2,3-b]indole (20),
9-benzenesulfonyl-6-bromo-4-chloro-9H-pyrido[2,3-b]indole (21),
9-benzenesulfonyl-6-bromo-9H-pyrido[2,3-b]indole (22),
9-(ethoxymethyl)-3-chloro-9H-pyrido[2,3-b]indole (23),
9-(ethoxymethyl)-4-chloro-9H-pyrido[2,3-b]indole (24),
9-(ethoxymethyl)-2-chloro-9H-pyrido[2,3-b]indole (25),
9-benzenesulfonyl-3-chloro-6-(4-methoxyphenyl)-9H-pyrido[2,3-b]indole (26),
9-benzenesulfonyl-3-chloro-6-(2'-phenylethenyl)-9H-pyrido[2,3-b]indole (27),
(E)-9-benzenesulfonyl-3-chloro-6-(Z-(4-methoxyphenyl)ethenyl)-9H-pyrido[2,3-b]indole (28),
9-benzenesulfonyl-2-chloro-6-(3-nitrophenyl)-9H-pyrido[2,3-b]indole (29),
9-benzenesulfonyl-3-chloro-6-(4-(morpholin-4-yl)methylphenyl)-9H-pyrido[2,3-b]indole (30),
9-benzenesulfonyl-3-chloro-6-(5-morpholin-4-yl-pyridin-2-yl)-9H-pyrido[2,3-b]indole (31),
9-benzenesulfonyl-2-chloro-6-(4-methoxyphenyl)-9H-pyrido[2,3-b]indole (32),
9-benzenesulfonyl-2-chloro-6-(2'-phenylethenyl)-9H-pyrido[2,3-b]indole (33),
9-benzenesulfonyl-4-chloro-6-(4-methoxyphenyl)-9H-pyrido[2,3-b]indole (34),
9-benzenesulfonyl-4-chloro-6-(2'-phenylethenyl)-9H-pyrido[2,3-b]indole (35),
9-benzenesulfonyl-2,6-di(4-methoxyphenyl)-9H-pyrido[2,3-b]indole (36),
9-benzenesulfonyl-4,6-di(4-methoxyphenyl)-9H-pyrido[2,3-b]indole (37),
4-(3-chloro-9-(benzenesulfonyl)-9H-pyrido[2,3-b]indol-6-yl)phenol (R353),
3-(4-(9-(benzenesulfonyl)-3-chloro-9H-pyrido[2,3-b]indol-6-yl)phenoxy)-N,
N-diethylpropan-1-amine (39),
9-(benzenesulfonyl)-3-chloro-6-(4-(2-(4-methylpiperazin-1-yl)ethoxy)phenyl)-9H-pyrido[2,3-b]indole (40),
3-chloro-6-(4-methoxyphenyl)-9H-pyrido[2,3-b]indole (R277),
3-chloro-6-(5-morpholin-4-yl-pyridin-2-yl)-9H-pyrido[2,3-b]indole (R308),
2-chloro-6-(2'-phenylethenyl)-9H-pyrido[2,3-b]indole (41),
(E)-3-chloro-6-(2'-(4-methoxyphenyl)ethenyl)-9H-pyrido[2,3-b]indole (R350),
3-chloro-6-(4-(morpholin-4-yl)methylphenyl)-9H-pyrido[2,3-b]indole (R313),
2,6-di(4-methoxyphenyl)-9H-pyrido[2,3-b]indole (R311),
3-(4-(3-chloro-9H-pyrido[2,3-b]indol-6-yl)phenoxy)-N,N-diethylpropan-1-amine (R337),
3-chloro-6-(4-(2-(4-methylpiperazin-1-yl)ethoxy)phenyl)-9H-pyrido[2,3-b]indole (R347),
3-(4-methoxyphenyl)-9H-pyrido[2,3-b]indole (R278),
3-(2'-phenylethenyl)-9H-pyrido[2,3-b]indole (R281),
3-(3-nitrophenyl)-9H-pyrido[2,3-b]indole (R328),
3-(furan-2-yl)-9H-pyrido[2,3-b]indole (R325),
3-(4-phenylphenyl)-9H-pyrido[2,3-b]indole (R329),
2-(4-methoxyphenyl)-9H-pyrido[2,3-b]indole (R299),
2-(2'-phenylethenyl)-9H-pyrido[2,3-b]indole (R300),
4-(4-methoxyphenyl)-9H-pyrido[2,3-b]indole (R309),
4-(2'-phenylethenyl)-9H-pyrido[2,3-b]indole (R310),
2-(3-nitrophenyl)-9H-pyrido[2,3-b]indole (42),
2-(furan-2-yl)-9H-pyrido[2,3-b]indole (R326),
2-(1H-pyrrol-2-yl)-9H-pyrido[2,3-b]indole (R355),
4-(3-nitrophenyl)-9H-pyrido[2,3-b]indole (R331),
4-(furan-2-yl)-9H-pyrido[2,3-b]indole (R327),
4-(4-phenylphenyl)-9H-pyrido[2,3-b]indole (R330),
9-benzenesulfonyl-6-(4-methoxyphenyl)-2-(2'-phenylethenyl)-9H-pyrido[2,3-b]indole (43),
9-benzenesulfonyl-2-(furan-2-yl)-6-(3-nitrophenyl)-9H-pyrido[2,3-b]indole (44),
9-benzenesulfonyl-6-(4-methoxyphenyl)-4-(2'-phenylethenyl)-9H-pyrido[2,3-b]indole (45),
6-(4-methoxyphenyl)-3-(2'-phenylethenyl)-9H-pyrido[2,3-b]indole (R315),
6-(5-morpholin-4-yl-pyridin-2-yl)-3-(2'-phenylethenyl)-9H-pyrido[2,3-b]indole (R307),
6-(4-(morpholin-4-yl)methylphenyl)-3-(2'-phenylethenyl)-9H-pyrido[2,3-b]indole (R314),
(E)-3-(2-(3-fluorophenyl)ethenyl)-6-(4-methoxyphenyl)-9H-pyrido[2,3-b]indole (R358),
N,N-diethyl-3-(4-(3-(2'-phenylethenyl)-9H-pyrido[2,3-b]indol-6-yl)phenoxy)propan-1-amine (R338),
N-(3-nitrophenyl)-9H-pyrido[2,3-b]indol-2-amine (R317),
N-(2-nitrophenyl)-9H-pyrido[2,3-b]indol-2-amine (R319),
N-(phenyl)-9H-pyrido[2,3-b]indol-2-amine (R318),
N-(3-nitrophenyl)-9H-pyrido[2,3-b]indol-4-amine (R322),
N-(2-nitrophenyl)-9H-pyrido[2,3-b]indol-4-amine (R323),
N-(3-methoxyphenyl)-9H-pyrido[2,3-b]indol-4-amine (R324),
N-(3-methoxyphenyl)-9H-pyrido[2,3-b]indol-3-amine (R344),
N-(phenyl)-9H-pyrido[2,3-b]indol-3-amine (46),
N-(phenyl)-6-(2'-phenylethenyl)-9H-pyrido[2,3-b]indol-2-amine (R320), N-(2-nitrophenyl)-6-(2'-phenylethenyl)-9H-pyrido[2,3-b]indol-2-amine (R332),
N-(3-methoxyphenyl)-6-(Z-phenylethyl)-9H-pyrido[2,3-b]indol-3-amine (R352),
2-(N,N-(diethylamino)ethylthio)-1-(2-(3-nitrophenylamino)-9H-pyrido[2,3-b]indol-6-yl)ethanone (R321),
9-(ethoxymethyl)-2-(3-nitrophenoxy)-9H-pyrido[2,3-b]indole (47),
9-(ethoxymethyl)-2-(3-methoxyphenoxy)-9H-pyrido[2,3-b]indole (48),
9-(ethoxymethyl)-4-(3-nitrophenoxy)-9H-pyrido[2,3-b]indole (49),
9-(ethoxymethyl)-4-(3-methoxyphenoxy)-9H-pyrido[2,3-b]indole (50),
2-(pent-1-ynyl)-9H-pyrido[2,3-b]indole (R341),
2-(phenylethynyl)-9H-pyrido[2,3-b]indole (R342),
2-(phenylethynyl)-9-(ethoxymethyl)-9H-pyrido[2,3-b]indole (51),
2-(pent-1-ynyl)-9-(ethoxymethyl)-9H-pyrido[2,3-b]indole (52),
2-cyclohex-1-enylethynyl-9-(ethoxymethyl)-9H-pyrido[2,3-b]indole (53),
2-cyclohexylethynyl-9-(ethoxymethyl)-9H-pyrido[2,3-b]indole (54),
3-(phenylethynyl)-9-(ethoxymethyl)-9H-pyrido[2,3-b]indole (55),
4-(phenylethynyl)-9-(ethoxymethyl)-9H-pyrido[2,3-b]indole (56),
4-(pent-I-ynyl)-9-(ethoxymethyl)-9H-pyrido[2,3-b]indole (57),
2-cyclohexyl-enylethynyl-9-(ethoxymethyl)-9H-pyrido[2,3-b]indole (58),
9-benzenesulfonyl-3-chloro-6-(2-phenylethynyl)-9H-pyrido[2,3-b]indole (59),
3-chloro-6-(2-phenylethynyl)-9H-pyrido[2,3-b]indole (60),
9-(benzenesulfonyl)-3-chloro-6-(2'-phenylethyl)-9H-pyrido[2,3-b]indole (61),
3-chloro-6-(2'-phenylethyl)-9H-pyrido[2,3-b]indole (R351),
3-(benzo[d][1,3]dioxol-5-yl)-6-phenethyl-9H-pyrido[2,3-b]indole (R354),
(E)-3-(2'-(3-fluorophenyl)ethenyl)-6-(4-hydroxyphenyl)-9H-pyrido[2,3-b]indole (R361),
3-((E)-2'-(3-fluorophenyl)ethenyl)-6-(E)-(2-(phenyl)ethenyl)-9H-pyrido[2,3-b]indole (R359),
6-(4-methoxyphenyl)-3-(3-nitrophenyl)-9H-pyrido[2,3-b]indole (R356),
3-(6-(4-methoxyphenyl)-9H-pyrido[2,3-b]indol-3-yl)benzenamine (R357), and
N-(3-(6-(4-methoxyphenyl)-9H-pyrido[2,3-b]indol-3-yl)phenyl)benzenesulfonamide (R360), General Procedure for the Synthesis of α-carbolines α-carbolines were synthesized by modified Graebe-Ullman reaction.[10] This approach was selected as the shortest route to access to chloropyrido[2,3-b]indoles from dichloropyridine in only two steps. The 4-chloro-α-carboline was prepared by chlorination of pyrido[2,3-b]indol-N-oxyde.[11]

[10] a) Vera-Luque, P.; Alajarin, R.; Alvarez-Builla, J.; Vaquero, J. J. Org. Lett. 2006, 8, 415. (b) Katritzky, A. R.; Lan, X.; Yang, J. Z.; Denisko, O. V. Chem. Rev. 1998, 98, 409. (c) Mehta, L. K.; Parrick, J.; Payne, F. J. Chem. Soc., Perkin Trans. 1 1993, 1261. (d) Semenov A. A.; Tolstikhina V. V. Chem. Heterocycl. Compd. 1984, 20, 345.
[11] Antiviral and neuroleptic α-carbolines. FR patent FR 19691114; Chem. Abstr. 1969, 72, 111444.

Synthesis of 6-acetyl-α-carbolines. General Procedure

To a 0.2 M stirred suspension of the α-carboline derivative (200 mg) in anhydrous $CH_2Cl_2$ was added $AlCl_3$ (4.5 equiv.) and acetyl chloride (2 equiv.) at room temperature under inert atmosphere. The mixture was stirred at reflux until completion of the reaction (as shown by t.l.c.). The resulting mixture was then cautiously quenched at 0° C. with $H_2O$. It was extracted with the mixture of EtOAc/DMF (99:1). The resulting organic layer was washed with a saturated aqueous solution of $NaHCO_3$, and brine, dried over $MgSO_4$, and filtered and the solvents were removed under reduced pressure.

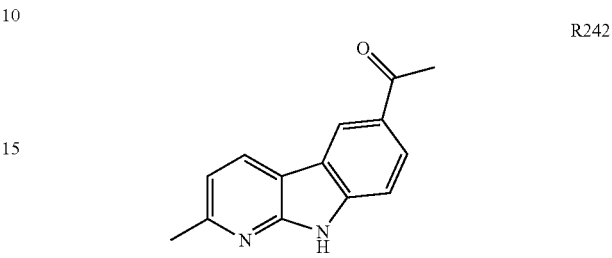

6-acetyl-2-methyl-9H-pyrido[2,3-b]indole (R242)

A white powder was obtained in 78% yield (184 mg) after trituration of the crude product in MeOH and filtration and flash chromatography (eluent: EtOAc/PE 1:1 to EtOAc) of residual filtrate; mp>139° C.; $^1$H-NMR (300 MHz, DMSO-$d_6$): δ 12.03 (bs, 1H), 8.82 (d, 1H, J=1.6 Hz), 8.51 (d, 1H, J=8.0 Hz), 8.03 (dd, 1H, J=1.6, 8.6 Hz), 7.52 (d, 1H, J=8.6 Hz), 7.15 (d, 1H, J=8.0 Hz), 2.69 (s, 3H), 2.60 (s, 3H); $^{13}$C-NMR (75 MHz, DMSO-$d_6$): δ 196.9 (C), 155.8 (C), 152.5 (C), 141.5 (C), 129.2 (CH), 128.9 (C), 126.1 (CH), 122.4 (CH), 120.3 (C), 115.5 (CH), 112.9 (C), 110.9 (CH), 26.6 ($CH_3$), 24.3 ($CH_3$); MS

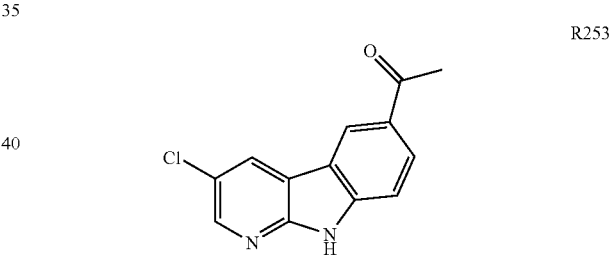

6-acetyl-3-chloro-9H-pyrido[2,3-b]indole (R253)

A white powder was obtained in 75% yield (184 mg) after trituration, filtration of crude product in THF and flash chromatography ($CH_2Cl_2$/AcOEt 9:1) of residual filtrate; $^1$H-NMR (300 MHz, DMSO-$d_6$): δ 12.4 (bs, 1H), 8.97 (s, 1H), 8.86 (d, 1H, J=2.1 Hz), 8.49 (d, 1H, J=2.1 Hz), 8.14 (d, 1H, J=8.6 Hz), 7.58 (d, 1H, J=8.6 Hz), 2.66 (s, 3H); $^{13}$C-NMR (75 MHz, DMSO-$d_6$): δ 196.8 (C), 161.9 (C), 144.7 (CH), 142.6 (C), 129.3 (C), 128.7 (CH), 127.3 (CH), 123.6 (CH), 122.5 (C), 119.3 (C), 116.8 (C), 111.3 (CH), 26.6 ($CH_3$); GC-MS (EI) m/z 244 [$M^+$]

Synthesis of 6-bromoacetyl-α-carbolines. General Procedure

To a 0.2 M stirred suspension of the α-carboline derivative (200 mg) in anhydrous $CH_2Cl_2$ was added $AlCl_3$ (4.5 equiv.) and bromoacetyl bromide (1.1 equiv.), at room temperature under inert atmosphere. The mixture was stirred at reflux until completion of the reaction (as shown by t.l.c.). The resulting mixture was then cautiously quenched at 0° C. with $H_2O$. It was extracted with the mixture of EtOAc/DMF (99:1). The resulting organic layer was washed with NaHCO3 a saturated aqueous solution of NaHCO3, and brine, dried over MgSO4, and filtered and the solvents were removed under reduced pressure.

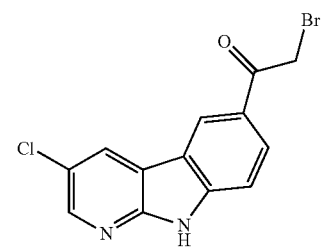

2-Bromo-1-(3-chloro-9H-pyrido[2,3-b]indol-6-yl)ethanone (R251)

A white powder was obtained in 69% yield (221 mg) after trituration of the crude product in MeOH and filtration and flash chromatography (CH$_2$Cl$_2$/EtOAc 9:1) of residual filtrate; $^1$H-NMR (300 MHz, DMSO-d$_6$): δ 12.52 (bs, 1H), 9.04 (d, 1H, J=1.1 Hz), 8.84 (d, 1H, J=2.3 Hz), 8.51 (d, 1H, J=2.5 Hz), 8.15 (dd, 1H, 1.7, 8.5 Hz), 7.61 (d, 1H, J=8.7 Hz), 4.96 (s, 2H); $^{13}$C-NMR (75 MHz, DMSO-d$_6$): δ 190.8 (C), 150.9 (C), 145.1 (CH), 142.9 (C), 128.8 (CH), 128.0 (CH), 126.2 (C), 124.3 (CH), 122.8 (C), 119.5 (C), 116.7 (C), 111.7 (CH), 33.7 (CH$_2$); MS (EI) m/z 244 [M$^+$-CH$_2$Br];

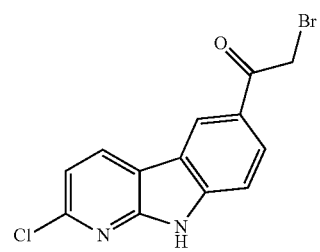

2-Bromo-1-(2-chloro-9H-pyrido[2,3-b]indol-6-yl)ethanone 1

A yellow powder was obtained in 31% yield (221 mg) after trituration of the crude product in MeOH and filtration; $^1$H NMR (300 MHz, DMSO-d$_6$): δ=12.54 (bs, 1H); 8.99 (d, 1H, J=1.5 Hz); 8.70 (d, 1H, J=8.1 Hz); 8.14 (dd, 1H, J=1.7 Hz, J=8.7 Hz); 7.63 (d, 1H, J=8.7 Hz); 7.39 (d, 1H, J=8.1 Hz); 4.99 (s, 2H).

The following compound can be prepared by the same method:
2-Bromo-1-(2-methyl-9H-pyrido[2,3-b]indol-6-yl)ethanone Synthesis of 6-benzoyl-α-carbolines. General Procedure To a 0.2 M stirred suspension of the α-carboline derivative (200 mg) in anhydrous CH$_2$Cl$_2$ was added AlCl$_3$ (4.5 equiv.) and benzoyl chloride (2 equiv.), at room temperature under inert atmosphere. The mixture was stirred at reflux until completion of the reaction (followed by t.l.c.). The resulting mixture was then cautiously quenched at 0° C. with H$_2$O. It was extracted with the mixture of EtOAc/DMF (99:1). The resulting organic layer was washed with NaHCO$_3$ saturated aqueous solution and brine, dried over MgSO$_4$, filtered and solvents were removed under reduced pressure.

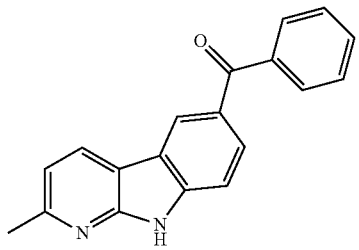

6-benzoyl-2-methyl-9H-pyrido[2,3-b]indole (R243)

A white powder was obtained in 87% yield (273 mg) after flash chromatography (eluent: EtOAc/PE 1:1 to EtOAc); mp 231° C.; $^1$H-NMR (300 MHz, DMSO-d$_6$): δ 12.10 (bs, 1H), 8.58 (s, 1H), 8.51 (d, 1H, J=7.9 Hz), 7.86 (dd, 1H, J=1.7, 8.5 Hz), 7.77-7.75 (m, 2H), 7.70-7.65 (m, 1H), 7.60-7.55 (m, 3H), 7.13 (d, 1H, J=8.22 Hz), 2.60 (s, 3H); $^{13}$C-NMR (75 MHz, DMSO-d$_6$): δ 195.4 (C), 161.8 (C), 155.9 (C), 152.5 (C), 141.4 (C), 138.3 (C), 131.8 (CH), 129.5 (CH), 129.4 (2 CH), 128.5 (2 CH), 128.1 (CH), 123.7 (CH), 120.3 (C), 115.9 (CH), 112.8 (C), 110.9 (CH), 24.4 (CH$_3$); MS (ESI) m/z 287 [M+H$^+$]

The following compounds can be prepared by the same method:
6-benzoyl-2-chloro-9H-pyrido[2,3-b]indole
6-benzoyl-3-chloro-9H-pyrido[2,3-b]indole
6-benzoyl-4-chloro-9H-pyrido[2,3-b]indole Synthesis of methyl α-oxo-α-carboline-6-acetate. General Procedure To a 0.2 M stirred suspension of the α-carboline derivative (200 mg) in anhydrous CH$_2$Cl$_2$ was added AlCl$_3$ (4.5 equiv.) and methyl oxalyl chloride (2 equiv.), at room temperature under inert atmosphere. The mixture was stirred at reflux until completion of the reaction (followed by t.l.c.). The resulting mixture was then cautiously quenched at 0° C. with H$_2$O. It was extracted with the mixture of EtOAc/DMF (99:1). The resulting organic layer was washed with NaHCO$_3$ saturated aqueous solution and brine, dried over MgSO$_4$, filtered and solvents were removed under reduced pressure.

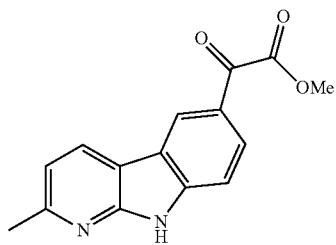

Methyl 2-oxo-2-[2-methyl-9H-pyrido[2,3-b]indol-6-yl]acetate: (R241)

A white powder was obtained in 83% yield (223 mg) after flash chromatography (eluent: $CH_2Cl_2$/EtOAc 8:2 to EtOAc); $^1$H-NMR (300 MHz, DMSO-$d_6$): δ 12.3 (bs, 1H), 8.77 (d, 1H, J=1.6 Hz), 8.59 (d, 1H, J=7.9 Hz), 8.00 (dd, 1H, J=1.6, 8.7 Hz), 7.62 (d, 1H, J=8.7 Hz), 7.20 (d, 1H, J=7.9 Hz), 3.99 (s, 3H), 2.61 (s, 3H); $^{13}$C-NMR (75 MHz, DMSO-$d_6$): δ 186.3 (C), 165.4 (C), 156.6 (C), 152.7 (C), 143.1 (C), 129.9 (CH), 127.4 (CH), 124.6 (CH), 123.3 (C), 120.9 (C), 116.1 (CH), 112.7 (C), 111.9 (CH), 52.9 ($CH_3$), 24.4 $CH_3$); MS (ESI) m/z 269.1 [M+H$^+$]; Anal. Calcd for $C_{15}H_{12}N_2O_3$: C, 67.16; H, 4.51; N, 10.44. Found: C, 67.10; H, 4.49; N, 10.33.

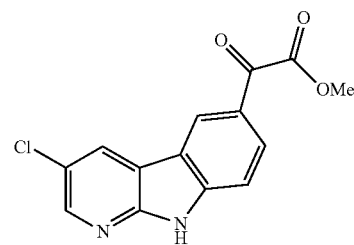

Methyl 2-oxo-2-[3-chloro-9H-pyrido[2,3-b]indol-6-yl]acetate (2)

A white powder was obtained in 70% yield (200 mg) after after flash chromatography (eluent: EtOAc/$CH_2Cl_2$ 2:8); $^1$H-NMR (300 MHz, DMSO-$d_6$): 12.7 (bs, 1H), 8.96 (d, 1H, J=2.4 Hz), 8.91 (d, 1H, J=1.3 Hz), 8.54 (d, 1H, J=2.4 Hz), 8.09 (dd, 1H, J=1.9, 8.6 Hz), 7.68 (d, 1H, J=8.6 Hz), 4.00 (s, 3H); $^{13}$C-NMR (75 MHz, DMSO-$d_6$): δ 186.2 (C), 165.2 (C), 150.9 (C), 145.4 (CH), 143.9 (C), 129.3 (CH), 128.3 (CH), 125.9 (CH), 123.8 (C), 123.2 (C), 119.8 (C), 116.5 (CH), 112.3 (C), 52.9 ($CH_3$); MS (ESI) m/z 287.1 [M+H$^+$]

The following compounds can be prepared by the same method:

Methyl 2-oxo-2-[2-chloro-9H-pyrido[2,3-b]indol-6-yl]acetate

Methyl 2-oxo-2-[4-chloro-9H-pyrido[2,3-b]indol-6-yl]acetate

Synthesis of 6-carboxaldehyde-α-carbolines. General Procedure

To a 0.02 M stirred suspension of the α-carboline derivative (200 mg) in anhydrous $CH_2Cl_2$ was added in portions $AlCl_3$ (4.5 equiv.) at −78° C. After stirring for 5 min, α,α-dichloromethyl methyl ether (3 equiv.) was added dropwise to the mixture. The reaction mixture was stirred at −78° C. and then allowed to warm to room temperature for 12 hours. The resulting mixture was then cautiously quenched at 0° C. with $H_2O$. It was extracted with the mixture of EtOAc/DMF (99:1). The combined organic layer was washed with aq. sat. $NaHCO_3$, dried with $MgSO_4$, filtered and solvents were removed under reduced pressure.

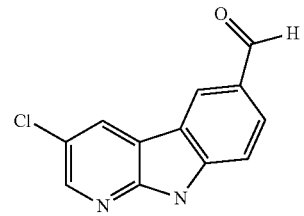

3-Chloro-9H-pyrido[2,3-b]indole-6-carbaldehyde (R267)

A white powder was obtained in 54% yield (123 mg) after after flash chromatography (eluent: $CH_2Cl_2$/EtOAc 85:15); $^1$H-NMR (300 MHz, DMSO-$d_6$) δ 12.56 (bs, H), 10.06 (s, H), 8.87 (d, 1H, J=2.4 Hz), 8.84 (d, 1H, J=1.5 Hz), 8.52 (dd, 1H, J=2.4 Hz), 8.04 (dd, 1H, J=1.5, 8.5 Hz), 7.67 (d, 1H, J=8.5 Hz); $^{13}$C-NMR (75 MHz, DMSO-$d_6$): δ 191.8 (CH), 150.8 (C), 145.1 (CH), 143.5 (C), 129.1 (C), 128.9 (CH), 128.2 (CH), 125.4 (CH), 122.8 (C), 119.8 (C), 116.6 (C), 112.0 (CH); MS (EI) m/z 230 [M$^+$]

The following compounds can be prepared by the same method:

2-Chloro-9H-pyrido[2,3-b]indole-6-carbaldehyde

4-Chloro-9H-pyrido[2,3-b]indole-6-carbaldehyde

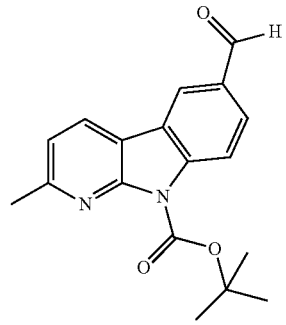

6-Formyl-2-methyl-9H-pyrido[2,3-b]indole-9-carboxylic acid tert-butyl ester (3)

The crude product 6-formyl-2-methyl-9H-pyrido[2,3-b]indole (231 mg, 1.1 mmol) was prepared and diluted immediately in anhydrous MeCN (9 mL). To a stirred suspension was added DMAP (cat. amount) and $Boc_2O$ (361 mg, 1.5 equiv.). The mixture was stirred at room temperature overnight and then poured with 5% aqueous $NaHCO_3$ and extracted with EtOAc. The combined organic layers were dried ($MgSO_4$), and the solvent was removed under reduced pressure to give an oil. A white powder was obtained in 54% yield (185 mg) after after flash chromatography (eluent: PE/EtOAc 85:15); $^1$H-NMR (300 MHz, $CDCl_3$): δ 10.06 (s, 1H), 8.46 (d, 1H, J=1.5 Hz), 8.43 (d, 1H, J=8.7 Hz), 8.22 (d, 1H, J=7.6 Hz), 8.00 (dd, 1H, J=1.5, 8.7 Hz), 7.24 (d, 1H, J=7.6 Hz), 2.75 (s, 3H), 1.78 (s, 9H); $^{13}$C-NMR (75 MHz, $CDCl_3$): δ 191.4 (CH), 157.8 (C), 151.7 (C), 149.4 (C), 141.3 (C), 131.7 (C), 128.9 (CH), 128.4 (CH), 123.2 (C), 121.4 (CH), 118.9 (CH), 116.3 (CH), 115.2 (C), 84.9 (C), 28.3 (3 CH$_3$), 25.2 (CH$_3$); MS (EI) m/z 311 [M+H$^+$], 333 [M+Na$^+$], 643 [2M+Na$^+$]

2-Methyl-9H-pyrido[2,3-b]indole-6-carbaldehyde (4)

A solution of 18 (56 mg, 0.177 mmol) in CH$_2$Cl$_2$ (2.5 mL) was stirred under argon and treated with CF$_3$CO$_2$H (700 µL). After 90 min at room temperature, the resulting mixture was then cautiously quenched at 0° C. with H$_2$O and a saturated aqueous NaHCO$_3$ was added until pH 10. The solution was diluted with CH$_2$Cl$_2$, washed with H$_2$O, dried with MgSO$_4$, filtered and concentrated.

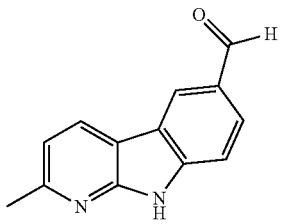

4

A white powder was obtained in 93% yield (35 mg) after trituration of the crude product in MeOH and filtration; $^1$H-NMR (300 MHz, DMSO-d$_6$): δ 12.20 (bs, 1H), 10.04 (s, 1H), 8.71 (d, 1H, J=1.2 Hz), 8.53 (d, 1H, J=7.9 Hz), 7.96 (dd, 1H, J=1.2, 8.4 Hz), 7.61 (d, 1H, J=8.4 Hz), 7.18 (d, 1H, J=7.9 Hz), 2.61 (s, 3H); $^{13}$C-NMR (300 MHz, DMSO-d$_6$): δ 192.1 (CH), 156.3 (C), 152.6 (C), 142.7 (C), 129.6 (CH), 128.8 (C), 126.9 (CH), 124.5 (CH), 120.9 (C), 115.9 (CH), 112.8 (C), 111.8 (C), 24.5 (CH$_3$); MS (ESI) [M+H$^+$]=211;

Synthesis of α-carboline-6-carboxylic Acids.
General Procedure

To a 0.2 M stirred suspension of the α-carboline derivative (200 mg) in anhydrous CH$_2$Cl$_2$ was added AlCl$_3$ (4.5 equiv.) and 2.2 M oxalyl chloride (2 equiv.) in anhydrous CH$_2$Cl$_2$, at room temperature under inert atmosphere. The mixture was stirred at room temperature until completion of the reaction (followed by t.l.c.). The resulting mixture was then cautiously quenched at 0° C. with H$_2$O. It was extracted with the mixture of EtOAc/DMF (99:1). The resulting organic layer was dried over MgSO$_4$, filtered and solvents were removed under reduced pressure.

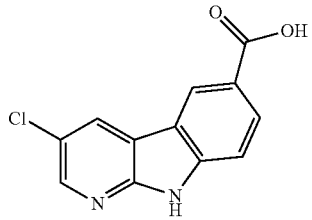

5

3-chloro-9H-pyrido[2,3-b]indol-6-carboxylic acid (5)

A white powder was obtained in 71% yield (181 mg) after trituration of the crude product in MeOH and filtration; mp>295° C. (MeOH); $^1$H-NMR (300 MHz, DMSO-d$_6$): δ 12.73 (bs, 1H), 12.36 (bs, 1H), 8.89 (d, 1H, J=1.5 Hz), 8.86 (d, 1H, J=2.2 Hz), 8.47 (d, 1H, J=2.2 Hz), 8.09 (dd, 1H, J=1.5, 8.5 Hz), 7.57 (d, 1H, J=8.5 Hz); MS (EI) m/z 247 [M+H]$^+$;

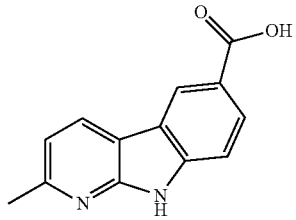

6

2-methyl-9H-pyrido[2,3-b]indol-6-carboxylic acid (6)

A white powder was obtained in 71% yield (181 mg) after trituration of the crude product in MeOH and filtration; mp>295° C. (MeOH); $^1$H-NMR (300 MHz, DMSO-d$_6$): δ 12.73 (bs, 1H), 12.02 (bs, 1H), 8.75 (d, 1H, J=1.5 Hz), 8.52 (d, 1H, J=7.8 Hz), 8.02 (dd, 1H, J=1.5, 8.5 Hz), 7.52 (d, 1H, J=8.5 Hz), 7.14 (d, 1H, J=7.8 Hz), 2.60 (s, 3H); MS (EI) m/z 227 [M+H]$^+$ The following compounds can be prepared by the same method:

2-Chloro-9H-pyrido[2,3-b]indol-6-carboxylic acid

4-Chloro-9H-pyrido[2,3-b]indol-6-carboxylic acid

Synthesis of α-carboline-6-carboxamides. General Procedure

To a 0.2 M stirred suspension of the α-carboline derivative (200 mg) in anhydrous CH$_2$Cl$_2$ was added AlCl$_3$ (4.5 equiv.) and 2.2 M oxalyl chloride (2 equiv.) in anhydrous CH$_2$Cl$_2$, at room temperature under inert atmosphere. The mixture was stirred at room temperature until completion of the reaction (followed by t.l.c.). The resulting mixture was then cautiously quenched at 0° C. with secondary amine. It was extracted with the mixture of EtOAc. The resulting organic layer was dried over MgSO$_4$, filtered and solvents were removed under reduced pressure. The product was purified by column chromatography (EtOAc) to afford product without protection. To a 0.5 M solution of this product in anhydrous DMF was added 60% sodium hydride (3 equiv.) at 0° C. After stirring at 0° C. for 20 min, iodomethane (2.5 equiv.) was added dropwise. The reaction mixture was stirred for 12 h and then poured with 5% aqueous saturated NaHCO$_3$ solution and extracted with EtOAc (3×50 mL). The combined organic layers were dried (MgSO$_4$), and the solvent was removed under reduced pressure.

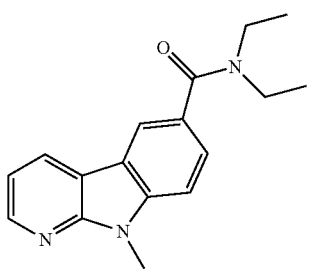

N,N-diethyl-9-methyl-9H-pyrido[2,3-b]indole-6-carboxamide (7)

The product was purified by column chromatography (EtOAc/PE 9:1) to afford 7 in 48% yield as an orange solid. $^1$H NMR (300 MHz, CDCl$_3$): δ 8.49 (dd, 1H, J=1.5, 4.9 Hz), 8.27 (dd, 1H, J=1.5, 7.7 Hz), 8.12 (d, 1H, J=1.5 Hz), 7.55 (dd, 1H, J=1.5, 8.3 Hz), 7.42 (d, 1H, J=8.3 Hz), 7.15 (dd, 1H, J=4.9, 7.7 Hz), 3.93 (s, 3H), 3.47 (bs, 4H), 1.23 (bs, 6H).

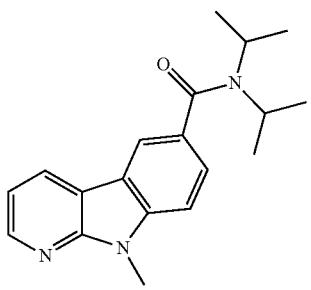

N,N-diisopropyl-9-methyl-9H-pyrido[2,3-b]indole-6-carboxamide (8)

The product was purified by column chromatography (EtOAc/PE 4:6) to afford 8 in 22% yield as an orange solid. $^1$H-NMR (300 MHz, CDCl$_3$): δ 8.41 (dd, 1H, J=1.5, 4.9 Hz), 8.19 (dd, 1H, J=1.5, 7.2 Hz), 7.99 (bs, 1H), 7.42 (dd, 1H, J=1.3, 8.5 Hz), 7.34 (d, 1H, J=8.5 Hz), 7.06 (dd, 1H, J=4.9, 7.2 Hz), 3.84 (s, 3H), 3.70 (bs, 2H), 1.31 (bs, 12H).

The following compounds can be prepared by the same method:
N,N-diisopropyl-2-methyl-9H-pyrido[2,3-b]indole-6-carboxamide
N,N-diisopropyl-2-chloro-9H-pyrido[2,3-b]indole-6-carboxamide
N,N-diisopropyl-3-chloro-9H-pyrido[2,3-b]indole-6-carboxamide
N,N-diisopropyl-4-chloro-9H-pyrido[2,3-b]indole-6-carboxamide
N,N-diethyl-2-methyl-9H-pyrido[2,3-b]indole-6-carboxamide
N,N-diethyl-2-chloro-9H-pyrido[2,3-b]indole-6-carboxamide
N,N-diethyl-3-chloro-9H-pyrido[2,3-b]indole-6-carboxamide
N,N-diethyl-4-chloro-9H-pyrido[2,3-b]indole-6-carboxamide Synthesis of 6-bromo-α-carbolines. General Procedure At room temperature and under inert atmosphere, a solution of 0.7 M bromine (1.2 equiv.) in anhydrous CH$_2$Cl$_2$ was added to a 0.45 M suspension of 2-, 3- or 4-chloro-9H-pyrido[2,3-b]indole (1 equiv.) in anhydrous CH$_2$Cl$_2$. The mixture was stirred for 1 h at room temperature Excess bromine was destroyed by addition of sat. aq Na$_2$S$_2$O$_3$ solution. The resulting mixture was extracted with EtOAc/DMF (99:1). The combined organic phases were washed with brine, dried over MgSO$_4$, filtered and evaporated under reduced pressure.

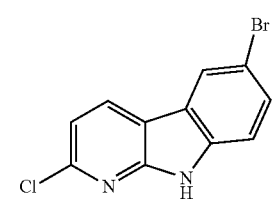

6-bromo-2-chloro-9H-pyrido[2,3-b]indole (9)

The compound 8a was obtained by trituration in MeOH. Yield: 75%; mp>220° C. (MeOH); IR 3135, 3053, 1626, 1597, 1574, 1404, 1273, 1202, 1128, 794, 771 cm$^{-1}$; $^1$H-NMR (300 MHz, DMSO-d$_6$): δ 12.21 (bs, 1H), 8.62 (d, 1H, J=8.1 Hz), 8.47 (d, 1H, J=1.5 Hz), 7.61 (dd, 1H, J=1.9, 8.7 Hz), 7.48 (d, 1H, J=8.7 Hz), 7.31 (d, 1H, J=8.1 Hz); $^{13}$C-NMR (75 MHz, DMSO-d$_6$): δ 151.2 (C), 147.1 (C), 137.5 (C), 132.2 (CH), 129.3 (CH), 123.9 (CH), 121.8 (C), 115.0 (CH), 113.6 (CH), 113.4 (C), 112.1 (C); MS (ESI) m/z 279 [M−H; $^{79}$Br], 281 [M−H; $^{81}$Br]; HRMS (EI): Calcd for C$_{11}$H$_6$BrClN$_2$: 279.9403. Found: 279.9405.

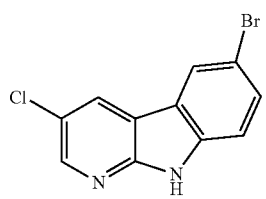

6-bromo-3-chloro-9H-pyrido[2,3-b]indole (R252)

The compound R252 was obtained by trituration in MeOH. Yield: 78%; mp>220° C. (MeOH); IR: 3031, 3005, 2957, 1577, 1604, 1486, 1269, 1232, 1089, 803, 700 cm$^{-1}$; $^1$H-NMR (300 MHz, DMSO-d$_6$): δ 12.19 (bs, 1H), 8.75 (d, 1H, J=2.5 Hz), 8.48 (d, 1H, J=1.9 Hz), 8.46 (d, 1H, J=2.5 Hz), 7.62 (dd, 1H, J=1.9, 8.6 Hz), 7.48 (d, 1H, J=8.6 Hz); $^{13}$C-NMR (75 MHz, DMSO-d$_6$): δ 150.3 (C), 145.0 (CH), 138.4 (C), 129.9 (CH), 128.8 (CH), 124.4 (CH), 122.1 (C), 121.5 (C), 115.4 (C), 113.6 (CH), 111.8 (C); MS (ESI) m/z 281 [M+H$^+$; $^{79}$Br], 283 [M+H$^+$; $^{81}$Br]; HRMS (EI): Calcd for C$_{11}$H$_6$BrClN$_2$: 279.9403. Found: 279.9405.

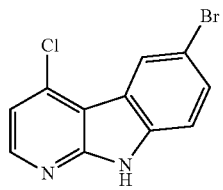

6-bromo-4-chloro-9H-pyrido[2,3-b]indole (10)

The compound 10 was obtained by trituration in MeOH. Yield: 76%; mp>220° C. (MeOH); IR: 3123, 2950, 1603, 1569, 1442, 1276, 870, 795 cm$^{-1}$; $^1$H-NMR (300 MHz, DMSO-d$_6$): δ 12.40 (bs, 1H), 8.43 (d, 1H, J=1.5 Hz), 8.42 (d, 1H, J=5.3 Hz), 7.69 (dd, 1H, J=1.5, 8.6 Hz), 7.54 (d, 1H, J=8.6 Hz), 7.38 (d, 1H, J=5.3 Hz); $^{13}$C-NMR (75 MHz, DMSO-d$_6$): δ 152.8 (C), 147.6 (CH), 137.6 (C), 136.9 (C), 129.9 (CH), 124.4 (CH), 120.7 (C), 115.9 (CH), 113.7 (CH), 111.9 (C), 111.7 (C); MS (ESI) m/z 281.1 [M+H$^+$; $^{79}$Br], 283.1 [M+H$^+$; $^{81}$Br]; HRMS (ESI): Calcd for C$_{11}$H$_6$BrClN$_2$: 280.9481. Found: 280.9485.

General Procedure for the Synthesis of 4-(chloro-9H-pyrido[2,3-b]indol-6-yl)-4-oxobutyric Acids At room temperature and under inert atmosphere, AlCl$_3$ (4.5 equiv.) and succinic anhydride (1.2 equiv.) were added to a 0.2 M suspension of (R248) or (R297) (1 equiv.) in anhydrous CH$_2$Cl$_2$. The mixture was stirred at reflux until completion of the reaction (monitored by t.l.c.). The reaction was refluxed for 2 h 30. The resulting mixture was then cautiously quenched at 0° C. with H$_2$O. The mixture was extracted with a mixture of EtOAc/DMF (99:1). The resulting organic layer was dried over MgSO$_4$, filtered, and solvents were removed under reduced pressure. Trituration of the crude residue from MeOH then filtration afforded desired products.

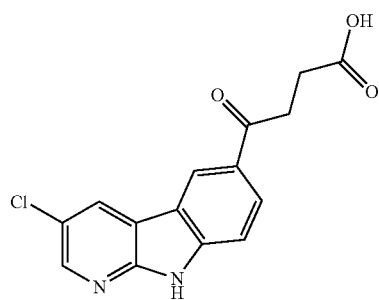

4-(3-Chloro-9H-pyrido[2,3-b]indol-6-yl)-4-oxo-butyric acid (11)

Orange solid. Yield=66%. mp 243.0° C.; IR (KBr): 3118, 1664, 1623, 1587, 1484, 1443, 1382, 1346, 1269, 1228, 1080, 527, 440 cm$^{-1}$; $^1$H-NMR (300 MHz, DMSO-d$_6$): δ12.41 (bs, 1H), 12.17 (bs, 1H), 9.01 (s, 1H), 8.87 (d, 1H, J=2.2 Hz), 8.48 (d, 1H, J=2.4 Hz), 8.12 (dd, 1H, J=1.5, 8.7 Hz), 7.58 (d, 1H, J=6.3 Hz), 3.36-(m, 2H), 2.64 (t, 2H, J=6.3 Hz); $^{13}$C-NMR (75 MHz, DMSO-d$_6$) δ197.4 (C), 174.0 (C), 150.8 (C), 144.8 (CH), 142.6 (C), 128.9 (CH), 128.8 (CH), 127.1 (CH), 123.4 (CH), 122.6 (C), 119.4 (C), 116.9 (C), 111.4 (CH), 32.9 (CH$_2$), 28.0 (CH$_2$); MS

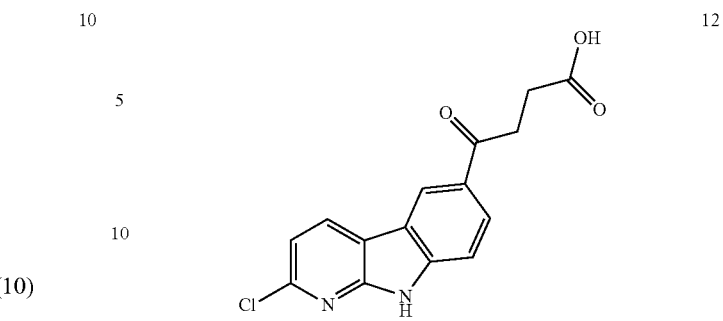

4-(2-Chloro-9H-pyrido[2,3-b]indol-6-yl)-4-oxo-butyric acid (12)

Yellow solid. Yield 31%. mp 280.8° C., IR (KBr): 3205, 3139, 3062, 2965, 1705, 1674, 1616, 1566, 1408, 1351, 1341, 1254, 1218, 1177, 1126, 931, 803, 773, 527 cm$^{-1}$, $^1$H NMR (300 MHz, DMSO-d$_6$): δ 12.45 (bs, 1H), 12.16 (bs, 1H), 8.97 (s, 1H), 8.74 (d, 1H, J=8.1 Hz), 8.12 (d, 1H, J=8.3 Hz), 7.60 (d, 1H, J=8.5 Hz), 7.37 (d, 1H, J=8.5 Hz) 3.37 (m, 2H), 2.64 (t, 2H, J=5.6 Hz), $^{13}$C NMR (75 MHz, DMSO-d$_6$): δ 197.4 (C), 173.9 (C), 151.7 (C), 146.9 (C), 141.7 (C), 132.1 (CH), 129.1 (C), 126.6 (CH), 122.7 (CH), 119.6 (C), 115.4 (CH), 114.6 (C), 111.4 (CH), 32.9 (CH$_2$), 27.9 (CH$_2$). MS (ESI) 303.0 [2M+H$^+$], 626.8 [2M+Na$^+$]

The following compound can be prepared by the same method:
4-(4-Chloro-9H-pyrido[2,3-b]indol-6-yl)-4-oxo-butyric acid Synthesis of 2-thio-substituted-1-(3-chloro-9H-pyrido[2,3-b]indol-6-yl)ethanones To the appropriate thiol (1.1 equiv.) in anhydrous DMF under argon at 0° C. was introduced NaH (1.2-1.4 equiv.). After 30 min, (R251) or (R228) were introduced. This solution was stirred at room temperature for 4 hours and then the crude mixture was concentrated under vacuum. This mixture was poured with 5% aqueous NaHCO$_3$ and extracted with EtOAc. The combined organic layers were dried (MgSO$_4$), and the solvent was removed under reduced pressure. The crude product was purified either by recrystallization from CH$_2$Cl$_2$/PE to afford R263, R284 and R283, or trituration in MeOH and filtration to give R264, R272, R273, R274 and R275 or flash chromatography to afford R279 and R280.

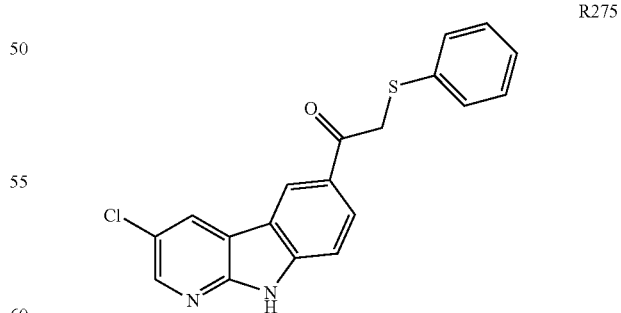

1-(3-Chloro-9H-pyrido[2,3-b]indol-6-yl)-2-phenyl-sulfanylethanone (R275)

Yield: 23%; mp 238-239° C. (MeOH); IR (KBr): 3436, 3200, 3113, 3026, 2995, 2847, 2749, 1669, 1618, 1592, 1454, 1382, 1264, 732, 522 cm$^{-1}$; $^1$H-NMR (300 MHz, DMSO-d$_6$): δ12.47 (bs, 1H), 9.05 (s, 1H), 8.83 (d, 1H, J=2.5 Hz), 8.50 (d, 1H, J=2.5 Hz), 8.16 (dd, 1H, J=1.5, 8.7 Hz), 7.60 (d, 1H, J=8.7 Hz), 7.35 (m, 4H), 7.20 (t, 1H, J=7.2 Hz), 4.74 (s, 2H); $^{13}$C-NMR (75 MHz, DMSO-d$_6$): δ193.3 (C), 150.9 (C), 144.9 (CH) 142.8 (C), 135.6 (C), 129.5 (C), 128.9 (CH), 128.8 (CH), 128.3 (CH), 127.9 (CH), 125.9 (CH), 124.2 (CH), 122.7 (C), 119.42 (C), 116.8 (C), 111.5 (CH), signal for CH$_2$ missing: must be behind DMSO $^1$H residual signal; MS (+ESI) 353.1 [M+H$^+$], HRMS Calculated for C$_{19}$H$_{13}$ClN$_2$OS: 352.0437. Found: 352.0437.

1H, J=2.3 Hz), 8.22 (dd, 1H, J=1.2, 8.7 Hz), 8.01 (dd, 1H, J=0.7, 7.9 Hz), 7.78 (dd, 1H, J=0.8, 7.5 Hz), 7.65 (d, 1H, J=8.7 Hz), 7.44 (td, 1H, J=1.4, 7.7 Hz), 7.35 (td, 1H, J=1.2, 7.5 Hz), 5.27 (s, 2H); $^{13}$C-NMR (75 MHz, DMSO-d$_6$): δ191.7 (C), 166.1 (C), 152.6 (C), 150.9 (C), 145.1 (CH), 143.0 (C), 134.8 (C), 128.9 (CH), 127.8 (CH), 127.7 (C), 126.4 (CH), 124.5 (CH), 124.1 (CH), 122.8 (C), 121.9 (CH), 121.1 (CH), 119.5 (C), 116.8 (C), 111.72 (CH), 41.07 (CH$_2$); MS (ESI) 410.1 [M+H$^+$]; HRMS Calculated for C$_{20}$H$_{12}$ClN$_3$OS$_2$: 409.0110. Found: 409.0110.

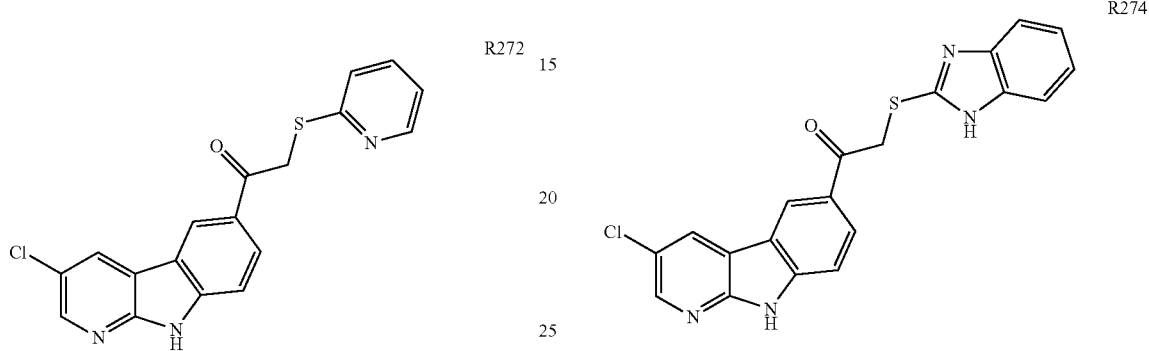

1-(3-Chloro-9H-pyrido[2,3-b]indol-6-yl)-2-(pyridin-2-ylsulfanyl)ethanone (R272)

2-(1H-Benzoimidazol-2-ylsulfanyl)-1-(3-chloro-9H-pyrido[2,3-b]indol-6-yl)ethanone (R274)

Yield: 67%; Mp 209-210° C. (Meoh); Ir (Kbr): 3400, 3200, 3113, 3031, 2842, 1669, 1572, 1413, 1259, 742 cm$^{-1}$, $^1$H-NMR (300 MHz, DMSO-d$_6$): δ12.47 (bs, 1H), 9.09 (s, 1H), 8.85 (s, 1H), 8.49 (s, 1H), 8.34 (d, 1H, J=3.6 Hz), 8.18 (d, 1H, J=8.3 Hz), 7.62 (m, 2H), 7.39 (d, 1H, J=7.9 Hz), 7.09 (t, 1H, J=5.7 Hz), 4.91 (s, 2H); $^{13}$C-NMR (75 MHz, DMSO-d$_6$): 6192.9 (C), 157.4 (C), 150.9 (C) 149.3 (CH), 144.6 (CH), 142.8 (C), 136.7 (CH), 128.8 (CH), 128.2 (C), 123.9 (CH), 122.7 (C), 121.7 (CH), 119.9 (CH), 119.43 (C), 116.8 (C), 111.5 (CH), 36.9 (CH$_2$); MS (+ESI) 354.1 [M+H$^+$], HRMS Calculated for C$_{18}$H$_{12}$ClN$_3$OS: 353.0390. Found: 353.0391.

Yield: 50%; mp 209-210° C. (MeOH); IR (KBr): 3267, 3047, 2959, 2350, 1659, 1618, 1587, 1377, 1259, 1157, 732, 747 cm$^{-1}$; $^1$H-NMR (300 MHz, DMSO-d$_6$): δ12.64 (s, 1H), 12.49 (s, 1H), 9.10 (s, 1H), 8.82 (d, 1H, J=1.3 Hz), 8.50 (s, 1H), 8.19 (d, 1H, J=8.3 Hz), 7.62 (d, 1H, J=8.7 Hz), 7.46 (bs, 1H), 7.38 (d, 1H, J=4.3 Hz), 7.11 (m, 2H), 5.15 (s, 2H); $^{13}$C-NMR (75 MHz, DMSO-d$_6$): δ192.4 (C), 150.9 (C), 149.7 (C) 145.0 (CH), 142.9 (CH), 132.2 (C), 128.9 (CH), 127.7 (CH), 124.0 (CH), 122.8 (C), 122.3 (C), 121.5 (CH), 119.4 (C), 116.8 (C), 111.6 (CH), 109.5 (C); signal for CH$_2$ missing: must be behind DMSO $^1$H residual signal, MS (ESI) 393.1 [M+H$^+$], 806.9 [2M+Na$^+$]

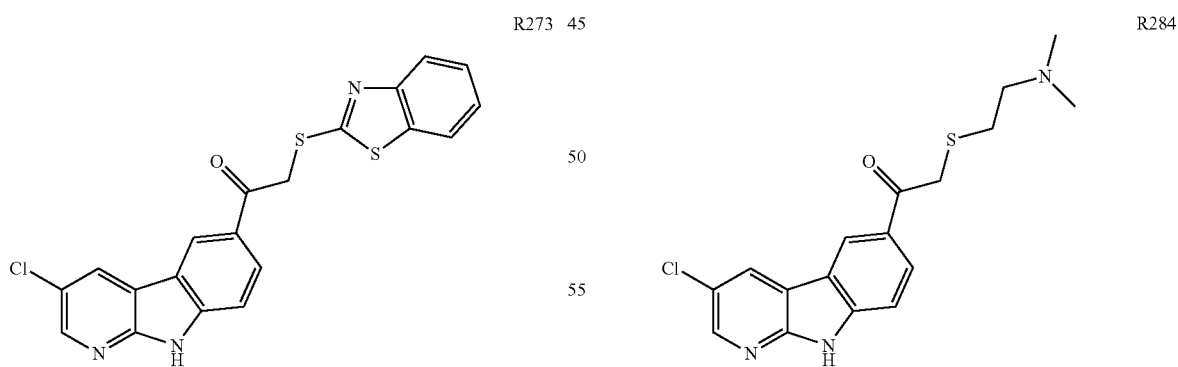

2-(Benzothiazol-2-ylsulfanyl)-1-(3-chloro-9H-pyrido[2,3-b]indol-6-yl)ethanone (R273)

1-(3-Chloro-9H-pyrido[2,3-b]indol-6-yl)-2-(2,2-dimethylaminoethylsulfanyl)ethanone (R284)

Yield: 54%; mp 241-242° C. (MeOH); IR (KBr): 3451, 3205, 3113, 2995, 2908, 2852, 2760, 2703, 1669, 1602, 1413, 998, 747 cm$^{-1}$; $^1$H-NMR (300 MHz, DMSO-d$_6$): δ12.52 (bs, 1H), 9.15 (d, 1H, J=1.2 Hz), 8.88 (d, 1H, J=2.3 Hz), 8.52 (d, Yield: 44%; mp 176-177° C. (CH$_2$Cl$_2$/PE); IR (KBr): 3441, 3103, 3057, 2945, 2781, 1654, 1613, 1588, 1449, 1372, 1260, 763 cm$^{-1}$; $^1$H-NMR (300 MHz, DMSO-d$_6$): δ12.44 (bs, 1H), 9.00 (d, 1H, J=1.3 Hz), 8.84 (d, 1H, J=2.2 Hz), 8.50

(d, 1H, J=2.2 Hz), 8.13 (dd, 1H, J=1.7, 8.6 Hz), 7.59 (d, 1H, J=8.6 Hz), 5.76 (s, 2H), 2.65 (t, 2H, J=6.6 Hz), 2.44 (t, 2H, J=6.6 Hz), 2.11 (s, 6H, CH$_3$); $^{13}$C-NMR (75 MHz, DMSO-d$_6$): δ194.2 (C), 150.9 (C), 144.9 (CH), 142.7 (C), 128.8 (CH), 127.9 (CH), 127.6 (C), 124.1 (CH), 122.7 (C), 119.4 (C), 116.8 (C), 111.5 (CH), 58.4 (CH$_2$), 44.8 (CH$_3$), 36.9 (CH$_2$), 29.3 (CH$_2$); MS (−ESI) 346.2 [M−H$^-$]

131.6 (C), 130.8 (CH), 129.8 (CH), 128.8 (CH), 128.6 (CH), 127.9 (CH), 126.9 (CH), 124.2 (CH), 122.7 (C), 122.16 (C), 119.4 (C), 116.8 (C), 111.5 (CH), signal for CH$_2$ missing: must be behind DMSO $^1$H residual signal; MS (−ESI) 431.0 [M−H$^-$], 466.7 [M+Cl$^-$]

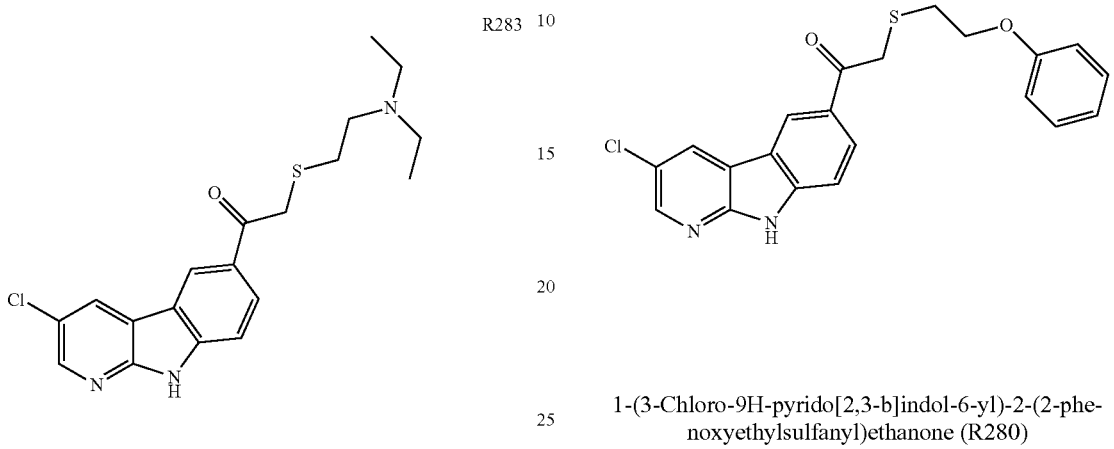

1-(3-Chloro-9H-pyrido[2,3-b]indol-6-yl)-2-(N,N-diethylaminoethylsulfanyl)ethanone (R283)

Yield: 56%; mp 137-138° C. (CH$_2$Cl$_2$/PE); IR (KBr): 3462, 3114, 3037, 2970, 1659, 1618, 1593, 1444, 1270, 533 cm$^{-1}$; $^1$H-NMR (300 MHz, DMSO-d$_6$): δ 12.44 (bs, 1H), 8.99 (d, 1H, J=1.1 Hz), 8.83 (d, 1H, J=2.4 Hz), 8.49 (d, 1H, J=2.4 Hz), 8.13 (dd, 1H, J=1.7, 8.7 Hz), 7.59 (d, 1H, J=8.7 Hz), 4.07 (s, 2H), 2.63 (s, 2H), 2.49 (m, 4H), 0.93 (t, 6H, J=7.2 Hz); $^{13}$C-NMR (75 MHz, DMSO-d$_6$): δ 194.3 (C), 150.9 (C), 144.9 (CH), 142.7 (C), 128.8 (CH), 128.0 (CH), 127.5 (C), 124.1 (CH), 122.7 (C), 119.4 (C), 116.8 (C), 111.5 (CFI), 51.9 (CH$_2$), 46.2 (CH$_3$), 36.7 (CH$_2$), 28.9 (CH$_2$), 11.7 (CR$_3$); MS (ESI) 376.1 [M+H$^+$]

1-(3-Chloro-9H-pyrido[2,3-b]indol-6-yl)-2-(2-phenoxyethylsulfanyl)ethanone (R280)

Yield: 41%; mp 167-168° C.; IR (KBr): 3436, 3200, 3113, 3026, 2995, 2847, 2749, 1669, 1618, 1592, 1454, 1382, 1264, 732, 522 cm$^{-1}$; $^1$H-NMR (300 MHz, DMSO-d$_6$): δ12.45 (bs, 1H), 9.02 (s, 1H), 8.82 (d, 1H, J=2.3 Hz), 8.50 (d, 1H, J=2.3 Hz), 8.15 (dd, 1H, J=1.5, 8.6 Hz), 7.59 (d, 1H, J=8.6 Hz), 7.24-7.30 (m, 2H), 6.89-6.94 (m, 3H); $^{13}$C-NMR (75 MHz, DMSO-d$_6$): δ194.3 (C), 158.1 (C), 150.1 (C) 144.9 (CH), 142.7 (C), 129.5 (CH), 128.8 (CH), 128.8 (CH), 127.9 (CH), 124.1 (CH), 120.7 (CH), 114.5 (CH), 111.5 (CH), 66.7 (CH$_2$), 37.2 (CH$_2$), 116.8 (C), 30.8 (CH$_2$), signal for CH$_2$ missing: must be behind DMSO $^1$H residual signal; MS (−ESI) 395.1 [M−H$^-$]

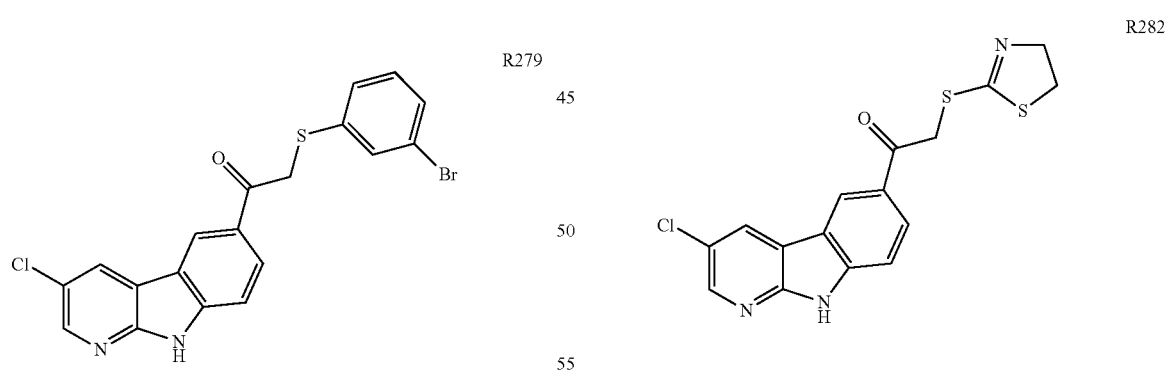

2-(3-Bromophenylsulfanyl)-1-(3-chloro-9H-pyrido[2,3-b]indol-6-yl)ethanone (R279)

Yield: 72%; mp 229-230° C.; IR (KBr): 3431, 3108, 3037, 2847, 1669, 1629, 1598, 1572, 1444, 1383, 1260, 758 cm$^{-1}$; $^1$H-NMR (300 MHz, DMSO-d$_6$): δ12.48 (bs, 1H), 9.06 (bs, 1H), 8.83 (d, 1H, J=2.3 Hz), 8.51 (d, 1H, J=2.2 Hz), 8.168 (d, 1H, J=8.7 Hz), 7.59-7.62 (m, 2H), 7.37-7.40 (m, 2H), 7.23-7.28 (m, 1H), 4.84 (s, 21-1); $^{13}$C-NMR (75 MHz, DMSO-d$_6$): δ 193.1 (C), 150.8 (C), 145.0 (CH) 142.9 (C), 138.7 (C), 1-(3-chloro-9H-pyrido[2,3-b]indol-6-yl)-2-(4,5-dihydrothiazol-2-ylsulfanyl)ethanone (R282)

The crude product was purified by flash chromatography (CH$_2$Cl$_2$/EtOAc 3:1) to afford R282 in 57% yield as a yellow solid, $^1$H-NMR (300 MHz, DMSO-d$_6$): δ 12.48 (bs, 1H), 9.06 (s, 1H), 8.88 (d, 1H, J=2.5 Hz), 8.50 (d, 1H, J=2.5 Hz), 8.14 (dd, 1H, J=1.5, 8.7 Hz), 7.60 (d, 1H, J=8.7 Hz), 4.93 (s, 2H), 4.09 (t, 2H, J=8.1 Hz), 3.46 (t, 2H, J=8.1 Hz); MS (ESI) m/z 361.9 [M+H$^+$]

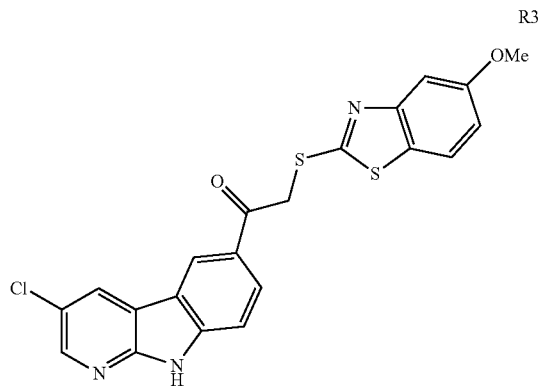

1-(3-chloro-9H-pyrido[2,3-b]indol-6-yl)-2-(5-methoxybenzothiazol-2-ylsulfanyl)éthanone (R301)

The crude product was purified by flash chromatography (EtOAc/PE 6:4) to afford R301 in 55% yield as a yellow solid, $^1$H-NMR (300 MHz, DMSO-$d_6$): δ 12.5 (bs, 1H), 9.12 (s, 1H), 8.84 (s, 1H), 8.50 (s, 1H), 8.20 (d, 1H, J=9.0 Hz), 7.84 (d, 1H, J=8.9 Hz), 7.63 (d, 1H, J=8.5 Hz), 7.33 (s, 1H), 6.97 (dd, 114, J=2.1. 9.0 Hz), 5.24 (s, 2H), 2.64 (s, 3H); $^{13}$C-NMR (75 MHz, DMSO-$d_6$): δ 191.7 (C), 167.0 (C), 161.8 (2C), 158.7 (C), 153.9 (C), 145.0 (CH), 142.9 (C), 128.9 (CH), 127.6 (CH), 126.3 (CH), 124.1 (CH), 122.7 (C), 122.0 (CH), 119.5 (C), 116.7 (C), 113.7 CH), 111.7 (CH), 104.4 (CH), 55.4 ($CH_3$), 41.0 ($CH_2$); MS (ESI) m/z 440.1 [M+H$^+$]

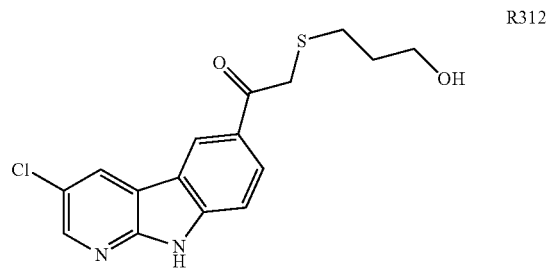 [SMILES: O=C(CSCCCO)c1ccc2[nH]c3ncc(Cl)cc3c2c1]

1-(3-chloro-9H-pyrido[2,3-b]indol-6-yl)-2-(3-hydroxypropylsulfanyl)ethan-1-one. (R312)

The crude product was purified by trituration with methanol and filtration to afford R312 in 22% yield as a yellow solid, $^1$H-NMR (300 MHz, DMSO-$d_6$): δ 12.45 (bs, 1H), 8.99 (d, 1H, J=1.3 Hz), 8.42 (d, 1H, J=2.5 Hz), 8.49 (d, 1H, J=2.4 Hz), 8.13 (dd, 1H, J=1.7, 8.7 Hz), 7.58 (d, 1H, J=8.7 Hz), 4.5 (bs, 1H), 4.05 (s, 2H), 3.45-3.43 (m, 2H), 2.58 (t, 2H, J=7.1 Hz), 1.71-1.66 (m, 2H); $^{13}$C-NMR (75 MHz, DMSO-$d_6$): δ 194.2 (C), 144.9 (C), 142.7 (C), 128.7 (CH), 127.9 (CH), 127.5 (C), 124.1 (CH), 122.7 (C), 119.4 (C), 116.8 (C), 111.4 (CH), 59.4 ($CH_2$), 36.8 ($CH_2$), 31.9 ($CH_2$), 28.3 ($CH_2$), MS (ESI) m/z 335.1 [M+H$^+$], 690.8 [2M+Na$^+$]; HRMS (EI): Calcd for $C_{16}H_{15}ClN_2O_2S$: 335.0621. Found: 335.0624.

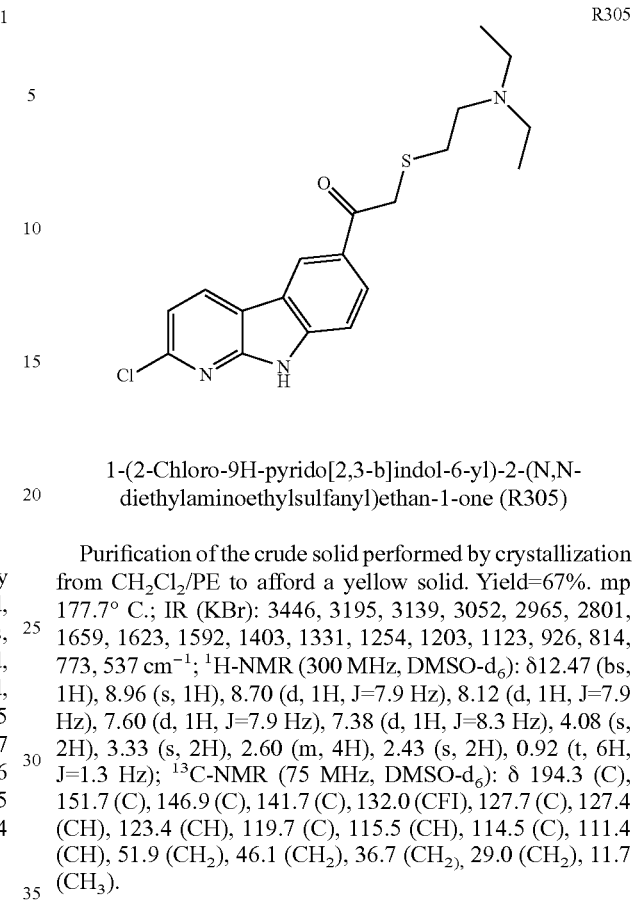

1-(2-Chloro-9H-pyrido[2,3-b]indol-6-yl)-2-(N,N-diethylaminoethylsulfanyl)ethan-1-one (R305)

Purification of the crude solid performed by crystallization from $CH_2Cl_2$/PE to afford a yellow solid. Yield=67%. mp 177.7° C.; IR (KBr): 3446, 3195, 3139, 3052, 2965, 2801, 1659, 1623, 1592, 1403, 1331, 1254, 1203, 1123, 926, 814, 773, 537 cm$^{-1}$; $^1$H-NMR (300 MHz, DMSO-$d_6$): δ12.47 (bs, 1H), 8.96 (s, 1H), 8.70 (d, 1H, J=7.9 Hz), 8.12 (d, 1H, J=7.9 Hz), 7.60 (d, 1H, J=7.9 Hz), 7.38 (d, 1H, J=8.3 Hz), 4.08 (s, 2H), 3.33 (s, 2H), 2.60 (m, 4H), 2.43 (s, 2H), 0.92 (t, 6H, J=1.3 Hz); $^{13}$C-NMR (75 MHz, DMSO-$d_6$): δ 194.3 (C), 151.7 (C), 146.9 (C), 141.7 (C), 132.0 (CFI), 127.7 (C), 127.4 (CH), 123.4 (CH), 119.7 (C), 115.5 (CH), 114.5 (C), 111.4 (CH), 51.9 ($CH_2$), 46.1 ($CH_2$), 36.7 ($CH_2$), 29.0 ($CH_2$), 11.7 ($CH_3$).

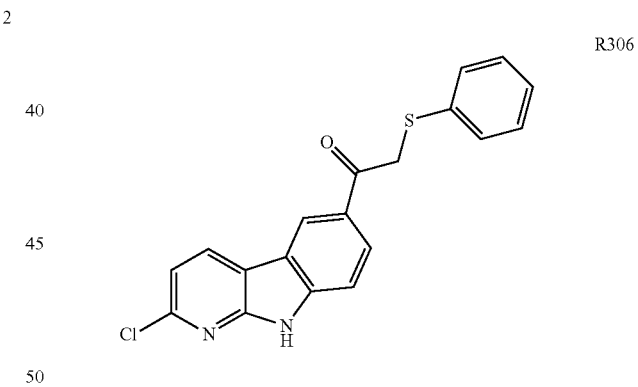

1-(2-Chloro-9H-pyrido[2,3-b]indol-6-yl)-2-phenylsulfanylethanone (R306)

Purification of the crude solid performed by trituration from $Et_2O$ to afford a yellow solid. Yield=60%; mp 255.9° C.; IR (KBr): 3190, 3129, 3052, 2975, 2893, 1659, 1918, 1597, 1571, 1479, 1397, 1280, 1172, 1126, 921, 732, 435 cm$^{-1}$; $^1$H-NMR (300 MHz, DMSO-$d_6$): δ12.50 (bs, 1H), 9.00 (s, 1H), 8.69 (d, 1H, J=8.1 Hz), 8.15 (dd, 1H, J=1.6, 8.6 Hz), 7.61 (d, 1H, J=8.7 Hz), 7.38 (m, 3H), 7.31 (t, 2H, J=7.6 Hz), 7.19 (t, 1H, J=7.2 Hz), 4.75 (s, 2H); $^{13}$C-NMR (75 MHz, DMSO-$d_6$): δ193.4 (C), 151.8 (C), 147.1 (C) 141.9 (C), 135.6 (C), 132.2 (CH), 128.9 (CH), 128.3 (CH), 127.9 (C), 127.4 (CH), 125.9 (CH), 123.6 (CH), 119.7 (C), 115.7 (CH), 114.7 (C), 111.6 (CH), 39.8 ($CH_2$); MS (−ESI) 726.8 [2M+Na$^+$], (−ESI) 351.1 [M−H$^-$], 740.6 [2M+Cl$^-$]

The following compounds can be prepared by the same method:
1-(4-Chloro-9H-pyrido[2,3-b]indol-6-yl)-2-phenylsulfanylethanone
1-(2-Chloro-9H-pyrido[2,3-b]indol-6-yl)-2-(pyridin-2-ylsulfanyl)ethanone
1-(4-Chloro-9H-pyrido[2,3-b]indol-6-yl)-2-(pyridin-2-ylsulfanyl)ethanone
2-(Benzothiazol-2-ylsulfanyl)-1-(2-chloro-9H-pyrido[2,3-b]indol-6-yl)ethanone
2-(Benzothiazol-2-ylsulfanyl)-1-(4-chloro-9H-pyrido[2,3-b]indol-6-yl)ethanone
2-(1H-Benzoimidazol-2-ylsulfanyl)-1-(2-chloro-9H-pyrido[2,3-b]indol-6-yl)ethanone
2-(1H-Benzoimidazol-2-ylsulfanyl)-1-(4-chloro-9H-pyrido[2,3-b]indol-6-yl)ethanone
1-(2-Chloro-9H-pyrido[2,3-b]indol-6-yl)-2-(2,2-dimethylaminoethylsulfanyl)ethanone
1-(4-Chloro-9H-pyrido[2,3-b]indol-6-yl)-2-(2,2-dimethylaminoethylsulfanyl)ethanone
1-(4-Chloro-9H-pyrido[2,3-b]indol-6-yl)-2-(N,N-diethylaminoethylsulfanyl)ethan-1-one
2-(3-Bromophenylsulfanyl)-1-(2-chloro-9H-pyrido[2,3-b]indol-6-yl)ethanone
2-(3-Bromophenylsulfanyl)-1-(4-chloro-9H-pyrido[2,3-b]indol-6-yl)ethanone
1-(2-Chloro-9H-pyrido[2,3-b]indol-6-yl)-2-(2-phenoxyethylsulfanyl)ethanone
1-(4-Chloro-9H-pyrido[2,3-b]indol-6-yl)-2-(2-phenoxyethylsulfanyl)ethanone
1-(2-chloro-9H-pyrido[2,3-b]indol-6-yl)-2-(4,5-dihydrothiazol-2-ylsulfanyl)éthanone
1-(4-chloro-9H-pyrido[2,3-b]indol-6-yl)-2-(4,5-dihydrothiazol-2-ylsulfanyl)éthanone
1-(2-chloro-9H-pyrido[2,3-b]indo-6-yl)-2-(5-methoxybenzothiazol-2-ylsulfanyl)éthanone
1-(4-chloro-9H-pyrido[2,3-b]indol-6-yl)-2-(5-methoxybenzothiazol-2-ylsulfanyl)éthanone
1-(2-chloro-9H-pyrido[2,3-b]indol-6-yl)-2-(3-hydroxypropylsulfanyl)ethan-1-one
1-(4-chloro-9H-pyrido[2,3-b]indol-6-yl)-2-(3-hydroxypropylsulfanyl)ethan-1-one Synthesis of 6-thiazolyl-α-carbolines. General Procedure To a 0.2 M stirred suspension of the α-carboline derivative (200 mg) in anhydrous CH$_2$Cl$_2$ was added AlCl$_3$ (4.5 equiv.) and bromoacetyl bromide (2.1 equiv.), at room temperature under inert atmosphere. The mixture was stirred at reflux until completion of the reaction (followed by t.l.c.). The resulting mixture was then cautiously quenched at 0° C. with H$_2$O. It was extracted with the mixture of EtOAc/DMF (99:1). The resulting organic layer was washed with NaHCO$_3$ saturated aqueous solution and brine, dried over MgSO$_4$, filtered and solvents were removed under reduced pressure. 2-Bromo-1-(9H-pyrido[2,3-b]indol-6-yl)ethanone was obtained in 61% yield after trituration of the crude product in MeOH and filtration $^1$H NMR (300 MHz, DMSO-d$_6$): δ 8.99 (d, 1H, J=1.7 Hz), 8.80 (dd, 1H, J=1.5, 7.7 Hz), 8.66 (d, 1H, J=9.0 Hz), 8.64 (d, 1H, J=1.7, 3.7 Hz), 8.26 (dd, 1H, J=1.7, 9.0 Hz), 7.60 (dd, 1H, J=4.5, 7.7 Hz), 5.42 (s, 2H), 5.0 (s, 1H)

A solution of potassium thiocyanate (73 mg, 0.73 mmol, 2 equiv.) in Ethanol (1 mL), was added dropwise a solution of compound 2-Bromo-1-(9H-pyrido[2,3-b]indol-6-yl)ethanone (150 mg, 0.366 mmol) in ethanol (1 mL). The mixture was stirred at reflux for 1 hour. The resulting mixture was then cautiously quenched at 0° C. with H$_2$O. It was extracted with EtOAc. The resulting organic layer was washed with NaCl saturated aqueous solution, dried over MgSO$_4$, and filtered. Solvent was removed under reduced pressure The crude product was triturated and filtered. The resulting product (82 mg, 0276 mmol) was dissolved in glacial acetic acid (1 mL), 50% sulfuric acid (200 µL) was added, and then the mixture was heated to reflux for 1 hour. The resulting mixture was quenched at 0° C. with H$_2$O. The aqueous layer is treated with Na$_2$CO$_3$ until pH=6 and then extracted with AcOEt (3×20 ml). The organic layers was washed with NaCl saturated aqueous solution, dried over MgSO$_4$, and filtered. Solvent was removed under reduced pressure. A white powder was obtained in 23% yield after trituration of the crude product in MeOH and filtration; $^1$H NMR (300 MHz, DMSO-d$_6$): δ 11.96 (bs, 1H), 11.78 (bs, 1H), 8.48-8.43 (m, 3H), 7.74 (dd, 1H, J=1.9, 8.5 Hz), 7.52 (d, 1H, J=8.5 Hz), 7.25 (dd, 1H, J=5.5, 7.2 Hz), 6.69 (d, 1H, J=1.9 Hz), 4.75 (bs, 1H); MS (ESI) m/z 268.1 [M+H$^+$]

The following compounds can be prepared by the same method:
4-(2-methyl-9H-pyrido[2,3-b]indol-6-yl)thiazol-2(3H)-one
4-(2-chloro-9H-pyrido[2,3-b]indol-6-yl)thiazol-2(3H)-one
4-(3-chloro-9H-pyrido[2,3-b]indol-6-yl)thiazol-2(3H)-one
4-(4-chloro-9H-pyrido[2,3-b]indol-6-yl)thiazol-2(3H)-one

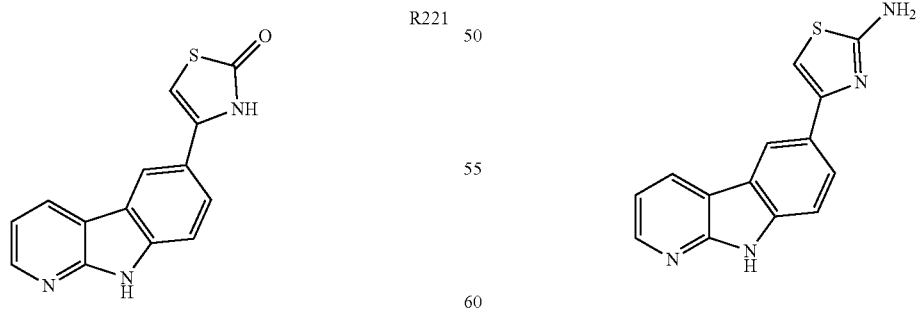

4-(9H-pyrido[2,3-b]indol-6-yl)thiazol-2(3H)-one (R221)

4-(9H-pyrido[2,3-b]indol-6-yl)thiazol-2-amine (13)

To a stirred suspension of 2-Bromo-1-(9H-pyrido[2,3-b]indol-6-yl)ethanone (100 mg, 0.346 mmol) in EtOH (2 mL) was added thiourea (26 mg, 1 equiv.) and the mixture was heated at 70° C. for 2 h. After cooling to room temperature, the solvent was evaporated to dryness. The resulting solid was stirred in a mixture of EtOAc/saturated aqueous NaHCO$_3$ solution (2:1) until dissolution, and then extracted with EtOAc. The organic layer was washed with brine, dried over anhydrous MgSO$_4$, filtered, and the solvent was removed under reduced pressure. Compound 13 was obtained as a white powder in 99% yield after trituration of the crude product in MeOH and filtration; $^1$H-NMR (300 MHz; DMSO-d$_6$): δ 12.07 (bs, 1H), 8.57-8.45 (m, 2H), 8.47 (dd, 1H, J=1.5, 4.9 Hz), 7.85 (dd, 1H, J=1.7, 8.5 Hz), 7.57 (d, 1H, J=8.5 Hz), 7.28 (dd, 1H, J=5.0, 7.7 Hz), 7.08 (s, 1H); $^{13}$C-NMR (75 MHz; DMSO-d$_6$): δ 170.1 (C), 150.9 (C), 145.1 (CH), 140.3 (C), 139.2 (C), 130.0 (CH), 125.0 (CH), 121.1 (C), 120.4 (C), 119.2 (CH), 116.0 (C), 115.6 (CH), 112.0 (CH), 100.7 (CH); MS (ESI) m/z 267.1 [M+H$^+$]; HRMS (ESI): Calcd for C$_{14}$H$_{10}$N$_4$S: 267.0704. Found: 267.0703

The following compounds can be prepared by the same method:
4-(2-methyl-9H-pyrido[2,3-b]indol-6-yl)thiazol-2-amine
4-(2-chloro-9H-pyrido[2,3-b]indol-6-yl)thiazol-2-amine
4-(3-chloro-9H-pyrido[2,3-b]indol-6-yl)thiazol-2-amine
4-(4-chloro-9H-pyrido[2,3-b]indol-6-yl)thiazol-2-amine

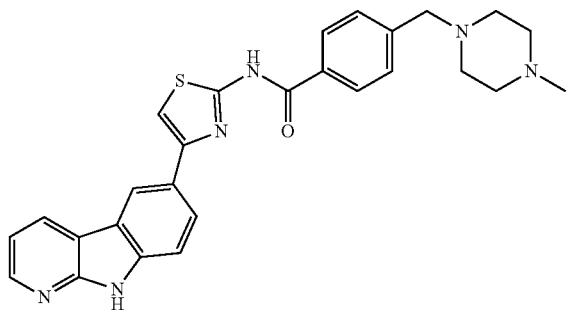

R222

4-(9H-pyrido[2,3-b]indol-6-yl)-4-((4-methylpiperazine-1-yl)methyl)benzamide (R222)

To a mixture of 4-(4-methylpiperazine)benzoic acid (741 mg, equiv.) in anhydrous DMF (1.6 mL) was added a solution of 4-(9H-pyrido[2,3-b]indol-6-yl)thiazol-2-amine (200 mg, 0.79 mmol) in anhydrous DMF (1.6 mL), a solution of EDCI (606 mg, equiv.) in dry DMF (1.6 mL) and DMAP (16 mg, equiv.). The reaction mixture was stirred at room temperature for 12 h and DMF was evaporated in vacuo. The product was purified by column chromatography (CH$_2$Cl$_2$/MeOH 9:1) to afford R222 in 13% yield. $^1$H-NMR (300 MHz; DMSO-d$_6$): δ 12.74 (bs, 1H), 11.90 (bs, 1H), 8.73 (s, 1H), 8.49 (d, 1H, J=7.3 Hz), 8.44 (d, 1H, J=3.6 Hz), 8.14-8.06 (m, 3H), 7.62 (s, 1H), 7.55 (d, 1H, J=8.5 Hz), 7.48 (d, 2H, J=8.1 Hz), 7.24 (dd, 1H, J=5.1, 7.6 Hz), 3.57 (s, 3H), 2.50 (bs, 4H), 2.26 (bs, 4H); MS (ESI) m/z 483.2 [M+H$^+$].

The following compounds can be prepared by the same method:
4-(2-methyl-9H-pyrido[2,3-b]indol-6-yl)-4-((4-methylpiperazine-1-yl)methyl)benzamide
4-(2-chloro-9H-pyrido[2,3-b]indol-6-yl)-4-((4-methylpiperazine-1-yl)methyl)benzamide
4-(3-chloro-9H-pyrido[2,3-b]indol-6-yl)-4-((4-methylpiperazine-1-yl)methyl)benzamide
4-(4-chloro-9H-pyrido[2,3-b]indol-6-yl)-4-((4-methylpiperazine-1-yl)methyl)benzamide General Procedure for the Preparation of 4-(chloro-9H-pyrido[2,3-b]indol-6-yl)-4-oxobutyric amides To the appropriate 4-(chloro-9H-pyrido[2,3-b]indol-6-yl)-4-oxo-butyric acid in anhydrous (0.2M) DMF were added amine (4 equiv.), N-Ethyl-N'-(3-dimethylaminopropyl)carbodiimide hydrochloride (4 equiv.) and a catalytic amount of DMAP under argon atmosphere. The reaction was stirred at room temperature for 12 h and then the resulting mixture was then cautiously quenched at 0° C. with H$_2$O. The mixture was extracted with EtOAc. The resulting organic layer was washed with a saturated aqueous NaHCO$_3$ solution and brine, dried over MgSO$_4$, filtered, and solvents were removed under reduced pressure. Trituration of the crude residue from dichloromethane then filtration and washing with PE afforded desired compounds.

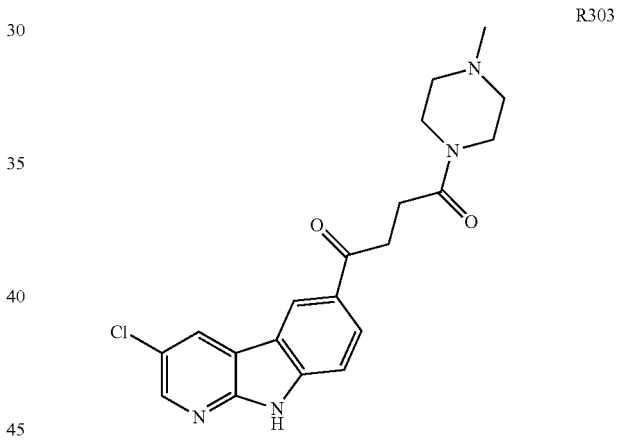

R303

1-(3-Chloro-9H-pyrido[2,3-b]indol-6-yl)-4-(4-methylpiperazin-1-yl)butane-1,4-dione (R303)

Yield=45%. mp 232.6° C.; IR (KBr): 3446, 3190, 3149, 2934, 2796, 1638, 1613, 1449, 1382, 1264, 1228, 1167, 527 cm$^{-1}$; $^1$H-NMR (300 MHz, DMSO-d$_6$): δ 12.40 (bs, 1H), 9.02 (s, 1H), 8.89 (d, 1H, J=2.2 Hz), 8.49 (d, 1H, J=2.4 Hz), 8.13 (dd, 1H, J=1.5, 8.7 Hz), 7.59 (d, 1H, J=8.6 Hz), 3.52 (t, 2H, J=4.5 Hz), 3.43 (t, 2H, J=4.2 Hz), 3.36 (m, 2H) 2.74 (t, 2H, J=5.9 Hz), 2.35 (t, 2H, J=3.9 Hz), 2.24 (t, 2H, J=4.9 Hz), 2.20 (s, 3H); $^{13}$C-NMR (75 MHz, DMSO-d$_6$): δ 197.8 (C), 169.7 (C), 150.8 (C), 144.8 (CH), 142.5 (C), 129.2 (C), 128.8 (CH), 127.2 (CH), 123.3 (CH), 122.6 (C), 119.3 (C), 116.9 (C), 111.4 (CH), 54.8 (CH$_2$), 54.3 (CH$_2$), 45.7 (CH$_3$), 44.6 (CH$_2$), 41.1 (CH$_2$), 32.9 (CH$_2$), 26.8 (CH$_2$); MS

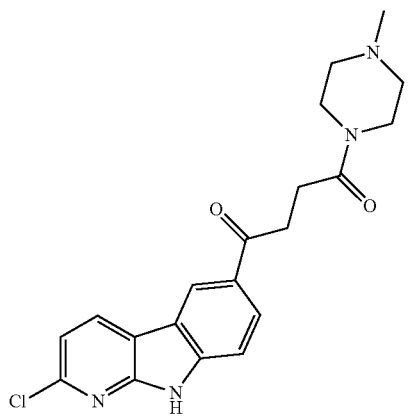

1-(2-Chloro-9H-pyrido[2,3-b]indol-6-yl)-4-(4-methylpiperazin-1-yl)butane-1,4-dione (R 302)

Yield=55%. mp 236.4° C.; ER (KBr): 3451, 3200, 3149, 2934, 2790, 1643, 1592, 1442, 1397, 1356, 1254, 1177, 1121, 993, 927, 794, 773 cm$^{-1}$; $^1$H-NMR (300 MHz, DMSO-d$_6$): δ12.43 (bs, 1H), 8.96 (s, 1H), 8.73 (d, 1H, J=7.2 Hz), 8.11 (d, 1H, J=7.2 Hz), 7.59 (d, 1H, J=8.3 Hz), 7.36 (d, 1H, J=6.9 Hz), 3.52 (s, 2H), 3.43 (s, 2H), 3.36 (m, 2H), 2.73 (t, 2H, J=5.9 Hz), 2.34 (s, 2H), 2.23 (s, 2H), 2.19 (s, 3H); $^{13}$C-NMR (75 MHz, DMSO-d$_6$): δ197.8 (C), 169.6 (C), 151.7 (C), 146.9 (C), 141.6 (C), 132.1 (CH), 129.4 (C), 126.6 (CH), 122.6 (CH), 119.6 (C), 115.4 (CH), 114.6 (C), 111.3 (CH), 54.7 (CH$_2$), 54.3 (CH$_2$), 45.6 (CH$_3$), 44.6 (CH$_2$), 41.0 (CH$_2$), 32.8 (CH$_2$), 26.7 (CH$_2$); MS

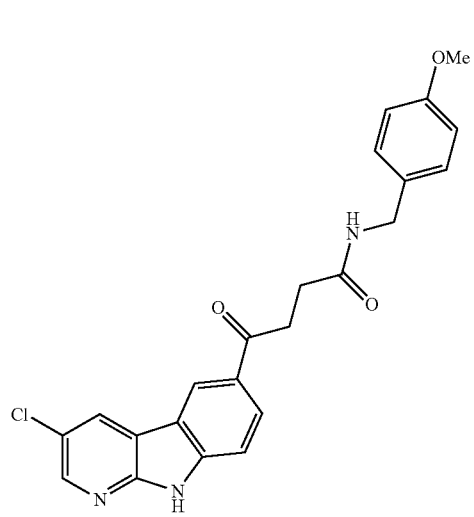

4-(3-Chloro-9H-pyrido[2,3-b]indol-6-yl)-N-(4-methoxybenzyl)-4-oxobutyramide (R304)

Yield=47%. mp 227.5° C.; IR (KBr): 3272, 3108, 2898, 1669, 1643, 1618, 1505, 1479, 1449, 1377, 1239, 1162, 1024, 814, 527 cm$^{-1}$; $^1$H-NMR (300 MHz, DMSO-d$_6$): δ 12.39 (bs, 1H), 9.02 (s, 1H), 8.88 (s, 1H), 8.49 (s, 1H), 8.37 (bs, 1H), 8.13 (d, 1H, J=7.5 Hz), 7.59 (d, 1H, J=8.3 Hz), 7.19 (d, 2H, J=7.7 Hz), 6.87 (d, 2H, J=7.9 Hz), 4.21 (s, 2H), 3.72 (s, 3H), 3.38 (s, 2H), 2.58 (s, 2H); $^{13}$C-NMR (75 MHz, DMSO-d$_6$): δ197.8 (C), 171.1 (C), 158.0 (C), 150.8 (C), 144.7 (CH), 142.5 (C), 132.5 (C), 128.9 (C), 128.7 (CH), 128.4 (CH), 127.1 (CH), 123.2 (CH), 122.5 (C), 119.3 (C), 116.8 (C), 113.5 (CH), 111.3 (CH), 54.9 (CH$_3$), 41.5 (CH$_2$), 33.2 (CH$_2$), 29.4 (CH$_2$); MS The following compounds can be prepared by the same method:

1-(4-Chloro-9H-pyrido[2,3-b]indol-6-yl)-4-(4-methylpiperazin-1-yl)butane-1,4-dione 4-(2-Chloro-9H-pyrido[2,3-b]indol-6-yl)-N-(4-methoxybenzyl)-4-oxobutyramide 4-(4-Chloro-9H-pyrido[2,3-b]indol-6-yl)-N-(4-methoxybenzyl)-4-oxobutyramide Synthesis of nitrovinyl- and ethylamino-substituted α-carbolines

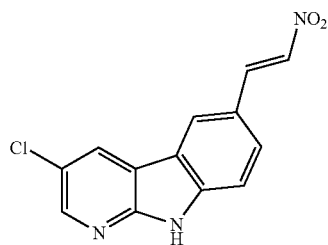

3-chloro-6-(2'-nitrovinyl)-9H-pyrido[2,3-b]indole (R266)

Solid ammonium acetate (509 mg, 6.6 mmol, 15 equiv.) was added to solution of R267 (100 mg, 0.44 mmol) in nitromethane (25 mL). The mixture was vigorously stirred and boiled at 120-130° C. for 48 h. Then the mixture was cooled in an ice bath and concentrated under reduced pressure. Trituration of the crude residue from methanol followed by filtration afforded R266 (69 mg, 57%). $^1$H-NMR (300 MHz, DMSO-d$_6$): δ 12.47 (bs, 1H), 8.76 (bs, 1H), 8.64 (d, 1H, J=2.1 Hz), 8.50 (d, 1H, J=2.5 Hz), 8.28 (d, 1H, J=13.5 Hz), 8.21 (d, 1H, J=13.5 Hz), 8.01 (bd, 1H, J=8.9 Hz), 7.58 (d, 1H, J=8.1 Hz); $^{13}$C-NMR (75 MHz, 80° C. DMSO-d$_6$): δ 150.5 (C), 144.6 (CH), 141.8 (C), 139.9 (CH), 135.3 (CH), 128.5 (CH), 127.9 (CH), 124.0 (CH), 122.3 (C), 121.6 (C), 119.9 (C), 115.9 (C), 111.9 (CH); MS (ESI) m/z 272 [M–H$^-$], HRMS (ESI): Calcd for C$_{13}$H$_8$ClN$_3$O$_2$: 274.0383. Found: 274.0386.

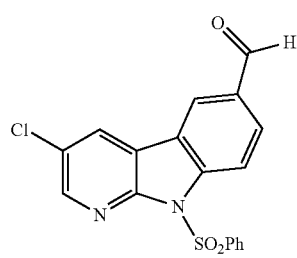

13

At 0° C., sodium hydride (60% in oil, 78 mg, 1.95 mmol 1.1 equiv.) was added to a stirred a solution of R266 (405 mg, 1.77 mmol) in anhydrous THF (12.4 mL). After stirring at 0° C. for 20 min, benzenesulfonyl chloride (273 μL, 2.13 mmol, 1.2 equiv.) was added dropwise. The reaction mixture was stirred for 12 h and then poured with 5% aqueous saturated NaHCO$_3$ solution and extracted with EtOAc (3×20 mL). The combined organic layers were dried (MgSO$_4$), and the solvent was removed under reduced pressure. The crude product was purified by flash chromatography (CH$_2$Cl$_2$/PE 8:2) to afford 13 in 80% yield as a white solid, $^1$H-NMR (300 MHz, CDCl$_3$): δ 10.11 (s, 1H), 8.59 (d, 1.14, J=8.9 Hz), 8.51 (d, 1H, J=2.3 Hz), 8.41 (d, 1H, J=1.4 Hz), 8.20 (d, 1H, J=2.3 Hz), 8.17-8.14 (m, 2H), 8.09 (dd, 1H, J=1.4, 8.9 Hz), 7.57 (tt, 1H, J=1.1, 7.3 Hz), 7.47 (d, 1H, J=7.9 Hz), 7.45 (td, 1H, J=1.5, 7.5 Hz); $^{13}$C-NMR (75 MHz, CDCl$_3$): δ 191.0 (C), 149.3 (C), 146.5 (CH), 141.9 (C), 138.2 (C), 134.7 (CH), 132.5 (C), 130.5 (CH), 129.3 (2 CH), 128.6 (CH), 128.1 (C), 127.9 (2 CH), 122.9 (CH), 122.2 (C), 119.0 (C), 115.4 (CH); MS (ESI) m/z 371 [M+H$^+$]

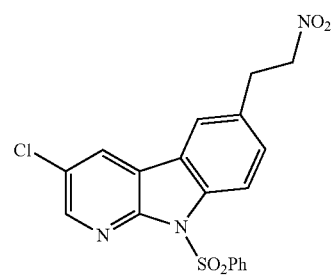

9-benzenesulfonyl-3-chloro-6-(2'-nitroethyl)-9H-pyrido[2,3-b]indole (15)

NaBH$_4$ (46 mg, 2.5 equiv.) was added in small portions to a suspension of 14 (200 mg, 0.48 mmol) and 240 mg of silica (40-60 mesh) in a solution of chloroform and isopropanol (11.6 mL, 8.6:3). The solution was stirred for 1 h 30 at room temperature and then filtered through celite. Solvents were removed under reduced pressure and the crude product was purified by flash chromatography (CH$_2$Cl$_2$/PE 7:3) to afford 15 in 73% yield as a white solid, $^1$H-NMR (300 MHz, CDCl$_3$): δ 8.49 (d, 1H, J=1.2 Hz), 8.41 (d, 1H, J=8.6 Hz), 8.14-8.10 (m, 3H), 7.74 (bs, 1H), 7.55 (t, 1H, J=7.5 Hz), 7.45-7.40 (m, 3H), 4.70 (t, 2H, J=7.1 Hz), 3.46 (t, 1H, J=7.1 Hz), $^{13}$C-NMR (75 MHz, CDCl$_3$): δ 162.4 (C), 149.0 (C), 145.8 (CH), 138.4 (C), 137.7 (C), 134.3 (CH), 131.9 (C), 129.9 (CH), 129.2 (2 CH), 128.2 (CH), 127.7 (2C), 122.3 (C), 121.0 (CH), 119.4 (C), 115.7 (CH), 76.4 (CH$_2$), 33.2 (CH$_2$), MS (ESI) m/z 416 [M+H$^+$]

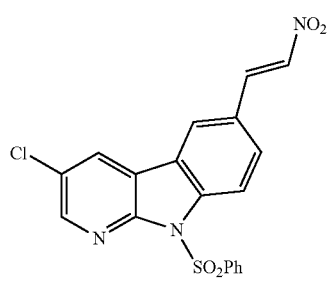

9-benzenesulfonyl-3-chloro-6-(2'-nitrovinyl)-9H-pyrido[2,3-b]indole (14)

Solid ammonium acetate (121 mg, 1.1 equiv. 1.56 mmol) was added to solution of 9-benzenesulfonyl-3-chloro-9H-pyrido[2,3-b]indole-6-carbaldehyde (524 mg, 1.42 mmol) in nitromethane (5.5 mL). The mixture was vigorously stirred and boiled at 100° C. for 2 h. Then the mixture was cooled in an ice bath and concentrated under reduced pressure. Trituration of the crude residue from ethanol followed by filtration afforded 14 (528 mg, 89.5%), $^1$H-NMR (300 MHz, CDCl$_3$): δ 8.81 (d, 1H, J=1.6 Hz), 8.70 (d, 1H, J=2.3 Hz), 8.65 (d, 1H, J=2.3 Hz), 8.42 (d, 1H, J=8.8 Hz), 8.25 (s, 2H), 8.17 (dd, 1H, J=1.6, 8.9 Hz), 8.09 (d, 1H, J=7.2 Hz), 8.09 (d, 1H, J=8.8 Hz), 7.71 (t, 1H, J=7.4 Hz), 7.60 (d, 1H, J=8.1 Hz), 7.58 (t, 1H, J=7.4 Hz); $^{13}$C-NMR (75 MHz, DMSO-d$_6$): δ 148.7 (C), 146.0 (CH), 139.4 (C), 138.7 (CH), 137.9 (CH), 137.3 (C), 135.2 (CH), 130.9 (CH), 129.8 (2 CH), 129.5 (CH), 127.3 (C), 127.1 (2 CH), 126.5 (C), 123.8 (CH), 122.2 (C), 118.9 (C), 115.0 (CH), MS (ESI) m/z 414 [M+H$^+$]

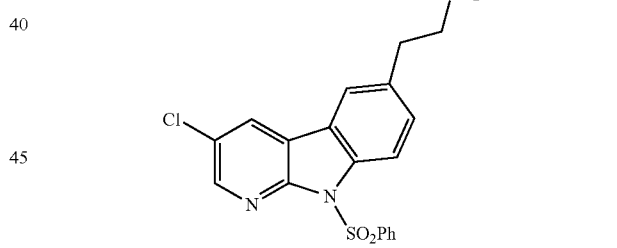

9-benzenesulfonyl-3-chloro-6-(2'-aminoethyl)-9H-pyrido[2,3-b]indole (16)

To a solution of 15 (72 mg, 0.17 mmol) in MeOH (1 mL) was added a catalytic amount of Ni Raney. This mixture was stirred overnight at 50° C. under nitrogen atmosphere. The solids were filtered off and the filtrate evaporated to give 16. $^1$H-NMR (300 MHz, DMSO-d$_6$): δ 8.78 (d, 1H, J=2.4 Hz), 8.60 (d, 1H, J=2.4 Hz), 8.30 (d, 1H, J=8.7 Hz), 8.14 (bs, 1H), 8.04 (d, 1H, J=8.7 Hz); 8.02 (d, 1H, J=7.2 Hz), 7.70 (t, 1H, J=7.2 Hz), 7.59-7.54 (m, 3H), 6.74 (bs, 2H); 3.05 (m, 2H), 2.96 (m, 2H); MS (ESI) m/z 386 [M-NH$_3^+$], 386 [M+H$^+$], 408 [M+Na$^+$].

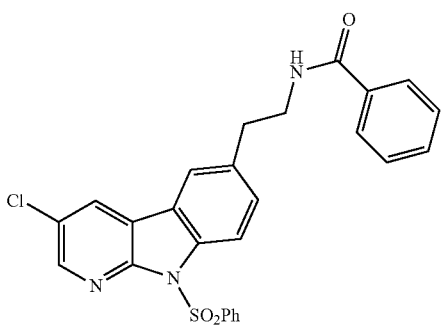

N-(2-(3-chloro-9-(benzenesulfonyl)-9H-pyrido[2,3-b]indol-6-yl)ethyl)benzamide (17)

To a cooled mixture (0° C.) of 16 (65 mg, 0.17 mmol) in CH$_2$Cl$_2$ (3 mL) were added Et$_3$N (100 μL, 4.2 equiv.) and benzoyl chloride (30 μL, 1.5 equiv.). The mixture was stirred for 12 h at room temperature. The resulting mixture was then quenched at 0° C. with NaHCO$_3$. It was extracted with the mixture of EtOAc. The resulting organic layer was washed with saturated aqueous NaHCO$_3$ solution and brine, dried over MgSO$_4$, filtered and solvents were removed under reduced pressure. The crude product was purified by flash chromatography (EtOAc/PE 1:1) to afford 17 in 48% yield as a white solid, $^1$H NMR (300 MHz, CDCl$_3$): δ 8.48 (d, 1H, J=2.3 Hz), 8.41 (d, 1H, J=8.5 Hz), 8.13-8.11 (m, 3H), 7.77 (bs, 1H), 7.70 (d, 1H, J=7.5 Hz), 7.57-7.41 (m, 7H), 6.19 (bs, 1H), 3.05 (q, 2H, J=6.9 Hz), 3.09 (t, 2H, J=6.9 Hz); MS (ESI) m/z 490 [M+H$^+$]

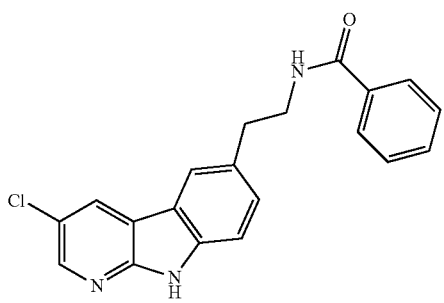

R265

N-(2-(3-chloro-9H-pyrido[2,3-b]indol-6-yl)ethyl)benzamide (R265)

At room temperature and under inert atmosphere, 1.0 M TBAF in THF (310 μL, 5 equiv.) was added a solution of 17 (30 mg, 0.061 mmol) in anhydrous THF (2.5 mL). The solution was refluxed for 2 h. The resulting mixture was then cautiously quenched at 0° C. with H$_2$O. The mixture was extracted with EtOAc (3×10 mL). The resulting organic layers were dried over MgSO$_4$, filtered, and solvents were removed under reduced pressure. The crude product was purified by flash chromatography (EtOAc) to afford R265 in 61% yield. $^1$H-NMR (300 MHz, DMSO-d$_6$): δ 11.91 (bs, 1H), 8.65 (d, 1H, J=2.3 Hz), 8.61 (bt, 1H, J=5.5 Hz), 8.39 (d, 1H, J=2.3 Hz), 8.07 (bs, 1H), 7.82 (d, 1H, J=7.5 Hz), 7.54-7.37 (m, 5H), 3.55 (q, 2H, J=7.7 Hz), 2.98 (t, 2H, J=7.7 Hz); MS (ESI) m/z 350.2 [M+H$^+$], 698.9 [2M+H$^+$], 721.0 [2M+Na$^+$], HRMS (ESI): Calcd for C$_{20}$H$_{16}$ClN$_3$O: 350.1060. Found: 350.10631.

The following compounds can be prepared by the same method

N-(2-(2-chloro-9H-pyrido[2,3-b]indol-6-yl)ethyl)benzamide

N-(2-(4-chloro-9H-pyrido[2,3-b]indol-6-yl)ethyl)benzamide

N-(2-(2-(4-methoxyphenyl)-9H-pyrido[2,3-b]indol-6-yl)ethyl)benzamide

N-(2-(3-(4-methoxyphenyl)-9H-pyrido[2,3-b]indol-6-yl)ethyl)benzamide

N-(2-(4-(4-methoxyphenyl)-9H-pyrido[2,3-b]indol-6-yl)ethyl)benzamide

N-(2-(2-(3-nitrophenyl)-9H-pyrido[2,3-b]indol-6-yl)ethyl)benzamide

N-(2-(3-(3-nitrophenyl)-9H-pyrido[2,3-b]indol-6-yl)ethyl)benzamide

N-(2-(4-(3-nitrophenyl)-9H-pyrido[2,3-b]indol-6-yl)ethyl)benzamide

N-(2-(2-(2-furyl)-9H-pyrido[2,3-b]indol-6-yl)ethyl)benzamide

N-(2-(3-(2-furyl)-9H-pyrido[2,3-b]indol-6-yl)ethyl)benzamide

N-(2-(4-(2-furyl)-9H-pyrido[2,3-b]indol-6-yl)ethyl)benzamide

N-(2-(2-(4-(morpholin-4-yl)methylphenyl)-9H-pyrido[2,3-b]indol-6-yl)ethyl)benzamide N-(2-(3-(4-(morpholin-4-yl)methylphenyl)-9H-pyrido[2,3-b]indol-6-yl)ethyl)benzamide N-(2-(4-(4-(morpholin-4-yl)methylphenyl)-9H-pyrido[2,3-b]indol-6-yl)ethyl)benzamide N-(2-(2-(5-morpholin-4-yl-pyridin-2-yl)-9H-pyrido[2,3-b]indol-6-yl)ethyl)benzamide N-(2-(3-(5-morpholin-4-yl-pyridin-2-yl)-9H-pyrido[2,3-b]indol-6-yl)ethyl)benzamide N-(2-(4-(5-morpholin-4-yl-pyridin-2-yl)-9H-pyrido[2,3-b]indol-6-yl)ethyl)benzamide N-(2-(2-(phenylphenyl)-9H-pyrido[2,3-b]indol-6-yl)ethyl)benzamide N-(2-(3-(phenylphenyl)-9H-pyrido[2,3-b]indol-6-yl)ethyl)benzamide N-(2-(4-(phenylphenyl)-9H-pyrido[2,3-b]indol-6-yl)ethyl)benzamide N-(2-(2-(2-phenylethenyl)-9H-pyrido[2,3-b]indol-6-yl)ethyl)benzamide N-(2-(3-(2-phenylethenyl)-9H-pyrido[2,3-b]indol-6-yl)ethyl)benzamide N-(2-(4-(2-phenylethenyl)-9H-pyrido[2,3-b]indol-6-yl)ethyl)benzamide N-(2-(2-(4-methoxyphenylethenyl)-9H-pyrido[2,3-b]indol-6-yl)ethyl)benzamide N-(2-(2-(3-(4-methoxyphenylethenyl)-9H-pyrido[2,3-b]indol-6-yl)ethyl)benzamide N-(2-(2-(4-(4-methoxyphenylethenyl)-9H-pyrido[2,3-b]indol-6-yl)ethyl)benzamide N-(2-(2-(2-(3-fluorophenylethenyl)-9H-pyrido[2,3-b]indol-6-yl)ethyl)benzamide N-(2-(2-(2-(3-fluorophenylethenyl)-9H-pyrido[2,3-b]indol-6-yl)ethyl)benzamide N-(2-(2-(2-(3-fluorophenylethenyl)-9H-pyrido[2,3-b]indol-6-yl)ethyl)benzamide N,N-(2-(3-nitrophenyl)-9H-pyrido[2,3-b]indol-6-yl)ethyl)benzamide-2-amine N,N-(2-(3-nitrophenyl)-9H-pyrido[2,3-b]indol-6-yl)ethyl)benzamide-3-amine N,N-(2-(3-nitrophenyl)-9H-pyrido[2,3-b]indol-6-yl)ethyl)benzamide-4-amine N,N-(2-(2-nitrophenyl)-9H-pyrido[2,3-b]indol-6-yl)ethyl)benzamide-2-amine N,N-(2-(2-nitrophenyl)-9H-pyrido[2,3-b]indol-6-yl)ethyl)benzamide-3-amine N,N-(2-(2-nitrophenyl)-9H-pyrido[2,3-b]indol-6-yl)ethyl)benzamide-4-amine N,N-(2-(3-methoxyphenyl)-9H-pyrido[2,3-b]indol-6-yl)ethyl)benzamide-2-amine N,N-(2-(3-methoxyphenyl)-9H-pyrido[2,3-b]indol-6-yl)ethyl)benzamide-3-amine N,N-(2-(3-methoxyphenyl)-9H-pyrido[2,3-b]indol-6-yl)ethyl)benzamide-4-amine N,N-(2-(phenyl)-9H-pyrido[2,3-b]indol-6-yl)ethyl)benzamide-2-amine N,N-(2-(phenyl)-9H-pyrido[2,3-b]indol-6-yl)ethyl)benzamide-3-amine N,N-(2-(phenyl)-9H-pyrido[2,3-b]indol-6-yl)ethyl)benzamide-4-amine General Procedure for the Benzenesulfonyl Protection Sodium hydride (60% in oil; 1.1 equiv.) was added to a stirred 0.15 M suspension of 8a-c (1 equiv.) in anhydrous THF at 0° C. After stirring at 0° C. for 20 min, benzenesulfonyl chloride (1.2 equiv.) was added dropwise. The reaction mixture was stirred for 12 h and then poured with 5% aqueous saturated NaHCO$_3$ solution and extracted with EtOAc (3×20 mL). The combined organic layers were dried (MgSO$_4$), and the solvent was removed under reduced pressure.

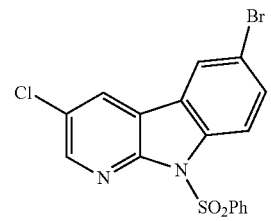

9-benzenesulfonyl-6-bromo-3-chloro-9H-pyrido[2,3-b]indole (20)

The crude product was purified by flash chromatography (CH$_2$Cl$_2$/PE 1:1) to afford 20 in 91% yield as a white solid; mp 242° C. (MeOH); IR: 3061, 1584, 1569, 1447, 1384, 1356, 1184, 1091, 970, 847, 815, 724 cm$^{-1}$; $^1$H-NMR (300 MHz, CDCl$_3$): δ 8.35 (d, 1H, J=8.9 Hz), 8.20 (s, 1H), 8.18 (s, 1H), 8.05 (d, 1H, J=8.1 Hz), 7.99 (d, 1H, J=1.5 Hz), 7.65 (dd, 1H, J=1.7, 8.9 Hz), 7.58 (t, 1H, J=7.4 Hz), 7.49-7.44 (m, 2H), 7.28 (d, 1H, J=8.1 Hz); $^{13}$C-NMR (75 MHz, CDCl$_3$): 149.2 (C), 138.1 (C), 136.4 (C), 134.5 (CH), 131.4 (CH), 130.7 (CH), 129.2 (2 CH), 128.2 (2 CH), 123.8 (C), 123.6 (CH), 119.8 (CH), 117.5 (CH), 116.6 (C); 115.9 (C); MS (ESI) 421.0 [M+H$^+$], 443.1 [M+Na$^+$]; HRMS (ESI): Calcd for C$_{17}$H$_{10}$BrClN$_2$O$_2$S: [M+Na$^+$]=442.9233. Found: [M+Na]$^+$=442.9229.

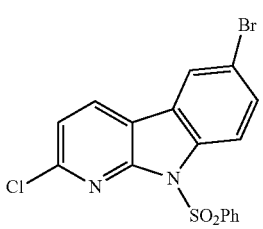

9-benzenesulfonyl-6-bromo-2-chloro-9H-pyrido[2,3-b]indole (19)

The crude product was purified by flash chromatography (CH$_2$Cl$_2$) to afford 19 in 88% yield as a solid. Mp 204-206° C. (CH$_2$Cl$_2$/PE 3:7); IR: 3060, 1614, 1573, 1448, 1380, 1371, 1187, 1173, 1128, 1088, 813, 727, 682 cm$^{-1}$; $^1$H-NMR (300 MHz, CDCl$_3$): δ 8.37 (d, 1H, J=8.9 Hz), 8.20 (d, 1H, J=7.2 Hz), 8.19 (d, 1H, J=8.7 Hz), 8.08 (d, 1H, J=8.1 Hz), 8.02 (d, 1H, J=1.8 Hz), 7.68 (dd, 1H, J=1.8, 8.9 Hz), 7.58-7.56 (m, 1H), 7.50-7.45 (m, 2H), 7.31 (d, 1H, J=8.1 Hz); $^{13}$C-NMR (75 MHz, CDCl$_3$): δ 149.2 (C), 138.1 (C), 136.5 (C), 134.5 (CH), 131.4 (CH), 130.7 (CH), 129.1 (2 CH), 128.2 (2 CH), 123.8 (C), 123.6 (CH), 119.8 (CH), 117.5 (CH), 116.6 (C); 115.9 (C); MS (ESI) m/z 421 [M+H$^+$, $^{79}$Br], 422.9 [M+H$^+$, $^{81}$Br]; HRMS (ESI): Calcd for C$_{17}$H$_{10}$BrClN$_2$O$_2$S: [M+Na$^+$]=442.9233. Found [M+Na]$^+$=442.9229.

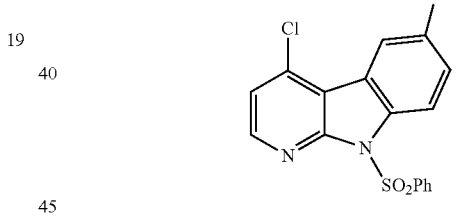

9-benzenesulfonyl-6-bromo-4-chloro-9H-pyrido[2,3-b]indole (21)

The crude product was purified by flash chromatography (CH$_2$Cl$_2$/PE 1:1) to afford 21 in 85% yield as a white solid; mp 212-214° C. (CH$_2$Cl$_2$/PE 1:1); IR (KBr): 3122, 3059, 1607, 1579, 1558, 1432, 1384, 1349, 1193, 1183, 995, 806, 722 cm$^{-1}$; $^1$H NMR (300 MHz, CDCl$_3$): δ 8.50 (d, 1H, J=2.1 Hz), 8.45 (d, 1H, J=5.3 Hz), 8.40 (d, 1H, J=8.9 Hz), 8.14-8.11 (m, 2H), 7.71 (dd, 1H, J=2.1 Hz, J=8.9 Hz), 7.55 (tt, 1H, J=1.3, 7.3 Hz), 7.45-7.40 (m, 2H), 7.29 (d, 1H, J=5.3 Hz); $^{13}$C-NMR (75 MHz, CDCl$_3$): δ 151.6 (C), 147.5 (CH), 138.8 (C), 138.3 (C), 136.4 (C), 134.5 (CH), 131.9 (CH), 129.2 (2 CH), 127.8 (2 CH), 125.9 (CH), 123.4 (C), 120.5 (CH), 117.4 (C), 116.4 (CH); 115.6 (C); MS (ESI) m/z 422.9 [M+H$^+$], 449.2 [M+Na$^+$]; HRMS (ESI): Calcd for C$_{17}$H$_{10}$BrClN$_2$O$_2$S: [M+Na$^+$]=442.9233. Found: [M+Na$^+$]=442.9233.

9-benzenesulfonyl-6-bromo-9H-pyrido[2,3-b]indole (22)

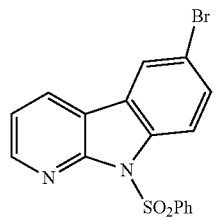

The crude product was purified by flash chromatography (CH$_2$Cl$_2$) to afford 22 in 72% yield as a white solid; $^1$H-NMR (300 MHz, CDCl$_3$): δ 8.59 (dd, 1H, J=1.5, 4.9 Hz), 8.38 (d, 1H, J=9.0 Hz), 8.16 (dd, 1H, J=1.5, 7.9 Hz), 8.13 (d, 3H, J=7.9 Hz), 8.06 (d, 1H, J=2.1 Hz), 7.67 (dd, 1H, J=2.1, 9.0. Hz), 7.53 (t, 1H, J=7.4 Hz), 7.44-7.39 (m, 2H), 7.31 (dd, 1H, J=4.9, 7.9 Hz); MS (ESI) m/z 388 [M+H$^+$];

General Procedure for the Protection by EOM

60% sodium hydride (3 equiv.) was added to a stirred 0.4M suspension of chloro-α-carboline (1 equiv.) in anhydrous DMF at 0° C. After stirring at 0° C. for 20 min, EOM-Cl (2.5 equiv.) was added dropwise. The reaction mixture was stirred for 12 hours and then poured with 5% aqueous saturated NaHCO$_3$ solution and extracted with EtOAc (3×20 mL). The combined organic layers were dried (MgSO$_4$), and the solvent was removed under reduced pressure.

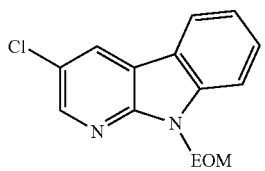

9-(ethoxymethyl)-3-chloro-9H-pyrido[2,3-b]indole (23)

The product was purified by column chromatography on silica gel (CH$_2$Cl$_2$) to afford 23 in 89% yield as a yellow solid; $^1$H NMR (300 MHz, CDCl$_3$): δ 8.42 (d, 1H, J=2.3 Hz); 8.28 (d, 1H, J=2.3 Hz); 8.03 (d, 1H, J=7.7 Hz); 7.62 (d, 1H, J=8.3 Hz); 7.56 (ddd, 1H, J=1.1, 7.1 Hz); 7.34 (ddd, 1H, J=1.1, 8.1 Hz), 5.90 (s, 2H); 3.54 (q, 2H, J=6.9 Hz); 1.15 (t, 3H, J=6.9 Hz).

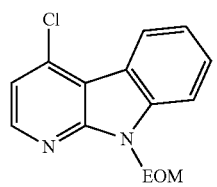

9-(ethoxymethyl)-4-chloro-9H-pyrido[2,3-b]indole (24)

The product was purified by column chromatography on silica gel (CH$_2$Cl$_2$/EP 9/1) to afford 24 in 55% yield as a white solid; $^1$H NMR (300 MHz, CDCl$_3$): δ 8.47 (d, 1H, J=7.9 Hz); 8.34 (d, 1H, J=5.3 Hz); 7.67 (d, 1H, J=8.3 Hz); 7.57 (td, 1H, J=1.3, 7.3 Hz); 7.37 (td, 1H, J=1.1, 8.1 Hz); 7.19 (d, 1H, J=5.3 Hz), 5.92 (s, 2H); 3.54 (q, 2H, J=6.9 Hz); 1.15 (t, 3H, J=6.9 Hz); $^{13}$C-NMR (75 MHz, CDCl$_3$): δ 152.8 (C), 146.0 (C), 139.5 (C), 138.2 (C), 127.7 (CH), 123.4 (CH), 121.3 (CH), 120.0 (C), 116.9 (CH), 114.2 (CH), 110.4 (CH), 71.3 (CH$_2$), 64.5 (CH$_2$), 15.1 (CH$_3$);

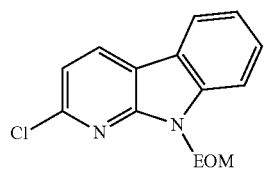

9-(ethoxymethyl)-2-chloro-9H-pyrido[2,3-b]indole (25)

The product was purified by column chromatography on silica gel (CH$_2$Cl$_2$/EP 1/1) to afford 25 in 99% yield as a white solid; $^1$H NMR (300 MHz, CDCl$_3$): δ 8.17 (d, 1H, J=7.9 Hz); 7.99 (d, 1H, J=7.7 Hz); 7.64 (d, 1H, J=8.3 Hz); 7.53 (td, 1H, J=1.0, 7.3 Hz); 7.33 (td, 1H, J=1.0, 7.7 Hz); 7.18 (d, 1H, J=7.9 Hz), 5.92 (s, 2H); 3.54 (q, 2H, J=6.9 Hz); 1.15 (t, 3H, J=6.9 Hz); $^{13}$C-NMR (75 MHz, CDCl$_3$): δ 151.2 (C), 147.6 (C), 139.4 (C), 130.4 (CH) 127.2 (CH), 121.3 (CH), 120.8 (CH), 120.4 (C), 115.8 (CH), 114.6 (C), 110.8 (CH), 71.1 (CH$_2$), 64.4 (CH$_2$), 15.0 (CH$_3$);

Typical Procedure for Suzuki Coupling at C-6

At room temperature and under inert atmosphere, Pd(PPh$_3$)$_4$ (0.08 equiv.), boronic acid (1.1 equiv.), and a 0.3M solution of K$_2$CO$_3$ (3 equiv.) in H$_2$O was added to a 0.1M suspension of 9a-c in anhydrous 1,4-dioxane or THF. This solution was stirred at 100° C. or 70° C. respectively for 12 h. After cooling to room temperature, the solution was filtered through celite and solvents were removed under reduced pressure.

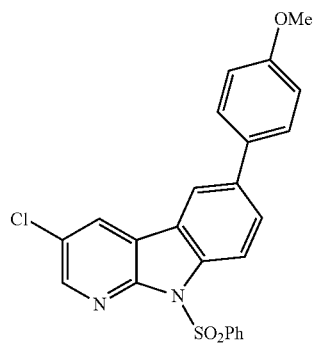

9-benzenesulfonyl-3-chloro-6-(4-methoxyphenyl)-9H-pyrido[2,3-b]indole (26)

The crude product was purified by flash chromatography (CH$_2$Cl$_2$/PE 7:3) to afford 26 in 75% yield as a yellow solid; mp>220° C. (CH$_2$Cl$_2$/PE 6:4); IR: 3016, 1607, 1683, 1520, 1473, 1361, 1216, 1182, 1091, 978, 822, 725 cm$^{-1}$; $^1$H-NMR (300 MHz, CDCl$_3$): δ 8.50 (d, 1H, J=8.9 Hz), 8.50 (d, 1H, J=2.3 Hz), 8.19 (d, 1H, J=2.3 Hz), 8.15-8.12 (m, 2H), 8.02 (d, 1H, J=1.5 Hz), 7.78 (dd, 1H, J=1.5, 8.9 Hz), 7.60-7.51 (m, 3H), 7.45-7.40 (m, 2H), 7.02 (dt, 1H, J=2.8, 8.9 Hz), 7.01 (d, 1H, J=8.9 Hz), 3.87 (s, 3H); $^{13}$C-NMR (75 MHz, CDCl$_3$): δ 159.5 (C), 159.0 (C), 150.7 (C), 149.2 (C), 145.7 (CH), 138.6 (C), 137.5 (C), 134.3 (CH), 132.9 (C) 129.2 (2 CH), 128.4 (2 CH), 128.3 (CH), 128.1 (CH), 127.6 (2 CH), 122.4 (C), 120.1 (C), 118.8 (CH), 115.5 (CH), 114.6 (2 CH), 54.5 (CH$_3$); MS (ESI) m/z 449.0 [M+H$^+$], 471.0 [M+Na$^+$], 918.8 [2M+Na$^+$]; HRMS (ESI): Calcd for C$_{24}$H$_{17}$ClN$_2$O$_3$S: [M+Na$^+$]= 471.0546. Found: [M+Na$^+$]=471.0546.

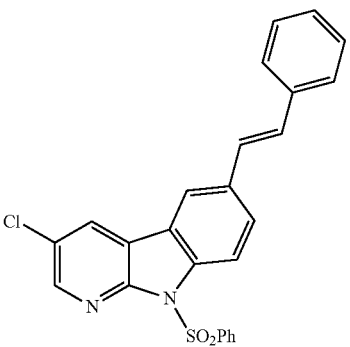

9-benzenesulfonyl-3-chloro-6-(2'-phenylethenyl)-9H-pyrido[2,3-b]indole (27)

The crude product was purified by flash chromatography (CH$_2$Cl$_2$/PE 6:4) to afford 11b in 71% yield as a yellow solid; mp 190-192° C. (MeOH); IR (KBr): 3025, 1568, 1474, 1433, 1366, 1176, 1090, 972, 727, 683 cm$^{-1}$; $^1$H-NMR (300 MHz, CDCl$_3$): δ 8.50 (d, 1H, J=2.4 Hz), 8.45 (d, 1H, J=8.9 Hz), 8.18 (d, 1H, J=2.4 Hz), 8.14-8.11 (m, 2H), 8.00 (d, 1H, J=1.7 Hz), 7.76 (dd, 1H, J=1.7, 8.9 Hz), 7.57-7.52 (m, 3H), 7.45-7.36 (m, 4H), 7.29 (tt, 1H, J=1.2, 7.4 Hz), 7.23 (d, 1H, J=16.4 Hz), 7.16 (d, 1H, J=16.4 Hz); $^{13}$C NMR (75 MHz, CDCl$_3$): δ 145.7 (CH), 138.5 (C), 137.8 (C), 137.1 (C), 134.3 (CH), 133.9 (C), 129.3 (CH), 129.2 (2 CH), 128.9 (2 CH), 128.4 (CH), 128.0 (CH), 127.8 (CH), 127.7 (CH), 127.6 (C) 127.6 (2 CH), 126.7 (2 CH), 122.4 (C), 119.9 (C), 118.6 (CH), 115.5 (CH); MS (ESI) m/z 445.0 [M+H$^+$], 466.9 [M+Na$^+$], 910.9 [2M+Na$^+$]; HRMS (ESI): Calcd for C$_{25}$H$_{17}$ClN$_2$O$_2$S: [M+Na$^+$]= 467.0597. Found: [M+Na$^+$]=467.0598.

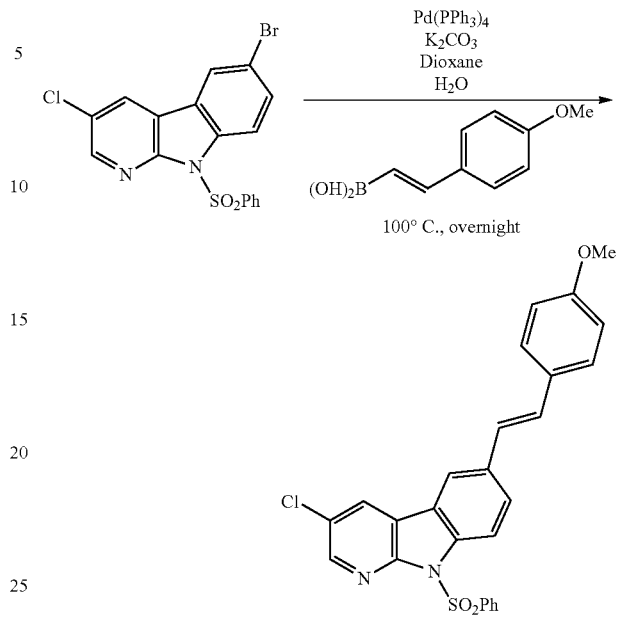

(E)-9-benzenesulfonyl-3-chloro-6-(2'-(4-methoxyphenyl)ethenyl)-9H-pyrido[2,3-b]indole (28)

To a solution of 9-benzenesulfonyl-6-bromo-3-chloro-9H-pyrido[2,3-b]indole (250 mg, 0.59 mmol, 1 equiv.) in anhydrous dioxane (25 ml) under Argon, Pd(PPh$_3$)$_4$ (102 mg, 0.09 mmol, 0.15 equiv.), K$_2$CO$_3$ (244 mg, 1.77 mmol, 3 equiv.), (E)-2'-(4-methoxyphenyl)ethenylboronic acid (110 mg, 0.77 mmol, 1.3 equiv.) and H$_2$O (5 ml) are added respectively. The mixture is stirred at 100° C. overnight and then filtered over celite which is washed with AcOEt (20 ml) and THF (10 ml). The filtrate is concentrated under reduced pressure and the crude residue is purified over silica gel column (eluant CH$_2$Cl$_2$/PE 7:3). The product is obtained as a white solid (212 mg, 0.40 mmol) in 68% yield.

$^1$H-NMR (300 MHz CDCl$_3$) δ 8.50 (d, 1H, J=2.5 Hz), 8.43 (d, 1, J=8.9 Hz), 8.18 (d, 1H, J=2.3 Hz), 8.13 (d, 1H, J=7.2 Hz), 8.12 (d, 1H, J=8.7 Hz), 7.97 (d, 1H, J=1.7 Hz), 7.74 (dd, 1H, J=1.7, 8.9 Hz), 7.57-7.40 (m, 5H), 7.11 (d, 2H, J=6.8 Hz), 6.93 (d, 2H, J=8.6 Hz), 3.85 (s, 3H).

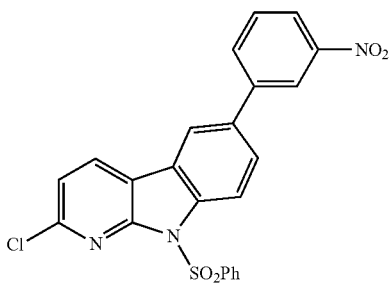

9-benzenesulfonyl-2-chloro-6-(3-nitrophenyl)-9H-pyrido[2,3-b]indole (29)

The crude product was purified by flash chromatography (CH$_2$Cl$_2$/PE 1:1) to afford 29 in 61% yield as a white solid; $^1$H-NMR (300 MHz, CDCl$_3$): 8.61 (d, 1H, J=8.9 Hz), 8.53 (t, 1H, J=2.1 Hz), 8.26-8.24 (m, 3H), 8.21 (d, 1H, J=8.1 Hz), 8.14 (d, 1H, J=1.3 Hz), 8.01-7.97 (m, 1H), 7.84 (d, 1H, J=1.9, 8.9 Hz), 7.67 (t, 1H, J=8.1 Hz), 7.58 (dd, 1H, J=2.4, 9.8 Hz), 7.50 (d, 1H, J=7.9 Hz), 7.35 (d, 1H, J=8.1 Hz); $^{13}$C-NMR (75 MHz, CDCl$_3$): δ 149.9 (C), 149.0 (C), 148.9 (CH), 142.3 (C), 138.3 (C), 137.7 (C), 134.9 (C), 134.5 (CH), 133.3 (CH), 130.7 (CH), 130.1 (CH), 129.1 (2 CH), 128.2 (2 CH), 127.7 (CH), 122.9 (C), 122.3 (CH), 122.2 (Cu), 119.8 (CH), 119.4 (CH), 116.8 (C), 115.7 (CH). MS (ESI) m/z 464.0 [M+H$^+$], 485.9 [M+Na$^+$], 948.3 [2M+Na$^+$]; HRMS (EI): Calcd for C$_{23}$H$_{14}$ClN$_3$O$_4$S: [M$^+$]=463.0394. Found: [M$^+$]=463.0394.

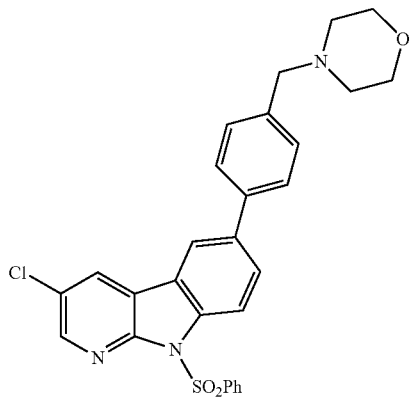

9-benzenesulfonyl-3-chloro-6-(4-(morpholin-4-yl) methylphenyl)-9H-pyrido[2,3-b]indole (30)

The crude product was purified by flash chromatography (CH$_2$Cl$_2$/EtOAc 8:2) to afford 30 in 78% yield as a white solid; $^1$H-NMR (300 MHz, CDCl$_3$): δ 8.53 (d, 1H, J=8.9 Hz), 8.51 (d, 1H, J=2.3 Hz), 8.20 (d, 1H, J=2.3 Hz), 8.15 (d, 1H, J=7.2 Hz), 8.07 (d, 1H, J=1.7 Hz), 7.82 (dd, 1H, J=1.7, 8.9 Hz), 7.61 (d, 2H, J=7.5 Hz), 7.55 (tt, 1H, J=1.3, 8.3 Hz), 7.46-7.41 (m, 4H), 3.76 (bs, 4H), 3.59 (bs, 2H), 2.52 (bs, 4H); $^{13}$C-NMR (75 MHz, CDCl$_3$): δ 149.2 (C), 145.7 (CH), 139.3 (C), 138.5 (C), 137.7 (CH), 137.4 (C), 137.3 (C), 134.2 (CH), 129.9 (2 CH), 129.1 (2 CH), 128.4 (CH), 128.1 (CH), 127.7 (CH), 127.6 (C), 127.2 (2 CH), 122.4 (C), 119.9 (C), 119.2 (CH), 115.5 (CH), 67.1 (2 CH$_2$), 63.1 (CH$_2$), 53.7 (2 CH$_2$); MS (ESI) m/z 518 [M+H$^+$];

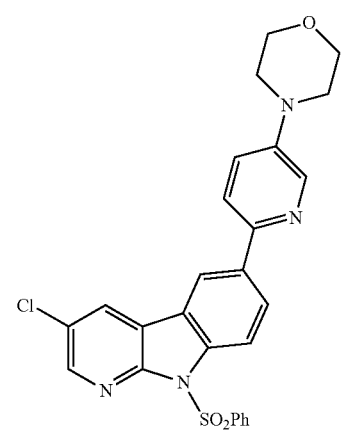

9-benzenesulfonyl-3-Chloro-6-(5-morpholin-4-yl-pyridin-2-yl)-9H-pyrido[2,3-b]indole (31)

The crude product was purified by flash chromatography (CH$_2$Cl$_2$) to afford 31 in 42% yield as a white solid; $^1$H-NMR (300 MHz, CDCl$_3$): δ 8.54-8.51 (m, 3H), 8.20 (d, 1H, J=2.3 Hz), 8.15-8.12 (m, 2H), 8.00 (d, 1H, J=1.7 Hz), 7.84-7.81 (m, 1H), 7.74 (dd, 1H, J=1.9, 8.7 Hz), 7.54 (d, 1H, J=7.5 Hz), 7.46-7.41 (m, 2H), 6.78 (d, 1H, J=9.2 Hz), 3.88-3.85 (m, 4H), 3.63-3.61 (m, 4H); $^{13}$C-NMR (75 MHz, CDCl$_3$): δ 158.7 (C), 149.7 (C), 149.3 (C), 146.0 (CH), 145.8 (CH), 138.5 (C), 137.5 (C), 136.6 (CH), 164.7 (C), 134.3 (CH), 129.2 (2 CH), 128.1 (2 CH), 127.7 (CH), 127.6 (3 CH), 126.0 (C), 122.6 (C), 119.8 (C), 118.3 (CH), 115.7 (CH), 10'7.1 (CH), 66.8 (2 CH$_2$), 45.7 (2 CH$_2$); MS (ESI) m/z 505.1 [M+H$^+$]; HRMS (EI): Calcd for C$_{26}$H$_{21}$ClN$_4$O$_3$S: 505.1101. Found: 505.1098.

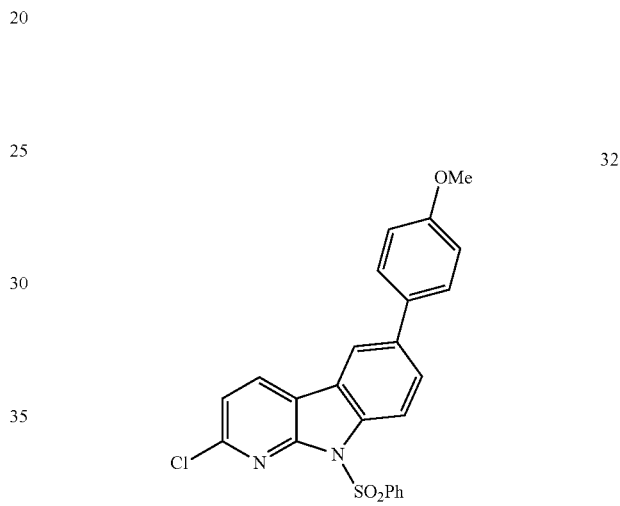

9-benzenesulfonyl-2-chloro-6-(4-methoxyphenyl)-9H-pyrido[2,3-b]indole (32)

The crude product was purified by flash chromatography (CH$_2$Cl$_2$/PE 3:7) to afford 32 in 58% yield as a white solid; mp 176-178° C. (CH$_2$Cl$_2$/PE 3:7); IR: 2932, 1606, 1587, 1567, 1519, 1465, 1450, 1369, 1172, 1039, 813, 732, 683 cm$^{-1}$; $^1$H-NMR (300 MHz, CDCl$_3$): δ 8.48 (d, J=8.6 Hz), 8.22 (d, 1H, J=7.5 Hz), 8.22 (d, 1H, J=8.9 Hz) 8.12 (d, 1H, J=8.1 Hz), 8.01 (d, 1H, J=1.5 Hz), 7.74 (dd, 1H, J=1.9, 8.9 Hz), 7.57 (d, 2H, 8.7 Hz), 7.56 (td, 1H, J=1.1, 8.1 Hz), 7.48-7.43 (m, 2H), 7.28 (d, 1H, J=8.1 Hz), 6.98 (d, 2H, J=8.7 Hz), 3.83 (s, 3H); $^{13}$C-NMR (75 MHz, CDCl$_3$): δ 162.4 (C), 159.4 (C), 148.4 (C), 138.4 (C), 137.3 (C), 136.7 (C), 134.3 (CH), 133.0 (C), 130.5 (CH), 129.1 (2 CH), 128.4 (2 CH), 128.1 (2 CH), 127.6 (CH), 122.7 (C), 119.5 (C), 118.5 (CH), 117.3 (C), 115.3 (CH), 114.5 (2 CH), 55.5 (CH$_3$); MS (ESI) m/z 448.9 [M+H$^+$], 471 HRMS (ESI): Calcd for C$_{24}$H$_{17}$ClN$_2$O$_3$S: [M+Na$^+$]=471.0546. Found: [M+Na$^+$]=471.0543.

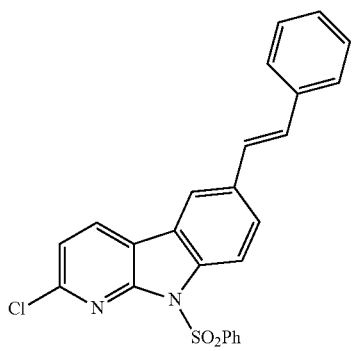

9-benzenesulfonyl-2-chloro-6-(2% phenylethenyl)-9H-pyrido[2,3-b]indole (33)

The crude product was purified by flash chromatography (CH$_2$Cl$_2$/PE 3:7) to afford 33 in 64% yield as a white solid; nip 180-182° C. (CH$_2$Cl$_2$/PE 3:7); IR: 3022, 1587, 1571, 1470, 1447, 1380, 1172, 980, 807, 753, 728, 682 cm$^{-1}$; $^1$H-NMR (300 MHz, CDCl$_3$): δ 8.46 (d, 1H, J=8.9 Hz), 8.22 (d, 1H, J=7.5 Hz), 8.22 (d, 1H, J=9.0 Hz), 8.11 (d, 1H, J=8.1 Hz), 8.00 (d, 1H, J=1.8 Hz), 7.75 (dd, 1H, J=1.8, 9.0 Hz), 7.57-7.54 (m, 3H), 7.47 (t, 2H, J=7.9 Hz), 7.39 (t, 2H, J=7.1 Hz), 7.31 (d, 1H, J=8.1 Hz), 7.31 (td, 1H, J=1.1, 7.2 Hz), 7.23 (d, 1H, J=16.3 Hz), 7.17 (d, 1H, J=16.3 Hz); $^{13}$C-NMR (75 MHz, CDCl$_3$): δ 162.4 (C), 148.5 (C), 138.4 (C), 137.2 (C), 137.1 (C); 134.3 (CH), 133.8 (C), 130.5 (CH), 129.2 (CH), 129.1 (2 CH); 128.9 (2 CH), 128.2 (2 CH), 127.9 (CH), 127.8 (CH), 127.1 (CH), 126.6 (2 CH), 122.6 (C), 119.6 (CH), 118.4 (CH), 117.1 (C), 115.3 (CH); MS (ESI) m/z 445.0 [M+H$^+$], 467.0 [M+Na$^+$], 910.6 [2M+Na$^+$]; HRMS (ESI): Calcd for C$_{25}$H$_{17}$ClN$_2$O$_2$S: [M+Na$^+$]=467.0597. Found: [M+Na$^+$]=467.0597.

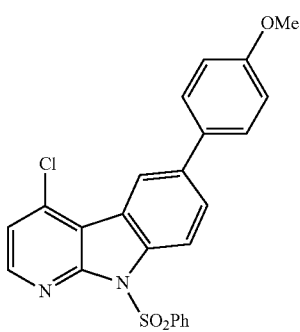

9-benzenesulfonyl-4-chloro-6-(4-methoxyphenyl)-9H-pyrido[2,3-b]indole (34)

The crude product was purified by flash chromatography (CH$_2$Cl$_2$/PE 1:1) to afford 34 in 70% yield as a white solid; mp 209-211° C. (CH$_2$Cl$_2$/PE); IR: 3022, 2835, 1607, 1583, 1521, 1467, 1441, 1375, 1234, 1172, 1020, 834, 770, 690 cm$^{-1}$; $^1$H-NMR (300 MHz, CDCl$_3$): δ 8.56 (d, 1H, J=9.0 Hz), 8.55 (d, 1H, J=7.4 Hz), 8.43 (d, 1H, J=5.5 Hz), 8.18-8.15 (m, 2H), 7.80 (dd, 1H, J=2.1, 8.7 Hz), 7.61 (d, 2H, J=8.7 Hz), 7.54 (tt, 1H, J=1.3, 7.4 Hz), 7.45-7.40 (m, 2H), 7.29 (d, 1H, J=5.5 Hz), 7.03 (d, 2H, J=8.7 Hz), 3.87 (s, 3H); $^{13}$C-NMR (75 MHz, CDCl$_3$): δ 159.4 (C), 151.9 (C), 146.8 (CH), 138.6 (C), 138.5 (C), 137.3 (C), 136.7 (C), 134.3 (CH), 133.2 (C), 129.1 (2 CH), 128.5 (2 CH), 128.0 (CH), 127.8 (2 CH), 122.5 (C), 121.2 (CH), 120.4 (CH), 116.8 (C), 115.0 (CH), 114.5 (2 CH); 55.5 (CH$_3$); MS (ESI) m/z 449.0 [M+H$^+$], 471.0 [M+Na$^+$], 918.8 [2M+Na$^+$]; FIRMS (ESI): Calcd for C$_{24}$H$_{17}$ClN$_2$O$_3$S: [M+Na$^+$] 471.0546. Found: [M+Na$^+$]= 471.0545.

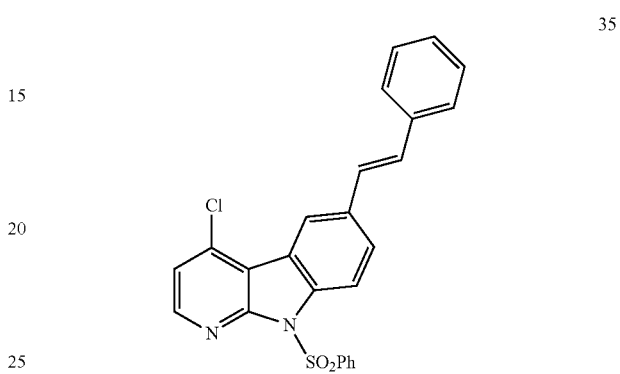

9-benzenesulfonyl-4-chloro-6-(2'-phenylethenyl)-9H-pyrido[2,3-b]indole (35)

The crude product was purified by flash chromatography (CH$_2$Cl$_2$/PE 6:4) to afford 35 in 68% yield as a white solid; mp 216-218° C. (CH$_2$Cl$_2$/PE); IR: 3063, 2924, 1614, 1583, 1562, 1442, 1371, 1170, 1006, 995, 814, 684 cm$^{-1}$; $^1$H-NMR (300 MHz, CDCl$_3$): δ 8.51 (d, 1H, J=8.6 Hz), 8.51 (d, 1H, J=1.5 Hz), 8.43 (d, 1H, J=5.5 Hz), 8.15 (d, 2H, J=8.6 Hz), 7.81 (dd, 1H, J=1.5, 8.6 Hz), 7.58-7.52 (m, 3H), 7.45-7.36 (m, 4H), 7.31-7.28 (m, 1H), 7.30 (d, 1H, J=5.5 Hz), 7.27 (d, 1H, J=16.4 Hz), 7.18 (d, 1H, J=16.4 Hz); $^{13}$C-NMR (75 MHz, CDCl$_3$): δ 162.4 (C), 149.8 (C), 146.9 (CH), 138.5 (C), 137.2 (C), 137.1 (C), 134.3 (CH), 133.8 (C), 129.2 (CH), 129.1 (2 CH), 128.9 (2 CH), 128.1 (CH), 127.9 (CH), 127.8 (2 CH), 127.3 (CH), 126.7 (2 CH), 122.4 (C), 121.2 (CH), 120.4 (CH), 116.7 (C), 115.0 (CH); MS (ESI) m/z 445.0 [M+H$^+$], 466.9 [M+Na$^+$], 910.8 [2M+Na$^+$]; HRMS (ESI): Calcd for C$_{25}$H$_{17}$ClN$_2$O$_2$S: [M+Na$^+$]=467.0597. Found: [M+Na$^+$]= 467.0598.

The following compounds can be prepared by the same method:
9-benzenesulfonyl-2-chloro-6-(4-(morpholin-4-yl)methylphenyl)-9H-pyrido[2,3-b]indole
9-benzenesulfonyl-4-chloro-6-(4-(morpholin-4-yl)methylphenyl)-9H-pyrido[2,3-b]indole
9-benzenesulfonyl-2-chloro-6-(5-morpholin-4-yl-pyridin-2-yl)-9H-pyrido[2,3-b]indole
9-benzenesulfonyl-4-chloro-6-(5-morpholin-4-yl-pyridin-2-yl)-9H-pyrido[2,3-b]indole
9-benzenesulfonyl-2-chloro-6-(2'-(4-methoxyphenyl)ethenyl)-9H-pyrido[2,3-b]indole
9-benzenesulfonyl-4-chloro-6-(2'-(4-methoxyphenyl)ethenyl)-9H-pyrido[2,3-b]indole
9-benzenesulfonyl-2-chloro-6-(2'-(3-fluorophenyl)ethenyl)-9H-pyrido[2,3-b]indole
9-benzenesulfonyl-3-chloro-6-(2'-(3-fluorophenyl)ethenyl)-9H-pyrido[2,3-b]indole 9-benzenesulfonyl-4-chloro-6-(2'-(3-fluorophenyl)ethenyl)-9H-pyrido[2,3-b]indole
9-benzenesulfonyl-3-chloro-6-(nitrophenyl)-9H-pyrido[2,3-b]indole
9-benzenesulfonyl-4-chloro-6-(nitrophenyl)-9H-pyrido[2,3-b]indole
9-benzenesulfonyl-2-chloro-6-(4-phenylphenyl)-9H-pyrido[2,3-b]indole
9-benzenesulfonyl-3-chloro-6-(4-phenylphenyl)-9H-pyrido[2,3-b]indole
9-benzenesulfonyl-4-chloro-6-(4-phenylphenyl)-9H-pyrido[2,3-b]indole
9-benzenesulfonyl-2-chloro-6-(furan-2-yl)-9H-pyrido[2,3-b]indole
9-benzenesulfonyl)-3-chloro-6-(furan-2-yl)-9H-pyrido[2,3-b]indole
9-benzenesulfonyl-4-chloro-6-(furan-2-yl)-9H-pyrido[2,3-b]indole Typical Procedure for Suzuki Reactions with 2 equiv. of Boronic Acid At room temperature and under inert atmosphere, Pd(PPh$_3$)$_4$ (0.08 equiv.), 4-methoxyphenyl boronic acid (2.2 equiv.), and a 0.3M solution of K$_2$CO$_3$ in H$_2$O were added to a solution of 19 or 21 in anhydrous 1,4-dioxane. This solution stirred at reflux for 12 h. After cooling to room temperature, solution was filtered through celite and solvents were removed under reduced pressure.

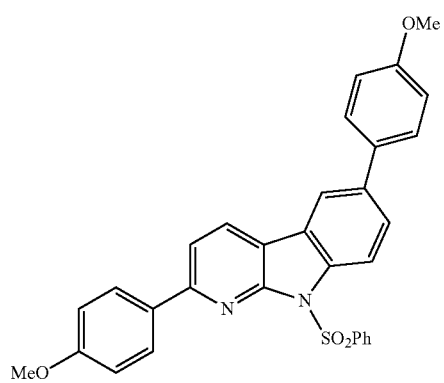

9-benzenesulfonyl-2,6-di(4-methoxyphenyl)-9H-pyrido[2,3-b]indole (36)

The crude product was purified by flash chromatography (CH$_2$Cl$_2$/PE 1/1) to afford 36 in 90% yield as a white solid; mp 206-208° C. (CH$_2$Cl$_2$/PE 6:4); IR: 2993, 1607, 1591, 1518, 1464, 1167, 1039, 978, 807 cm$^{-1}$; $^1$H-NMR (300 MHz, CDCl$_3$): δ 8.51 (d, 1H, J=8.7 Hz), 8.22 (d, 2H, J=7.4 Hz), 8.16 (d, 1H, J=7.7 Hz), 8.15 (d, 2H, J=8.9 Hz), 8.02 (d, 1H, J=1.5 Hz), 7.72 (dd, 1H, J=1.5, 8.7 Hz), 7.66 (d, 1H, J=8.1 Hz), 7.60 (d, 2H, J=8.9 Hz), 7.48 (t, 1H, J=7.4 Hz), 7.41-7.36 (m, 2H), 7.04 (d, 2H, J=8.6 Hz), 7.02 (d, 2H, J=8.6 Hz), 3.89 (s, 3H), 3.87 (s, 3H); 13C-NMR (75 MHz, CDCl$_3$): δ 160.8 (C), 159.3 (C), 154.6 (C), 151.3 (C), 139.9 (C), 136.9 (2×C), 133.9 (CH), 133.4 (C), 131.6 (C), 128.9 (2 CH), 128.5 (2 CH), 128.4 (2 CH), 127.8 (2 CH), 126.9 (CH), 123.7 (C), 118.4 (CH), 116.6 (C), 115.2 (CH), 115.1 (CH), 114.5 (3 CH), 114.3 (2 CH); 55.5 (2 CH$_3$); MS (ESI) m/z 521.1 [M+H+], 543.0 [M+Na+]; HRMS (ESI): Calcd for C$_{31}$H$_{24}$N$_2$O$_3$S: [M+Na]+=543.1354. Found: [M+Na]+=543.1355.

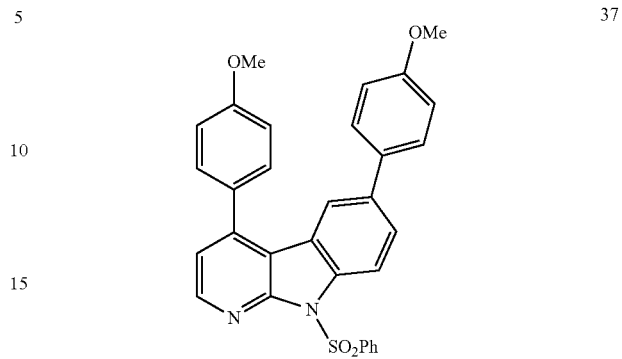

9-benzenesulfonyl-4,6-di(4-methoxyphenyl)-9H-pyrido[2,3-b]indole (37)

The crude product was purified by flash chromatography (CH$_2$Cl$_2$/PE 1:1) to afford 37 in 89% yield as a white solid; mp 162-164° C. (CH$_2$Cl$_2$/PE 1:1); IR: 3010, 2965, 1608, 1515, 1464, 1232, 1170, 822 cm$^{-1}$; $^1$H-NMR (300 MHz, CDCl$_3$): δ 8.55 (d, 1H, J=5.0 Hz), 8.53 (dd, 1H, J=0.8, 8.5 Hz), 8.22-8.20 (m, 2H), 7.72 (d, 1H, J=1.9 Hz), 7.70 (dd (H, J=1.9, 8.5 Hz), 7.54-7.36 (m, 7H), 7.14 (d, 1H, J=5.0 Hz), 7.07 (d, 2H, J=8.7 Hz), 6.94 (d, 2H, J=8.7 Hz), 3.90 (s, 3H), 3.84 (s, 3H); $^{13}$C-NMR (75 MHz, CDCl$_3$): δ 160.5 (C), 159.2 (C), 151.7 (C), 149.5 (2C), 146.6 (CH), 145.7 (C), 138.9 (C), 136.7 (C), 136.3 (C), 134.0 (CH), 133.2 (C), 130.0 (2 CH), 129.0 (2 CH), 128.1 (2 CH), 127.8 (2 CH), 126.9 (CH), 123.5 (C), 120.7 (CH), 120.5 (CH), 115.0 (CH), 114.5 (2 CH), 114.3 (2 CH); 55.6 (CH$_3$), 55.5 (CH$_3$); MS (ESI) m/z 521.1 [M+H+], 1062.9 [2M+Na+]; HRMS (ESI): Calcd for C$_{31}$H$_{24}$N$_2$O$_3$S: 521.1535. Found: 521.1537.

The following compounds can be prepared by the same method:
9-benzenesulfonyl-2,6-di(4-(morpholin-4-yl)methy)phenyl)-9H-pyrido[2,3-b]indole
9-benzenesulfonyl-4,6-di(4-(morpholin-4-yl)methylphenyl)-9H-pyrido[2,3-b]indole
9-benzenesulfonyl-2,6-di(5-morpholin-4-yl)-pyridin-2-yl)-9H-pyrido[2,3-b]indole
9-benzenesulfonyl-4,6-di(5-morpholin-4-yl-pyridin-2-yl)-9H-pyrido[2,3-b]indole
9-benzenesulfonyl-2,6-di(2'-phenylethenyl)-9H-pyrido[2,3-b]indole
9-benzenesulfonyl-4,6-di(2'-phenylethenyl)-9H-pyrido[2,3-b]indole
9-benzenesulfonyl-2,6-di(2'-(4-methoxyphenyl)ethenyl)-9H-pyrido[2,3-b]indole
9-benzenesulfonyl-4,6-di(2'-(4-methoxyphenyl)ethenyl)-9H-pyrido[2,3-b]indole
9-benzenesulfonyl-2,6-di(2'-(3-fluorophenyl)ethenyl)-9H-pyrido[2,3-b]indole
9-benzenesulfonyl-4,6-di(2'-(3-fluorophenyl)ethenyl)-9H-pyrido[2,3-b]indole
9-benzenesulfonyl-2,6-di(nitrophenyl)-9H-pyrido[2,3-b]indole
9-benzenesulfonyl-4,6-di(nitrophenyl)-9H-pyrido[2,3-b]indole
9-benzenesulfonyl-2,6-di(2-furyl)-9H-pyrido[2,3-b]indole
9-benzenesulfonyl-4,6-di(2-furyl)-9H-pyrido[2,3-b]indole 9-benzenesulfonyl-2,6-di(4-phenylphenyl)-9H-pyrido[2,3-b]indole 9-benzenesulfonyl-4,6-di(4-phenylphenyl)-9H-pyrido[2,3-b]indole Typical Procedure for the Demethylation of the Methoxyphenyl Group and Mitsunobu Substitution

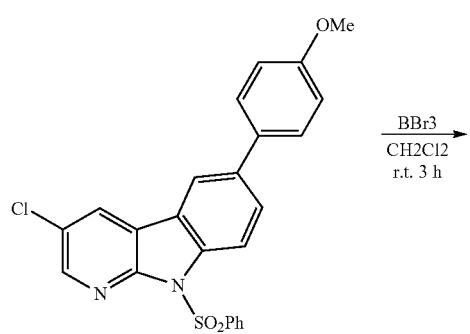

R353

Typical procedure for the Mitsunobu substitution of the phenol group

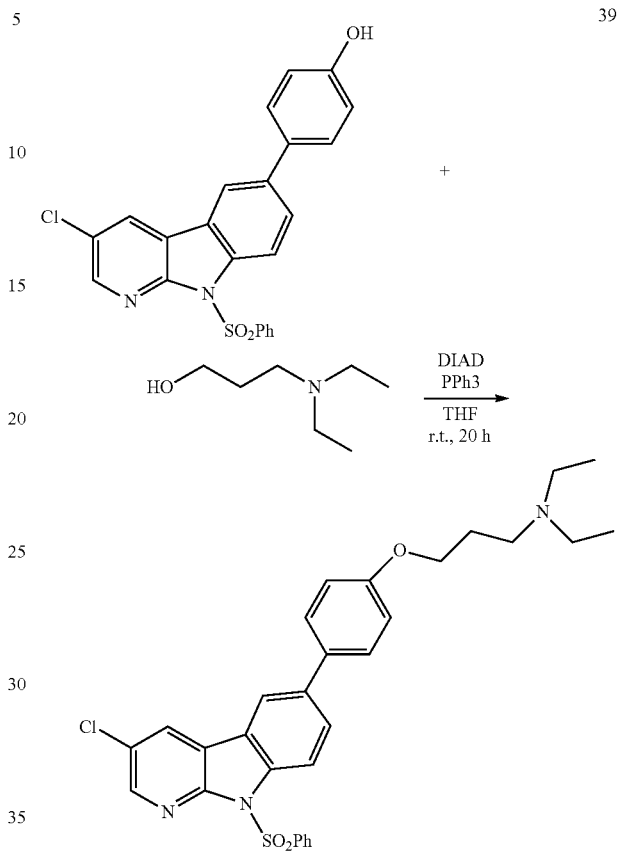

3-(4-(3-chloro-9-(benzenesulfonyl)-9H-pyrido[2,3-b]indol-6-yl)phenoxy)-N,N-diethylpropan-1-amine (39)

4-(3-chloro-9-(benzenesulfonyl)-9H-pyrido[2,3-b]indol-6-yl)phenol (R353)

To a solution of 3-chloro-6-(4-methoxyphenyl)-9-(benzenesulfonyl)-9H-pyrido[2,3-b]indole (222 mg, 1.11 mmol, 1eq.) in CH$_2$Cl$_2$ at 0° C., BBr$_3$ (4.46 ml, 1M in CH$_2$Cl$_2$ 4.46 mmol) was added dropwise. After 3 h at room temperature, the reaction mixture is hydrolysed with H$_2$O and extracted with AcOEt (3×50 ml), dried with MgSO$_4$, then filtered. The solvents were removed under reduced pressure and the crude material was purified by flash chromatography (CH$_2$Cl$_2$ then AcOEt) to afford 4-(3-chloro-9-(benzenesulfonyl)-9H-pyrido[2,3-b]indol-6-yl)phenol (409 mg, 0.94 mmol, 85% yield). $^1$H NMR $^1$H ((CD$_3$)$_2$CO, 300 MHz), δ 8.67 (d, 1H, J=2.3 Hz), 8.45-8.51 (m, 4H), 8.16-8.20 (m, 2H), 7.93 (dd, 1H, J=2.1 Hz, 8.9 Hz), 7.54-7.68 (m, 5H), 6.98 (d, 2H, J=8.6 Hz).

The following compounds can be prepared by the same method:

4-(2-chloro-9-(benzenesulfonyl)-9H-pyrido[2,3-b]indol-6-yl)phenol 4-(4-chloro-9-(benzenesulfonyl)-9H-pyrido[2,3-b]indol-6-yl)phenol To a solution of 4-(3-chloro-9-(benzenesulfonyl)-9H-pyrido[2,3-b]indol-6-yl)phenol (180 mg, 0.41 mmol, 1 eq.), triphenylphosphine (430 mg, 1.64 mmol, 4 eq.) and 3-(diethylamino)propan-1-ol (264 mg, 2.05 mmol, Seq.) in THF (10 ml) was added diisopropyldiazodicarboxylate (DIAD, 332 mg, 1.64 mmol, 4 eq.). The resulting solution was stirred at room temperature under Ar for 20 h and concentrated under reduced pressure. The crude residue was chromatographed over silica gel column (eluted with mixtures of AcOEt and EP and then AcOEt and MeOH). The product was then dissolved in dichloromethane and precipitated with EP. The solid was then filtered and washed with EP to give 3-(4-(3-chloro-9-(benzenesulfonyl)-9H-pyrido[2,3-b]indol-6-yl)phenoxy)-N,N-diethylpropan-1-amine (113 mg, 0.21 mmol, 51% yield). $^1$H NMR (CDCl$_3$ 300 MHz) δ ppm 8.47 (dd, 2H, J=2.6 Hz, 8.3 Hz), 8.18 (d, 1H, J=2.3 Hz), 8.13 (d, 2H, J=7.4 Hz), 8.01 (d, 1H, J=1.5 Hz), 7.77 (dd, 1H, J=1.8 Hz, 8.7 Hz), 7.54 (dd, 3H, J=8.7 Hz, 9.0 Hz), 7.42 (dd, 2H, J=7.3 Hz, 7.9 Hz), 7.01 (d, 2H, J=8.6 Hz), 4.08 (t, 2H, J=6.1 Hz), 2.58-2.72 (m, 6H), 2.00 (dd, 2H, J=6.8 Hz, 7.5 Hz), 1.08 (t, 6H, J=7.2 Hz). NMR $^{13}$C 75 MHz CDCl$_3$ δ ppm 162.5 (C), 158.9 (C), 149.3 (C), 145.6 (CH), 138.6 (C), 137.5 (C), 137.4 (C), 134.3 (CH), 129.1 (2×CH), 128.3 (2×CH), 128.3 (C), 128.1 (CH), 127.6 (2×CH), 122.4 (C), 120.1 (C), 118.8 (CH), 115.5 (CH), 115.1 (2×CH), 66.5 (CH$_2$), 49.5 (CH$_2$), 47.1 (2×CH$_2$), 26.8 (CH$_2$), 11.6 (2×CH$_3$). MS [ESI] 548 [M+H $^{35}$Cl], 550 [M+H $^{37}$Cl]. HRMS: calc. 548.1775; observed: 548.1776.

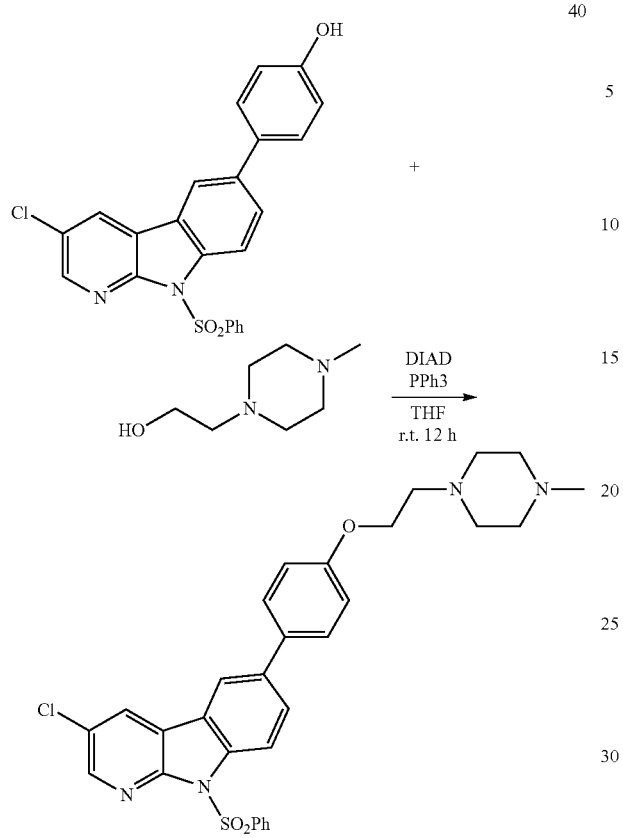

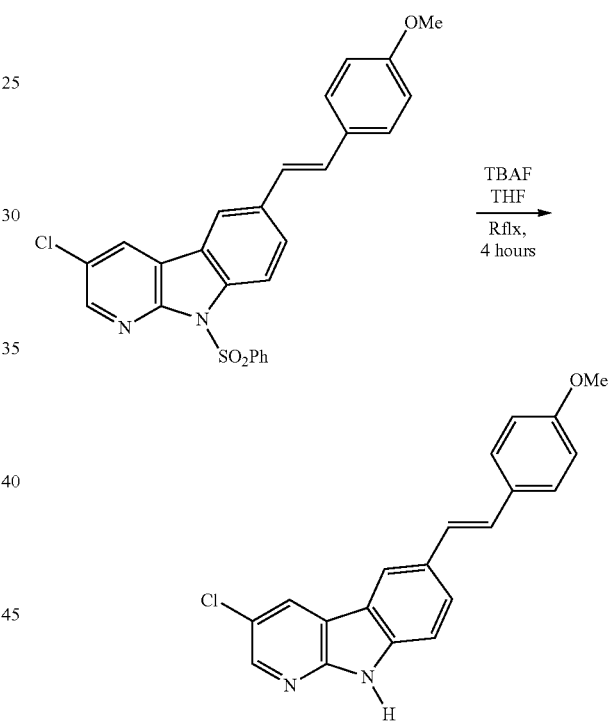

3-chloro-6-(4-(2-(4-methylpiperazin-1-yl)ethoxy)
phenyl)-9-(benzenesulfonyl)-9H-pyrido[2,3-b]indole
(40)

To a solution of 4-(3-chloro-9-(benzenesulfonyl)-9H-pyrido[2,3-b]indol-6-yl)phenol (240 mg, 0.55 mmol, 1 equiv.) in anhydrous THF (14 ml), triphenylphosphin (577 mg, 2.2 mmol, 4 equiv.) and 2-(4-methylpiperazin-1-yl)ethanol (397 mg, 2.75 mmol, 5 equiv.) are added. DIAD (445 mg, 2.2 mmol, 4 equiv.) is then added dropwise to the solution which is stirred at room temperature for 12 hours. The mixture is then extracted with a solution of HCl 0.1M (3×10 ml). The aqueous layer is treated with $Na_2CO_3$ until pH=9 and then extracted with AcOEt (3×20 ml). The organic layers are dried over $MgSO_4$, filtered and concentrated under reduced pressure. The residue (yellow solid) is purified over silica chromatography (eluted with AcOEt/MeOH 9:1 and then THF/MeOH 9:1) to give the product as a white solid (259 mg, 0.44 mmol) in 80% yield. $^1$H NMR (300 MHz, $CDCl_3$) δ 8.47 (dd, 2H, J=2.5, 7.7 Hz), 8.17 (d, 1H, J=2.1 Hz), 8.13 (d, 2H, J=7.5 Hz), 8.00 (d, 1H, J=0.9 Hz), 7.76 (dd, 1H, J=1.5, 8.6 Hz), 7.57-7.39 (m, 5H), 7.55 (d, 2H, J=8.6 Hz), 7.01 (d, 2H, J=8.5 Hz), 4.17 (t, 2H, J=5.6 Hz), 2.87 (t, 2H, J=5.6 Hz), 2.70-2.58 (br d, 8H), 2.35 (s, 3H).

The following compounds can be prepared by the same method:
3-(4-(2-chloro-9-(benzenesulfonyl)-9H-pyrido[2,3-b] indol-6-yl)phenoxy)-N,N-diethylpropan-1-amine
3-(2-chloro-9-(benzenesulfonyl)-9H-pyrido[2,3-b]indol-6-yl)phenoxy)-N,N-dimethylpropan-1-amine
3-(4-(4-chloro-9-(benzenesulfonyl)-9H-pyrido[2,3-b]indol-6-yl)phenoxy)-N,N-diethylpropan-1-amine
3-(4-(4-chloro-9-(benzenesulfonyl)-9H-pyrido[2,3-b]indol-6-yl)phenoxy)-N,N-dimethylpropan-1-amine
2-chloro-6-(4-(2-(4-methy)piperazin 1-yl)ethoxy)phenyl)-9-(benzenesulfonyl)-9H-pyrido[2,3-b]indole
4-chloro-6-(4-(2-(4-methylpiperazin-1-yl)ethoxy)phenyl)-9-(benzenesulfonyl)-9H-pyrido[2,3-b]indole Typical Procedure for Deprotection of the Benzenesulfonyl Group with TBAF in THF To a 1 M mixture of compound in anhydrous THF was added 4 equiv. of TBAF (1.0 M solution in THF), under inert atmosphere. The mixture was refluxed until completion of the reaction (followed by T.L.C, 2-3 hours). Solvent was removed and the residue was dissolved in $CH_2Cl_2$. The organic layer was washed with water, brine, dried over anhydrous $MgSO_4$, filtered and the solvent was removed under reduced pressure.

(E)-3-chloro-6-(2'-(4-methoxyphenyl)ethenyl)-9H-pyrido[2,3-b]indole (R350)

To a Solution of (E)-9-Benzenesulfonyl-3-Chloro-6-(2'-(4-methoxyphenyl)ethenyl)-9H-pyrido[2,3-b]indole (127 mg, 0.25 mmol, 1 equiv.) in anhydrous THF (11 ml) under Argon, TBAF 1M in THF (1.26 ml, 1.26 mmol, 5 equiv.) is added dropwise. The reaction is carried out at reflux for 4 hours and then concentrated under reduced pressure. The crude product is washed with MeOH and then filtered. The product R350 is obtained as a white solid (17 mg, 0.04 mmol) in 21% yield. $^1$H NMR (300 MHz, DMSO $d_6$) δ 12.05 (br s, 1H), 8.68 (d, 1H, J=2.1 Hz), 8.42 (d, 1H, J=2.3 Hz), 8.41 (s, 1H), 7.74 (d, 1H, J=8.3 Hz), 7.55 (d, 2H, J=8.5 Hz), 7.50 (d, J=8.3 Hz), 7.21 (d, 2H, J=1.5 Hz), 6.97 (d, 2H, J=8.5 Hz), 3.78 (s, 3H).

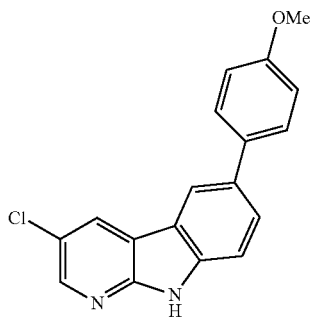

3-chloro-6-(4-methoxyphenyl)-9H-pyrido[2,3-b]indole (R277)

At room temperature and under inert atmosphere, 1.0 M TBAF in THF (1.9 mL, 5 equiv.) was added a solution of 9-benzenesulfonyl-3-chloro-6-(4-methoxyphenyl)-9H-pyrido[2,3-b]indole (26) (169 mg, 0.376 mmol) in anhydrous THF (17 mL). The solution was refluxed for 2 h. The resulting mixture was then cautiously quenched at 0° C. with H$_2$O. The mixture was extracted with EtOAc (3×10 mL). The resulting organic layers were dried over MgSO$_4$, filtered, and solvents were removed under reduced pressure. The crude product was purified by flash chromatography (CH$_2$Cl$_2$/EtOAc 9:1) to afford R277 in 85% yield as a yellow solid; mp>220° C. (MeOH); IR: 3109, 3035, 2935, 2848, 1630, 1603, 1578, 1483, 1232, 1090, 1033, 800, 778, 700 cm$^{-1}$; $^1$H-NMR (300 MHz, DMSO-d$_6$): δ 12.02 (bs, 1H), 8.74 (d, 1H, J=2.4 Hz), 8.49 (d, 1H, J=1.8 Hz), 8.42 (d, 1H, J=2.4 Hz), 7.76 (dd, 1H, J=1.8, 8.6 Hz), 7.55 (d, 1H, J=8.5 Hz), 7.06 (d, 1H, J=8.7 Hz), 3.81 (s, 3H); $^{13}$C-NMR (75 MHz, DMSO-d$_6$): δ 158.4 (C), 150.7 (C), 144.1 (CH), 138.8 (C), 133.2 (C), 132.1 (C), 128.3 (CH), 127.7 (2 CH), 126.2 (CH), 121.7 (C), 120.2 (C), 119.3 (CH), 126.6 (C), 114.4 (2 CH), 111.8 (CH), 55.2 (CH$_3$); MS (ESI) m/z 309.1 [M+H]$^+$; HRMS (EI): Calcd for C$_{18}$H$_{13}$ClN$_2$O: 308.0716. Found: 308.0714.

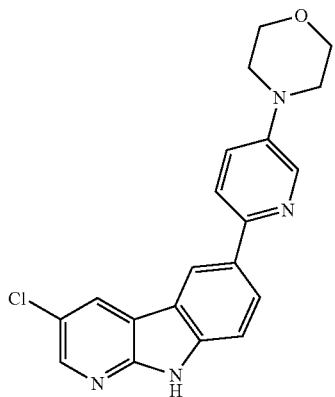

3-Chloro-6-(5-morpholin-4-yl-pyridin-2-yl)-9H-pyrido[2,3-b]indole (R308)

At Room Temperature and Under Inert Atmosphere, 1.0 M TBAF in Ti-if (0.94 mL, 5 equiv.) was added a solution of R308 (95 mg, 0.0.188 mmol) in anhydrous THF (8.5 mL). The solution was refluxed for 2 h. The resulting mixture was then cautiously quenched at 0° C. with H$_2$O. The mixture was extracted with EtOAc (3×10 mL). The resulting organic layers were dried over MgSO$_4$, filtered, and solvents were removed under reduced pressure. The crude product was purified by flash chromatography (PE/EtOAc 1:1 to EtOAc) to afford R308 in 85% yield as a yellow solid; $^1$H-NMR (300 MHz, DMSO-d$_6$): δ 12.02 (bs, 1H), 8.72 (d, 1H, J=2.1 Hz), 8.55 (d, 1H, J=2.4 Hz), 8.50 (d, 1H, J=1.5 Hz), 8.43 (d, 1H, J=2.3 Hz), 7.96 (dd, 1H, J=2.6, 8.9 Hz), 7.77 (dd, 1H, J=1.7, 8.5 Hz), 7.56 (d, 1H, J=8.5 Hz), 6.97 (d, 1H, J=8.9 Hz), 3.73 (t 4H, J=4.6 Hz), 3.49 (t, 4H, J=4.6 Hz); $^{13}$C-NMR (75 MHz, DMSO-d$_6$): δ 158.2 (C), 150.5 (C), 145.3 (CH), 144.2 (C), 138.8 (C), 135.8 (CH), 129.6 (C), 128.2 (CH), 126.1 (C), 125.7 (CH), 121.7 (C), 120.3 (C), 118.8 (CH), 116.5 (C), 111.9 (CH), 107.1 (CH), 65.9 (2 CH$_2$), 45.3 (2 CH$_2$); MS (ESI) m/z 365.2 [M+H$^+$]; HRMS (EI): Calcd for C$_{20}$H$_{17}$ClN$_4$O: 365.1169. Found: 365.1169.

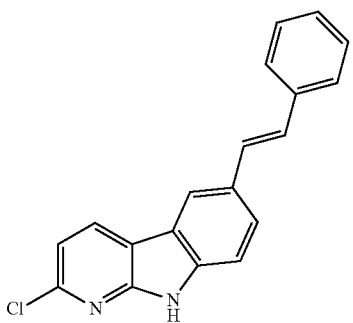

2-chloro-6-(2'-phenylethenyl)-9H-pyrido[2,3-b]indole (41)

At room temperature and under inert atmosphere, 1.0 M TBAF in THF (1.6 mL, 5 equiv.) was added a solution of 11a (140 mg, 0.315 mmol) in anhydrous THE (15 mL). The solution was refluxed for 4 h. The resulting mixture was then cautiously quenched at 0° C. with H$_2$O. The mixture was extracted with EtOAc (3×20 mL). The resulting organic layers were dried over MgSO$_4$, filtered, and solvents were removed under reduced pressure. Solvent was removed. The crude product was purified by flash chromatography (eluent: PE/EtOAc 1:1 to EtOAc) to afford 42 in 73% yield as a yellow solid; $^1$H-NMR (300 MHz, DMSO-d$_6$): δ 12.12 (bs, 1H), 8.57 (d, 1H, J=8.1 Hz), 8.43 (bs, 1H), 7.77 (dd, 114, J=1.1, 8.5 Hz), 7.61 (d, 2H, J=7.1 Hz), 7.52 (d, 1H, J=8.3 Hz), 7.40 (d, 1H, J=16.4 Hz), 7.40 (d, 1H, J=7.5 Hz), 7.38 (d, 1H, J=7.9 Hz), 7.29 (d, 1H, J=7.9 Hz), 7.27 (d 1H, J 7.5 Hz), 7.26 (d, 1H, J=16.4 Hz); $^{13}$C-NMR (75 MHz, DMSO-d$_6$): δ 151.4 (C), 146.5 (C), 138.5 (C), 137.4 (C), 131.5 (CH), 129.5 (CH), 129.0 (C), 128.7 (2 CH), 126.3 (CH), 126.2 (2 CH), 125.9 (CH), 120.3 (C), 119.3 (CH), 114.7 (C), 114.3 (C), 111.8 (CH); MS (ESI) m/z 304 [M+H$^+$];

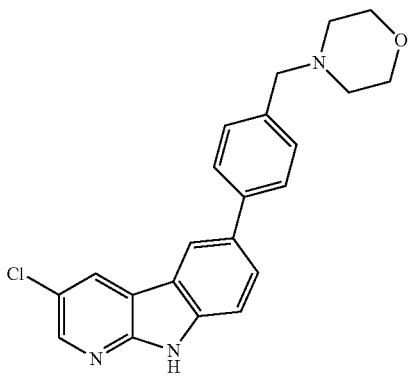

3-chloro-6-(4-(morpholin-4-yl)methylphenyl)-9H-pyrido[2,3-b]indole (R313)

At Room Temperature and Under Inert Atmosphere, 1.0 M TBAF in THF (1.75 mL, 5 equiv.) was added a solution of 30 (181 mg, 0.35 mmol) in anhydrous THF (16 mL). The solution was refluxed for 4 h. The resulting mixture was then cautiously quenched at 0° C. with $H_2O$. The mixture was extracted with EtOAc (3×20 mL). The resulting organic layers were dried over $MgSO_4$, filtered, and solvents were removed under reduced pressure. The crude product was purified by flash chromatography (eluent: $CH_2Cl_2$/EtOAc 7:3 to EtOAc) to afford R313 in 61% yield as a yellow solid; $^1$H-NMR (300 MHz, DMSO-$d_6$): δ 12.05 (bs, 1H), 8.75 (d, 1H, J=2.4 Hz), 8.55 (d, 1H, J=1.7 Hz), 8.43 (d, 1H, J=2.4 Hz), 7.81 (dd, 1H, J=1.7, 8.7 Hz), 7.70 (d, 2H, J=8.1 Hz), 7.58 (d, 1H, J=8.7 Hz), 7.41 (d, 2H, J=8.1 Hz), 3.59 (t, 4H, J=4.4 Hz), 3.51 (s, 2H), 2.39 (t, 4H, J=4.4 Hz); $^{13}$C-NMR (75 MHz, DMSO-$d_6$): δ 150.6 (C), 144.2 (C), 139.5 (C), 139.2 (C), 136.3 (C), 132.3 (C), 129.6 (2 CH), 128.3 (C), 126.5 (2 CH), 126.4 (CH), 121.8 (C), 120.2 (C), 119.8 (CH), 116.7 (C), 111.9 (CH), 66.2 (2 $CH_2$), 62.1 ($CH_2$), 53.2 (2 $CH_2$); MS (ESI) m/z 378 [M+H$^+$]

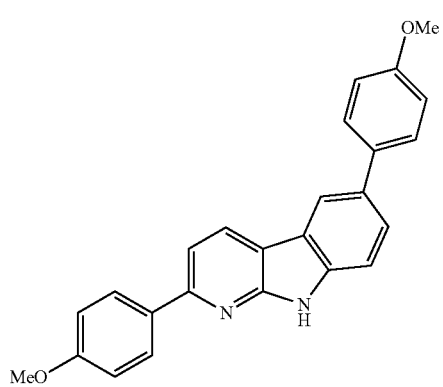

2,6-di(4-methoxyphenyl)-9H-pyrido[2,3-b]indole (R311)

The crude product was purified by flash chromatography (eluent: $CH_2Cl_2$/EtOAc 9:1) to afford R311 in 95% yield as brown solid; $^1$H-NMR (300 MHz, DMSO-$d_6$): δ 11.81 (s, 1H), 8.59 (d, 1H, J=8.1 Hz), 8.40 (d, 1H, J=1.1 Hz), 8.15 (d, 2H, J=8.7 Hz), 7.76 (d, 1H, J=8.1 Hz), 7.71-7.68 (m, 3H), 7.52 (d, 1H, J=8.5 Hz), 7.08 (d, 2H, J=8.7 Hz), 7.05 (d, 2H, J=8.7 Hz), 3.84 (s, 3H), 3.82 (s, 3H); $^{13}$C-NMR (75 MHz, DMSO-$d_6$): δ 159.9 (C), 158.3 (C), 153.0 (C), 152.5 (C), 138.3 (C), 133.5 (C), 131.9 (C), 131.7 (C), 129.4 (CH), 128.0 (2 CH), 127.7 (2 CH), 125.0 (CH), 121.2 (C), 118.5 (CH), 114.3 (2 CH), 114.3 (2 CH), 113.8 (C), 111.5 (CH), 111.3 (CH), 55.2 ($CH_3$), 55.1 ($CH_3$); MS (ESI) m/z 381.2 [M+H]$^+$; HRMS (EI): Calcd for $C_{25}H_{20}N_2O_2$: 380.1525. Found: 380.1527.

The following compounds can be prepared by the same method:

2-chloro-6-(4-methoxyphenyl)-9H-pyrido[2,3-b]indole
4-chloro-6-(4-methoxyphenyl)-9H-pyrido[2,3-b]indole
3-chloro-6-(2'-phenyl)ethenyl)-9H-pyrido[2,3-b]indole
4-chloro-6-(2'-phenylethenyl)-9H-pyrido[2,3-b]indole
2-chloro-6-(4-(morpholin-4-yl)methy)phenyl)-9H-pyrido[2,3-b]indole
4-chloro-6-(4-(morpholin-4-yl)methylphenyl)-9H-pyrido[2,3-b]indole
2-chloro-6-(5-morpholin-4-yl-pyridin-2-yl)-9H-pyrido[2,3-b]indole
4-chloro-6-(5-morpholin-4-yl-pyridin-2-yl)-9H-pyrido[2,3-b]indole
2-chloro-6-(2'-(4-methoxyphenyl)ethenyl)-9H-pyrido[2,3-b]indole
4-chloro-6-(2'-(4-methoxyphenyl)ethenyl)-9H-pyrido[2,3-b]indole
2-chloro-6-(2'-(3-fluorophenyl)ethenyl)-9H-pyrido[2,3-b]indole
3-chloro-6-(2'-(3-fluorophenyl)ethenyl)-9H-pyrido[2,3-b]indole
4-chloro-6-(2'-(3-fluorophenyl)ethenyl)-9H-pyrido[2,3-b]indole
2-chloro-6-(nitrophenyl)-9H-pyrido[2,3-b]indole
3-chloro-6-(nitrophenyl)-9H-pyrido[2,3-b]indole
4-chloro-6-(nitrophenyl)-9H-pyrido[2,3-b]indole
2-chloro-6-(2-furyl)-9H-pyrido[2,3-b]indole
3-chloro-6-(2-furyl)-9H-pyrido[2,3-b]indole
4-chloro-6-(2-furyl)-9H-pyrido[2,3-b]indole
2-chloro-6-(4-phenylphenyl)-9H-pyrido[2,3-b]indole
3-chloro-6-(4-phenylphenyl)-9H-pyrido[2,3-b]indole
4-chloro-6-(4-phenylphenyl)-9H-pyrido[2,3-b]indole
2,6-di(4-(morpholin-4-yl)methylphenyl)-9H-pyrido[2,3-b]indole
4,6-di(4-(morpholin-4-yl)methylphenyl)-9H-pyrido[2,3-b]indole
2,6-di(5-morpholin-4-yl-pyridin-2-yl)-9H-pyrido[2,3-b]indole
4,6-di(5-morpholin-4-yl-pyridin-2-yl)-9H-pyrido[2,3-b]indole
2,6-di(2'-(4-methoxyphenyl)ethenyl)-9H-pyrido[2,3-b]indole
4,6-di(2'-(4-methoxyphenyl)ethenyl)-9H-pyrido[2,3-b]indole
2,6-di(2'-(3-fluorophenyl)ethenyl)-9H-pyrido[2,3-b]indole
4,6-di(2'-(3-fluorophenyl)ethenyl)-9H-pyrido[2,3-b]indole
2,6-di(nitrophenyl)-9H-pyrido[2,3-b]indole
4,6-di(nitrophenyl)-9H-pyrido[2,3-b]indole
2,6-di(2-furyl)-9H-pyrido[2,3-b]indole
4,6-di(2-furyl)-9H-pyrido[2,3-h]indole 2,6-di(4-phenylphenyl)-9H-pyrido[2,3-b]indole
4,6-di(4-phenylphenyl)-9H-pyrido[2,3-b]indole
2,6-di(2'-(phenyl)ethenyl)-9H-pyrido[2,3-b]indole
4,6-di(2'-(phenyl)ethenyl)-9H-pyrido[2,3-b]indole Typical Procedure for the Sodium Methoxide-catalyzed Deprotection of the Benzenesulfonyl Group

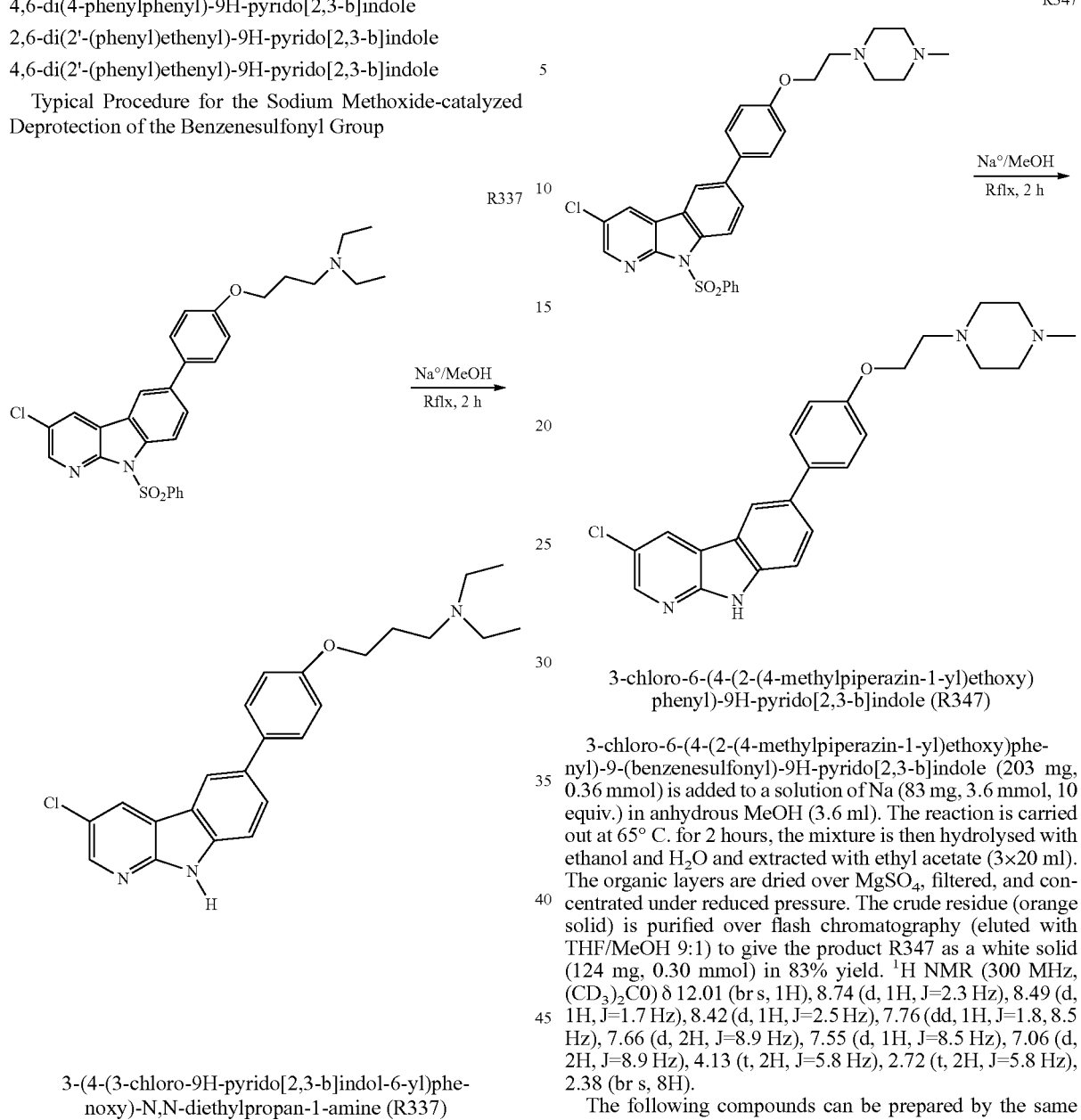

3-(4-(3-chloro-9H-pyrido[2,3-b]indol-6-yl)phenoxy)-N,N-diethylpropan-1-amine (R337)

3-(4-(3-chloro-9-(benzenesulfonyl)-9H-pyrido[2,3-b]indol-6-yl)phenoxy)-N,N-diethylpropan-1-amine (57 mg, 0.10 mmol) is added to a solution of Na° (23 mg, 1 mmol, 10 eq) in methanol (0.1 ml). The reaction is carried out at 65° C. for 2 hours, the mixture is then hydrolysed with ethanol and H$_2$O and extracted with ethyl acetate (3×20 ml). The organic layers are dried over MgSO$_4$, filtered, and concentrated under reduced pressure. The crude residue (orange solid) is purified over flash chromatography (eluted with THF/MeOH 9:1) to give the product R337 as a white solid (29 mg, 0.07 mmol) with a 70% yield. $^1$H NMR (CDCl$_3$ 300 MHz) δ ppm 8.42 (br s, 1H), 8.28 (br. s, 1H), 8.14 (br.s, 1H), 7.70 (dd, 1H, J=1.7, 8.5 Hz); 7.60-7.45 (m, 3H), 7.57 (d, 2'-1, J=8.6 Hz), 7.01 (d, 2'-1, J=8.7 Hz), 4.08 (t, 2H, J=6.3 Hz), 2.67 (t, 2H, J=7.3 Hz), 2.59 (q, 4H, J=7.1 Hz), 1.98 (p, 2H, J=6.8 Hz), 1.07 (t, 6H, J=7.1 Hz).

3-chloro-6-(4-(2-(4-methylpiperazin-1-yl)ethoxy)phenyl)-9H-pyrido[2,3-b]indole (R347)

3-chloro-6-(4-(2-(4-methylpiperazin-1-yl)ethoxy)phenyl)-9-(benzenesulfonyl)-9H-pyrido[2,3-b]indole (203 mg, 0.36 mmol) is added to a solution of Na (83 mg, 3.6 mmol, 10 equiv.) in anhydrous MeOH (3.6 ml). The reaction is carried out at 65° C. for 2 hours, the mixture is then hydrolysed with ethanol and H$_2$O and extracted with ethyl acetate (3×20 ml). The organic layers are dried over MgSO$_4$, filtered, and concentrated under reduced pressure. The crude residue (orange solid) is purified over flash chromatography (eluted with THF/MeOH 9:1) to give the product R347 as a white solid (124 mg, 0.30 mmol) in 83% yield. $^1$H NMR (300 MHz, (CD$_3$)$_2$CO) δ 12.01 (br s, 1H), 8.74 (d, 1H, J=2.3 Hz), 8.49 (d, 1H, J=1.7 Hz), 8.42 (d, 1H, J=2.5 Hz), 7.76 (dd, 1H, J=1.8, 8.5 Hz), 7.66 (d, 2H, J=8.9 Hz), 7.55 (d, 1H, J=8.5 Hz), 7.06 (d, 2H, J=8.9 Hz), 4.13 (t, 2H, J=5.8 Hz), 2.72 (t, 2H, J=5.8 Hz), 2.38 (br s, 8H).

The following compounds can be prepared by the same method:
3-(4-(2-chloro-9H-pyrido[2,3-b]indol-6-yl)phenoxy)-N,N-diethylpropan-1-amine
3-(4-(2-chloro-9H-pyrido[2,3-b]indol-6-yl)phenoxy)-N,N-dimethylpropan-1-amine
3-(4-(4-chloro-9H-pyrido[2,3-b]indol-6-yl)phenoxy)-N,N-diethylpropan-1-amine
3-(4-(4-chloro-9H-pyrido[2,3-b]indol-6-yl)phenoxy)-N,N-dimethylpropan-1-amine
2-chloro-6-(4-(2-(4-methylpiperazin-1-yl)ethoxy)phenyl)-9H-pyrido[2,3-b]indole
4-chloro-6-(4-(2-(4-methylpiperazin-1-yl)ethoxy)phenyl)-9H-pyrido[2,3-b]indole Procedure A for Suzuki-Miyaura Coupling at the 2, 3, and 4 Positions with Pd(OAc)$_2$/S Phos A sealed pressure tube with stir bar was charged with Pd(OAc)$_2$ (0.08 equiv.), 2-dicyclohexylphosphino-2',6'- dimethoxyphenyl (0.16 equiv.), R248 (1 equiv.), boronic acid (1.2 equiv.) and K$_3$PO$_4$ (2.5 equiv.). The tube was evacuated and back-filled with argon (this was repeated three additional times). 1,4-Dioxane (2.5 mL/mmol) was added (when degassed solvent was used) and the reaction mixture was allowed to stir at 100° C. overnight. After cooling to room temperature, the products were extracted from the water layer with ethyl acetate, dried over MgSO$_4$, filtered through celite and solvents were removed under reduced pressure.

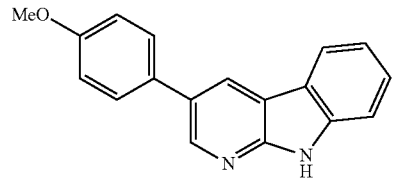

3-(4-methoxyphenyl)-9H-pyrido[2,3-b]indole (R278)

The product was purified by column chromatography (CH$_2$Cl$_2$/EtOAc 9:1) to afford R278 in 73% yield as a yellow solid; mp>220° C. (MeOH); IR:3125, 2979, 1607, 1587, 1570, 1519, 1455, 1244, 1231, 1034, 742 cm$^{-1}$; $^1$H-NMR (300 MHz, DMSO-d$_6$): δ 11.80 (bs, 1H), 8.75 (d, 1H, J=2.1 Hz), 8.67 (d, 1H, J=2.1 Hz), 8.23 (d, 1H, J=7.9 Hz), 7.72 (d, 2H, J=8.6 Hz), 7.51-7.43 (m, 2H), 7.23 (td, 1H, J=1.5, 8.1 Hz), 7.07 (d, 2H, J=8.6 Hz), 3.82 (s, 3H); $^{13}$C-NMR (75 MHz, DMSO-d$_6$): 158.6 (C), 151.1 (C), 144.4 (CH), 139.4 (C), 130.9 (C), 127.9 (2 CH), 127.4 (C), 126.7 (CH), 126.0 (CH), 121.4 (CH), 120.5 (C), 119.3 (CH), 115.3 (C), 114.5 (2 CH), 111.3 (CH), 55.2 (CH$_3$); MS (ESI) m/z 275.2 [M+H]$^+$; HRMS (ESI): Calcd for C$_{18}$H$_{14}$N$_2$: 275.1184. Found: 275.1186.

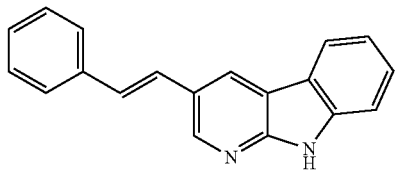

3-(2'-phenylethenyl)-9H-pyrido[2,3-b]indole (R281)

The product was purified by column chromatography (CH$_2$Cl$_2$/EtOAc 9:1) to afford R281 in 68% yield as a white solid. Mp>220° C. (MeOH); IR 2973, 1604, 1496, 1456, 1403, 1243, 1109, 961, 741, 685 cm$^{-1}$; $^1$H-NMR (300 MHz, DMSO-d$_6$): δ 11.85 (bs, 1H), 8.84 (d, 1H, J=2.1 Hz), 8.62 (d, 1H, J=2.1 Hz), 8.19 (d, 1H, J=7.7 Hz), 7.64 (d, 2H, J=7.4 Hz), 7.51-7.34 (m, 6H), 7.30-7.22 (m, 2H); $^{13}$C-NMR (75 MHz, DMSO-d$_6$): δ 151.6 (C), 146.2 (CH), 139.4 (C), 137.4 (C), 128.7 (2 CH), 127.3 (C), 126.9 (CH), 126.8 (CH), 126.4 (CH), 126.2 (2 CH), 124.8 (CH), 124.7 (C), 121.3 (CH), 120.4 (C), 119.7 (CH), 115.5 (C), 111.4 (CH); MS (ESI) m/z 271.2 [M+H]$^+$; HRMS (ESI): Calcd for C$_{19}$H$_{14}$N$_2$: 271.1235. Found: 271.1236.

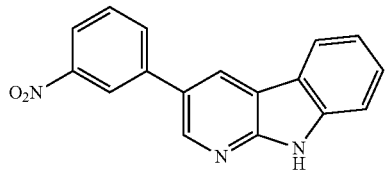

3-(3-nitrophenyl)-9H-pyrido[2,3-b]indole (R328)

The product was purified by column chromatography on silica gel (CH$_2$Cl$_2$/EtOAc 8/2) to afford R 328 in 70% yield as a yellow solid. mp>220° C. (MeOH); $^1$H NMR (300 MHz, DMSO-d$_6$): δ 11.99 (bs, NH); 9.02 (d, 1H, J=2.3 Hz); 8.85 (d, 1H, J=2.3 Hz); 8.62 (t, 1H, J=1.9 Hz); 830 (t, 2H, J=7.7 Hz); 8.23 (dd, 1H, J=1.0, 2.3 Hz); 7.81 (t, 1H, J=8.1 Hz); 7.55-7.46 (m, 2H); 7.27 (td, 1H, J=1.5, 7.2 Hz); $^{13}$C NMR (75 MHz, DMSO-d6): δ 152.2 (C), 148.8 (C), 145.3 (CH), 140.7 (C), 139.8 (C), 133.6 (CH), 130.8 (CH), 127.3 (2×CH), 125.6 (C), 122.0 (C14), 121.9 (CH), 121.4 (CH), 120.9 (C), 120.1 (CH), 115.8 (C), 111.8 (CH); MS (ESI) m/z 290.1 [M+H]$^+$; HRMS (ESI): Calcd for C$_{17}$H$_{11}$N$_3$O$_2$: 290.0930. Found: 290.0934.

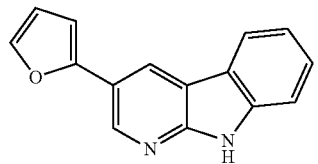

3-(furan-2-yl)-9H-pyrido[2,3-b]indole (R325)

The product was purified by column chromatography on silica gel (CH$_2$Cl$_2$/EtOAc 9/1) to afford R325 in 65% yield as a yellow solid. mp>220° C. (MeOH); $^1$H NMR (300 MHz, DMSO-d6): δ 11.91 (bs, NH); 8.80 (s, 2H); 8.23 (d, 1H, J=7.9 Hz); 7.79 (dd, 1H, J=0.5, 1.7 Hz); 7.52-7.44 (m, 2H); 7.24 (td, 1H, J=1.9, 7.2 Hz); 6.99 (d, 1H, J=0.8, 3.4 Hz); 6.64 (dd, 1H, J=1.9, 3.4 Hz); $^{13}$C NMR (75 MHz, DMSO-d6): δ 152.2 (C), 151.1 (C), 142.5 (CH), 142.4 (CH), 139.4 (C), 126.9 (CH), 123.3 (CH), 121.5 (CH), 120.4 (C), 119.7 (CH), 118.7 (C), 115.1 (C), 112.0 (CH), 111.4 (CH), 104.6 (CH); MS (EI) m/z 234.0 [M$^+$]; HRMS (EI): Calcd for C$_{15}$H$_{10}$N$_2$O: 234.0793. Found: 234.0792.

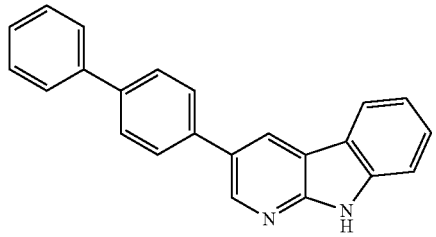

3-(4-phenylphenyl)-9H-pyrido[2,3-b]indole (R329)

The product was purified by column chromatography (CH$_2$Cl$_2$/EtOAc 8:2) to afford R329 in 63% yield as a white solid. ¹H-NMR (300 MHz, DMSO-d₆): δ 11.89 (bs, 1H); 8.89 (d, 1H, J=2.1 Hz); 8.80 (d, 1H, J=2.3 Hz); 8.26 (d, 1H, J=7.7 Hz); 7.92 (d, 1H, J=8.5 Hz); 7.82 (d, 1H, J=8.3 Hz); 7.75 (d, 1H, J=8.3 Hz); 7.53-7.45 (m, 3H); 7.41-7.36 (m, 1H); 7.04 (ddd, 1H, J=1.3, 6.6 Hz).

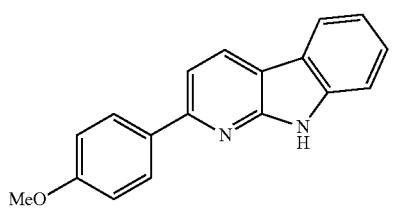

2-(4-methoxyphenyl)-9H-pyrido[2,3-b]indole (R299)

The product was purified by column chromatography (CH₂Cl₂) to afford R299 in 70% yield as a white solid. mp>220° C. (MeOH); IR 3136, 3083, 2958, 1596, 1583, 1572, 1457, 1415, 1028, 818 cm⁻¹; ¹H NMR (300 MHz, DMSO-d₆) δ 11.80 (br s, 1H), 8.52 (d, 1H, J=8.1 Hz), 8.14 (d, 2H, J=8.9 Hz), 8.13 (d, 1H, J=7.9 Hz), 7.74 (d, 1H, J=8.1 Hz), 7.48 (d, 1H, 7.3 Hz), 7.42 (td, 1H, J=1.3 and 6.9 Hz), 7.21 (td, 1H, J=1.3 and 7.9 Hz), 7.07 (d, 2H, J=8.9 Hz), 3.83 (s, 3H); ¹³C NMR (75 MHz, DMSO-d₆) δ 159.8 (C), 152.8 (C), 152.0 (C), 139.1 (C), 131.9 (C), 129.1 (CH), 128.0 (2 CH), 126.2 (CH), 120.9 (CH), 120.5 (C), 119.4 (CH), 114.1 (2 CH), 113.5 (C), 111.2 (CH), 111.1 (CH), 55.2 (CH₃); MS (ESI) m/z 275.2 [M+H]⁺; HRMS (ESI): Calcd for $C_{18}H_{14}N_2O$: 275.1184. Found: 275.1186.

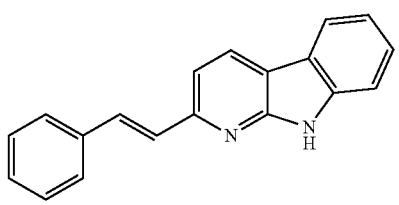

2-(2'-phenylethenyl)-9H-pyrido[2,3-b]indole (R300)

The product was purified by column chromatography (CH₂Cl₂) to afford R300 in 72% yield as a yellow solid. mp>220° C. (MeOH); IR 3159, 3089, 3041, 2888, 1601, 1579, 1458, 1413, 1227, 954, 726, 685 cm⁻¹; ¹H NMR (300 MHz, DMSO-d₆) δ 11.75 (br s, 1H), 8.48 (d, 1H, J=7.7 Hz), 8.12 (d, 1H, J=8.1 Hz), 7.72 (d, 1H, J=16.0 Hz), 7.69 (d, 2H, J=7.2 Hz), 7.46-7.40 (m, 6H), 7.34-7.29 (m, 1H), 7.21 (td, 1H, J=1.3, 8.1 Hz); ¹³C NMR (75 MHz, DMSO-d₆) δ 152.0 (C), 151.8 (C), 139.4 (C), 136.5 (C), 131.0 (CH), 128.9 (CH), 128.8 (2 CH), 128.1 (CH), 126.9 (2 CH), 126.5 (CH), 120.9 (CH), 120.5 (C), 119.5 (CH), 114.9 (CH), 114.6 (C), 111.1 (CH); MS (ESI) m/z 271.2 [M+H]⁺; HRMS (ESI): Calcd for $C_{19}H_{14}N_2$: 271.1235. Found: 271.1236.

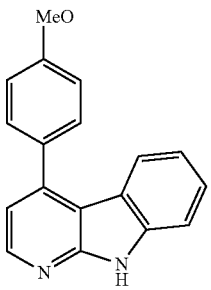

4-(4-methoxyphenyl)-9H-pyrido[2,3-b]indole (R309)

The product was purified by column chromatography (CH₂Cl₂/EtOAc 9:1) to afford R309 in 70% yield as a yellow solid. Mp 208-210° C. (MeOH); IR 3062, 2968, 2835, 1599, 1560, 1515, 1456, 1252, 1176, 1029, 809, 745, 724 cm⁻¹; ¹H-NMR (300 MHz, DMSO-d₆): δ 11.93 (bs, 1H), 8.41 (d, 1H, J=-4.9 Hz), 7.64-7.60 (m, 3H), 7.5 (d, 1H, J=8.1 Hz), 7.40 (ddd, 1H, J=0.9, 7.2 Hz), 7.17 (d, 2H, J=8.7 Hz), 7.06 (d, 1H, J=5.1 Hz), 7.04 (td, 1H, J=1.1, 7.5 Hz), 3.88 (s, 3H); ¹³C-NMR (75 MHz, DMSO-d₆): δ 159.6 (C), 149.2 (C), 145.9 (CH), 144.1 (C), 138.9 (C), 130.6 (C), 129.8 (2 CH), 126.4 (CH), 121.9 (CH), 119.9 (C), 119.0 (CH), 115.9 (CH), 114.2 (2 CH), 112.1 (C), 111.3 (CH), 55.3 (CH₃); MS (ESI) m/z 275.2 [M+H]⁺; HRMS (EI): Calcd for $C_{18}H_{14}N_2$: 274.1106. Found: 274.1105.

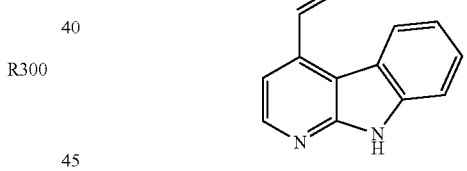

4-(2'-phenylethenyl)-9H-pyrido[2,3-b]indole (R310)

The product was purified by column chromatography (CH₂Cl₂/EtOAc 9:1) to afford R310 in 72% yield as a yellow solid. Mp>220° C. (MeOH); IR: 3059, 2972, 1633, 1599, 1580, 1561, 1455, 1397, 1255, 957, 730, 690 cm⁻¹; ¹H-NMR (300 MHz, DMSO-d₆): δ 11.87 (bs, 1H), 8.39 (d, 1H, J=5.3 Hz), 8.32 (d, 1H, J=8.0 Hz), 8.07 (d, 1H, J=16.3 Hz), 7.85 (d, 2H, J=7.2 Hz), 7.65 (d, 1H, J=16.3 Hz), 7.54-7.45 (m, 5H), 7.41-7.36 (m, 1H), 7.27 (td, 1H, J=1.5, 8.0 Hz); ¹³C-NMR (75 MHz, DMSO-d₆): δ 152.7 (C), 145.9 (CH), 139.8 (C), 139.0 (C), 136.3 (C), 134.5 (CH), 128.9 (2 CH), 128.8 (CH), 127.4 (2 CH), 126.3 (CH), 123.7 (CH), 123.4 (CH), 120.4 (C), 119.7 (CH), 112.3 (C), 111.2 (CH), 110.9 (CH); MS (ESI) m/z 270 [M⁺]; HRMS (ESI): Calcd for $C_{19}H_{14}N_2$: 271.1235. Found: 271.1235.

Procedure B for Suzuki-Miyaura Coupling at the 2 and 4 Positions with Pd(PPh₃)₄

At room temperature and under an inert atmosphere, Pd(PPh₃)₄ (0.08 equiv.), boronic acid (1.1 equiv.), and a 0.3 M solution of K$_2$CO$_3$ (3 equiv.) in H$_2$O were added to a 0.1M solution of R297 or R296 in anhydrous 1,4-dioxane. This solution was stirred at 100° C. for 12 h. After cooling to room temperature, the solution was filtered through celite and solvents were removed under reduced pressure.

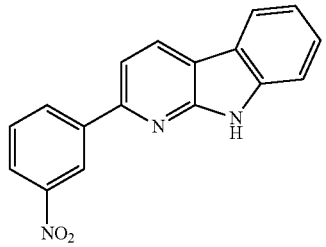

2-(3-nitrophenyl)-9H-pyrido[2,3-b]indole (42)

The product was purified by column chromatography on silica gel (CH$_2$Cl$_2$/EP 9/1) to afford 42 in 83% yield as a yellow solid. mp 185.187° C. (MeOH); $^1$H NMR (300 MHz, DMSO-d$_6$): δ 12.01 (bs, NH); 9.06 (t, 1H, J=1.9 Hz); 8.62 (d, 1H, J=8.0 Hz); 8.60 (d, 1H J=8.1 Hz); 8.25 (dd, 1H, J=1.5, 8.1 Hz); 8.19 (d, 1H, J=7.7 Hz); 7.96 (d, 1H, J=18.0 Hz); 7.79 (t, 1H, J=8.1 Hz); 7.51 (d, 1H, J=8.9 Hz); 7.47 (td, 1H, J=0.8, 8.9 Hz); 7.25 (td, 1H, J=1.5, 7.9 Hz); $^{13}$C NMR (75 MHz, DMSO-d6): δ 152.0 (C), 150.0 (C), 148.5 (C), 141.0 (C), 139.6 (C), 132.7 (CH), 130.3 (CH), 128.9 (CH), 129.5 (CH), 127.0 (CH), 123.1 (CH), 121.4 (CH), 120.9 (CH), 120.1 (C), 119.7 (CH), 115.4 (C), 112.2 (C), 111.3 (CH); MS (ESI) m/z 290.2, 244.3 [M+H]$^+$, [M-NO$_2$+H]$^+$; HRMS (ESI): Calcd for C$_{17}$H$_{11}$N$_3$O$_2$: 290.0930. Found:290.09314.

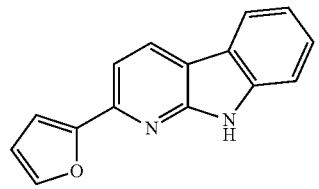

2-(furan-2-yl)-9H-pyrido[2,3-b]indole (R326)

The product was purified by column chromatography on silica gel (CH$_2$Cl$_2$) to afford R326 in 81% yield as a brown solid. mp=208-210° C. (MeOH); $^1$H-NMR (300 MHz, DMSO-d$_6$): δ 11.85 (bs, 1H), 8.54 (d, 1H, J=7.9 Hz), 8.13 (d, 1H, J=7.7 Hz), 7.85 (dd, 1H, J=1.1, 1.7 Hz), 7.62 (d, 1H, J=8.1 Hz), 7.48-7.41 (m, 2H), 7.22 (ddd, 1H, J=1.9, 6.8, 8.1 Hz), 7.13 (d, 1H, J=3.4 Hz), 6.68 (dd, 1H, J=1.7, 3.4 Hz); $^{13}$C NMR (75 MHz, DMSO-d$_6$): δ 154.0 (C), 151.8 (C), 145.3 (CH), 143.8 (C), 139.3 (C), 129.1 (CH), 126.5 (CH), 120.9 (CH), 120.4 (CH), 119.6 (CH), 114.3 (C), 112.3 (CH), 111.2 (CH), 110.2 (CH), 108.3 (CH); MS (CI) m/z 235 [M+H]$^+$ 100° C.; HRMS (CI): Calcd for C$_{15}$H$_{10}$N$_2$O: 235.0871. Found: 235.08727.

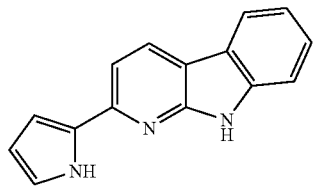

2-(1H-pyrrol-2-yl)-9H-pyrido[2,3-b]indole (R355)

At room temperature and under an inert atmosphere, Pd(PPh$_3$)$_4$ (0.08 equiv.), boronic acid (1.1 equiv.), and a 0.3 M solution of K$_2$CO$_3$ (3 equiv.) in H$_2$O were added to a 0.1M solution of 2-chloro-α-carboline in anhydrous 1,4-dioxane. This solution was stirred at 100° C. for 12 h. After cooling to room temperature, the solution was filtered through celite and solvents were removed under reduced pressure. A solution of crude product in CH$_2$Cl$_2$ (3.5 mL) was stirred under argon and treated with CF$_3$CO$_2$H (1 mL). After 90 min at room temperature, the resulting mixture was then cautiously quenched at 0° C. with H$_2$O and a saturated aqueous NaHCO$_3$ was added until pH 10. The solution was diluted with CH$_2$Cl$_2$, washed with H$_2$O, dried with MgSO$_4$, filtered and concentrated. The product was purified by column chromatography on silica gel (CH$_2$Cl$_2$) to afford R355 in 10% yield as a yellow solid. $^1$H-NMR (300 MHz, CDCl$_3$): δ 9.90 (bs, 1H), 8.89 (bs, NH), 8.28 (d, 1H, J=8.0 Hz), 7.98 (d, 1H, J=8.0 Hz), 7.51 (d, 1H, J=8.1 Hz), 7.43-7.40 (m, 1H); 7.33-7.27 (m, 2H), 6.97 (s, 1H), 6.85 (s, 1H), 6.34 (dd, 1H, J=2.6, 5.5 Hz).

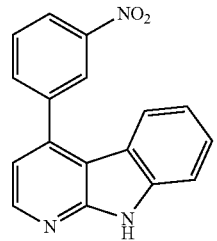

4-(3-nitrophenyl)-9H-pyrido[2,3-b]indole (R331)

The product was purified by column chromatography on silica gel (CH$_2$Cl$_2$/EtOAc 8/2) to afford R331 in 77% yield as a yellow solid. mp>220° C. (MeOH); $^1$H-NMR (300 MHz, DMSO-d$_6$): δ 12.11 (bs, 1H), 8.52 (d, 1H, J=5.0 Hz), 8.48 (t, 1H, J=1.8 Hz), 8.43 (ddd, 1H, J=1.1, 2.3, 7.9 Hz), 8.18 (ddd, 1H, J=1.0, 1.7, 7.9 Hz), 7.93 (t, 1H, J=8.1 Hz), 7.55 (d, 1H, J=7.9 Hz), 7.46 (d, 1H, J=7.9 Hz), 7.45 (td, 1H, J=1.0, 7.9 Hz 7.21 (d, 1H, J=5.0 Hz), 7.04 (td, 1H, J=1.0, 7.9 Hz); $^{13}$C-NMR (75 MHz, DMSO-d$_6$): δ 152.3 (C), 148.1 (C), 146.2 (CH), 141.6 (C), 139.9 (C), 139.2 (C), 135.2 (CH), 130.6 (CH), 126.8 (CH), 123.5 (CH), 123.1 (CH), 121.7 (CH), 119.4 (C), 119.2 (C), 115.8 (CH), 111.9 (C), 111.6 (CH); MS (ESI) m/z 290.2, 244.3 [M+H]$^+$, [M-NO$_2$+H]$^+$; HRMS (ESI): Calcd for C$_{17}$H$_{11}$N$_3$O$_2$: 290.0930. Found: 290.09255; Anal. Calcd for C$_{17}$H$_{11}$N$_3$O$_2$:: C, 70.58; H, 3.83; N, 14.52. Found: C, 70.30; H, 3.85; N, 14.20.

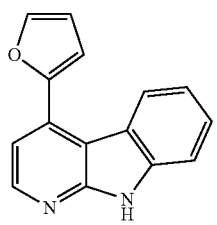

4-(furan-2-yl)-9H-pyrido[2,3-b]indole (R327)

The product was purified by column chromatography on silica gel (CH$_2$Cl$_2$/EtOAc 8/2) to afford R327 in 76% yield as a green solid. mp>220° C. (MeOH); $^1$H NMR (300 MHz, DMSO-d6): δ 12.00 (bs, NH); 8.50 (d, 1H, J=8.5 Hz); 8.42 (d, 1H, J=5.3 Hz); 8.13 (dd, 1H, J=0.6, 1.7 Hz); 7.54-7.51 (m, 1H); 7.48 (td, 1H, J=1.1, 6.9 Hz); 7.43 (d, 1H, J=5.1 Hz); 7.31 (dd, 1H, J=0.8, 3.4 Hz); 7.21 (ddd, 1H, J=1.5, 6.8, 8.2 Hz). $^{13}$C NMR (75 MHz, DMSO-d6): δ 153.0 (C), 151.7 (C), 145.8 (CH), 144.5 (CH), 139.2 (C2), 131.7 (C), 126.7 (CH), 123.7 (CH), 119.7 (C), 119.5 (CH), 112.5 (2×CH), 111.2 (CH), 111.1 (CH), 109.8 (C); MS (CI) m/z 235 [M+H]$^+$; HRMS (CI): Calcd for C$_{15}$H$_{10}$N$_2$O: 235.0871. Found: 235.0872.

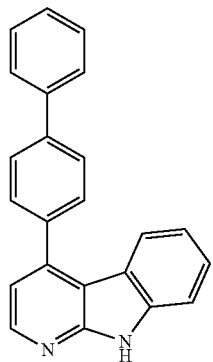

4-(4-phenylphenyl)-9H-pyrido[2,3-b]indole (R330)

The product was purified by column chromatography (CH$_2$Cl$_2$/EtOAc 7:3) to afford R330 in 58% yield as a green solid. $^1$H-NMR (300 MHz, DMSO-d$_6$): δ 12.00 (bs, 1H), 8.47 (d, 1H, J=5.1 Hz), 7.93 (d, 1H, J=8.2 Hz), 7.83 (d, 1H, J=7.3 Hz), 7.79 (d, 1H, J=7.8 Hz), 7.64 (d, 1H, J=8.7 Hz), 7.56-7.51 (m, 3H), 7.45-7.40 (m, 2H), 7.15 (d, 1H, J=4.9 Hz), 7.04 (ddd, 1H, J=0.5, 6.8 Hz).

Typical Procedure Suzuki-Miyaura on 6-substituted 2- and 4-chloropyrido[2,3-b]indoles At room temperature and under an inert atmosphere, Pd(PPh$_3$)$_4$, (0.08 equiv.), trans vinyl phenyl boronic acid (1.1 equiv.), and a 0.3M solution of K$_2$CO$_3$ (3 equiv.) in H$_2$O were added to a 0.1M solution of 32 or 34 in 1,4-dioxane. This solution was stirred at 100° C. for 12 h. After cooling to room temperature, solution was filtered through celite and solvents were removed under reduced pressure.

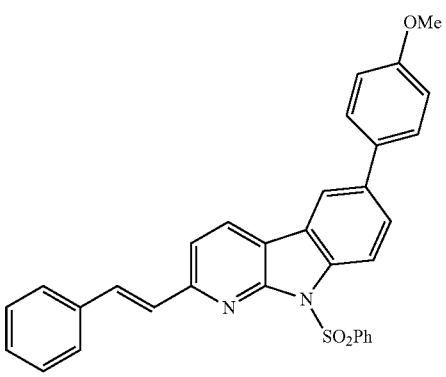

9-benzenesulfonyl-6-(4-methoxyphenyl)-2-(2'-phenylethenyl)-9H-pyrido[2,3-b]indole (43)

The crude product was purified by flash chromatography (CH$_2$Cl$_2$/PE 1:1) to afford 43 in 84% yield as a yellow solid; mp 193-195° C. (CH$_2$Cl$_2$/PE); IR: 2926, 1607, 1586, 1518, 1465, 1382, 1172, 1090, 967, 812 cm$^{-1}$; $^1$H-NMR (300 MHz, CDCl$_3$): δ 8.58 (d, 1H, J=8.9 Hz), 8.33 (d, 1H, J=7.4 Hz), 8.32 (d, 1H, J=8.9 Hz), 8.14 (d, 1H, J=7.9 Hz), 8.06 (d, 1H, J=1.7 Hz), 7.91 (d, 1H, J=16.0 Hz), 7.78 (dd, 1H, J=1.9, 8.6 Hz), 7.71 (d, 2H, J=7.4 Hz), 7.66 (d, 2H, J=8.7 Hz), 7.60-7.36 (m, 6H), 7.34 (d, 1H, J=2.6 Hz), 7.28 (d, 1H, J=16.0 Hz), 7.09 (d, 2H, J=8.6 Hz), 3.94 (s, 3H); $^{13}$C-NMR (75 MHz, CDCl$_3$): δ 159.3 (C), 153.5 (C), 151.2 (C), 139.0 (C), 137.1 (C), 136.9 (C), 136.8 (C), 134.0 (CH), 133.4 (CH), 133.2 (C), 128.9 (4 CH), 128.6 (CH), 128.5 (CH); 128.3 (2 CH), 127.9 (3 CH), 127.3 (2 CH), 127.0 (CH), 123.6 (C), 118.5 (CH), 118.3 (CH), 117.4 (C), 115.2 (CH), 114.4 (2 CH); 55.4 (CH$_3$); MS (ESI) m/z 517.1 [M+H$^+$], 539 [M+Na$^+$]; HRMS (ESI): Calcd for C$_{32}$H$_{24}$N$_2$O$_3$S: 517.1586. Found: 517.1589.

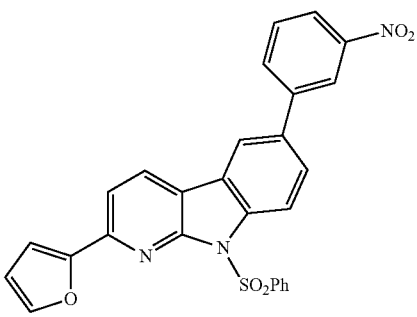

9-benzenesulfonyl-2-(furan-2-yl)-6-(3-nitrophenyl)-9H-pyrido[2,3-b]indole (44)

The crude product was purified by flash chromatography (CH$_2$Cl$_2$/PE 6:4) to afford 44 in 81% yield as a white solid; $^1$H-NMR (300 MHz, CDCl$_3$): δ 8.59 (d, 1H, J=8.6 Hz), 8.53 (m, 1H), 8.28-8.21 (m, 4H), 8.12 (d, 1H, J=1.9 Hz), 8.00 (dd, 1H, J=16 Hz), 7.78 (dd, J=1.0, 7.7 Hz), 7.78 (dd, 1H, J=1.9, 8.6 Hz), 7.72 (d, 1H, J=8.1 Hz), 7.66 (t, 1H, J=7.9 Hz), 7.57-7.51 (m, 2H), 7.46 (d, 1H, J=8.1 Hz), 7.43 (d, 1H, J=8.5 Hz), 7.26 (d, 1H, J=5.6 Hz), 6.61 (dd, 1H, J=1.7, 3.4 Hz).

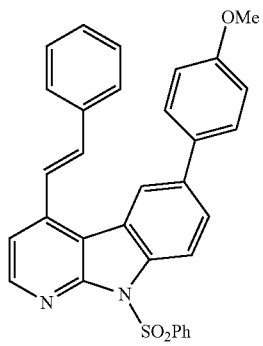

9-benzenesulfonyl-6-(4-methoxyphenyl)-4-(2'-phenylethenyl)-9H-pyrido[2,3-b]indole (45)

The crude product was purified by flash chromatography (CH$_2$Cl$_2$/PE 7:3) to afford 45 in 87% yield as a yellow solid; mp 190-192° C. (CH$_2$Cl$_2$/PE); IR: 3073, 2838, 1633, 1607, 1587, 1517, 1462, 1443, 1377, 1179, 1047, 810, 728, 688 cm$^{-1}$; $^1$H-NMR (300 MHz, CDCl$_3$): δ 8.59 (d, 1H, J=8.7 Hz), 8.52 (d, 1H, J=5.1 Hz), 8.23 (d, 1H, J=1.7 Hz), 8.20-8.17 (m, 2H), 7.84 (d, 1H, J=16.2 Hz), 7.75 (dd, 1H, J=1.8, 8.7 Hz), 7.62-7.57 (m, 4H), 7.55-7.50 (m, 1H), 7.45-7.36 (m, 5H), 7.35 (d, 1H, J=16.2 Hz), 7.02 (d, 2H, J=8.9 Hz), 3.88 (s, 3H); $^{13}$C-NMR (75 MHz, CDCl$_3$): δ 162.4 (C), 159.4 (C), 146.7 (CH), 141.6 (C), 138.9 (C), 137.1 (C), 136.8 (C), 136.2 (C), 135.8 (CH), 134.0 (CH), 133.5 (C), 129.2 (3 CH), 129.0 (2 CH), 128.4 (2 CH), 127.7 (2 CH), 127.3 (2 CH), 127.1 (CH), 124.0 (C), 123.4 (CH), 121.2 (CH), 116.0 (CH), 115.9 (C), 115.3 (CH), 114.6 (2 CH), 55.5 (CH$_3$); MS (ESI) m/z 517.1 [M+H$^+$], 1055.0 [2M+Na$^+$]; HRMS (EI): Calcd for C$_{31}$H$_{24}$N$_2$O$_3$S: 517.1586. Found: 517.1585.

The following compounds can be prepared by the same method:

9-benzensulfonyl-2-aryl-6-(4-methoxyphenyl)-9H-pyrido[2,3-b]indole
where aryl is chosen from: (3-nitrophenyl), (phenylphenyl), (4-(morpholin-4-yl)methylphenyl), (5-morpholin-4-yl-pyridin-2-yl), (2-furyl), (1H-pyrrol-2-yl)

9-benzensulfonyl-2-aryl-6-(3-nitrophenyl)-9H-pyrido[2,3-b]indole
where aryl is chosen from: (4-methoxyphenyl), (phenylphenyl), (4-(morpholin-4-yl)methylphenyl), (5-morpholin-4-yl-pyridin-2-yl), (1H-pyrrol-2-yl)

9-benzensulfonyl-2-aryl-6-(2-furyl)-9H-pyrido[2,3-b]indole
where aryl is chosen from: (4-methoxyphenyl), (3-nitrophenyl), (phenylphenyl), (4-(morpholin-4-yl)methylphenyl), (5-morpholin-4-yl-pyridin-2'-yl), (1H-pyrrol-2-yl)

9-benzensulfonyl-2-aryl-6-(4-phenylphenyl)-9H-pyrido[2,3-b]indole
where aryl is chosen from: (4-methoxyphenyl), (3-nitrophenyl), (4-(morpholin-4-yl)methylphenyl), (5-morpholin-4-yl-pyridin-2-yl), (2-furyl), (1H-pyrrol-2-yl)

9-benzensulfonyl-2-aryl-6-(4-(morpholin-4-yl)methylphenyl)-9H-pyrido[2,3-b]indole
where aryl is chosen from: (4-methoxyphenyl), (3-nitrophenyl), (phenylphenyl), (5-morpholin-4-yl-pyridin-2-yl), (2-furyl), (1H-pyrrol-2-yl)

9-benzensulfonyl-2-aryl-6-(5-morpholin-4-yl-pyridin-2-yl)-9H-pyrido[2,3-b]indole
where aryl is chosen from: (4-methoxyphenyl), (3-nitrophenyl), (4-(morpholin-4-yl)methylphenyl), (phenylphenyl), (2-furyl), (1H-pyrrol-2-yl)

9-benzensulfonyl-2-aryl-6-(2-phenylethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

9-benzensulfonyl-2-aryl-6-(2-(4-methoxyphenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

9-benzensulfonyl-2-aryl-6-(2'-(3-fluorophenyl)ethenyl)-9H-pyrido[2,3-b]indole
where aryl is chosen from: (4-methoxyphenyl), (3-nitrophenyl), (4-(morpholin-4-yl)methylphenyl), 1-phenyl), (5-morpholin-4-yl-pyridin-2-yl), (2-furyl), (1H-pyrrol-2-yl)

9-benzensulfonyl-4-aryl-6-(4-methoxyphenyl)-9H-pyrido[2,3-b]indole
where aryl is chosen from: (3-nitrophenyl), (phenylphenyl), (4-(morpholin-4-yl)methylphenyl), (5-morpholin-4-yl-pyridin-2-yl), (2-furyl), (1H-pyrrol-2-yl)

9-benzensulfonyl-4-aryl-6-(3-nitrophenyl)-9H-pyrido[2,3-b]indole
where aryl is chosen from: (4-methoxyphenyl)), (phenylphenyl), (4-(morpholin-4-yl)methylphenyl), (5-morpholin-4-yl-pyridin-2-yl), (2-furyl), (1H-pyrrol-2-yl)

9-benzensulfonyl-4-aryl-6-(2-furyl)-9H-pyrido[2,3-b]indole
where aryl is chosen from: (4-methoxyphenyl), (3-nitrophenyl), (phenyl)phenyl), (4-(morpholin-4-yl)methylphenyl), (5-morpholin-4-yl-pyridin-2-yl), (2-furyl), (1H-pyrrol-2-yl)

9-benzensulfonyl-4-aryl-6-(4-phenylphenyl)-9H-pyrido[2,3-b]indole
where aryl is chosen from: (4-methoxyphenyl), (3-nitrophenyl), (4-(morpholin-4-yl)methylphenyl), (5-morpholin-4-yl-pyridin-2-yl), (2-furyl), (1H-pyrrol-2-yl)

9-benzensulfonyl-4-aryl-6-(4-(morpholin-4-yl)methylphenyl)-9H-pyrido[2,3-b]indole
where aryl is chosen from: (4-methoxyphenyl), (3-nitrophenyl), (phenylphenyl), (5-morpholin-4-yl-pyridin-2-yl), (2-furyl), (1H-pyrrol-2-yl)

9-benzensulfonyl-4-aryl-6-(5-morpholin-4-yl-pyridin-2-yl)-9H-pyrido[2,3-b]indole
where aryl is chosen from: (4-methoxyphenyl), (3-nitrophenyl), (4-(morpholin-4-yl)methylphenyl), (phenylphenyl), (2-furyl), (1H-pyrrol-2-yl)

9-benzensulfonyl-4-aryl-6-(2-phenylethenyl)-9H-pyrido[2,3-b]indole where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

9-benzensulfonyl-4-aryl-6-(2-(4-methoxyphenyl)ethenyl)-9H-pyrido[2,3-b]indole
where aryl is chosen from: (4-methoxyphenyl), (3-nitrophenyl), (4-(morpholin-4-yl)methy)phenyl), (phenylphenyl), (5-morpholin-4-yl-pyridin-2-yl), (2-furyl), (1H-pyrrol-2-yl)

9-benzensulfonyl-4-aryl-6-(2'-(3-fluorophenyl)ethenyl)-9H-pyrido[2,3-b]indole where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
2-aryl-6-(4-methoxyphenyl)-9H-pyrido[2,3-b]indole where aryl is chosen from: (3-nitrophenyl), (phenylphenyl), (4-(morpholin-4-yl)methylphenyl), (5-morpholin-4-yl-pyridin-2-yl), (2-furyl), (1H-pyrrol-2-yl)
2-aryl-6-(3-nitrophenyl)-9H-pyrido[2,3-b]indole
where aryl is chosen from: (4-methoxyphenyl), (phenylphenyl), (4-(morpholin-4-yl)methylphenyl), (5-morpholin-4-yl-pyridin-2-yl), (2-furyl), (1H-pyrrol-2-yl)
2-aryl-6-(2-furyl)-9H-pyrido[2,3-b]indole where aryl is chosen from: (4-methoxyphenyl), (3-nitrophenyl), (phenylphenyl), (4-(morpholin-4-yl)methylphenyl), (5-morpholin-4-yl-pyridin-2-yl), (2-furyl), (1H-pyrrol-2-yl)
2-aryl-6-(4-phenylphenyl)-9H-pyrido[2,3-b]indole
where aryl is chosen from: (4-methoxyphenyl), (3-nitrophenyl), (4-(morpholin-4-yl)methylphenyl), (5-morpholin-4-yl-pyridin-2-yl), (2-furyl), (1H-pyrrol-2-yl)
2-aryl-6-(4-(morpholin-4-yl)methylphenyl)-9H-pyrido[2,3-b]indole
where aryl is chosen from: (4-methoxyphenyl), (3-nitrophenyl), (phenylphenyl), (5-morpholin-4-yl-pyridin-2-yl), (2-furyl), (1H-pyrrol-2-yl)
2-aryl-6-(5-morpholin-4-yl-pyridin-2-yl)-9H-pyrido[2,3-b]indole
where aryl is chosen from: (4-methoxyphenyl), (3-nitrophenyl), (4-(morpholin-4-yl)methylphenyl), (phenylphenyl), (2-furyl), (1H-pyrrol-2-yl)
2-aryl-6-(2-phenylethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
2-aryl-6-(2-(4-methoxyphenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
2-aryl-6-(2'-(3-fluorophenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-aryl-6-(4-methoxyphenyl)-9H-pyrido[2,3-b]indole
where aryl is chosen from: (3-nitrophenyl), (phenylphenyl), (4-(morpholin-4-yl)methylphenyl), (5-morpholin-4-yl-pyridin-2-yl), (2-furyl), (1H-pyrrol-2-yl)
4-aryl-6-(3-nitrophenyl)-9H-pyrido[2,3-b]indole
where aryl is chosen from: (4-methoxyphenyl), (phenylphenyl), (4-(morpholin-4-yl)methylphenyl), (5-morpholin-4-yl-pyridin-2-yl), (2-furyl), (1H-pyrrol-2-yl)
4-aryl-6-(2-furyl)-9H-pyrido[2,3-b]indole
where aryl is chosen i from: (4-methoxyphenyl), (3-nitrophenyl), (phenylphenyl), (4-(morpholin-4-yl)methylphenyl), (5-morpholin-4-yl-pyridin-2-yl), (2-furyl), (1H-pyrrol-2-yl)
4-aryl-6-(4-phenylphenyl)-9H-pyrido[2,3-b]indole
where aryl is chosen from: (4-methoxyphenyl), (3-nitrophenyl), (4-(morpholin-4-yl)methylphenyl), (5-morpholin-4-yl-pyridin-2-yl), (2-furyl), (1H-pyrrol-2-yl)
4-aryl-6-(4-(morpholin-4-yl)methylphenyl)-9H-pyrido[2,3-b]indole
where aryl is chosen from: (4-methoxyphenyl), (3-nitrophenyl), (phenylphenyl), (5-morpholin-4-yl-pyridin-2-yl), (2-furyl), (1H-pyrrol-2-yl)
4-aryl-6-(5-morpholin-4-yl-pyridin-2-yl)-9H-pyrido[2,3-b]indole
where aryl is chosen from: (4-methoxyphenyl), (3-nitrophenyl), (4-(morpholin-4-yl)methylphenyl), (phenylphenyl), (2-furyl), (1H-pyrrol-2-yl)
4-aryl-6-(2-phenylethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-aryl-6-(2-(4-methoxyphenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-aryl-6-(2'-(3-fluorophenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-(2-aryl-9H-pyrido[2,3-b]indol-6-yl)-4-oxo-butyric acid
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-(4-aryl-9H-pyrido[2,3-b]indol-6-yl)-4-oxo-butyric acid
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
1-(2-aryl-9H-pyrido[2,3-b]indol-6-yl)-4-(4-methylpiperazin-1-yl)butane-1,4-dione
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
1-(4-aryl-9H-pyrid)[2,3-b]indol-6-yl)-4-(4-methylpiperazin-1-yl)butane-1,4-dione
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-(2-aryl-9H-pyrido[2,3-b]indol-6-yl)-N-(4-methoxybenzyl)-4-oxobutyramide
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
4-(4-aryl-9H-pyrido[2,3-b]indol-6-yl)-N-(4-methoxybenzyl)-4-oxobutyramide
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
3-(4-(2-aryl-9H-pyrido[2,3-b]indol-6-yl)phenoxy)-N,N-dimethylpropan-1-amine
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)
3-(4-(4-aryl-9H-pyrido[2,3-b]indol-6-yl)phenoxy)-N,N-dimethylpropan-1-amine where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

3-(4-(2-aryl-9H-pyrido[2,3-b]indol-6-yl)phenoxy)-N,N-diethylpropan-1-amine
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

3-(4-(4-aryl-9H-pyrido[2,3-b]indol-6-yl)phenoxy)-N,N-diethylpropan-1-amine
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

2-aryl-6-(4-(2-(4-methylpiperazin-1-yl)ethoxy)phenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

4-aryl-6-(4-(2-(4-methylpiperazin-1-yl)ethoxy)phenyl)-9H-pyrido[2,3-b]indole
where aryl is chosen from: (4-methoxyphenyl), (3-nitrophenyl), (4-(morpholin-4-yl)methylphenyl), (phenylphenyl), (5-morpholin-4-yl-pyridin-2-yl), (2-furyl), (1H-pyrrol-2-yl)

9-benzensulfonyl-2-(2-arylethenyl)-6-(4-methoxyphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(4-methoxyphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 2-(2-arylethenyl)-6-(4-methoxyphenyl)-9H-pyrido[2,3-b]indole where arylethenyl is chosen from:
(2-(4-methoxyphenyl)ethenyl), (2'-(3-fluorophenyl)ethenyl), or 2-phenylethenyl 4-(2-arylethenyl)-6-(4-methoxyphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
(2-(4-methoxyphenyl)ethenyl), (2'-(3-fluorophenyl)ethenyl), or 2-phenylethenyl
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(3-nitrophenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(3-nitrophenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(2-furyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(2-furyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(4-phenylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(4-phenylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(4-(morpholin-4-yl)methylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(4-(morpholin-4-yl)methylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(5-morpholin-4-yl-pyridin-2-yl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(5-morpholin-4-yl-pyridin-2-yl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(2-phenylethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(2-phenylethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl)

9-benzensulfonyl-2-(2-arylethenyl)-6-(2-(4-methoxyphenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(2-(4-methoxyphenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-2-(2-arylethenyl)-6-(2'-(3-fluorophenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 9-benzensulfonyl-4-(2-arylethenyl)-6-(2'-(3-fluorophenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl 2-(2-arylethenyl)-6-(3-nitrophenyl)-9H-pyrido[2,3-b]indole
where arylethenyl is chosen from:

4-(2-arylethenyl)-6-(3-nitrophenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
2-(2-arylethenyl)-6-(2-furyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-arylethenyl)-6-(2-furyl)-9H-pyrido[2,3-b]indole
where arylethenyl is chosen from:
(2-(4-methoxyphenyl)ethenyl), (2'-(3-fluorophenyl)ethenyl), or 2-phenylethenyl
2-(2-arylethenyl)-6-(4-phenylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-arylethenyl)-6-(4-phenyl)phenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
2-(2-arylethenyl)-6-(4-(morpholin-4-yl)methylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-arylethenyl)-6-(4-(morpholin-4-yl)methylphenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
2-(2-arylethenyl)-6-(5-morpholin-4-yl-pyridin-2-yl)-9H-pyrido[2,3-b]indole
where arylethenyl is chosen from:
(2-(4-methoxyphenyl)ethenyl), (2'-(3-fluorophenyl)ethenyl), or 2-phenylethenyl)
4-(2-arylethenyl)-6-(5-morpholin-4-yl-pyridin-2-yl)-9H-pyrido[2,3-b]indole
where arylethenyl is chosen from:
(2-(4-methoxyphenyl)ethenyl), (2'-(3-fluorophenyl)ethenyl), or 2-phenylethenyl
2-(2-arylethenyl)-6-(2-phenylethenyl)-9H-pyrido[2,3-b]indole
where arylethenyl is chosen from:
(2-(4-methoxyphenyl)ethenyl), (2'-(3-fluorophenyl)ethenyl or 2-phenylethenyl
4-(2-arylethenyl)-6-(2-phenylethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
2-(2-arylethenyl)-6-(2-(4-methoxyphenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-(2-arylethenyl)-6-(2-(4-methoxyphenyl)ethenyl)-9H-pyrido[2,3-b]indole
where arylethenyl is chosen from:
(2-(4-methoxyphenyl))ethenyl), (2'-(3-fluorophenyl)ethenyl), or 2-phenylethenyl
2-(2-arylethenyl)-6-(2'-(3-fluorophenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-arylethenyl)-6-(2'-(3-fluorophenyl)ethenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-(2-arylethenyl)-9H-pyrido[2,3-b]indol-6-yl)-4-oxo-butyric acid
where arylethenyl is chosen from:
(2-(4-methoxyphenyl)ethenyl), (2'-(3-fluorophenyl)ethenyl), or 2-phenylethenyl
4-(4-(2-arylethenyl)-9H-pyrido[2,3-b]indol-6-yl)-4-oxo-butyric acid
where arylethenyl is chosen from:
(2-(4-methoxyphenyl)ethenyl), (2'-(3-fluorophenyl)ethenyl), or 2-phenylethenyl
1-(2-(2-arylethenyl)-9H-pyrido[2,3-b]indol-6-yl)-4-(4-methylpiperazin-1-yl)butane-1,4-dione
where arylethenyl is chosen from:
(2-(4-methoxyphenyl)ethenyl), (2'-(3-fluorophenyl)ethenyl), or 2-phenylethenyl
1-(4-(2-arylethenyl)-9H-pyrido[2,3-b]indol-6-yl)-4-(4-methylpiperazin-1-yl) butane-1,4-dione
where arylethenyl is chosen from:
(2-(4-methoxyphenyl)ethenyl), (2'-(3-fluorophenyl)ethenyl), or 2-phenylethenyl
4-(2-(2-arylethenyl)-9H-pyrido[2,3-b]indol-6-yl)-N-(4-methoxybenzyl)-4-oxobutyramide
where arylethenyl is chosen from:
(2-(4-methoxyphenyl)ethenyl), (2'-(3-fluorophenyl)ethenyl), or 2-phenylethenyl
4-(4-(2-arylethenyl)-9H-pyrido[2,3-b]indol-6-yl)-N-(4-methoxybenzyl)-4-oxobutyramide
where arylethenyl is chosen from:
(2-(4-methoxyphenyl)ethenyl), (2'-(3-fluorophenyl)ethenyl), or 2-phenylethenyl
3-(4-(2-(2-arylethenyl)-9H-pyrido[2,3-b]indol-6-yl)phenoxy)-N,N-dimethylpropan-1-amine
where arylethenyl is chosen from:
(2-(4-methoxyphenyl)ethenyl), (2'-(3-fluorophenyl)ethenyl), or 2-phenylethenyl
3-(4-(4-(2-arylethenyl)-9H-pyrido[2,3-b]indol-6-yl)phenoxy)-N,N-dimethylpropan-1-amine
where arylethenyl is chosen from:
(2-(4-methoxyphenyl)ethenyl), (2'-(3-fluorophenyl)ethenyl), or 2-phenylethenyl
3-(4-(2-(2-arylethenyl)-9H-pyrido[2,3-b]indol-6-yl)phenoxy)-N,N-diethylpropan-1-amine
where arylethenyl is chosen from:
(2-(4-methoxyphenyl)ethenyl), (2'-(3-fluorophenyl)ethenyl), or 2-phenylethenyl
3-(4-(4-(2-arylethenyl)-9H-pyrido[2,3-b]indol-6-yl)phenoxy)-N,N-diethylpropan-1-amine
where arylethenyl is chosen from:
(2-(4-methoxyphenyl)ethenyl), (2'-(3-fluorophenyl)ethenyl), or 2-phenyl)ethenyl
2-(2-arylethenyl)-6-(4-(2-(4-methylpiperazin-1-yl)ethoxy)phenyl)-9H-pyrido[2,3-b]indole
where arylethenyl is chosen from:
(2-(4-methoxyphenyl)ethenyl), (2'-(3-fluorophenyl)ethenyl), or 2-phenylethenyl
4-(2-arylethenyl)-6-(4-(2-(4-methy)piperazin-1-yl)ethoxy)phenyl)-9H-pyrido[2,3-b]indole
where arylethenyl is chosen from:
(2-(4-methoxyphenyl)ethenyl), (2'-(3-fluorophenyl)ethenyl), or 2-phenylethenyl

Typical Procedure Suzuki-Miyaura on 6-substituted 3-chloropyrido[2,3-b]indoles

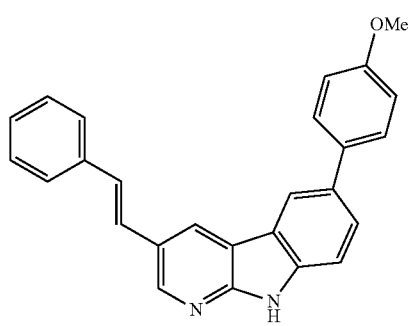

6-(4-methoxyphenyl)-3-(2'-phenylethenyl)-9H-pyrido[2,3-b]indole (R315)

In sealed pressure tube and stir bar was charged Pd(OAc)$_2$ (5 mg, 0.08 equiv.), 2-dicyclohexylphosphino-2',6'-dimethoxyphenyl 1 (18 mg, 0.16 equiv.), a-carbolines (83 mg, 0.267 mmol), trans vinyl phenyl boronic acid (119 mg, 3.0 equiv.) and K$_3$PO$_4$ (142 mg, 2.5 equiv.). The tube was evacuated and back-filled with argon (this was repeated three additional times). 700 µl of anhydrous 1,4-dioxane was added (when degassed solvent was used) and the reaction mixture was allowed to stir at 100° C. overnight. After cooling to room temperature, the products were extracted from the water layer with ethyl acetate, dried over MgSO$_4$, filtered through celite and solvents were removed under reduced pressure. The crude product was purified by flash chromatography (CH$_2$Cl$_2$/EtOAc 9:1) to afford R315 in 65% yield as a white solid; mp>220° C. (MeOH); IR: 3060, 2994, 2833, 1606, 1517, 1485, 1460, 1232, 957, 813, 740, 692 cm$^{-1}$; $^1$H-NMR (300 MHz, DMSO-d$_6$): δ 11.86 (bs, 1H), 8.95 (d, 1H, J=2.1 Hz), 8.61 (d, 1H, J=2.1 Hz), 8.47 (d, 1H, J=1.3 Hz), 7.74 (dd, 1H, J=1.9, 8.5 Hz), 7.71 (d, 214, J=8.9 Hz), 7.63 (d, 2H, J=7.1 Hz), 7.54 (d, 1H, J=8.5 Hz), 7.46 (d, 1H, J=16.4 Hz), 7.43-7.39 (m, 2H), 7.37 (d, 1H, J=16.4 Hz), 7.27 (t, 1H, J=7.4 Hz), 7.07 (d, 2H, J=8.9 Hz), 3.82 (s, 3H); $^{13}$C-NMR (75 MHz, DMSO-d$_6$): δ 158.4 (C), 152.0 (C), 146.5 (CH), 138.5 (C), 137.4 (C), 133.4 (C), 131.9 (C), 128.8 (2 CH), 127.7 (2 CH), 127.4 (CH), 126.8 (CH), 126.3 (CH), 126.2 (2 CH), 125.6 (CH), 124.9 (CH), 127.8 (C), 121.1 (C), 118.9 (CH), 115.8 (C), 114.4 (2 CH), 111.7 (CH), 55.2 (CH$_3$); MS (ESI) m/z 377.3 [M+H$^+$]; HRMS (ESI): Calcd for C$_{26}$H$_{20}$N$_2$O: 377.1654. Found: 377.1653.

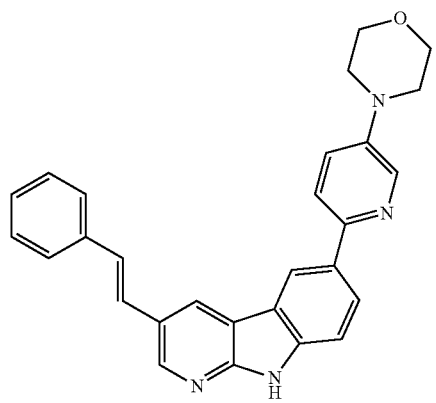

6-(5-morpholin-4-yl-pyridin-2-yl)-3-(2'-phenylethenyl)-9H-pyrido[2,3-b]indole (R307)

In sealed pressure tube and stir bar was charged Pd(OAc)$_2$ (2.5 mg, 0.08 equiv.), 2-dicyclohexylphosphino-2',6'-dimethoxyphenyl 1 (9 mg, 0.16 equiv.), α-carbolines (50 mg, 0.137 mmol), trans vinyl phenyl boronic acid (41 mg, 3 equiv.) and K$_3$PO$_4$ (117 mg, 4 equiv.). The tube was evacuated and back-filled with argon (this was repeated three additional times). 200 µL of anhydrous 1,4-dioxane was added (when degassed solvent was used) and the reaction mixture was allowed to stir at 100° C. overnight. After cooling to room temperature, the products were extracted from H$_2$O layer with EtOAc, dried over MgSO$_4$, filtered through celite and solvents were removed under reduced pressure. The crude product was purified by flash chromatography (eluent: EtOAc/PE 1:1 to EtOAc) to afford R307 in 72% yield as a yellow solid; $^1$H-NMR (300 MHz, DMSO-d$_6$): δ 11.89 (bs, 1H), 8.92 (d, 1H, 2.1 Hz), 8.63 (d, 1H, J=2.1 Hz), 8.57 (d, 1H, J=2.5 Hz), 8.49 (bs, 1H), 7.99 (dd, 1H, J=2.5, 8.9 Hz), 7.74 (dd, 1H, J=1.9, 8.5 Hz), 7.64 (d, 2H, J=7.6 Hz), 7.55 (d, 1H, J=8.5 Hz), 7.46 (d, 1H, J=16.4 Hz), 7.43-7.39 (m, 2H), 7.36 (d, 1H, J=16.4 Hz), 7.30-7.25 (m, 1H), 6.98 (d, 1H, J=8.9 Hz), 3.76-3.73 (m, 4H), 3.52-3.49 (m, 4H); $^{13}$C-NMR (75 MHz, DMSO-d$_6$): δ 158.1 (C), 152.0 (C), 146.5 (CH), 145.3 (C), 138.5 (C), 137.3 (C) 135.7 (CH), 129.4 (C), 128.8 (2 CH), 127.4 (CH), 126.8 (CH), 126.4 (CH), 126.3 (C), 126.2 (2 CH), 125.1 (CH), 124.9 (CH), 124.7 (C), 121.2 (C), 118.5 (CH), 115.7 (C), 111.9 (CH), 107.1 (CH), 66.2 (2 CH$_2$), 45.3 (2 CH$_2$); MS (ESI) m/z 433.3 [M+H$^+$]; HRMS (ESI): Calcd for C$_{28}$H$_{24}$N$_4$O: 433.2028. Found: 433.2029.

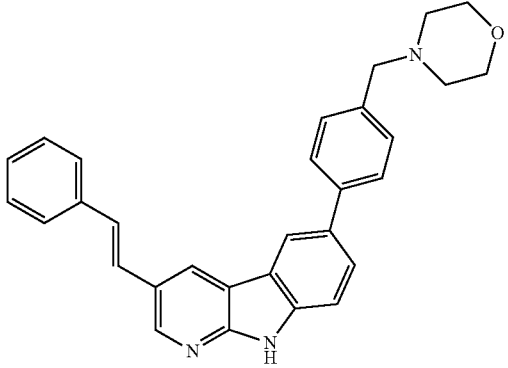

6-(4-(morpholin-4-yl)methylphenyl)-3-(2'-phenylethenyl)-9H-pyrido[2,3-b]indole (R314)

In sealed pressure tube and stir bar was charged Pd(OAc)$_2$ (0.08 equiv., 2 mg, 0.08 mmol), 2-dicyclohexylphosphino-2',6'-dimethoxyphenyl 1 (0.16 equiv., 7 mg, 0.16 mmol), R313 (40 mg, 0.106 mmol), trans vinyl phenyl boronic acid (3 equiv., 48 mg, 0.318 mmol) and K$_3$PO$_4$ (4 equiv., 90 mg, 0.424 mmol). The tube was evacuated and back-filled with argon (this was repeated three additional times). 270 µL of anhydrous 1,4-dioxane was added (when degassed solvent was used) and the reaction mixture was allowed to stir at 100° C. overnight. After cooling to room temperature, the products were extracted from the water layer with EtOAc, dried over MgSO$_4$, filtered through celite and solvents were removed under reduced pressure. The crude product was purified by flash chromatography (EtOAc) to afford R314 in 72% yield as a yellow solid; ¹H-NMR (300 MHz, DMSO-d₆): δ 11.91 (bs, 1H), 8.95 (d, 1H, J=2.1 Hz), 8.63 (d, 1H, J=2.1 Hz), 8.54 (d, 1H, J=1.3 Hz), 7.80 (dd, 1H, J=1.9, 8.7 Hz), 7.73 (d, 2H, J=8.5 Hz), 7.63 (d, 2H, J=7.4 Hz), 7.57 (d, 2H, J=8.4 Hz), 7.46 (d, 1H, J=16.0 Hz), 7.39 (d, 1H, J=16.0 Hz), 7.44-7.39 (m, 3H), 7.29 (m, 1H), 3.60 (bs, 4H), 3.52 (s, 2H), 2.40 (bs, 4H); ¹³C-NMR (75 MHz, DMSO-d₆): δ 152.0 (C), 146.5 (CH), 139.7 (C), 138.9 (C), 137.3 (C), 136.2 (C) 131.8 (C), 129.6 (2 CH), 128.8 (2 CH), 127.4 (CH), 126.8 (CH), 126.4 (2 CH), 126.3 (CH), 126.2 (2 CH), 125.8 (CH), 124.9 (CH), 124.8 (C), 121.1 (C), 119.4 (CH), 115.7 (C), 111.8 (CH), 66.2 (2 CH), 62.1 (CH₂), 53.2 (2 CH₂); MS (ESI) m/z 446 [M+H⁺]

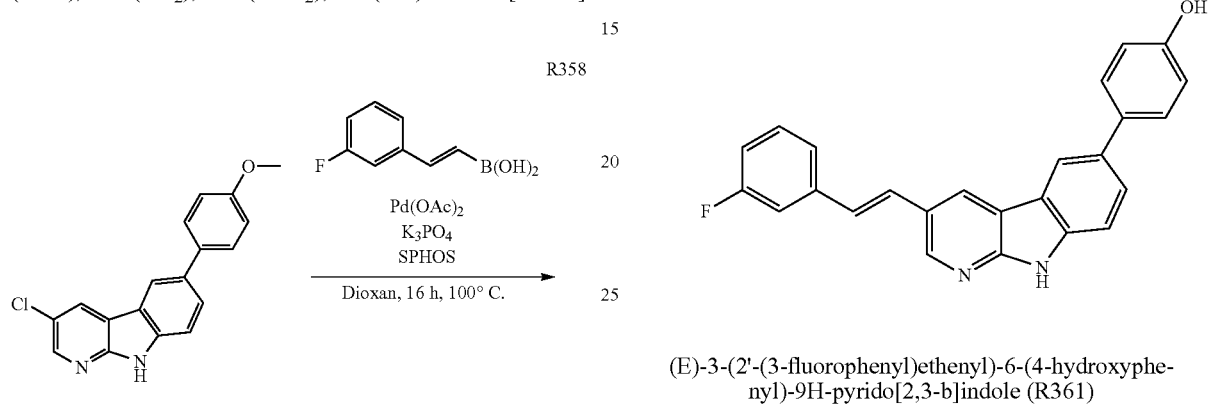

R358

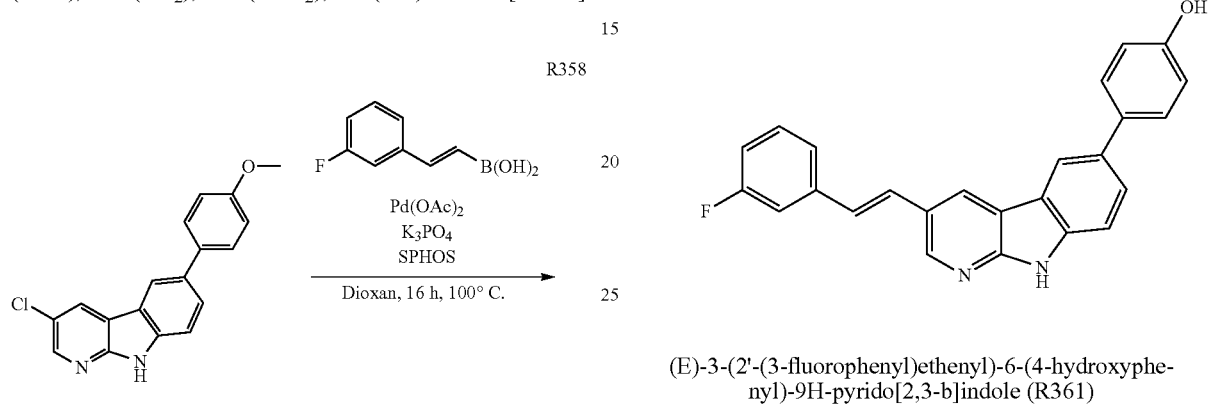

(E)-3-(2'-(3-fluorophenyl)ethenyl)-6-(4-methoxyphenyl)-9H-pyrido[2,3-b]indole (R358)

3-chloro-6-(4-methoxyphenyl)-9H-pyrido[2,3-b]indole (50 mg, 0.16 mmol, 1 equiv.), (E)-2'-(3-fluorophenyl)ethenylboronic acid (80 mg, 0.48 mmol, 3 equiv.), K₃PO₄ (136 mg, 0.64 mmol, 4 equiv.), S-PHOS (13.1 mg, 0.032 mmol, 0.2 equiv.), Pd(OAc)₂ (3.6 mg, 0.016 mmol, 0.1 equiv.) are introduced in a schlenk tube which is flushed with N₂. Freshly distilled dioxan (0.433 ml) is then injected and the reaction is carried out at 100° C. overnight. The mixture is filtered through celite and concentrated under reduced pressure. The crude product is purified over silica gel chromatography (eluant CH₂Cl₂/AcOEt 9:1). The slightly yellow solid obtained is washed with methanol to give the product as a white solid (51 mg, 0.13 mmol) in 81% yield. ¹H NMR (300 MHz, DMSO-d₆) δ 11.91 (br s, 1H), 8.94 (d, 1H, J=1.5 Hz), 8.62 (d, 1H, J=1.9 Hz), 8.47 (s, 1H), 7.75-7.68 (m, 3H), 7.57-7.36 (m, 6H), 7.10-7.05 (m, 3H), 3.82 (s, 3H).

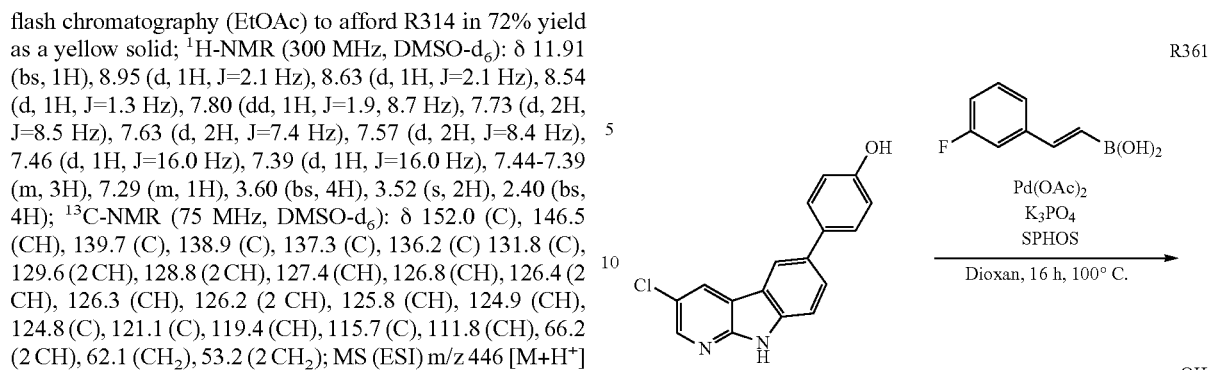

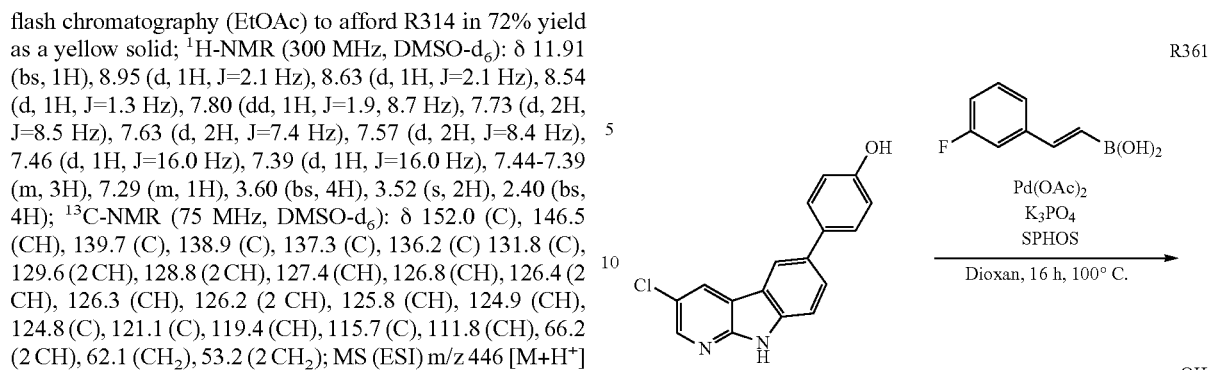

(E)-3-(2'-(3-fluorophenyl)ethenyl)-6-(4-hydroxyphenyl)-9H-pyrido[2,3-b]indole (R361)

¹H NMR (300 MHz, DMSO-d₆) δ 11.91 (br s, 1H), 8.94 (d, 1H, J=1.5 Hz), 8.62 (d, 1H, J=1.9 Hz), 8.47 (s, 1H), 7.75-7.68 (m, 3H), 7.57-7.36 (m, 6H), 7.10-7.05 (m, 3H).

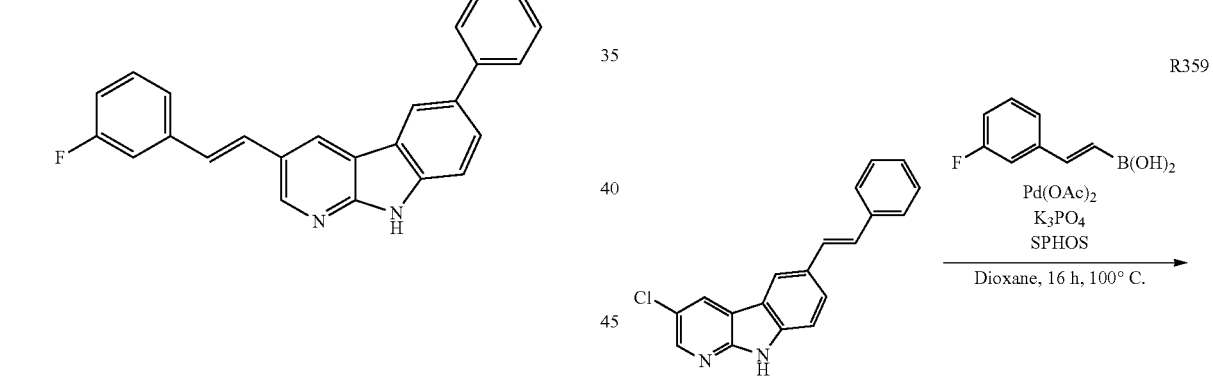

R359

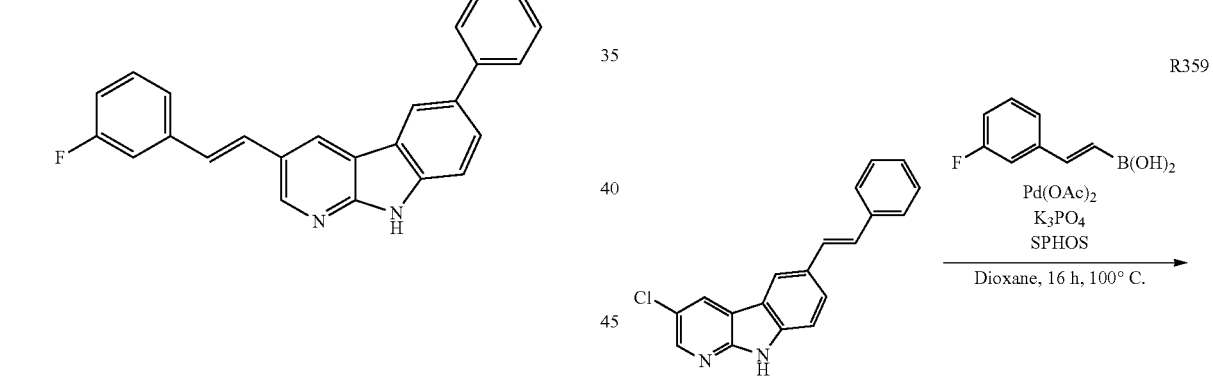

3-((E)-2'-(3-fluorophenyl)ethenyl)-6-(E)-(2-(phenyl)ethenyl)-9H-pyrido[2,3-b]indole (R359)

(E)-3-chloro-6-(2-(phenyl)ethenyl)-9H-pyrido[2,3-b]indole (50 mg, 0.16 mmol, 1 equiv.), (E)-2'-(3-fluorophenyl)ethenylboronic acid (81 mg, 0.49 mmol, 3 equiv.), K₃PO₄ (136 mg, 0.64 mmol, 4 equiv.), S-PHOS (13.1 mg, 0.032 mmol, 0.2 equiv.), Pd(OAc)₂ (4.0 mg, 0.016 mmol, 0.1 equiv.) are introduced in a schlenk tube which is flushed with N₂. Freshly distilled dioxane (0.433 ml) is then injected and the reaction is carried out at 100° C. overnight. The mixture is filtered through celite and concentrated under reduced pressure. The crude product is purified over silica gel chromatography (eluant CH₂Cl₂/AcOEt 6:4). The white solid obtained is washed with methanol to give the product as a white solid (44 mg, 0.11 mmol) in 69% yield.

¹H NMR (300 MHz, DMSO-d₆) δ 11.98 (br s, 1H), 8.87 (s, 1H), 8.65 (s, 1H), 8.45 (s, 1H), 7.77-7.10 (m, 15H); ¹³C NMR (75 MHz, DMSO-d₆) δ 164.3 (C), 161.1 (C), 152.1 (C), 146.6 (CH), 140.1 (C), 139.2 (C), 137.5 (C), 130.7 (CH), 129.2 (CH), 128.7 (2×CH), 128.0 (CH), 127.2 (CH), 126.2 (2×CH), 126.1 (CH), 126.0 (CH), 125.6 (CH), 125.1 (CH), 124.6 (C), 122.7 (CH), 120.9 (C), 119.3 (CH), 115.6 (C), 114.1 (CH), 112.3 (CH), 111.7 (CH).

¹H NMR (300 MHz, DMSO-d₆) δ 12.00 (br s, 1H), 9.12 (d, 1H, J=2.1 Hz), 8.88 (d, 1H, J=2.3 Hz), 8.64 (t, 1H, J=2.0 Hz), 8.59 (d, 1H, J=1.7 Hz), 8.34-8.22 (m, 2H), 7.85-7.70 (m, 4H), 7.58 (d, 1H, J=8.6 Hz), 7.07 (d, 2H, J=8.6 Hz), 3.82 (s, 3H); MS (+ESI) [M+H⁺]=396.2.

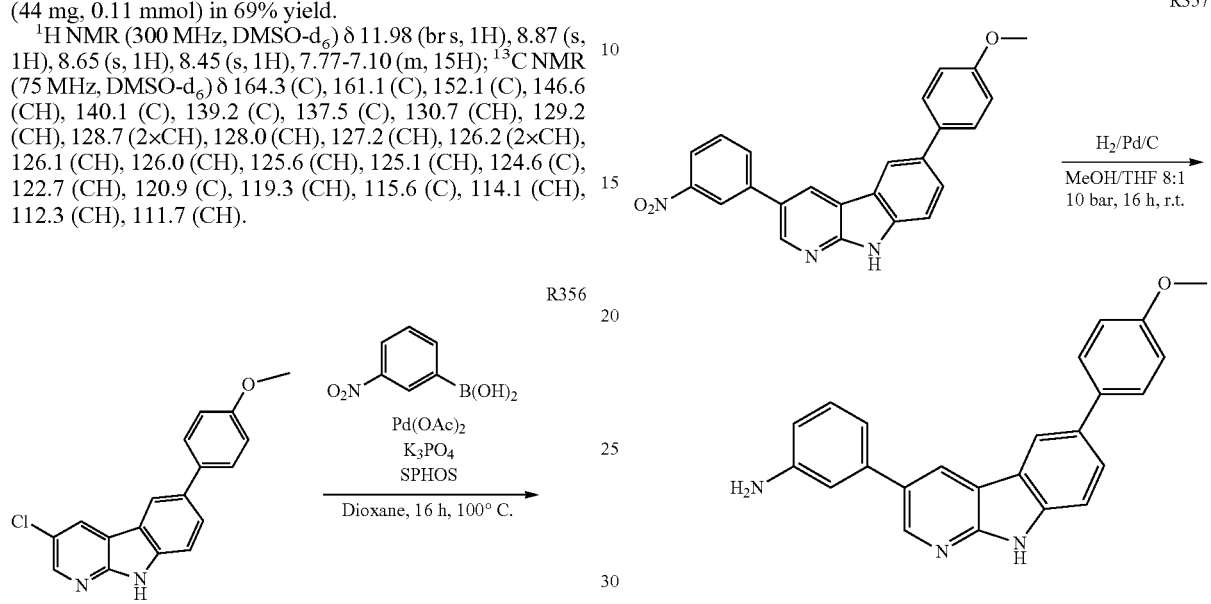

6-(4-methoxyphenyl)-3-(3-nitrophenyl)-9H-pyrido[2,3-b]indole (R356)

3-chloro-6-(4-methoxyphenyl)-9H-pyrido[2,3-b]indole (50 mg, 0.16 mmol, 1 equiv.), 3-nitrophenylboronic acid (81 mg, 0.48 mmol, 3 equiv.), K₃PO₄ (136 mg, 0.64 mmol, 4 equiv.), S-PHOS (13.1 mg, 0.032 mmol, 0.2 equiv.), Pd(OAc)₂ (4.0 mg, 0.016 mmol, 0.1 equiv.) are introduced in a schlenk tube which is flushed with N₂. Freshly distilled dioxane (0.433 ml) is then injected and the reaction is carried out at 100° C. overnight. The mixture is filtered through celite and concentrated under reduced pressure. The crude product is purified over silica gel chromatography (eluant CH₂Cl₂/AcOEt 6:4). The white solid obtained is washed with methanol to give the product as a white solid (43 mg, 0.11 mmol) in 69% yield.

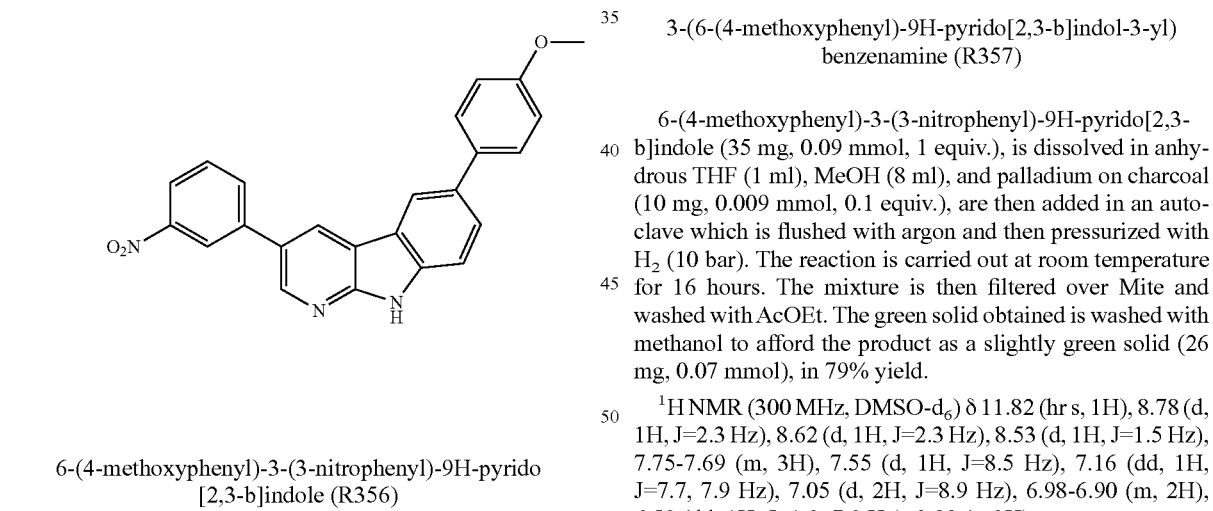

3-(6-(4-methoxyphenyl)-9H-pyrido[2,3-b]indol-3-yl)benzenamine (R357)

6-(4-methoxyphenyl)-3-(3-nitrophenyl)-9H-pyrido[2,3-b]indole (35 mg, 0.09 mmol, 1 equiv.), is dissolved in anhydrous THF (1 ml), MeOH (8 ml), and palladium on charcoal (10 mg, 0.009 mmol, 0.1 equiv.), are then added in an autoclave which is flushed with argon and then pressurized with H₂ (10 bar). The reaction is carried out at room temperature for 16 hours. The mixture is then filtered over Mite and washed with AcOEt. The green solid obtained is washed with methanol to afford the product as a slightly green solid (26 mg, 0.07 mmol), in 79% yield.

¹H NMR (300 MHz, DMSO-d₆) δ 11.82 (hr s, 1H), 8.78 (d, 1H, J=2.3 Hz), 8.62 (d, 1H, J=2.3 Hz), 8.53 (d, 1H, J=1.5 Hz), 7.75-7.69 (m, 3H), 7.55 (d, 1H, J=8.5 Hz), 7.16 (dd, 1H, J=7.7, 7.9 Hz), 7.05 (d, 2H, J=8.9 Hz), 6.98-6.90 (m, 2H), 6.59 (dd, 1H, J=1.3, 7.9 Hz), 3.82 (s, 3H).

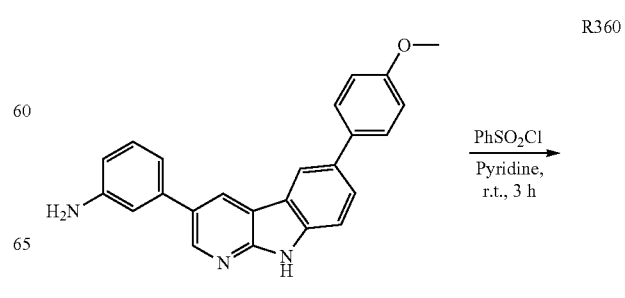

-continued

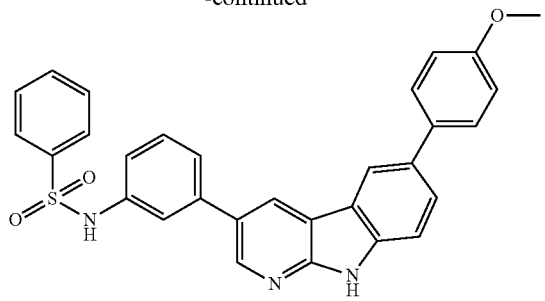

N-(3-(6-(4-methoxyphenyl)-9H-pyrido[2,3-b]indol-3-yl)phenyl)benzenesulfonamide (R360)

To a solution of 3-(6-(4-methoxyphenyl)-9H-pyrido[2,3-b]indol-3-yl)benzenamine (23 mg, 0.06 mmol, 1 equiv.), in anhydrous pyridine (0.300 ml), benzenesulfonyl chloride (0.009 ml) is added under argon. The reaction is carried out at room temperature for 3 hours and is then quenched with H₂O (5 ml). The aqueous layer is extracted with AcOEt (3×5 ml) and CH₂Cl₂ (5 ml). The organic layers are dried over MgSO₄ and concentrated under reduced pressure. The crude product is purified over silica gel chromatography (eluant CH₂Cl₂/AcOEt 7:3) to afford the product as a white solid (15 mg, 0.03 mmol) in 50% yield.

¹H NMR (300 MHz, DMSO-d₆) δ 11.98 (br s, 1H), 10.50 (br s, 1H), 8.83 (d, 1H, J=2.1 Hz), 8.60 (d, 1H, J=2.3 Hz), 8.59 (d, 1H, J=1.5 Hz), 7.92 (d, 1H, J=1.5 Hz), 7.89 (d, H, J=1.7 Hz), 7.82 (dd, 1H, J=1.9, 8.6 Hz), 7.77 (d, 1H, J=8.9 Hz), 7.70-7.67 (m, 2H), 7.62 (d, 2H, J=8.7 Hz), 7.53 (d, 1H, J=1.7 Hz), 7.52 (d, 1H, J=3.0 Hz), 7.44 (dd, 1H, J=7.9, 8.1 Hz), 7.17 (d, 1H, J=1.7 Hz), 7.13 (d, 2H, J=8.9 Hz), 3.82 (s, 3H).

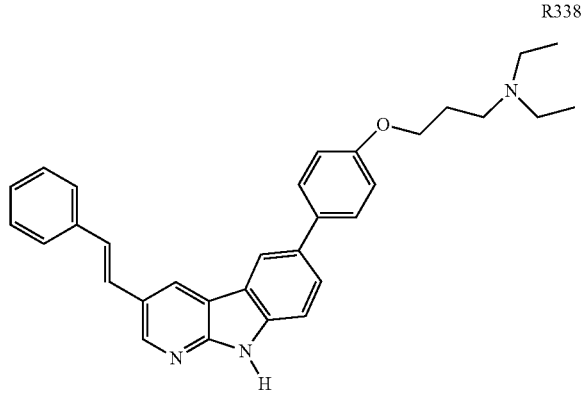 [SMILES: CCN(CC)CCCOc1ccc(-c2ccc3[nH]c4ncc(/C=C/c5ccccc5)cc4c3c2)cc1]

R338

N,N-diethyl-3-(4-(3-(2'-phenylethenyl)-9H-pyrido[2,3-b]indol-6-yl)phenoxy)propan-1-amine (R338)

To a solution of 3-(4-(3-chloro-9H-pyrido (100 mg, mmol, 1 eq) in anhydrous dioxane (50 ml), Pd(PPh₃)₄ (mg, mmol, 0.15 eq), K₂CO₃ (mg, mmol, eq), (E)-2'-(phenyl)ethenylboronic acid (mg, mmol, eq) and H₂O (ml) are respectively added under argon. The mixture is stirred at 100° C. overnight, filtered over Mite which is washed with AcOEt and THF. The crude product (brown oil) is purified over silica chromatography (eluted with CH₂Cl₂/PE 7:3) to give the product R338 as a white solid (39 mg, 0.08 mmol) with a 77% yield. ¹HNMR (CDCl₃ 300 MHz) δ ppm 8.60 (br s, 1H), 8.56 (br. s, 1H), 8.25 (br.s, 1H), 7.70 (br. d, 1H, J=8.7 Hz); 7.62 (d, 2H, J=5.9 Hz), 7.60-7.52 (m, 3H), 7.40 (br. t, 2H, J=7.1 Hz), 7.33-7.16 (3H, m), 7.01 (d, 2H, J=5.9 Hz), 4.11 (t, 2H, J=5.5 Hz), 2.75 (br. s, 6H), 2.11 (br. s, 2H), 1.17 (br. s, 6H).

The following compounds can be prepared by the same method 3-aryl-6-(4-methoxyphenyl)-9H-pyrido[2,3-b]indole
where aryl is chosen from: (4-methoxyphenyl), (3-nitrophenyl), (phenylphenyl), (4-(morpholin-4-yl)methylphenyl), (5-morpholin-4-yl-pyridin-2-yl), (2-furyl), (1H-pyrrol-2-yl), (3-aminophenyl), (3-benzenesulfonamidophenyl)

3-aryl-6-(3-nitrophenyl)-9H-pyrido[2,3-b]indole
where aryl is chosen from: (4-methoxyphenyl), (4-phenylphenyl), (4-(morpholin-4-yl)methylphenyl), (5-morpholin-4-yl-pyridin-2-yl), (2-furyl), (1H-pyrrol-2-yl), (3-aminophenyl), (3-benzenesulfonamidophenyl), (3-nitrophenyl)

2-aryl-6-(2-furyl)-9H-pyrido[2,3-b]indole
where aryl is chosen from: (4-methoxyphenyl), (3-nitrophenyl), (phenylphenyl), (4-(morpholin-4-yl)methylphenyl), (5-morpholin-4-yl-pyridin-2-yl), (2-furyl), (1H-pyrrol-2-yl), (3-aminophenyl), (3-benzenesulfonamidophenyl)

3-aryl-6-(4-phenylphenyl)-9H-pyrido[2,3-b]indole
where aryl is chosen from: (4-methoxyphenyl), (3-nitrophenyl), (4-(morpholin-4-yl)methylphenyl), (5-morpholin-4-yl-pyridin-2-yl), (2-furyl), (1H-pyrrol-2-yl), (3-aminophenyl), (3-benzenesulfonamidophenyl), (4-phenylphenyl)

3-aryl-6-(4-(morpholin-4-yl)methylphenyl)-9H-pyrido[2,3-b]indole
where aryl is chosen from: (4-methoxyphenyl), (3-nitrophenyl), (phenylphenyl), (5-morpholin-4-yl-pyridin-2-yl), (2-furyl), (1H-pyrrol-2-yl), (3-aminophenyl), (3-benzenesulfonamidophenyl), (4-(morpholin-4-yl)ethylphenyl)

3-aryl-6-(5-morpholin-4-yl-pyridin-2-yl)-9H-pyrido[2,3-b]indole
where aryl is chosen from: (4-methoxyphenyl), (3-nitrophenyl), (4-(morpholin-4-yl)methylphenyl), (phenylphenyl), (2-furyl), (5-morpholin-4-yl-pyridin-2-yl)

3-aryl-6-(2-phenylethenyl)-9H-pyrido[2,3-b]indole
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)

3-aryl-6-(2-(4-methoxyphenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl)), (5-morpholin-4-yl)-pyridin-2-yl), (2-furyl), (1H-pyrrol-2-yl), (3-aminophenyl), (3-benzenesulfonamidophenyl)

3-aryl-6-(2'-(3-fluorophenyl)ethenyl)-9H-pyrido[2,3-b]indole
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)

4-(3-aryl-9H-pyrido[2,3-b]indol-6-yl)-4-oxo-butyric acid
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)

1-(3-aryl-9H-pyrido[2,3-b]indol-6-yl)-4-(4-methylpiperazin-1-yl)butane-1,4-dione
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)

4-(3-aryl-9H-pyrido[2,3-b]indol-6-yl)-N-(4-methoxybenzyl)-4-oxobutyramide
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)), 3-(4-(3-aryl-9H-pyrido[2,3-b]indol-6-yl)phenoxy)-N,N-dimethylpropan-1-amine
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)), 3-(4-(3-aryl-9H-pyrido[2,3-b]indol-6-yl)phenoxy)-N,N-diethylpropan-1-amine
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)), 3-aryl-6-(4-(2-(4-methylpiperazin-1-yl)ethoxy)phenyl)-9H-pyrido[2,3-b]indole
where aryl is chosen from: (4-methoxyphenyl), (3-nitrophenyl), (4-(morpholin-4-yl)methylphenyl), (phenylphenyl)), (5-morpholin-4-yl-pyridin-2-yl), (2-furyl), (1H-pyrrol-2-yl), (3-aminophenyl), (3-benzenesulfonamidophenyl)), 3-(2-arylethenyl)-6-(4-methoxyphenyl)-9H-pyrido[2,3-b]indole
Where arylethenyl) is chosen from:
(2-phenylethenyl), (2-(4-methoxyphenyl)ethenyl), fluorophenyl)ethenyl)

3-(2-arylethenyl)-6-(3-nitrophenyl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

3-(2-arylethenyl)-6-(2-furyl)-9H-pyrido[2,3-b]indole
Where arylethyenyl is chosen from:
(2-phenylethenyl), (2-(4-methoxyphenyl)ethenyl), (2'-(3-fluorophenyl))ethenyl)

3-(2-arylethenyl)-6-(4-phenylphenyl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

3-(2-arylethenyl)-6-(4-(morpholin-4-yl)methylphenyl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

3-(2-arylethenyl)-6-(5-morpholin-4-yl-pyridin-2-yl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

3-(2-arylethenyl)-6-(2-phenylethenyl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

3-(2-arylethenyl)-6-(2-(4-methoxyphenyl)ethenyl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

3-(2-arylethenyl)-6-(2'-(3-fluorophenyl)ethenyl)-9H-pyrido[2,3-b]indole
Where arylethyenyl is chosen from:
(2-phenylethenyl), (2-(4-methoxyphenyl)ethenyl), (2'-(3-fluorophenyl)ethenyl)

4-(3-(2-arylethenyl)-9H-pyrido[2,3-b]indol-6-yl)-4-oxo-butyric acid
Where arylethyenyl is chosen from:
(2-phenylethenyl), (2-(4-methoxyphenyl)ethenyl), (2'-(3-fluorophenyl)ethenyl)

1-(3-(2-arylethenyl)-9H-pyrido[2,3-b]indol-6-yl)-4-(4-methylpiperazin-1-yl)butane-1,4-dione
Where arylethyenyl is chosen from:
(2-phenylethenyl), (2-(4-methoxyphenyl)ethenyl), (2'-(3-fluorophenyl)ethenyl)

4-(3-(2-arylethenyl)-9H-pyrido[2,3-b]indol-6-yl)-N-(4-methoxybenzyl)-4-oxobutyramide
Where arylethyenyl is chosen from:
(2-phenylethenyl), (2-(4-methoxyphenyl)ethenyl), (2'-(3-fluorophenyl)ethenyl)

3-(4-(3-(2-arylethenyl)-9H-pyrido[2,3-b]indol-6-yl)phenoxy)-N,N-dimethylpropan-1-amine
Where arylethyenyl is chosen from:
(2-phenylethenyl), (2-(4-methoxyphenyl))ethenyl), (2'-(3-fluorophenyl)ethenyl)

3-(4-(3-(2-arylethenyl)-9H-pyrido[2,3-b]indol-6-yl)phenoxy)-N,N-diethylpropan-1-amine
Where arylethyenyl is chosen from:
(2-phenylethenyl), (2-(4-methoxyphenyl)ethenyl), (2'-(3-fluorophenyl)ethenyl)

3-(2-arylethenyl)-6-(4-(2-(4-methylpiperazin-1-yl)ethoxy)phenyl)-9H-pyrido[2,3-b]indole
Where arylethyenyl is chosen from:
(2-phenyl)ethenyl), (2-(4-methoxyphenyl)ethenyl), (2'-(3-fluorophenyl)ethenyl)

Typical Procedure for the Buchwald Coupling with Arylamines

A solution of R296 or R297, aniline (1.2 equiv.), tris(dibenzylideneacetone)palladium (0.05 equiv.), dicyclohexylphosphino-2',4',6'-triisopropylbiphenyl (0.1 equiv.), and $K_2CO_3$ (3 equiv.) in degassed t-BuOH (1.5 mL/mmol R296 or R297) was stirred overnight at 100° C. in a sealed tube. After cooling at room temperature, the mixture was quenched with water and extracted with EtOAc. The organic layer was dried over $MgSO_4$, filtered through Celite and concentrated under reduced pressure.

C—N Coupling at C2

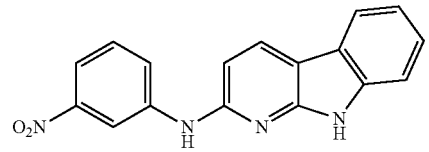

N-(3-nitrophenyl)-9H-pyrido[2,3-b]indol-2-amine (R317)

The crude product was purified by flash chromatography ($CH_2Cl_2$/PE 9:1) to afford R317 in 55% yield as a red solid; $^1$H-NMR (300 MHz, DMSO-$d_6$): δ 11.62 (bs, 1H), 9.76 (bs, 1H), 8.93 (t, 1H, J=2.3 Hz), 8.31 (d, 1H, J=8.3 Hz), 8.15 (ddd, 1H, J=0.8, 2.3, 8.2 Hz), 7.95 (d, 1H, J=7.5 Hz), 7.73 (ddd, 1H, J=0.8, 2.3, 8.2 Hz), 7.56 (t, 1H, J=8.2 Hz), 7.43 (d, 1H, J=7.9 Hz), 7.30 (td, 1H, J=1.0, 7.4 Hz), 7.15 (td, 1H, J=1.0, 7.4 Hz), 6.74 (d, 1H, J=8.3 Hz); MS (ESI) m/z 304 [M+H$^+$].

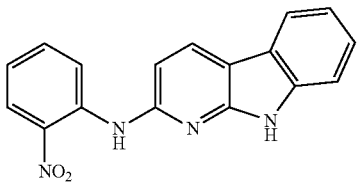

N-(2-nitrophenyl)-9H-pyrido[2,3-b]indol-2-amine (R319)

The crude product was purified by flash chromatography (CH$_2$Cl$_2$/PE 9:1) to afford R319 in 53% yield as a red solid; $^1$H-NMR (300 MHz, DMSO-d$_6$): δ 10.38 (bs, 1H), 8.87 (d, 1H, J=8.7 Hz), 8.53 (bs, 1H), 8.25 (t, 2H, J=8.5 Hz), 7.96 (d, 1H, J=7.9 Hz), 7.57 (td, 1H, J=1.5, 8.9 Hz), 7.42-7.37 (m, 3H), 6.95 (td, 1H, J=1.1, 8.5 Hz), 6.87 (d, 1H, J=8.3 Hz); MS (ESI) m/z 304 [M+H$^+$].

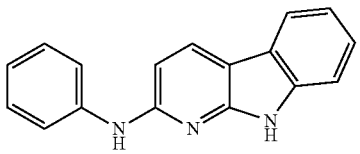

N-(phenyl)-9H-pyrido[2,3-b]indol-2-amine (R318)

Using the general procedure, R297 (100 mg, 0.498 mmol), Pd$_2$dba$_3$ (37.0 mg, 0.04 mmol, 0.08 equiv.), X-Phos (37.0 mg, 0.080 mmol, 0.16 equiv.), aniline (60 μL, 0.650 mmol, 1.3 equiv.) and LiN(TMS)$_2$ (1.5 mL, 1.0 M in THF, 3.00 mmol, 6 equiv.) were heated to 65° C. overnight. The crude material was purified by column chromatography (CH$_2$Cl$_2$) to give the desired product as a white solid (80 mg, 62%). $^1$H-NMR (300 MHz, acetone-d$_6$): δ 10.56 (bs, 1H), 8.40 (bs, 1H), 8.20 (d, 1H, J=8.5 Hz), 7.91 (d, 1H, J=7.7 Hz), 7.85 (d, 2H, 17.7 Hz), 7.48 (d, 1H, J=8.1 Hz), 7.31-7.25 (m, 3H), 7.15 (t, 1H, J=7.5 Hz), 6.92 (t, 1H, J=7.2 Hz), 6.73 (d, 1H, J=8.5 Hz); MS (ESI) m/z 258 [M+H$^+$].

C—N Coupling at C4

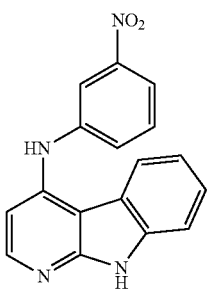

N-(3-nitrophenyl)-9H-pyrido[2,3-b]indol-4-amine (R322)

The crude product was purified by flash chromatography (CH$_2$Cl$_2$/PE 9:1) to afford R322 in 80% yield as a yellow solid; $^1$H-NMR (300 MHz, DMSO-d$_6$): δ 11.62 (bs, 1H), 9.76 (bs, 1H), 8.23 (d, 1H, J=5.5 Hz), 8.06 (t, 1H, J=2.2 Hz), 8.00 (d, 1H, J=7.4 Hz), 7.82 (ddd, 1H, J=0.8, 2.5, 8.3 Hz), 7.67 (dt, 1H, J=0.9, 7.5 Hz), 7.58 (t, 1H, J=7.9 Hz), 7.39 (td, 1H, J=1.1, 7.5 Hz), 7.15 (td, 1H, J=1.1, 7.5 Hz), 6.98 (d, 1H, J=5.5 Hz); MS (ESI) m/z 305.2 [M+H$^+$], HRMS (ESI): Calcd for C$_{17}$H$_{11}$N$_3$O$_2$: 305.1039. Found: 305.1041.

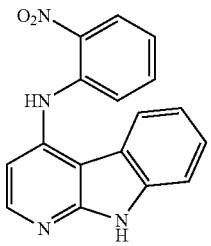

N-(2-nitrophenyl)-9H-pyrido[2,3-b]indol-4-amine (R323)

The crude product was purified by flash chromatography (CH$_2$Cl$_2$/PE 9:1) to afford R323 in 73% yield as a red solid, $^1$H-NMR (300 MHz, DMSO-d$_6$): δ 11.93 (bs, 1H), 9.71 (bs, 1H), 8.31 (d, 1H, J=5.5 Hz), 8.24 (dd, 1H, J=1.3, 8.0 Hz), 7.86 (d, 1H, J=7.9 Hz), 7.61 (td, 1H, J=1.5, 7.9 Hz), 7.53-7.40 (m, 3H), 7.19-7.10 (m, 3H); $^{13}$C-NMR (75 MHz, DMSO-d$_6$): δ 153.6 (C), 147.0 (CH), 142.2 (C), 138.3 (C), 138.2 (C), 136.6 (C), 135.8 (CH), 126.3 (CH), 125.9 (CH), 121.8 (CH), 121.0 (CH), 119.9 (CH), 119.5 (CH), 119.2 (C), 111.1 (CH), 106.1 (C), 105.8 (CH); MS (ESI) m/z 305.2 [M+H$^+$], HRMS (ESI): Calcd for C$_{17}$H$_{11}$N$_3$O$_2$: 305.1039. Found: 305.1036.

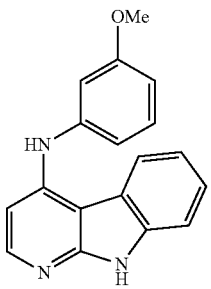

N-(3-methoxyphenyl)-9H-pyrido[2,3-b]indol-4-amine (R324)

The crude product was purified by flash chromatography (CH$_2$Cl$_2$/EtOAc 6:4) to afford R324 in 64% yield as a red solid, $^1$H-NMR (300 MHz, DMSO-d$_6$): δ 11.64 (bs, 1H), 8.5 (bs, 1H), 8.11-8.07 (m, 2H), 7.44 (d, 1H, J=7.7 Hz), 7.36 (td, 1H, 0.9, 7.5 Hz), 7.25 (t, 1H, J=8.5 Hz), 7.14 (td, 1H, J=0.9, 7.5 Hz), 6.89-6.86 (m, 2H), 6.85 (d, 1H, J=5.6 Hz), 6.63 (dt, 1H, J=1.7, 8.3 Hz); $^{13}$C-NMR (75 MHz, DMSO-d$_6$): δ 153.7 (C), 146.8 (C), 145.9 (C), 142.7 (C), 137.6 (C), 129.9 (CH), 124.9 (CH), 122.7 (CH), 120.0 (C), 118.8 (CH), 112.9 (CH), 110.5 (CH), 108.1 (CH), 106.4 (CH), 103.6 (C), 102.3 (CH), 54.9 (CH$_3$); MS (ESI) m/z 290.3 [M+H$^+$], HRMS (ESI): Calcd for $C_{18}H_{14}N_2O$: 290.1293. Found: 290.1288.

C—N Coupling at C3

A solution of the corresponding 3-chloro α-carboline(1 equiv.), aniline (1.2 equiv.), tris(dibenzylideneacetone)palladium (0.05 equiv.), dicyclohexylphosphino-2',4',6'-triisopropylbiphenyl (0.1 equiv.), and NaOtBu (3 equiv.) in degassed t-BuOH (1.5 mL/mmol R 248) was stirred overnight at 100° C. in a sealed tube. After cooling at room temperature, the mixture was quenched with water and extracted with EtOAc. The organic layer was dried over $MgSO_4$, filtered through celite and concentrated under reduced pressure.

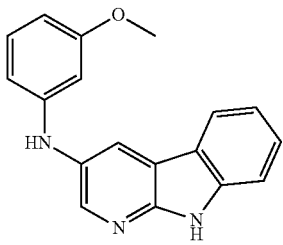

R344

N-(3-methoxyphenyl)-9H-pyrido[2,3-b]indol-3-amine (R344)

The crude product was purified by flash chromatography ($CH_2Cl_2$/EtOAc 8:2) to afford R344 in 82% yield as a yellow solid, $^1$H-NMR (300 MHz, DMSO-$d_6$): δ 11.62 (bs, NH), 8.30 (d, 1H, J=2.3 Hz); 8.23 (d, 1H, J=2.3 Hz), 8.14 (d, 1H, J=7.7 Hz), 8.01 (bs, NH), 7.46 (d, 1H, J=7.5 Hz); 7.42 (td, 1H, J=0.8, 8.1 Hz), 7.16 (td, 1H, J=1.3, 7.7 Hz), 7.08 (t, 1H, J=7.9 Hz), 6.48 (dd, 1H, J=1.7, 7.9 Hz), 6.45 (t, 1H, J=2.3 Hz), 6.31 (dd, 1H, J=2.3, 8.1 Hz), 3.68 (s, 3H);

46

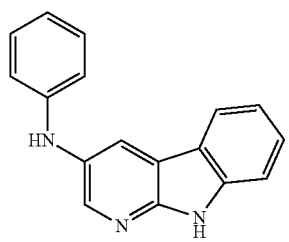

N-(phenyl)-9H-pyrido[2,3-b]indol-3-amine (46)

The crude product was purified by flash chromatography ($CH_2Cl_2$/EtOAc 6:4) to afford 47 in 64% yield as a red solid, $^1$H-NMR (300 MHz, DMSO-$d_6$): δ 11.61 (bs, 1H), 8.30 (d, 1H, J=2.4 Hz), 8.24 (d, 1H, J=2.4 Hz), 8.13 (d, 1H, J=7.7 Hz), 8.01 (bs, NH), 7.47-7.73 (m, 1H), 7.41 (td, 1H, J=1.1, 8.1 Hz), 7.19 (d, 2H, J=7.5 Hz), 7.16 (td, 1H, J=1.5, 6.57 Hz), 6.93 (d, 2H, J=7.7 Hz), 6.72 (t, 1H, J=7.1 Hz); MS (ESI) m/z 260.3 [M+H$^+$], HRMS (ESI): Calcd for $C_{17}H_{13}N_3$: 260.1188. Found 260.1189.

C—N Coupling at C2 with 6-substituted-α-carbolines:

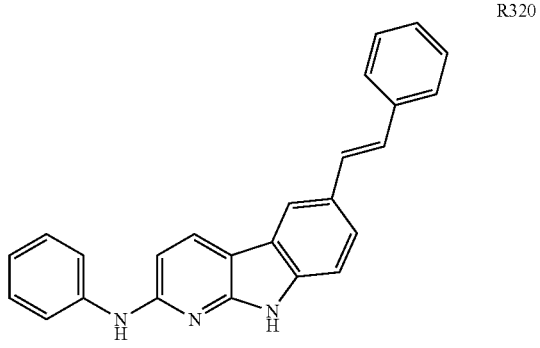 [SMILES: C(=C\c1ccc2[nH]c3nc(Nc4ccccc4)ccc3c2c1)/c1ccccc1]

R320

N-(phenyl)-6-(2'-phenylethenyl)-9H-pyrido[2,3-b]indol-2-amine (R320)

Using the general procedure, 2-chloro-6-(2'-phenylethenyl)-9H-pyrido[2,3-b]indole (54 mg, 0.178 mmol), $Pd_2dba_3$ (13.0 mg, 0.014 mmol, 0.08 equiv.), X-Phos (13.0 mg, 0.029 mmol, 0.16 equiv.), aniline (21 μL, 0.231 mmol, 1.3 equiv.), $K_2CO_3$ (74 mg, 0.53 mmol, 3 equiv.) and t-BuOH (0.4 mL) were heated to 65° C. overnight. The crude material was purified by column chromatography (EtOAc/PE 15:85) to give the desired product as a yellow solid (40 mg, 62%). $^1$H-NMR (300 MHz, DMSO-$d_6$): δ 11.59 (bs, 1H), 9.23 (bs, 1H), 8.24 (d, 1H, J=8.5 Hz), 8.15 (d, 1H, J=0.8 Hz), 7.84 (d, 2H, J=7.5 Hz), 7.60 (d, 2H, J=7.3 Hz), 7.55 (d, 1H, J=1.3, 8.3 Hz), 7.40-7.18 (m, 8H), 6.93-6.88 (m, 1H), 6.71 (d, 1H, J=8.5 Hz); $^{13}$C-NMR (75 MHz, DMSO-$d_6$): δ 154.4 (C), 151.4 (C), 141.8 (C), 137.6 (C), 137.3 (C), 130.1 (CH), 129.7 (CH), 128.7 (2 CH), 128.6 (2 CH), 128.5 (C), 126.9 (CH), 126.0 (2 CH), 125.3 (CH), 122.8 (CH), 122.0 (C), 120.3 (CH), 118.0 (2 CH), 117.3 (CH), 110.9 (CH), 106.5 (C), 103.7 (CFI); MS (ESI) m/z 362 [M+H$^+$], HRMS (ESI): Calcd for $C_{25}H_{19}N_3$: 362.1657. Found: 362.1653.

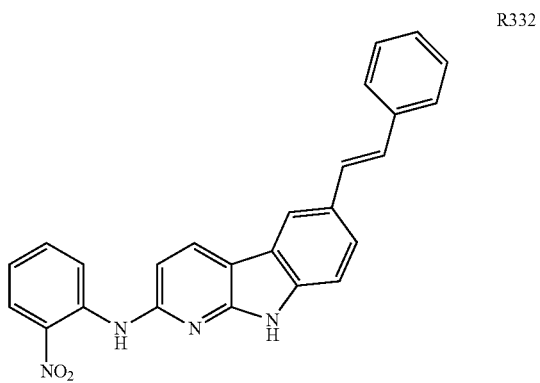 [SMILES: O=[N+]([O-])c1ccccc1Nc1ccc2c(n1)[nH]c1ccc(/C=C/c3ccccc3)cc12]

R332

N-(2-nitrophenyl)-6-(2'-phenylethenyl)-9H-pyrido[2,3-b]indol-2-amine (R320)

Using the general procedure, 2-Chloro-6-(2'-phenylethenyl)-9H-pyrido[2,3-b]indole (43 mg, 0.142 mmol), $Pd_2dba_3$ (11.0 mg, 0.011 mmol, 8 mol % Pd), L (11.0 mg, 0.023 mmol, 16 mol %), 2-nitro-aniline (23 μL, 0.185 mmol, 1.3 equiv.), $K_2CO_3$ (59 mg, 0.426 mmol, 3 equiv.) and t-BuOH (0.3 mL) were heated to 100° C. overnight. The crude material was purified by column chromatography ($CH_2Cl_2$/PE 7:3) to give the desired product as a yellow solid (40 mg, 62%). $^1$H-NMR (300 MHz, DMSO-d$_6$): δ 11.68 (bs, 1H), 9.90 (bs, 1H), 8.39 (d, 1H, J=8.3 Hz), 8.33 (d, 1H, J=8.5 Hz), 8.25 (d, 1H, J=0.6 Hz), 8.09 (dd, 1H, J=1.3, 8.5 Hz), 7.69 (td, 1H, J=1.1, 8.1 Hz), 7.62-7.59 (m, 3H), 7.41-7.35 (m, 4H), 7.27-7.19 (m, 3H), 7.13 (td, 1H, J=1.0, 8.3 Hz), 6.94 (d, 1H, J=8.3 Hz)

C—N Coupling at C3 with 6-substituted-α-carbolines:

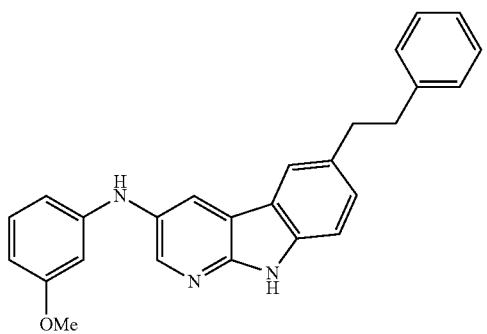

R352

N-(3-methoxyphenyl)-6-(2'-phenylethyl)-9H-pyrido[2,3-b]indol-3-amine (R352)

3-chloro-6-(2'-phenylethyl)-9H-pyrido[2,3-b]indole (50 mg, 0.16 mmol, 1 equiv.), Pd$_2$dba$_3$ (8.2 mg, 0.008 mmol, 0.05 equiv.), 2-Dicyclohexyl phosphino-2',4',6'-Triisopropylbiphenyl (L$_2$)(8.1 mg, 0.016 mmol, 0.1 equiv.), sodium tert-butoxide (36 mg, 0.37 mmol, 2.2 equiv.) are introduced in a schlenk tube and flushed with N$_2$. tert-butanol (0.255 ml) and m-Anisidine (25 mg, 0.20 mmol, 1.2 equiv.) are then added. The reaction is carried out at 100° C. overnight and then filtered over celite and evaporated under reduced pressure. The crude product (yellow oil) is purified over silica gel chromatography (eluant AcOEt/PE 4:6, 6:4) to afford the product as a green solid (18 mg, 0.046 mmol) in 29% yield. mp=161-165; IR 3359, 3145, 3022, 1595, 1494, 1467, 1383, 1218, 1151, 1038, 968, 891, 809, 771, 685 cm$^{-1}$; $^1$H NMR (300 MHz, CDCl$_3$) 9.94 (br s, 1H, H$_9$), 8.18 (s, 1H, H$_2$), 7.78 (s, 1H, H$_4$), 7.41 (d, 1H, J=8.3 Hz, H$_8$), 7.32-7.14 (m, 71-1, CH$_{Ph}$+CH$_{An}$), 6.52 (d, 1H, J=8.1 Hz, H$_7$), 6.47-6.44 (m, 2H, H$_5$+CH$_{Ph}$ or CH$_{An}$), (br s, 1H, NH$_{An}$), 3.77 (s, 3H, OCH$_3$), 3.12-2.97 (m, 4H, 2CH$_2$); MS (+ESI) [M+H$^+$]=394.3

The Following Compounds can be Prepared by the Same Method 2-aminoaryl-6-(4-methoxyphenyl)-9H-pyrido[2,3-b]indole
3-aminoaryl-6-(4-methoxyphenyl)-9H-pyrido[2,3-b]indole
4-aminoaryl-6-(4-methoxyphenyl)-9H-pyrido[2,3-b]indole
2-aminoaryl-6-(3-nitrophenyl)-9H-pyrido[2,3-b]indole
3-aminoaryl-6-(3-nitrophenyl)-9H-pyrido[2,3-b]indole
3-aminoaryl-6-(3-nitrophenyl)-9H-pyrido[2,3-b]indole
2-aminoaryl-6-(2-furyl)-9H-pyrido[2,3-b]indole
3-aminoaryl-6-(2-furyl)-9H-pyrido[2,3-b]indole
4-aminoaryl-6-(2-furyl)-9H-pyrido[2,3-b]indole
2-aminoaryl-6-(4-phenylphenyl)-9H-pyrido[2,3-b]indole
3-aminoaryl-6-(4-phenylphenyl)-9H-pyrido[2,3-b]indole
4-aminoaryl-6-(4-phenylphenyl)-9H-pyrido[2,3-b]indole
2-aminoaryl-6-(4-(morpholin-4-yl)methylphenyl)-9H-pyrido[2,3-b]indole
3-aminoaryl-6-(4-(morpholin-4-yl)methylphenyl)-9H-pyrido[2,3-b]indole
4-aminoaryl-6-(4-(morpholin-4-yl)methylphenyl)-9H-pyrido[2,3-b]indole
2-aminoaryl-6-(5-morpholin-4-yl-pyridin-2-yl)-9H-pyrido[2,3-b]indole
3-aminoaryl-6-(5-morpholin-4-yl-pyridin-2-yl)-9H-pyrido[2,3-b]indole
4-aminoaryl-6-(5-morpholin-4-yl-pyridin-2-yl)-9H-pyrido[2,3-b]indole
2-aminoaryl-6-(2-phenylethenyl)-9H-pyrido[2,3-b]indole
3-aminoaryl-6-(2-phenylethenyl)-9H-pyrido[2,3-b]indole
4-aminoaryl-6-(2-phenylethenyl)-9H-pyrido[2,3-b]indole
2-aminoaryl-6-(2-(4-methoxyphenyl)ethenyl)-9H-pyrido[2,3-b]indole
3-aminoaryl-6-(2-(4-methoxyphenyl)ethenyl)-9H-pyrido[2,3-b]indole
4-aminoaryl-6-(2-(4-methoxyphenyl)ethenyl)-9H-pyrido[2,3-b]indole
2-aminoaryl-6-(2'-(3-fluorophenyl)ethenyl)-9H-pyrido[2,3-b]indole
3-aminoaryl-6-(2'-(3-fluorophenyl)ethenyl)-9H-pyrido[2,3-b]indole
4-aminoaryl-6-(2'-(3-fluorophenyl)ethenyl)-9H-pyrido[2,3-b]indole
4-(2-aminoaryl-9H-pyrido[2,3-b]indol-6-yl)-4-oxo-butyric acid
4-(3-aminoaryl-9H-pyrido[2,3-b]indol-6-yl)-4-oxo-butyric acid
4-(4-aminoaryl-9H-pyrido[2,3-b]indol-6-yl)-4-oxo-butyric acid
1-(2-aminoaryl-9H-pyrido[2,3-b]indol-6-yl)-4-(4-methy)piperazin-1-yl)butane-1,4-dione
1-(3-aminoaryl-9H-pyrido[2,3-b]indol-6-yl)-4-(4-methylpiperazin-1-yl)butane-1,4-dione
1-(4-aminoaryl-9H-pyrido[2,3-b]indol-6-yl)-4-(4-methylpiperazin-1-yl)butane-1,4-dione
4-(2-aminoaryl-9H-pyrido[2,3-b]indol-6-yl)-N-(4-methoxybenzyl)-4-oxobutyramide
4-(3-aminoaryl-9H-pyrido[2,3-b]indol-6-yl)-N-(4-methoxybenzyl)-4-oxobutyramide
4-(4-aminoaryl-9H-pyrido[2,3-b]indol-6-yl)-N-(4-methoxybenzyl)-4-oxobutyramide
3-(4-(2-aminoaryl-9H-pyrido[2,3-b]indol-6-yl)phenoxy)-N,N-dimethylpropan-1-amine
4-(3-aminoaryl-9H-pyrido[2,3-b]indol-6-yl)phenoxy)-N,N-dimethylpropan-1-amine
4-(4-aminoaryl-9H-pyrido[2,3-b]indol-6-yl)phenoxy)-N,N-dimethylpropan-1-amine
3-(4-(2-aminoaryl-9H-pyrido[2,3-b]indol-6-yl)phenoxy)-N,N-diethylpropan-1-amine
3-(4-(3-aminoaryl-9H-pyrido[2,3-b]indol-6-yl)phenoxy)-N,N-diethylpropan-1-amine
3-(4-(4-aminoaryl-9H-pyrido[2,3-b]indol-6-yl)phenoxy)-N,N-diethylpropan-1-amine
2-aminoaryl-6-(4-(2-(4-methylpiperazin-1-yl)ethoxy)phenyl)-9H-pyrido[2,3-b]indole
3-aminoaryl-6-(4-(2-(4-methylpiperazin-1-yl)ethoxy)phenyl)-9H-pyrido[2,3-b]indole
4-aminoaryl-6-(4-(2-(4-methylpiperazin-1-yl)ethoxy)phenyl)-9H-pyrido[2,3-b]indole
where aminoaryl is chosen independently from:
(3-nitroaminophenyl), (2-nitroaminophenyl), (4-methoxyaminophenyl), or aminophenyl

Typical Procedure for the Preparation of Disubstituted α-carbolines by Electrophilic Aromatic Substitution on arylamino-α-carbolines

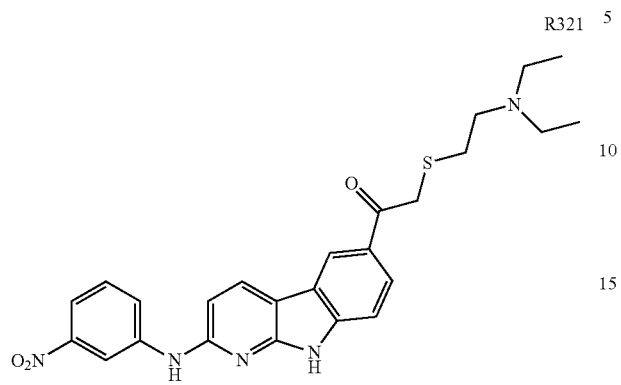

2-(2'-(N,N-diethylamino)ethylthio)-1-[2-(3-nitrophenylamino)-9H-pyrido[2,3-b]indol-6-yl]ethanone (R321)

To a solution of R317 (104 mg, 0.343 mmol) in anhydrous $CH_2Cl_2$ (3 mL) was added $AlCl_3$ (206 mg, 1.54 mmol, 4.5 equiv.) and bromoacetyl bromide (33 µL, 0.377 mmol, 1.1 equiv.) diluted in $CH_2Cl_2$ (1 mL) at room temperature under inert atmosphere. The mixture was stirred at reflux until completion of the reaction (followed by t.l.c.). The resulting mixture was then cautiously quenched at 0° C. with $H_2O$. It was extracted with the mixture of EtOAc/DMF (99:1). The resulting organic layer was washed with saturated aqueous $NaHCO_3$ solution and brine, dried over $MgSO_4$, filtered and solvents were removed under reduced pressure. To diethylamino)ethylthiol (64 mg, 0.376 mmol, 1.1 equiv.) in anhydrous DMF (700 µL) under argon at 0° C. was introduced NaH (17 mg, 0.414 mmol). After 30 min, the product obtained in the previous step (80 mg, 0.188 mmol) was introduced. This solution was stirred at room temperature for 4 h and then the crude mixture was concentrated under vacuum. This mixture was poured with 5% aqueous $NaHCO_3$ and extracted with EtOAc. The combined organic layers were dried ($MgSO_4$), and the solvent was removed under reduced pressure. The crude product was purified by recrystallization from $CH_2Cl_2$/PE to furnish desired compound R321. $^1$H-NMR (300 MHz, DMSO-$d_6$): δ 12.07 (bs, 1H), 9.87 (bs, 1H), 8.93-8.92 (m, 1H), 8.71 (s, 1H), 8.44 (d, 1H, J=8.7 Hz), 8.17-8.14 (m, 1H), 7.97 (dd, 1H, J=1.7, 8.5 Hz), 7.76 (d, 1H, J=6.8 Hz), 7.58 (t, 1H, J=8.3 Hz), 7.49 (d, 1H, J=8.3 Hz), 4.07 (s, 2H), 2.61 (s, 4H), 2.44 (s, 2H), 0.92 (t, 6H, J=Hz), 0.83 (bs, 2H), MS (ESI) m/z 478 [M+H$^+$];

Typical Procedure for the Buchwald Coupling with phenols. General Procedure

A solution of 9-EOM protected 2- or 4-chloro α-carbolines, the appropriate phenol (1.3 equiv), tris(dibenzylideneacetone)dipalladium (0.08 equiv), dicyclohexylphosphino-2',4',6'-triisopropylbiphenyl (0.16 equiv), and $K_2CO_3$ (2.2 equiv) in degassed toluene (1.5 mL per mmol) was stirred overnight at 110° C. in a sealed tube. After cooling to r.t., the products were extracted from the water layer with ethyl acetate, dried over $MgSO_4$, filtered through celite and solvents were removed under reduced pressure.

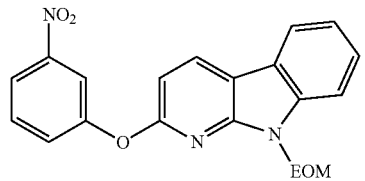

47

9-(ethoxymethyl)-2-(3-nitrophenoxy)-9H-pyrido[2,3-b]indole (47)

The product was purified by column chromatography on silica gel ($CH_2Cl_2$/EP 1/1) and recrystallisation in EtOH to afford 47 in 62% yield as a yellow solid; $^1$H NMR (300 MHz, CDCl$_3$): δ 8.35 (d, 1H, J=8.1 Hz); 8.16-8.15 (m, 1H); 8.08 (ddd, 1H, J=2.1, 3.2, 5.85 Hz); 8.00 (d, 1H, J=7.7 Hz); 7.63-7.55 (m, 3H); 7.48 (td, 1H, J=1.1, 7.4 Hz); 7.32 (td, 1H, J=1.1, 8.3 Hz), 5.68 (s, 2H); 3.41 (q, 2H, J=6.9 Hz); 1.06 (t, 3H, J=6.9 Hz); $^{13}$C NMR (75 MHz, CDCl$_3$) δ=160.6 (C), 155.3 (CH), 150.1 (C), 149.0 (C), 139.2 (C), 132.1 (CH), 130.0 (CH), 127.3 (CH), 126.2 (CH), 121.2 (CH), 121.0 (C), 120.2 (CH), 119.1 (CH), 116.3 (CH), 112.2 (C), 110.6 (CH), 104.0 (CH), 70.9 ($CH_2$), 64.4 ($CH_2$), 14.9 ($CH_3$); MS (SIMS) m/z 363 [M$^+$]; HRMS (LSIMS): Calcd for $C_{18}H_{13}N_3O_3$: 363.1219. Found: 363.1218.

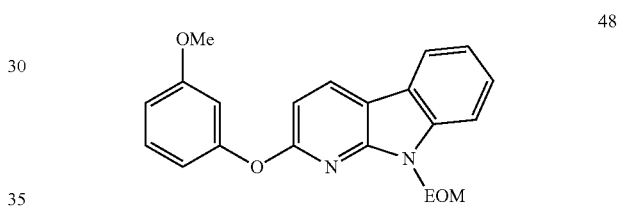

48

9-(ethoxymethyl)-2-(3-methoxyphenoxy)-9H-pyrido[2,3-b]indole (48)

The product was purified by column chromatography on silica gel ($CH_2Cl_2$) to afford 48 in 89% yield as a yellow solid; $^1$H NMR (300 MHz, CDCl$_3$): δ 8.42 (d, 1H, J=2.3 Hz); 8.28 (d, 1H, J=2.3 Hz); 8.03 (d, 1H, J=7.7 Hz); 7.62 (d, 1H, J=8.3 Hz); 7.56 (ddd, 1H, J=1.1, 7.1 Hz); 7.34 (ddd, 1H, J=1.1, 8.1 Hz), 5.90 (s, 2H); 3.54 (q, 2H, J=6.9 Hz); 1.15 (t, 3H, J=6.9 Hz);

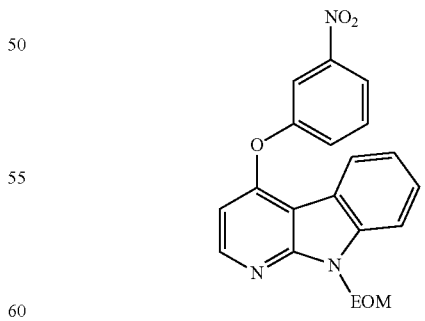

49

9-(ethoxymethyl)-4-(3-nitro-phenoxy)-9H-pyrido[2,3-b]indole (49)

The product was purified by column chromatography on silica gel ($CH_2Cl_2$/EP 9/1) to afford 49 in 86% yield as a white solid; ¹H NMR (300 MHz, CDCl₃): δ 8.37 (d, 1H, J=5.6 Hz); 8.13 (d, 2H, J=7.9 Hz); 8.08 (t, 1H, J=2.1 Hz); 7.68 (d, 1H, J=8.3 Hz); 7.62 (d, 1H, J=7.9 Hz); 7.58-7.51 (m, 2H); 7.31 (td, 1H, J=1.0, 7.9 Hz); 6.59 (d, 1H, J=5.6 Hz); 5.96 (s, 2H); 3.59 (q, 2H, J=6.9 Hz); 1.17 (t, 3H, J=6.9 Hz);

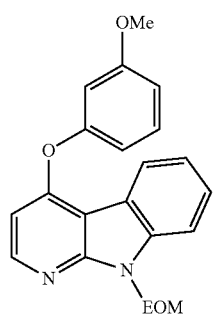

50

9-(ethoxymethyl)-4-(3-methoxy-phenoxy)-9H-pyrido[2,3-b]indole (50)

The product was purified by column chromatography on silica gel (CH₂Cl₂) to afford 50 in 78% yield as a yellow oil; ¹H NMR (300 MHz, CDCl₃): δ 8.29 (d, 1H, J=5.6 Hz); 8.26 (d, 1H, J=7.7 Hz); 7.66 (d, 1H, J=8.1 Hz); 7.52 (td, 1H, J=1.3, 7.3 Hz); 7.38-7.29 (m, 2H); 6.85-6.79 (m, 1H); 6.55 (d, 1H, J=5.9 Hz); 5.94 (s, 2H); 3.82 (s, 3H); 3.58 (q, 2H, J=6.9 Hz); 1.16 (t, 3H, J=6.9 Hz);

Sonogashira Reaction with Unprotected α-carbolines; General Procedure

A Schlenk tube with stir bar was charged with Pd(Cl)₂(CH₃CN)₂ (8 mg, 0.08 equiv), 2-dicyclohexylphosphino-2',4',6'-triisopropylbiphenyl (30 mg, 0.16 equiv), chloro-α-carbolines (100 mg, 1 equiv), Cs₂CO₃ (325 mg, 2.6 equiv.). The tube was evacuated and back-filled with argon (this was repeated three additional times). A anhydrous acetonitrile (700 µL) was added (when degassed solvent was used) and then the alkyne (1.3 equiv.) was injected and the reaction mixture was allowed to stir at desired temperature overnight. After cooling to r.t., the products were extracted from the water layer with ethyl acetate, dried over MgSO₄, filtered through celite and solvents were removed under reduced pressure.

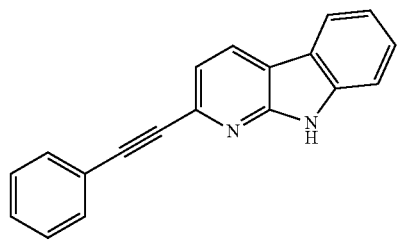

2-(phenylethynyl)-9H-pyrido[2,3-b]indole (R342)

The product was purified by column chromatography on silica gel (CH₂Cl₂) to afford R342 in 64% yield as a yellow solid; ¹H NMR (300 MHz, DMSO-d₆): δ 11.87 (bs, NH); 8.54 (d, 1H, J=7.9 Hz); 8.19 (d, 1H, J=7.7 Hz); 7.66-7.62 (m, 2H); 7.52-7.46 (m, 6H); 7.25 (ddd, 1H, J=1.5, 6.8 Hz).

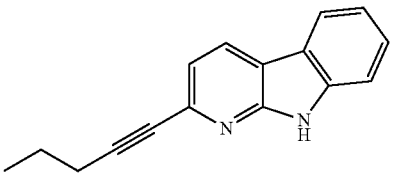

2-(pent-1-ynyl)-9H-pyrido[2,3-b]indole (R341)

The product was purified by column chromatography on silica gel (CH₂Cl₂/EtOAc 9/1) to afford R341 in 61% yield as a yellow solid; ¹H NMR (300 MHz, Acetone-d₆): δ 11.75 (bs, NH); 8.45 (d, 1H, J=7.7 Hz); 8.14 (d, 1H, J=7.7 Hz); 7.50 (d, 1H, J=7.5 Hz); 7.45 (ddd, 1H, J=1.1, 6.8 Hz); 7.27 (d, 1H, J=7.8 Hz); 7.22 (ddd, 1H, J=1.7, 8.1 Hz), 2.47 (t, 2H, J=7.0 Hz); 1.62-1.57 (m, 2H); 1.04 (t, 3H, J=7.8 Hz).

Sonogashira Reaction with N-EOM Protected α-carbolines; General Procedure

A Schlenk tube with stir bar was charged with Pd(Cl)₂(CH₃CN)₂ (0.08 equiv), 2-dicyclohexylphosphino-2',4',6'-triisopropylbiphenyl (0.16 equiv), N-EOM protected chloro-α-carbolines (1 equiv), Cs₂CO₃ (2.6 equiv.). The tube was evacuated and back-filled with argon (this was repeated three additional times). An anhydrous acetonitrile (0.6 mmol/mL) was added (when degassed solvent was used) and then the alkyne (1.3 equiv.) was injected and the reaction mixture was allowed to stir at desired temperature overnight. After cooling to r.t., the products were extracted from the water layer with ethyl acetate, dried over MgSO₄, filtered through celite and solvents were removed under reduced pressure.

C—C(sp) at C2

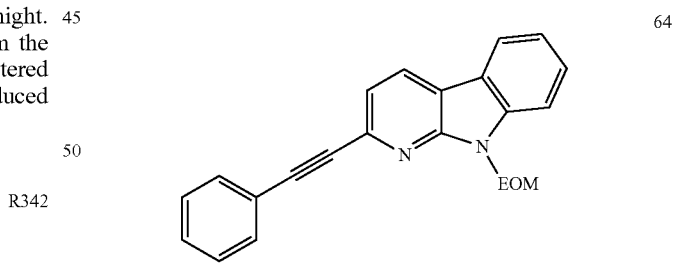

2-(phenylethynyl)-9-(ethoxymethyl)-9H-pyrido[2,3-b]indole (64)

The product was purified by column chromatography on silica gel (CH₂Cl₂/EP 7/3) to afford 64 in 80% yield as a yellow solid; ¹H NMR (300 MHz, CDCl₃): δ 8.28 (d, 1H, J=7.9 Hz); 8.05 (d, 1H, J=7.7 Hz); 7.69-7.64 (m, 3H); 7.54 (td, 1H, J=1.1, 7.3 Hz); 7.49 (d, 1H, J=7.7 Hz); 7.39-7.37 (m, 3H); 7.33 (td, 1H, J=1.0, 7.1 Hz); 5.97 (s, 1H); 3.57 (q, 2H, J=6.9 Hz); 1.16 (t, 3H, J=6.9 Hz);

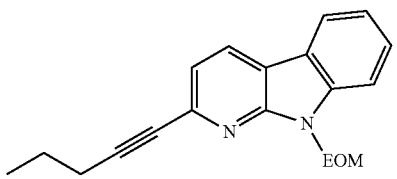

2-(pent-1-ynyl) 9-(ethoxymethyl)-9H-pyrido[2,3-b]indole (65)

The product was purified by column chromatography on silica gel (CH$_2$Cl$_2$/EP 6/4) to afford 65 in 85% yield as a yellow solid; $^1$H NMR (300 MHz, CDCl$_3$): δ 8.21 (d, 1H, J=7.9 Hz); 8.02 (d, 1H, J=7.7 Hz); 8.15 (d, 1H, J=8.1 Hz); 7.51 (td, 1H, J=1.3, 7.4 Hz); 7.33 (d, 1H, J=7.9 Hz); 7.31 (td, 1H, J=1.0, 8.3 Hz); 5.94 (s, 1H); 3.53 (q, 2H, J=7.0 Hz); 2.48 (t, 2H, J=7.3 Hz); 1.71 (sex, 2H, J=7.3 Hz); 1.13 (t, 3H, J=7.0 Hz); 1.09 (t, 3H, J=7.3 Hz)

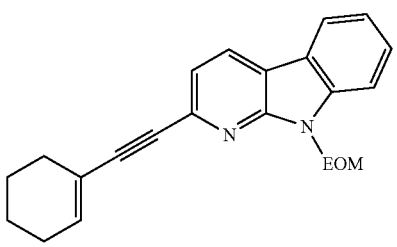

2-Cyclohex-1-enylethynyl-9-(ethoxymethyl)-9H-pyrido[2,3-b]indole (66)

The product was purified by column chromatography on silica gel (CH$_2$Cl$_2$/EP 4/6) to afford 66 in 87% yield as a yellow oil; $^1$H NMR (300 MHz, CDCl$_3$): 8.22 (d, 1H, J=7.9 Hz); 8.02 (d, 1H, J=7.9 Hz); 7.65 (d, 1H, J=8.3 Hz); 7.51 (ddd, 1H, J=1.1, 7.1, 8.3 Hz); 7.36 (d, 1H, J=7.9 Hz); 7.31 (d, 1H, J=1.1, 7.9 Hz); 6.36 (sept, 1H, J=1.9 Hz); 5.94 (s, 2H); 3.54 (q, 2H, J=7.1 Hz); 2.33-2.28 (m, 2H); 2.20-2.15 (m, 2H); 1.73-1.61 (m, 4H); 1.13 (t, 3H, J=7.1 Hz).

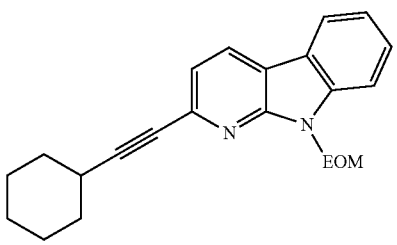

2-cyclohexylethynyl-9-(ethoxymethyl)-9H-pyrido[2,3-b]indole (67)

The product was purified by column chromatography on silica gel (CH$_2$Cl$_2$/EP 4/6) to afford 67 in 79% yield brown oil; $^1$H NMR (300 MHz, CDCl$_3$): δ 8.20 (d, 1H, J=7.9 Hz); 8.01 (d, 1H, J=7.9 Hz); 7.64 (d, 1H, J=8.3 Hz); 7.51 (td, 1H, J=1.1, 7.2 Hz); 7.33 (d, 1H, J=7.9 Hz); 7.30 (td, 1H, J=0.75, 7.9 Hz); 5.93 (s, 2H); 3.53 (q, 2H, J=7.1 Hz); 2.72-2.63 (m, 1H); 1.98-1.94 (m, 2H); 1.82-1.78 (m, 2H); 1.68-1.56 (m, 3H); 1.44-1.33 (m, 3H); 1.13 (t, 3H, J=7.0 Hz); $^{13}$C-NMR (75 MHz, CDCl$_3$): δ 151.7 (C), 139.9 (C), 139.9 (C), 128.1 (CH), 127.2 CH), 120.9 (CH), 120.9 (CH), 120.8 (C), 120.1 (CH), 115.2 (C), 110.7 (CH), 94.7 (C), 81.5 (C), 71.1 (CH$_2$), 64.2 (2×CH$_2$), 32.5 (2×CH$_2$), 29.9 (CH$_2$), 26.0 (CH), 25.1 (CH$_2$), 15.1 (CH$_3$).

C—C(sp) at C3

A Schlenk tube with stir bar was charged with Pd(Cl)$_2$(CH$_3$CN)$_2$ (0.08 equiv), 2-dicyclohexylphosphino-2',4',6'-triisopropylbiphenyl (0.16 equiv), chloro-α-carbolines (1 equiv), Cs$_2$CO$_3$ (2.6 equiv.). The tube was evacuated and back-filled with argon (this was repeated three additional times). An anhydrous acetonitrile (0.6 mmol/mL) was added (when degassed solvent was used) and then the alkyne (1.3 equiv.) was injected and the reaction mixture was allowed to stir at desired temperature overnight. After cooling to r.t., the products were extracted from the water layer with ethyl acetate, dried over MgSO$_4$, filtered through celite and solvents were removed under reduced pressure.

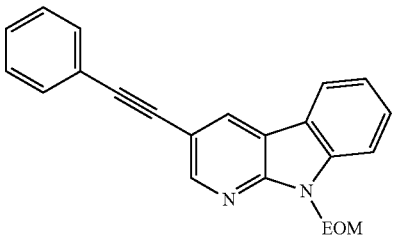

3-(phenylethynyl)-9-(ethoxymethyl)-9H-pyrido[2,3-b]indole (68)

The product was purified by column chromatography on silica gel (CH$_2$Cl$_2$/EP 8/2) to afford 68 in 96% yield as a yellow solid; $^1$H NMR (300 MHz, CDCl$_3$): δ 8.66 (d, 1H, J=1.9 Hz); 8.45 (d, 1H, J=1.9 Hz); 8.06 (d, 1H, J=7.7 Hz); 7.66 (d, 1H, J=8.31 Hz); 7.60-7.53 (m, 3H); 7.41-7.32 (m, 4H); 5.93 (s, 1H); 3.57 (q, 2H, J=6.9 Hz); 1.16 (t, 3H, J=6.9 Hz); MS (ESI) m/z 281.3, 327.0 [M+H$^+$-EtOH]$^+$, [M+H]$^+$;

C—C(sp) at C4

A Schlenk tube with stir bar was charged with Pd(Cl)$_2$(CH$_3$CN)$_2$ (0.08 equiv), 2-dicyclohexylphosphino-2',4',6'-triisopropylbiphenyl (0.16 equiv), chloro-α-carbolines (1 equiv), Cs$_2$CO$_3$ (2.6 equiv.). The tube was evacuated and back-filled with argon (this was repeated three additional times). An anhydrous acetonitrile (0.6 mmol/mL) was added (when degassed solvent was used) and then the alkyne (1.3 equiv.) was injected and the reaction mixture was allowed to stir at desired temperature overnight. After cooling to r.t., the products were extracted from the water layer with ethyl acetate, dried over MgSO$_4$, filtered through celite and solvents were removed under reduced pressure

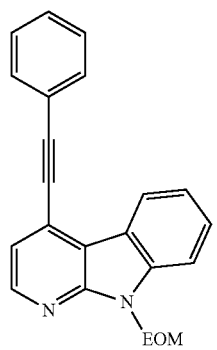

4-(phenylethynyl)-9-(ethoxymethyl)-9H-pyrido[2,3-b]indole (69)

The product was purified by column chromatography on silica gel (CH$_2$Cl$_2$/EP 9/1) to afford 69 in 96% yield as a yellow solid; NMR (300 MHz, CDCl$_3$): δ 8.61 (d, 1H, J=7.7 Hz); 8.45 (d, 1H, J=5.1 Hz); 7.72 (dd, 1H, J=3.8, 7.5 Hz); 7.68 (d, 1H, J=8.1 Hz); 7.57 (td, 1H, J=1.0, 7.1 Hz); 7.48-7.43 (m, 3H); 7.37 (d, 1H, J=1.0, 7.9 Hz); 7.30 (d, 1H, J=5.3 Hz); 5.95 (s, 2H); 3.52 (q, 2H, J=6.9 Hz); 1.16 (t, 3H, J=6.9 Hz);

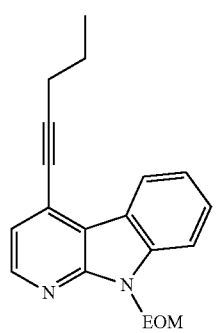

4-(pent-1-ynyl) 9-(ethoxymethyl)-9H-pyrido[2,3-b]indole (70)

The product was purified by column chromatography on silica gel (CH$_2$Cl$_2$) to afford 70 in 90% yield as a yellow oil; $^1$H NMR (300 MHz, CDCl$_3$): δ 8.52 (d, 1H, J=7.7 Hz); 8.38 (d, 1H, J=5.2 Hz); 7.65 (d, 1H, J=8.3 Hz); 7.54 (td, 1H, J=1.1, 7.2 Hz); 7.33 (td, 1H, J=1.1, 8.2 Hz); 7.17 (d, 1H, J=5.2 Hz); 5.92 (s, 2H); 3.54 (q, 2H, J=7.0 Hz); 2.63 (t, 2H, J=7.3 Hz); 1.81 (sex, 2H, J=7.3 Hz); 1.16 (t, 3H, J=7.3 Hz); 1.14 (t, 3H, J=7.0 Hz).

2-Cyclohexyl-enylethynyl-9-(ethoxymethyl)-9H-pyrido[2,3-b]indole (71)

The product was purified by column chromatography on silica gel (CH$_2$Cl$_2$/EP 8/2) to afford 71 in 77% yield as a yellow oil; NMR (300 MHz, CDCl$_3$): δ 8.52 (d, 1H, J=7.7 Hz); 8.39 (d, 1H, J=5.1 Hz); 7.65 (d, 1H, J=8.3 Hz); 7.55 (td, 1H, J=1.1, 7.1 Hz); 7.34 (td, 1H, J=1.1, 8.2 Hz); 7.18 (d, 1H, J=5.1 Hz); 6.46 (sept, 1H, J=1.9 Hz), 5.92 (s, 2H); 3.54 (q, 2H, J=7.0 Hz); 2.39-2.37. (m, 2H); 2.28-2.22 (m, 2H); 1.81-1.65 (m, 4H); 1.14 (t, 3H, J=7.0 Hz).

C—C(sp) at C6

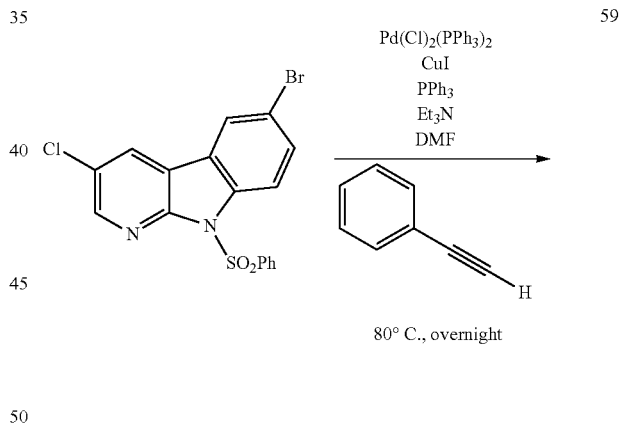

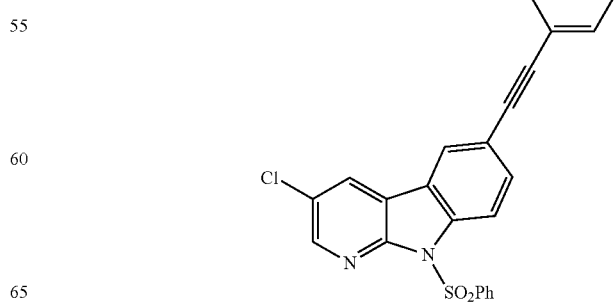

9-benzenesulfonyl-3-chloro-6-(2-phenylethynyl)-9H-pyrido[2,3-b]indole (59)

To a solution of 9-benzenesulfonyl-6-bromo-3-chloro-9-9H-pyrido[2,3-b]indole (100 mg, 0.24 mmol, 1 equiv.) in anhydrous DMF (1.5 ml) under argon, $Pd(Cl)_2(PPh_3)_2$ (17 mg, 0.024 mmol, 0.1 equiv.), CuI (9 mg, 0.048 mmol, 0.2 equiv.), $PPh_3$ (6 mg, 0.024 mmol, 0.1 equiv.), 1-ethynylbenzene (0.079 ml, 0.72 mmol, 3 equiv.) and triethylamine (3 ml) are respectively added. The mixture is stirred at 80° C. overnight and then poured over water (5 ml) and extracted with $CH_2Cl_2$ (3×10 ml). The combined organic layers are washed with brine (3×10 ml) and concentrated under reduced pressure. The crude residue is purified over silica gel column (eluant $CH_2Cl_2$/PE 1:1) to afford the product 59 as a white solid (98 mg, 0.28 mmol) in 92% yield. NMR (300 MHz, $CDCl_3$) δ 8.51 (d, 1H, J=2.3 Hz), 8.46 (d, 1H, J=8.9 Hz), 8.15 (d, 2H, J=2.3 Hz), 8.10 (dd, 2H, J=1.6, 15 Hz), 7.76 (dd, 1H, J=1.7, 8.9 Hz), 7.58-7.54 (m, 3H), 7.44 (dd, 2H, J=7.3, 8.3 Hz), 7.38 (d, 1H, J=1.7 Hz), 7.36 (d, 2H, J=2.3 Hz).

The following compound can be prepared by the same method:

9-benzenesulfonyl-3-chloro-6-(2-cyclohexylethynyl)-9H-pyrido[2,3-b]indole
9-benzenesulfonyl-3-chloro-6-(2-cyclohex-1-enylethynyl)-9H-pyrido[2,3-b]indole
9-benzenesulfonyl-3-chloro-6-(1-pentynyl)-9H-pyrido[2,3-b]indole
9-benzenesulfonyl-2-chloro-6-(2-phenylethynyl)-9H-pyrido[2,3-b]indole
9-benzenesulfonyl-2-chloro-6-(2-cyclohexylethynyl)-9H-pyrido[2,3-b]indole
9-benzenesulfonyl-2-chloro-6-(2-cyclohex-1-enylethynyl)-9H-pyrido[2,3-b]indole
9-benzenesulfonyl-2-chloro-6-(1-pentynyl)-9H-pyrido[2,3-b]indole
9-benzenesulfonyl-4-chloro-6-(2-phenylethynyl)-9H-pyrido[2,3-b]indole
9-benzenesulfonyl-4-chloro-6-(2-cyclohexylethynyl)-9H-pyrido[2,3-b]indole
9-benzenesulfonyl-4-chloro-6-(2-cyclohex-1-enylethynyl)-9H-pyrido[2,3-b]indole
9-benzenesulfonyl-4-chloro-6-(1-pentynyl)-9H-pyrido[2,3-b]indole

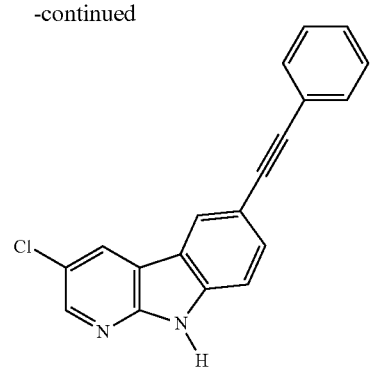

3-chloro-6-(2-phenylethynyl)-9H-pyrido[2,3-b]indole (60)

To a solution of 9-benzenesulfonyl-3-chloro-6-(2-phenylethynyl)-9H-pyrido[2,3-b]indole (88 mg, 0.20 mmol, 1 equiv.) in anhydrous THF under argon, TBAF 1M in THF (1 ml, 1 mmol, 5 equiv.) is added dropwise. The reaction is carried out at reflux for 4 hours and then evaporated. The crude product (yellow solid) is purified over silica gel chromatography ($CH_2Cl_2$/AcOEt 9:1) to afford the product 60 as a white solid (53 mg, 0.18 mmol) in 88% yield. $^1$H NMR (300 MHz, DMSO $d_6$) δ 12.25 (br s, 1H), 8.77 (d, 1H, J=2.5 Hz), 8.49 (br s, 1H), 8.47 (d, 1H, J=2.5 Hz), 7.67 (dd, 1H, J=1.5, 8.5 Hz), 7.59-7.54 (m, 3H), 7.45-7.42 (m, 3H).

The following compound can be prepared by the same method:

3-chloro-6-(2-cyclohexylethynyl)-9H-pyrido[2,3-b]indole
3-chloro-6-(2-cyclohex-1-enylethynyl)-9H-pyrido[2,3-b]indole
3-chloro-6-(1-pentynyl)-9H-pyrido[2,3-b]indole
2-chloro-6-(2-phenylethynyl)-9H-pyrido[2,3-b]indole
2-chloro-6-(2-cyclohexylethynyl)-9H-pyrido[2,3-b]indole
2-chloro-6-(2-cyclohex-1-enylethynyl)-9H-pyrido[2,3-b]indole
2-chloro-6-(1-pentynyl)-9H-pyrido[2,3-b]indole
4-chloro-6-(2-phenylethynyl)-9H-pyrido[2,3-b]indole
4-chloro-6-(2-cyclohexylethynyl)-9H-pyrido[2,3-b]indole
4-chloro-6-(2-cyclohex-1-enylethynyl)-9H-pyrido[2,3-b]indole
4-chloro-6-(1-pentynyl)-9H-pyrido[2,3-b]indole Typical Procedure for the Synthesis of alkyl linked α-carbolines by Hydrogenation

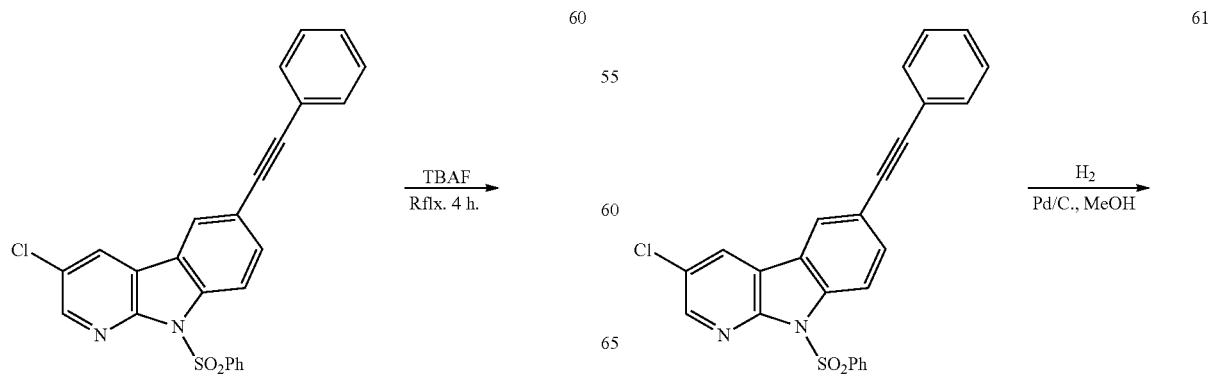

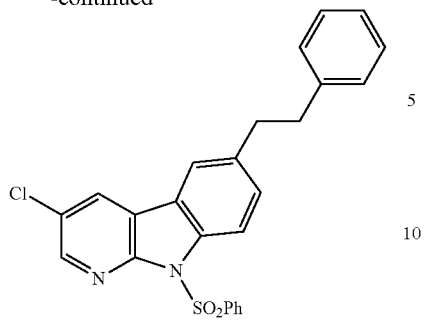

9-(benzenesulfonyl)-3-chloro-6-(2'-phenylethyl)-9H-pyrido[2,3-b]indole (61)

A solution of 9-benzenesulfonyl-3-chloro-6-(2-phenylethynyl)-9H-pyrido[2,3-b]indole (200 mg, 0.45 mmol, 1 equiv.) in anhydrous ethanol (25 ml) was treated with 10% palladium on carbon (50 mg, 0.047 mmol, 0.1 equiv.) and then stirred at room temperature under an atmosphere of $H_2$ overnight. The reaction mixture was filtered through celite and then concentrated under reduced pressure. The crude product (pale yellow solid) was purified over silica gel chromatography (eluant $CH_2Cl_2$/PE 7:3) to afford the product 61 as a white solid (183 mg, 0.41 mmol) in 91% yield. mp=158-162° C.; IR 3057, 3023, 2926, 1494, 1475, 1432, 1376, 1366, 1255, 1182, 1712, 1090, 977, 908, 713, 683 cm$^{-1}$; $^1$H NMR (300 MHz, CDCl$_3$) δ 8.48 (d, 1H, J=2.3 Hz, H$_2$), 8.36 (d, 1H, J=8.7 Hz, H$_8$), 8.12 (m, 3H, H$_4$+H$_7$+CH$_P$), 7.67 (s, 1H, H$_5$), 7.56-7.52 (m, 1H, CH$_P$+CH$_{Ph}$), 7.45-7.38 (m, 3H, 3CH$_P$ or CH$_{Ph}$), 7.32-7.18 (m, 5H, CH$_P$+CH$_{Ph}$), 3.12-2.97 (m, 4H, 2CH$_2$); $^{13}$C NMR (75 MHz, CDCl$_3$) δ 149.2 (C), 145.4 (CH), 141.4 (C), 138.7 (C), 138.1 (C), 137.0 (C), 134.2 (CH), 130.0 (CH), 129.1 (2×CH), 128.6 (2×CH), 128.6 (2×CH), 128.9 (2×CH), 127.6 (CH), 127.5 (C), 126.3 (CH), 122.0 (C), 120.6 (CH), 120.0 (C), 115.1 (CH), 38.2 (CH$_2$), 38.8 (CH$_2$); MS (+ESI) [M+H$^+$]=447.1

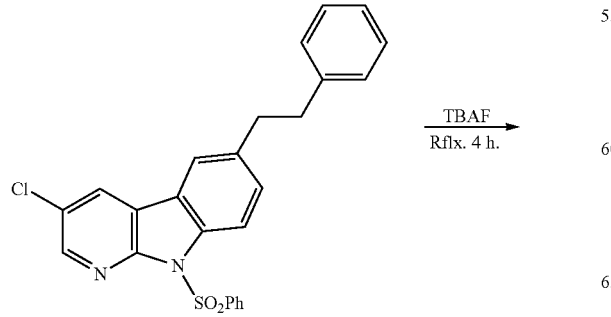

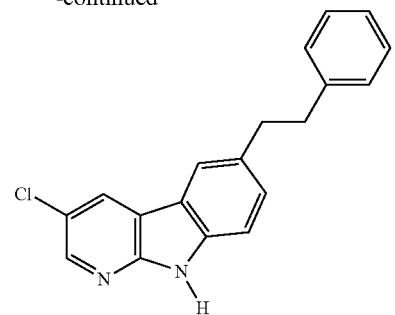

3-chloro-6-(2'-phenylethyl)-9H-pyrido[2,3-b]indole (R351)

To a solution of 9-(benzenesulfonyl)-3-chloro-6-(2'-phenylethyl)-9H-pyrido[2,3-b]indole (170 mg, 0.38 mmol, 1 equiv.) in THF (18 ml) under argon TBAF 1M in THF (1.91 ml, 1.91 mmol, 5 equiv.) was added dropwise. The reaction was carried out at reflux for 4 hours and then evaporated. The crude product (brown oil) was purified over silica gel chromatography (eluant AcOEt/PE 1:1) to afford the product R351 as a white solid (108 mg, 0.35 mmol) in 91% yield. mp=216-220° C.; IR 3111, 3028, 2921, 2851, 1600, 1490, 1453, 1389, 1271, 1236, 1087, 1030, 931, 732, 682 cm$^{-1}$; $^1$H NMR (300 MHz, DMSO d$_6$) δ 12.31 (br s, 1H, H$_9$), 9.02 (d, 1H, J=2.5 Hz, H$_2$), 8.80 (d, 1H, J=2.4 Hz, H$_4$), 8.48 (s, 1H, H$_5$), 7.85-7.77 (m, 2H, H$_8$+H$_7$), 7.72 (m, 4H, CH$_{Ph}$), 7.61-7.57 (m, 1H, CH$_{Ph}$), 3.46-3.36 (m, 4H, 2CH$_2$); $^{13}$C NMR (75 MHz, DMSO d$_6$) δ 150.3 (C), 143.8 (CH), 141.6 (C), 138.2 (C), 133.0 (C), 128.4 (2×CH), 128.3 (CH), 128.2 (2×CH), 127.8 (CH), 125.8 (CH), 121.5 (C), 120.9 (CH), 119.6 (C), 116.3 (C), 111.2 (CH), 37.7 (CH$_2$), 37.3 (CH$_2$); MS (+ESI) [M+H$^+$]=307.2

The following compound can be prepared by the same method:
3-chloro-6-(2-cyclohexylethyl)-9H-pyrido[2,3-b]indole
3-chloro-6-(1-pentyl)-9H-pyrido[2,3-b]indole
2-chloro-6-(2'-phenylethyl)-9H-pyrido[2,3-b]indole
2-chloro-6-(2-cyclohexylethyl)-9H-pyrido[2,3-b]indole
2-chloro-6-(1-pentyl)-9H-pyrido[2,3-b]indole
4-chloro-6-(2'-phenylethyl)-9H-pyrido[2,3-b]indole
4-chloro-6-(2-cyclohexylethyl)-9H-pyrido[2,3-b]indole
4-chloro-6-(1-pentyl)-9H-pyrido[2,3-b]indole

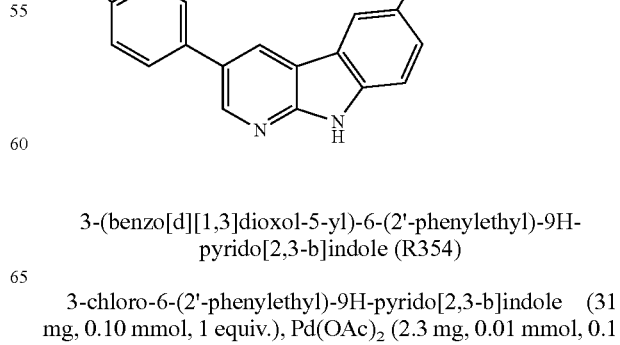

3-(benzo[d][1,3]dioxol-5-yl)-6-(2'-phenylethyl)-9H-pyrido[2,3-b]indole (R354)

3-chloro-6-(2'-phenylethyl)-9H-pyrido[2,3-b]indole (31 mg, 0.10 mmol, 1 equiv.), Pd(OAc)$_2$ (2.3 mg, 0.01 mmol, 0.1 equiv.), 2-Dicyclohexyl phosphino-2',6'-dimethoxylbiphenyl (L) (8.2 mg, 0.02 mmol, 0.2 equiv.), $K_3PO_4$ (43 mg, 0.20 mmol, 2 equiv.) and benzo[d][1,3]dioxol-5-ylboronic acid (24.9 mg, 0.15 mmol, 1.5 equiv.) are introduced in a schlenk tube and flushed with $N_2$. Freshly distilled dioxane (0.40 ml) is then injected and the reaction is carried out at 100° C. overnight. The mixture is filtered over Mite and evaporated under reduced pressure. The crude product is purified over silica gel chromatography (eluant AcOEt/PE 4:6, 6:4). The resulting solid is washed with methanol and filtered under vacuum to give the product as a white solid (12 mg, 0.03 mmol) in 30% yield. mp=231-235° C.; IR 3028, 2901, 2837, 1610, 1512, 1490, 1466, 1446, 1396, 1279, 1225, 1034, 800, 697 cm$^{-1}$; $^1$H NMR (300 MHz, DMSO d$_6$) δ 11.71 (br s, 1H, H$_9$), 8.71 (d, 1H, J=2.3 Hz, H$_2$), 8.64 (d, 1H, J=2.3 Hz, H$_4$), 8.10 (s, 1H, HO, 7.42-7.16 (m, 9H, H$_7$+CH$_{Ph}$+CH$_{An}$), 7.05 (d, 1H, J=8.1 Hz, H$_8$); 6.08 (s, 2H, OCH$_2$O), 3.06-2.96 (m, 4H, CH$_2$); $^{13}$C NMR (75 MHz, DMSO d$_6$) δ 151.3 (C), 148.1 (C), 146.5 (C), 144.2 (CH), 141.7 (C), 137.9 (C), 132.9 (C), 132.7 (C), 128.4 (2×CH), 128.3 (2×CH), 127.3 (C), 126.3 (CH), 125.8 (CH), 120.7 (CH), 120.5 (CH), 120.4 (C), 120.2 (CH), 115.3 (C), 111.1 (C), 108.8 (CH), 107.3 (CH), 101.1 (CH$_2$), 37.8 (CH$_2$), 37.4 (CH$_2$); MS (+ESI) [M+H$^+$]=393.3

36. Alk Kinase Inhibitory Activity

Method: ELISA-Based In Vitro Kinase Assay

Recombinant ALK kinase was expressed in Sf9 insect cells using the pBlueBacHis2C baculovirus vector system and purified using an anion exchange Fast Flow Q-sepharose column (Amersham-Pharmacia Biotech) followed by HiTrap™-nickel affinity column (Amersham-Pharmacia Biotech). Purified ALK protein was used to screen inhibitors in the ELISA-based kinase assay. A Nunc Immuno 96 well plate was incubated overnight at 37° C. with coating solution (125 μL/well) containing ALK peptide substrate (ARDIYRASFFRKGGCAMLPVK) (SEQ ID NO: 1) at various concentrations in PBS. Wells were then washed with 200 μL of wash buffer (PBS-Tween 0.05%) and left to dry for at least 2 h at 37° C. The kinase reaction was performed in the presence of 50 mM Tris pH 7.5, 5 mM MnCl$_2$, 5 mM MgCl$_2$, 0.3 mM ATP and purified rALK in a total volume of 100 μL/well at 30° C. for 15 min. For inhibitor testing the reaction mix was preincubated with the inhibitor or solvent control for 10 min at room temperature before transferring to the ELISA plate. After the reaction wells were washed 5 times with 200 μL of wash buffer. Phosphorylated peptide was detected using 100 μL/well of a mouse monoclonal anti-phosphotyrosine antibody (clone 4G10 Upstate Biotech Ltd) diluted 1:2000 in PBS+4% BSA. After 30 min incubation at room temperature the antibody was removed and wells were washed as described above. 100 μL of a secondary antibody (anti-mouse IgG, Horseradish Peroxidase linked whole antibody, Amersham Pharmacia Biotech) diluted 1:1000 in PBS+4% BSA was added to each well and the plate was incubated again for 30 min at room temperature before washing as above. The plate was developed using 100 μL/well TMB Substrate Solution (Endogen) and the reaction was stopped by adding an equiv.ual volume of $H_2SO_4$ 0.36 M. Finally, the absorbance was read at 450 nm using an Ultrospec® 300 spectrophotometer (Amersham-Pharmacia Biotech). The concentration of the test solution showing 50% inhibition as compared with the control was expressed as IC$_{50}$ (μM).

37. Abl T315I Mutant Kinase Inhibitory Activity

Method: ELISA-Based In Vitro Kinase Assay

Recombinant Abl T315I protein was expressed in Sf9 cells using the pBlueBacHis2C baculovirus expression vector. Abl T315I was purified using an anion exchange Fast Flow Q-sepharose column (Amersham-Pharmacia Biotech) followed by HiTrap™-nickel affinity column (Amersham-Pharmacia Biotech). Purified Abl T315I was used in the ELISA-based kinase assay to screen inhibitors as described above. The kinase reaction was performed in the presence of 50 mM Tris pH 7.5, 1 mM MnCl$_2$, 5 mM MgCl$_2$, 0.3 mM ATP, peptide substrate (ARDIYRASFFRKGGCAMLPVK) (SEQ ID NO: 1) and purified Abl T315I. The concentration of the test solution showing 50% inhibition as compared with the control was expressed as IC$_{50}$ (μM).

38. RET Kinase Inhibitory Activity

Method: ELISA-Based In Vitro Kinase Assay

Recombinant Ret protein was expressed in Sf9 cells using the pBlueBacHis2C baculovirus expression vector. Ret was purified using an anion exchange Fast Flow Q-sepharose column (Amersham-Pharmacia Biotech) followed by HiTrap™-nickel affinity column (Amersham-Pharmacia Biotech). Purified Ret was used in the ELISA-based kinase assay to screen inhibitors as described above. The kinase reaction was performed in the presence of 50 mM Tris pH 7.5, 1 mM MnCl$_2$, 5 mM MgCl$_2$, 0.3 mM ATP, peptide substrate (ARDIYRASFFRKGGCAMLPVK) (SEQ ID NO: 1) and purified Ret. The concentration of the test solution showing 50% inhibition as compared with the control was expressed as IC$_{50}$ (μM).

Inhibition of the proliferation of NPM/ALK positive cells

Method: Tritiated Thymidine Uptake Cell Proliferation Assay

The following procedure was used with parent untransformed BaF3 cells, BaF3 cells transformed with the oncogenic fusion protein NPM/ALK, NPM/ALK positive SUDHL-1 cells, ALK-negative U937 cells, NPM/ALK positive KARPAS-299 cells. The parent untransformed BaF3 cells and Alk-negative U937 cells are used as controls. Cells were seeded in U-bottomed 96-well plates at 10 000 cells/well in a volume of 100 μL in supplemented medium. In the case of the parent untransformed BaF3 cells, the medium was supplemented with IL-3. Serial dilutions of inhibitors were added to the appropriate wells and volumes adjusted to 200 μL. Controls were treated with the equivalent volume of vehicle, DMSO, alone. Plates were incubated at 37° C. for 72 h. $^3$[H]-thymidine (1 μCi/well) was added for the last 16 h of incubation. Cells were harvested on to paper filters and $^3$[H]-thymidine incorporation was measured using a β scintillation counter (1430 MicroBeta, Wallac, Turku, Finland). The 50% inhibitory concentration (IC$_{50}$) was defined as the concentration of inhibitor, expressed in micromolar, that gave a 50% decrease in $^3$[H]-thymidine uptake compared with controls.

Inhibition of the Proliferation of Bcr/Abl Positive Cells

Method: Tritiated Thymidine Uptake Cell Proliferation Assay

The following procedure was used with parent untransformed BaF3 cells, BaF3 cells transformed with the oncogenic fusion protein bcr-abl, Abl-negative U937 cells, or Bcr-abl positive LAMA-84 cells. The parent untransformed BaF3 cells and Abl-negative U937 cells are used as controls. Cells were seeded in U-bottomed 96-well plates at 10 000 cells/well in a volume of 100 μL in supplemented medium. In the case of the parent untransformed BaF3 cells, the medium was supplemented with IL-3. Serial dilutions of inhibitors were added to the appropriate wells and volumes adjusted to 200 μL. Controls were treated with the equivalent volume of vehicle, DMSO, alone. Plates were incubated at 37° C. for 72 h. $^3$[H]-thymidine (1 µCi/well) was added for the last 16 h of incubation. Cells were harvested on to paper filters and $^3$[H]-thymidine incorporation was measured using a β scintillation counter (1430 MicroBeta, Wallac, Turku, Finland). The 50% inhibitory concentration ($IC_{50}$) was defined as the concentration of inhibitor, expressed in micromolar, that gave a 50% decrease in $^3$H-thymidine uptake compared with controls.

Inhibition of the Proliferation of RET-positive Cells

Method: Tritiated Thymidine Uptake Cell Proliferation Assay

The following procedure was used with parent untransformed BaF3 cells, BaF3 cells transformed with the oncogenic fusion protein RET-PTC2, or RET-negative 11937 cells. The parent untransformed BaF3 cells and RET-negative U937 cells are used as controls. Cells were seeded in U-bottomed 96-well plates at 10 000 cells/well in a volume of 100 µL in supplemented medium. In the case of the parent untransformed BaF3 cells, the medium was supplemented with IL-3. Serial dilutions of inhibitors were added to the appropriate wells and volumes adjusted to 200 µL. Controls were treated with the equivalent volume of vehicle, DMSO, alone. Plates were incubated at 37° C. for 72 h. $^3$[H]-thymidine (1 µCi/well) was added for the last 16 h of incubation. Cells were harvested on to paper filters and $^3$[H]-thymidine incorporation was measured using a β scintillation counter (1430 MicroBeta, Wallac, Turku, Finland). The 50% inhibitory concentration ($IC_{50}$) was defined as the concentration of inhibitor, expressed in micromolar, that gave a 50% decrease in $^3$[H]-thymidine uptake compared with controls.

Results from ELISA Kinase and Tritiated Thymidine Uptake Cell Proliferation Assays

| cpd | structure | ALK | ABL | RET | BaF parental | BaF NPM/ALK | BaF BCR/ABL | BaF RET/PTC | SUDHL (NPM/ALK+) |
|---|---|---|---|---|---|---|---|---|---|
| R221 | 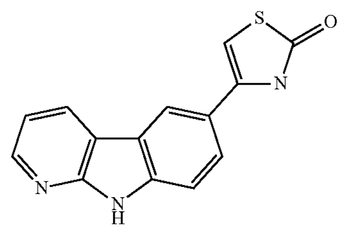 [SMILES: O=c1[nH]c(-c2ccc3[nH]c4ncccc4c3c2)cs1] | 19 ± 1.8 | 53 ± 16 | 82 ± 3.2 | | | | | |
| R222 | 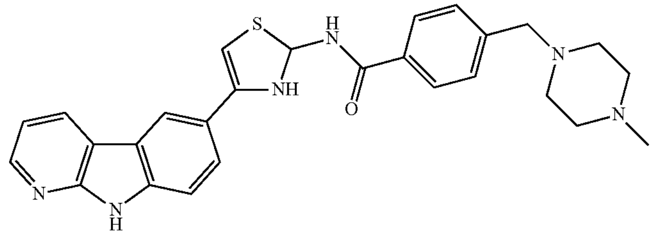 [SMILES: CN1CCN(Cc2ccc(C(=O)NC3NC(c4ccc5[nH]c6ncccc6c5c4)=CS3)cc2)CC1] | 88 ± 4.3 | >100 | 8.8 ± 1.6 | 1.5 | 1.5 | 2.5 | 1.6 | |
| R228 | 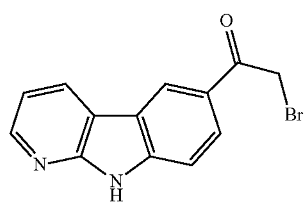 [SMILES: O=C(CBr)c1ccc2[nH]c3ncccc3c2c1] | 1.8 ± 1.0 | 13 ± 4.6 | 16 | 13 | 8 | 18 | 11 | |
| R241 | 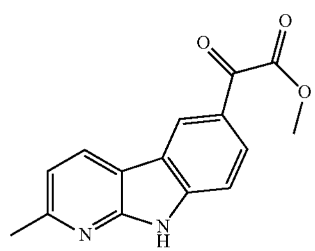 [SMILES: COC(=O)C(=O)c1ccc2[nH]c3nc(C)ccc3c2c1] | 25.3 ± 2.6 | | | | | | | |

| cpd | structure | ALK | ABL | RET | BaF parental | BaF NPM/ALK | BaF BCR/ABL | U937 (ALK−) | K299 (NPM/ALK+) |
|---|---|---|---|---|---|---|---|---|---|
| R242 | 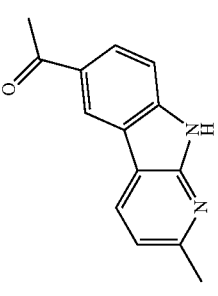 | 87.1 ± 1.3 | | | | | | | |
| R243 | 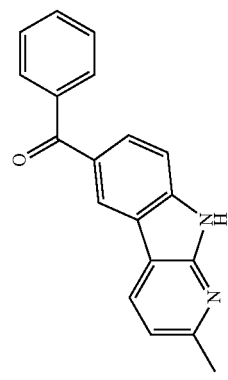 | 15.3 ± 1.5 | | | | | | | |
| R244 | 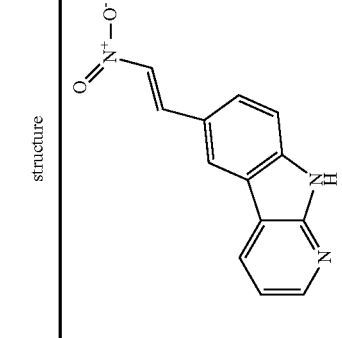 | 14.6 ± 2.8 | | | | | | | |
| R245 | 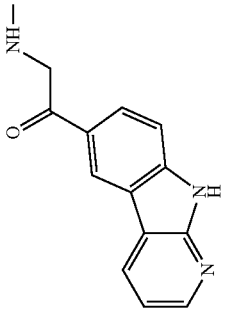 | 82.4 ± 8.1 | | | | | | | |

-continued
| | | |
|---|---|---|
| R246 | 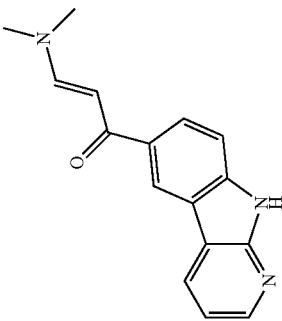 | 55.1 ± 16.9 |
| R247 | 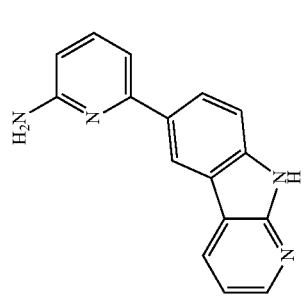 | >100 |
| R249 | 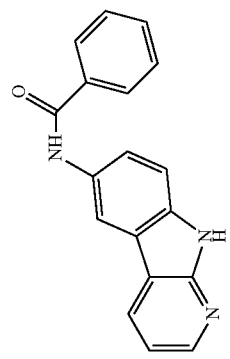 | >100 |
| R250 | 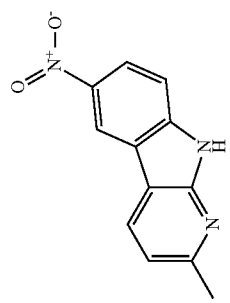 | 7.7 ± 0.8 |

| cpd | structure | ALK | ABL | RET | BaF parental | BaF NPM/ALK | BaF BCR/ABL | U937 (ALK−) | SUDHL (NPM/ALK+) |
|---|---|---|---|---|---|---|---|---|---|
| R251 | 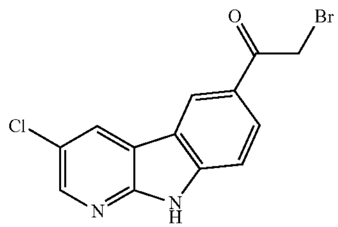 [SMILES: O=C(CBr)c1ccc2[nH]c3ncc(Cl)cc3c2c1] | 9.7 ± 1.3 | | | | | | | |
| R252 | 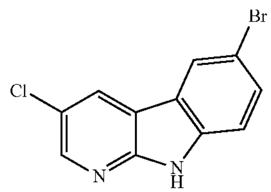 [SMILES: Clc1cnc2[nH]c3ccc(Br)cc3c2c1] | 1.7 ± 0.4 | | | >20 | >20 | >20 | | >20 |
| R253 | 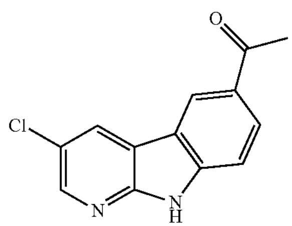 [SMILES: CC(=O)c1ccc2[nH]c3ncc(Cl)cc3c2c1] | 6.6 ± 0.67 | | | | | | | |
| R263 | 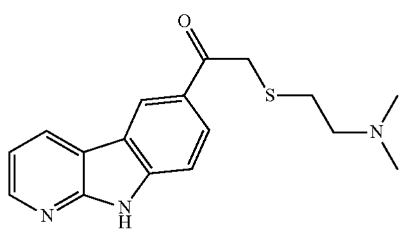 [SMILES: CN(C)CCSCC(=O)c1ccc2[nH]c3ncccc3c2c1] | >100 | >100 | >100 | >25 | >25 | >25 | | 13 |

-continued

| | | | | | | | |
|---|---|---|---|---|---|---|---|
| R264 | [structure] | 13 ± 0.58 | 49 ± 1.1 | 24 ± 6.1 | 19 | 13 | 23 | 24 |
| R265 | [structure] | 40 ± 1.9 | 54 ± 43 | 26 ± 4.7 | >25 | >25 | >25 | >25 |
| R266 | [structure] | 3.3 ± 0.4 | 9.8 ± 0.67 | 4.6 ± 0.39 | 3.4 | 3.4 | 2.0 | 0.81 |
| R267 | [structure] | 20 ± 3.2 | 20 ± 0.67 | 34 ± 27 | 17 | 14 | 8.3 | 9.4 |
| R268 | [structure] | 2.9 ± 0.4 | 3.6 ± 0.19 | 3.3 ± 1.5 | >25 | >25 | >25 | 0.6 |

-continued

| cpd | structure | ALK | ABL | RET | BaF parental | BaF NPM/ALK | LAMA (BCR/ABL+) | U937 (ALK−) | SUDHL (NPM/ALK+) |
|---|---|---|---|---|---|---|---|---|---|
| R272 | 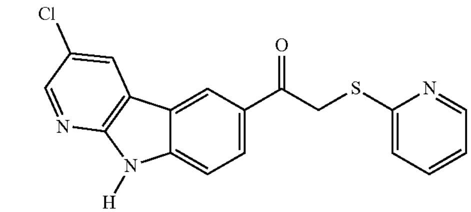 [SMILES: O=C(CSc1ccccn1)c1ccc2[nH]c3ncc(Cl)cc3c2c1] | 7.9 ± 2.3 | 41 | 19 | 2 | 2.5 | | | >25 |
| R273 | 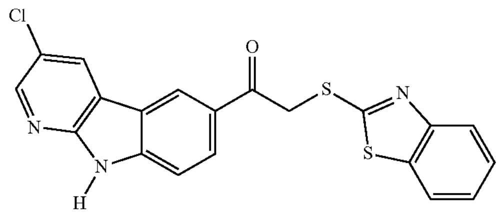 [SMILES: O=C(CSc1nc2ccccc2s1)c1ccc2[nH]c3ncc(Cl)cc3c2c1] | 0.4 ± 0.03 | 4.4 | 2 | 14 | 19 | | | >25 |
| R274 | 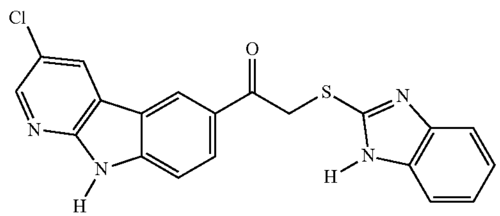 [SMILES: O=C(CSc1nc2ccccc2[nH]1)c1ccc2[nH]c3ncc(Cl)cc3c2c1] | 6.3 ± 2.3 | 19 | 14 | 0.9 | 1 | | | 0.6 |
| R275 | 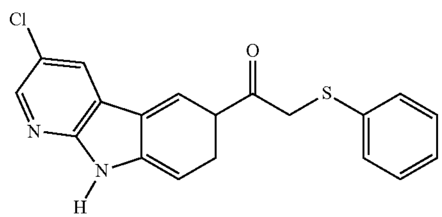 [SMILES: O=C(CSc1ccccc1)C1C=c2c([nH]c3ncc(Cl)cc23)=CC1] | 20 ± 0.6 | >100 | 27 | 2 | 8 | | | >25 |

-continued

| | | | | | |
|---|---|---|---|---|---|
| R276 | [structure] | 0.5 ± 0.1 | 50 | 1.0 | >25 | >25 |
| R277 | [structure] | 0.8 ± 0.2 | >25 | 2.0 | >13 | >13 |
| R278 | [structure] | 1.2 ± 0.2 | 23 | 1.0 | >50 | >50 |
| R279 | [structure] | 0.8 ± 0.2 | >100 | 3.6 | >50 | >50 |

-continued

| | | | | | | |
|---|---|---|---|---|---|---|
| R280 | [structure: chloro-α-carboline with phenoxyethylthio acetyl group] | 1.4 ± 0.3 | 33 | 3.6 | 37 | >50 |
| R281 | [structure: α-carboline with styryl group] | 0.5 ± 0.3 | 1.8 | 1.1 | >100 | >100 |
| R282 | [structure: chloro-α-carboline with thiazoline-thio-acetyl group] | 7.0 ± 1.1 | 36 | 9.5 | 32 | 14 | 0.7 |
| R283 | [structure: chloro-α-carboline with diethylaminoethylthio acetyl group] | 6.8 ± 1.5 | 48 | 5.7 | 3.6 ± 1.8 | 0.5 ± 0.2 | 0.2 ± 0.02 |

-continued

| | | | | | |
|---|---|---|---|---|---|
| R284 | [structure] | 36 ± 14 | >100 | 41 | |
| R299 | [structure] | 2.1 ± 0.5 | >100 | 4.1 | >100 | 59 |
| R300 | [structure] | 1.2 ± 0.3 | >100 | 4.8 | >100 | 80 | >100 |
| R301 | [structure] | 38 ± 16 | | | | |

-continued

| | | | | | | |
|---|---|---|---|---|---|---|
| R302 | [structure] | 24 ± 2 | 50 | 5.8 | 4.8 | |
| R303 | [structure] | 93 ± 1 | 87 | 9.5 | 5.1 | |
| R304 | [structure] | 5.1 ± 1.9 | 5.0 | 19 ± 7 | 2.6 ± 1.0 | 1.6 | 8.4 |

-continued

| | | | | | | | |
|---|---|---|---|---|---|---|---|
| R305 | | 17 ± 1 | 16 | | 5.5 | 5.2 | |
| R306 | | 0.8 ± 0.3 | 3.5 ± 0.03 | 1.3 | 25 ± 3 | 7.3 ± 0.3 | 1.4 |
| R307 | | 0.5 ± 0.1 | 3.1 ± 0.1 | >100 | >100 | 40 | 5.7 |

| | | | | | | |
|---|---|---|---|---|---|---|
| R308 | [structure: chloro-pyridyl-morpholine carboline] | >100 | | 50 60 | | |
| R309 | [structure: MeO-phenyl carboline] | 4 ± 0.2 | 1.6 | 15 | 25 | |
| R311 | [structure: bis-OMe-phenyl carboline] | 3.2 ± 0.1 | 8.3 | >100 | 15 ± 3 | 55 32 |

-continued

| | | | | | | |
|---|---|---|---|---|---|---|
| R312 | [structure] | 7.4 ± 2.2 | 17 | 42 | 5.3 | |
| R313 | [structure] | 8.8 ± 2.7 | >10 | 0.50 | 0.64 | |
| R314 | [structure] | 2.9 ± 1.1 | >50 | 5.3 ± 1.0 | 1.6 ± 0.1 | 2.1 | 2.1 |

-continued

| | | | | | | |
|---|---|---|---|---|---|---|
| R315 | [structure] | 1.1 ± 0.3 | 6.5 | 25 ± 10 | 3.9 ± 1.1 | 21 | 2 |
| R316 | [structure] | >33 | | >33 | 10 | | |
| R317 | [structure] | 8.2 ± 2.1 | 26 | 6.3 | 2.6 | | |
| R319 | [structure] | 4.7 ± 0.2 | 16 | 44 | 11 | | |

| | | | | |
|---|---|---|---|---|
| R320 | [structure] | 2.8 ± 0.4 | 23 | 17 |
| R321 | [structure] | 18 ± 1 | 0.7 | 0.3 |
| R322 | [structure] | 20 ± 4 | >100 | 57 |

| | -continued | | | |
|---|---|---|---|---|
| R323 | 23 ± 12 | >100 | 0.21 ± 0.01 | 13 | >100 |
| R324 | >100 | 1.7 | 3.8 | | |
| R325 | 33 ± 1 | >100 | >100 | | |
| R326 | 100 ± 3 | 8.8 | 19 | | |

-continued

| | | | | |
|---|---|---|---|---|
| R327 | [structure] | 33 ± 12 | >100 | 26 |
| R328 | [structure] | 48 ± 17 | 6.8 | 13 |
| R329 | [structure] | 12 ± 7 | >100 | >100 |
| R330 | [structure] | 14 ± 2 | >100 | >100 |

| cpd | structure | ALK | ABL | RET | BaF parental | BaF NPM/ALK | U937 (ALK−) | SUDHL (NPM/ALK+) |
|---|---|---|---|---|---|---|---|---|
| R331 | 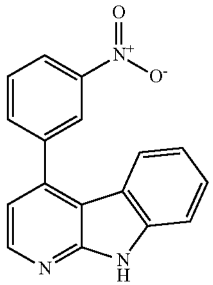 [SMILES: O=[N+]([O-])c1cccc(-c2ccnc3[nH]c4ccccc4c23)c1] | >100 | | | >100 | 40 | | |
| R332 | 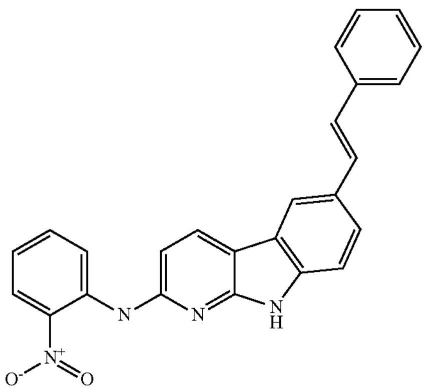 [SMILES: O=[N+]([O-])c1ccccc1Nc1ccc2c(n1)[nH]c1ccc(/C=C/c3ccccc3)cc12] | 13 ± 2 | | | 20 ± 1 | 3 ± 0.8 | 1.9 | 3.6 |
| R337 | 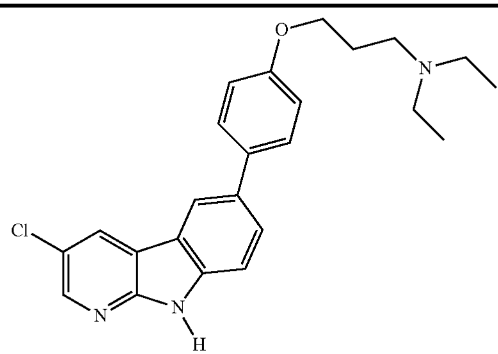 | 31 ± 9 | | | 2.6 | 2.5 | 1.1 | 2.4 |

-continued

| | | | | | |
|---|---|---|---|---|---|
| R338 | [structure] | 7 ± 1.8 | 0.4 | 0.5 | 0.4 | 0.4 |
| R340 | [salt of R338] | 7 ± 1.5 | 1 | 1.2 | 0.5 | 0.7 |
| R341 | [structure] | 11 ± 0.1 | 70 | 74 | 17 | 48 |
| R342 | [structure] | 4.1 ± 0.2 | >100 | >180 | 33 | 21 |
| R344 | [structure] | >100 | | | | |

-continued
| | | | | | | |
|---|---|---|---|---|---|---|
| R347 | 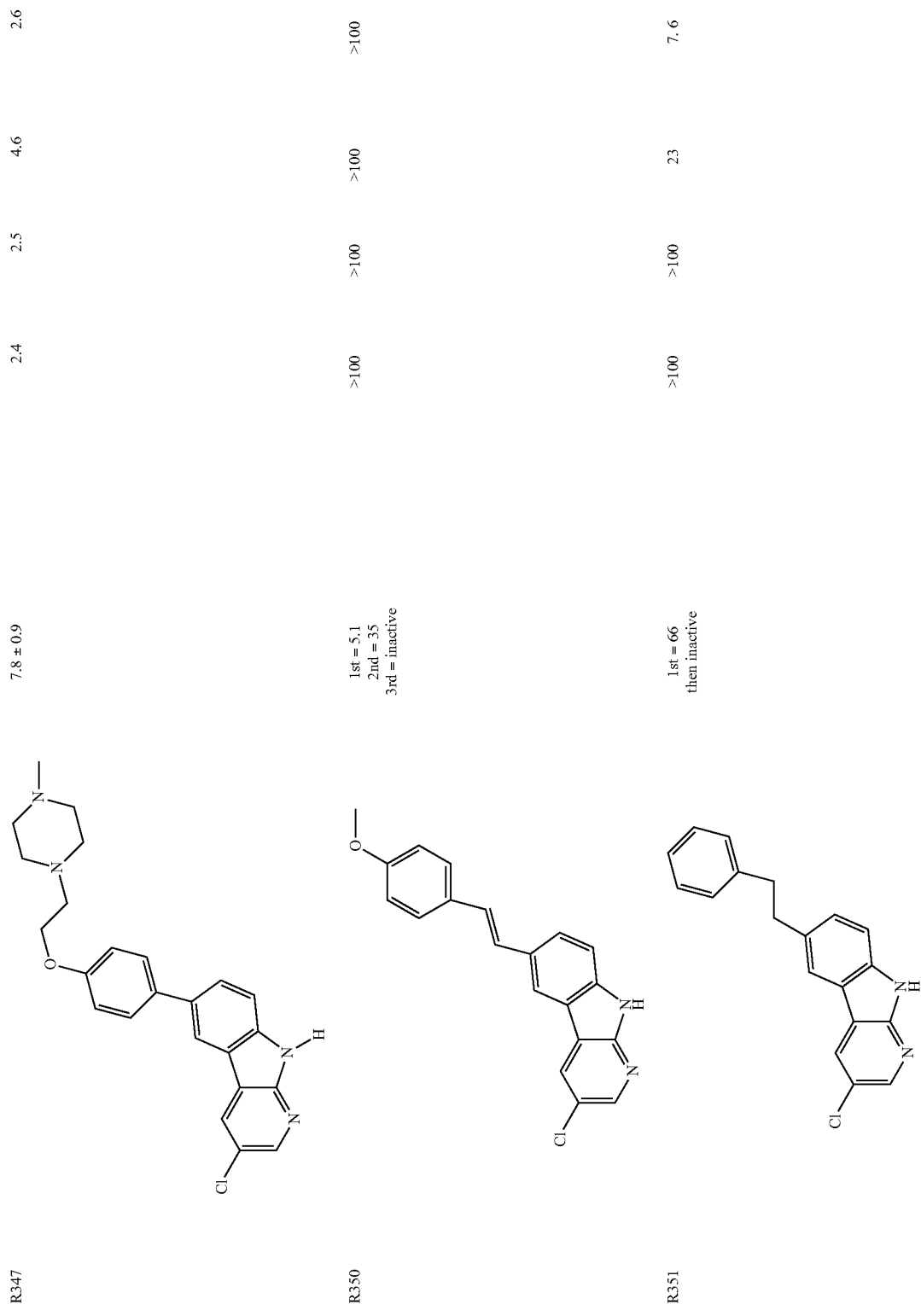 | 7.8 ± 0.9 | 2.4 | 2.5 | 4.6 | 2.6 |
| R350 | | 1st = 5.1<br>2nd = 35<br>3rd = inactive | >100 | >100 | >100 | >100 |
| R351 | | 1st = 66<br>then inactive | >100 | >100 | 23 | 7.6 |

| | | | | | | |
|---|---|---|---|---|---|---|
| R352 | [structure] | 1st = 19 then inactive | 5.3 | 5.2 | 13 | 8.6 |
| R353 | [structure] | 19 | 0.94 | 1.2 | 0.37 | 0.07 |
| R354 | [structure] | 13 | 27 | 22 | 27 | 25 |

-continued
| | | |
|---|---|---|
| R355 | 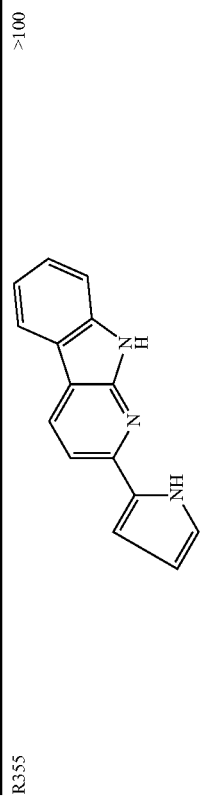 | >100 |
| R356 | 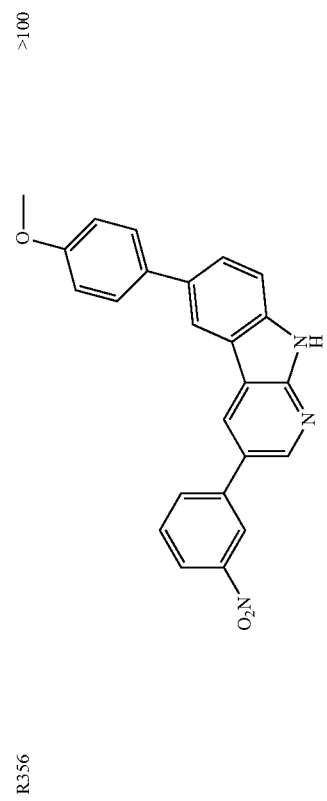 | >100 |
| R357 | 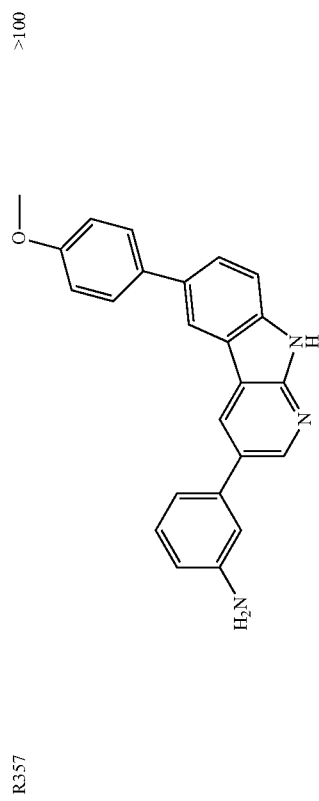 | >100 |

-continued
| R358 | 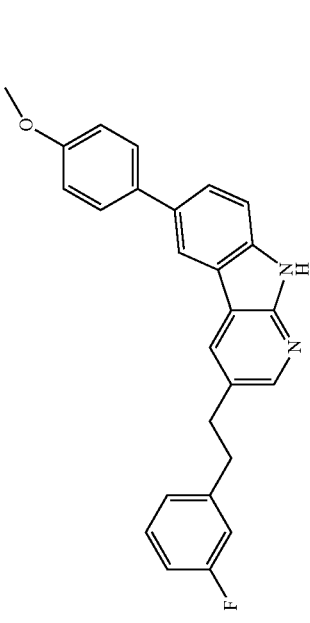 | >100 |
| R359 | 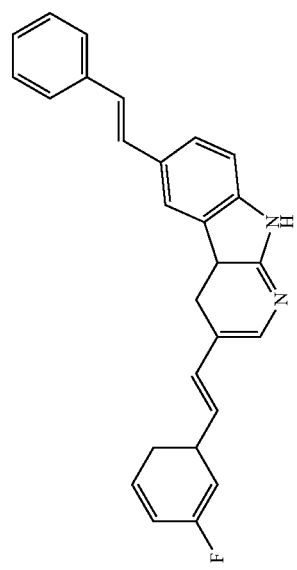 | >100 |

The invention claimed is:

1. A compound of formula (I):

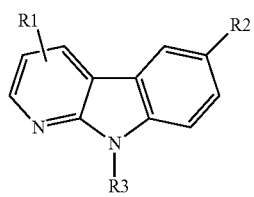

wherein when R1 is nil or when R1 is attached in the 2 position of the α-carboline ring, R1 is selected from the group consisting of:

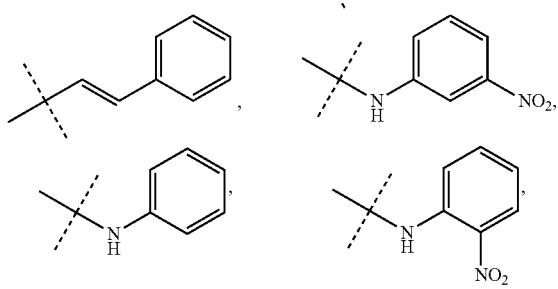

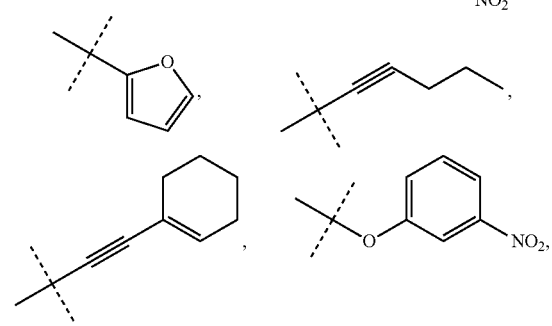

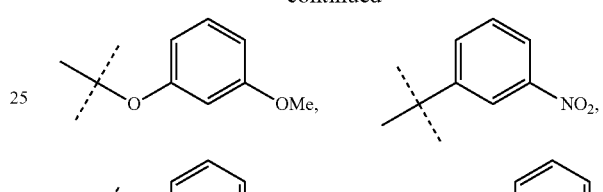

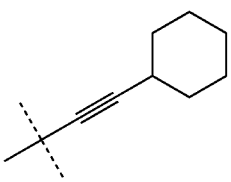

and 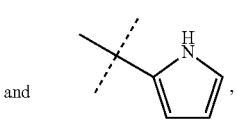

when R1 is attached in the 3 position of the α-carboline ring, R1 is selected from the group consisting of:

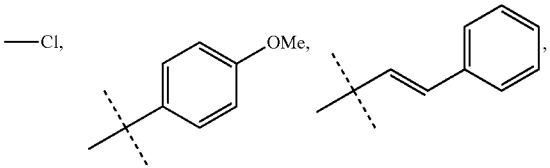

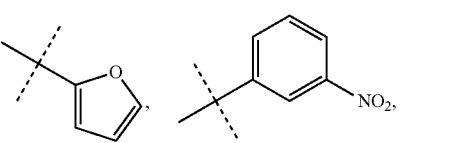

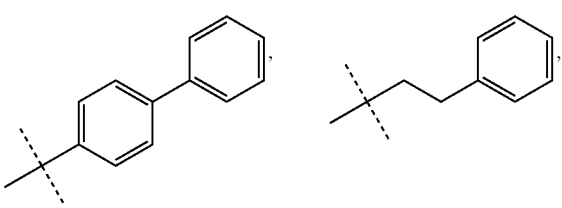

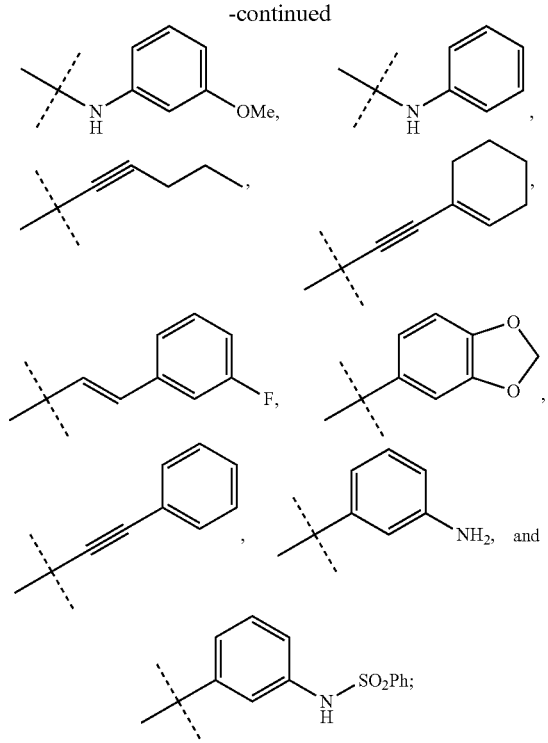
when R1 is attached in the 4 position of the α-carboline ring, R1 is selected from the group consisting of:
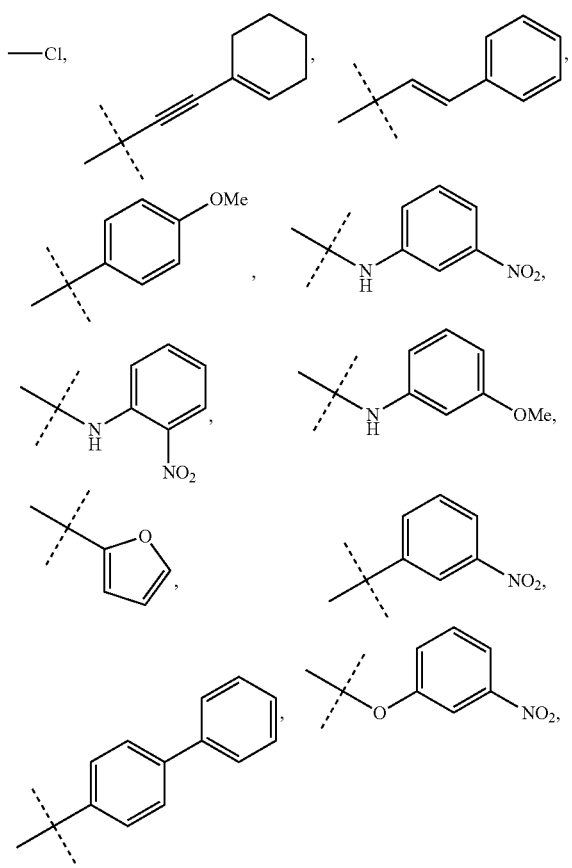
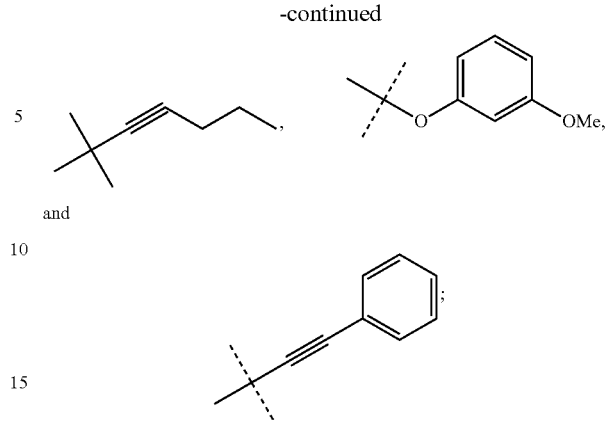
and
wherein R2 is selected from the group consisting of:
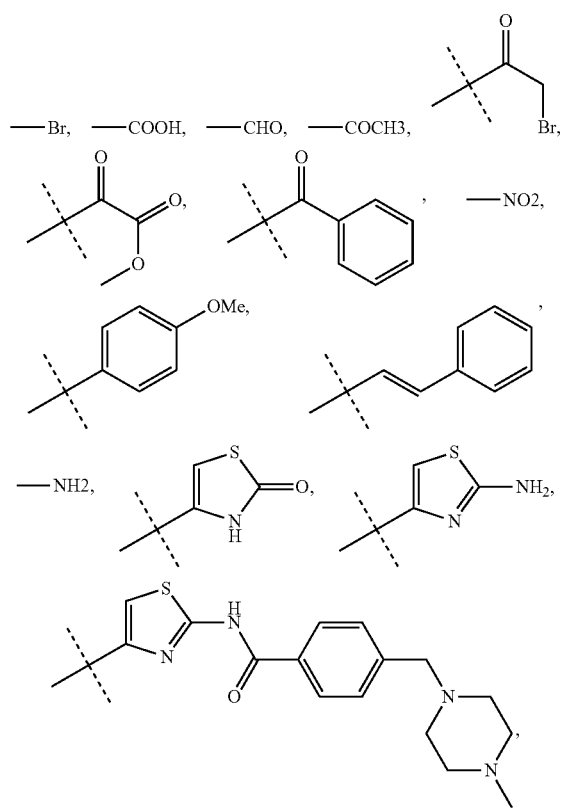

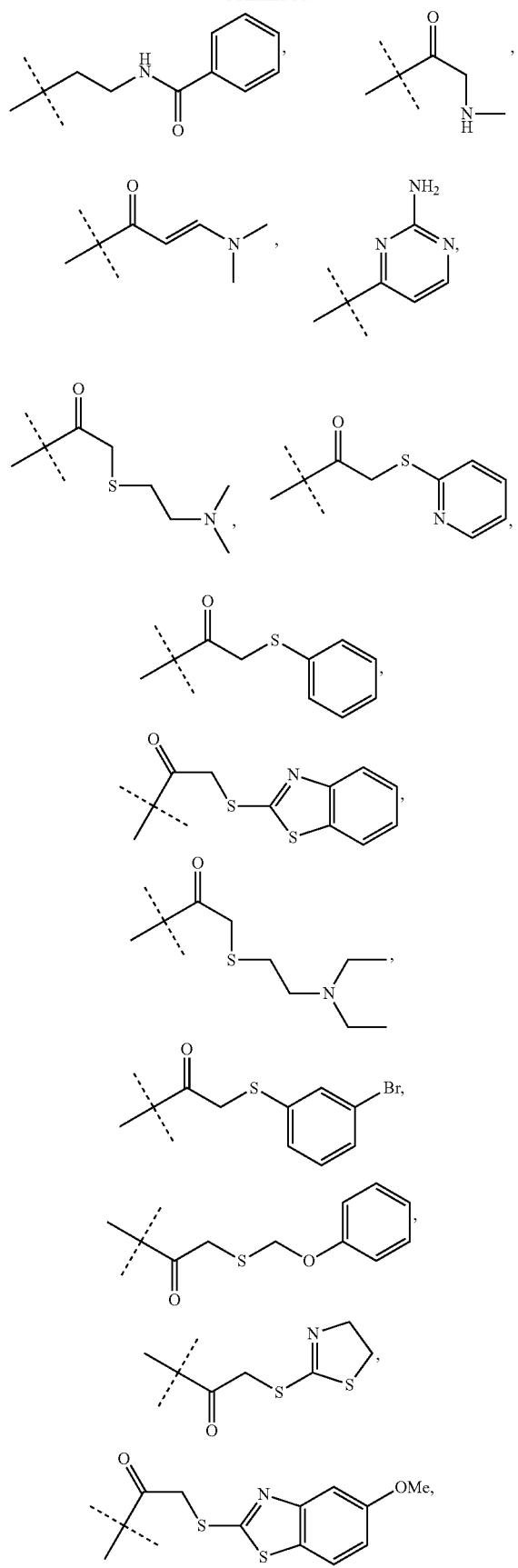
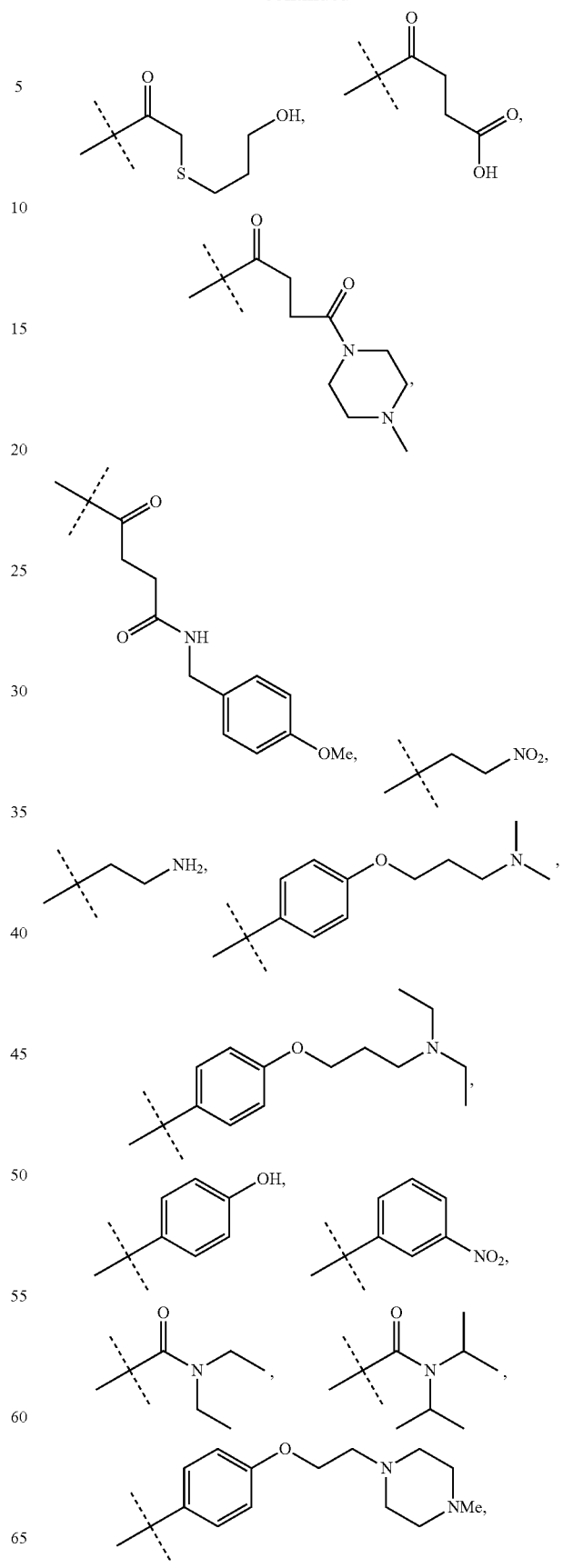

-continued

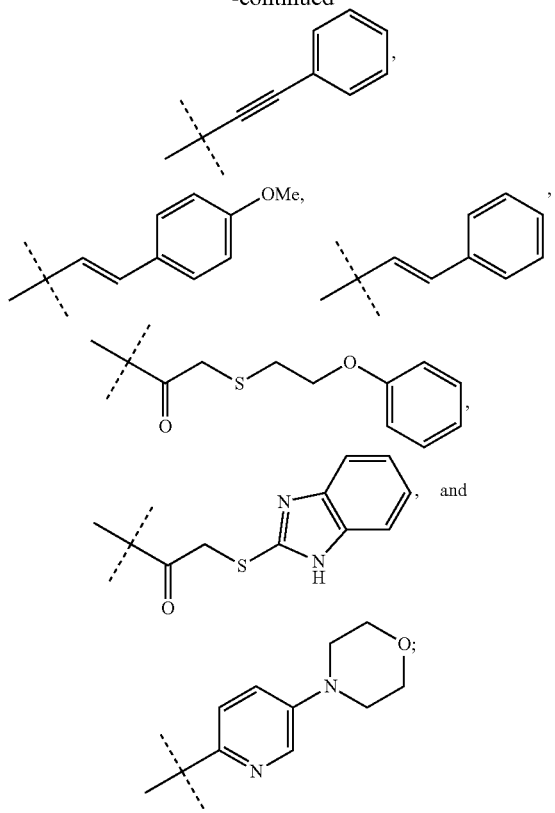

wherein R3 is selected from the group consisting of hydrogen, methyl, ethoxymethyl, tert-butyloxycarbonyl and benzenesulfonyl;

wherein a dashed line across a bond indicates the point of attachment of the group to the α-carboline ring, or a stereoisomer, enantiomer, diastereoisomer or a pharmaceutically acceptable salt thereof.

2. The compound according to claim 1, wherein when R1 is attached in the 2 position of the α-carboline ring, R1 is selected from the group consisting of:

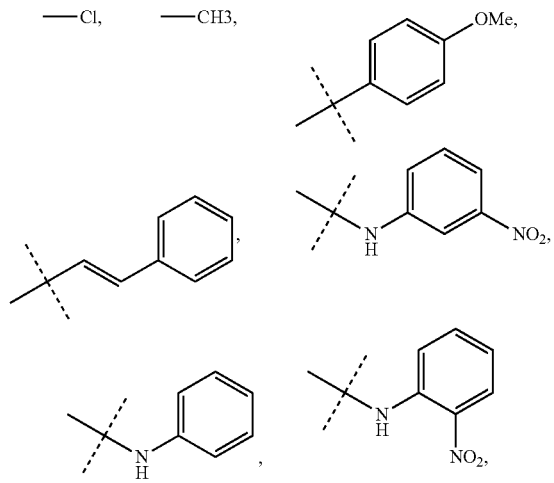

-continued

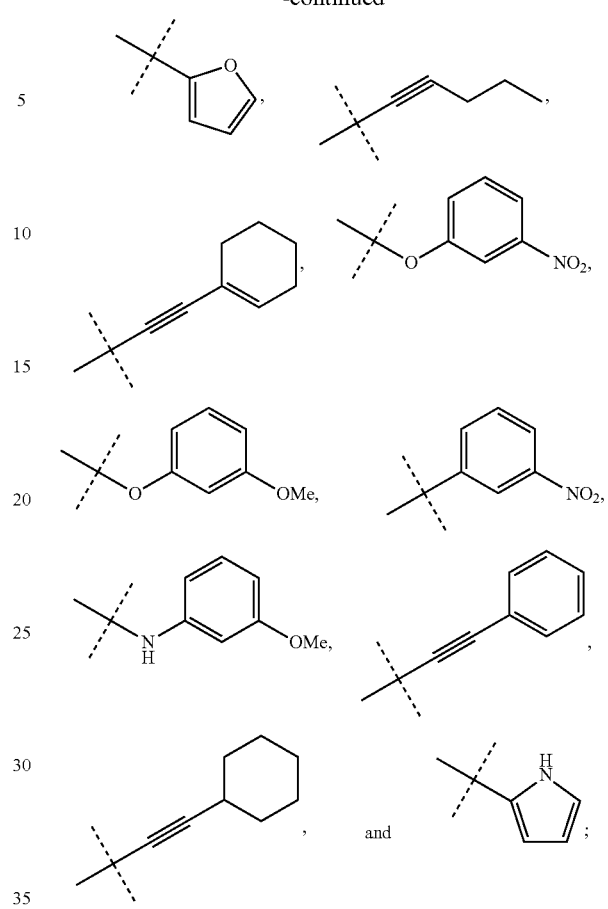

when R1 is attached in the 3 position of the α-carboline ring, R1 is selected from the group consisting of:

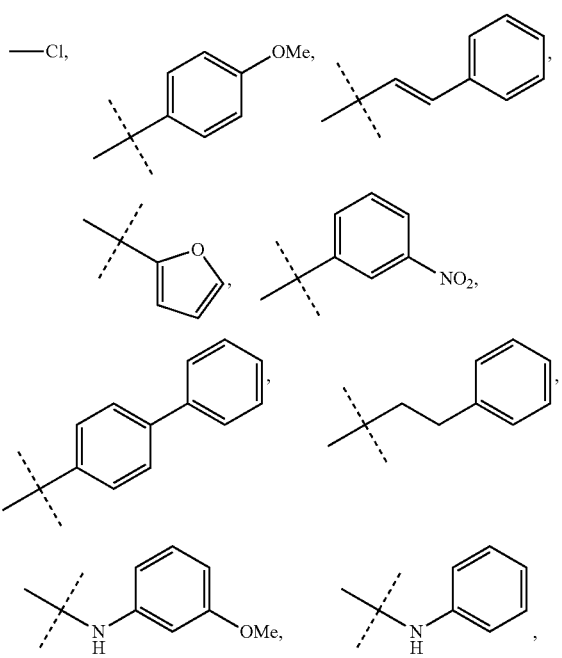

-continued
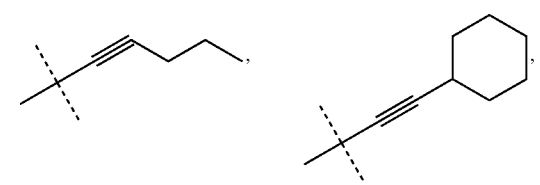
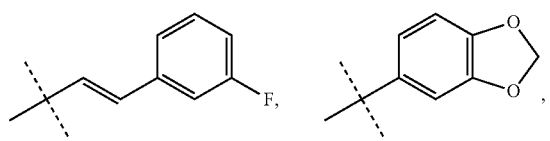
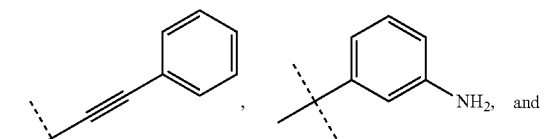
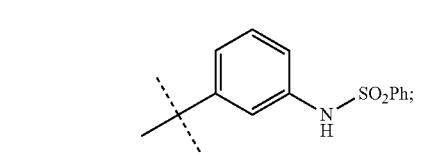
when R1 is attached in the 4 position of the α-carboline ring, R1 is selected from the group consisting of:
—Cl,
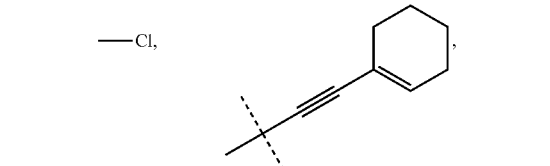
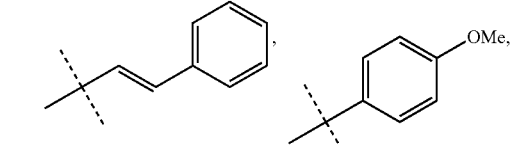
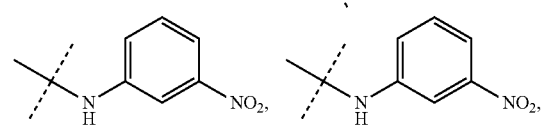
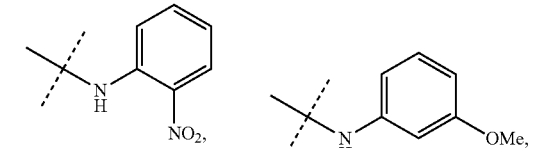
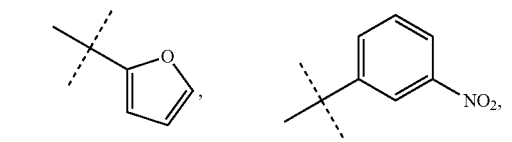
-continued
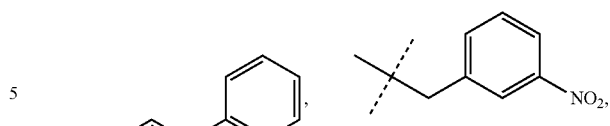
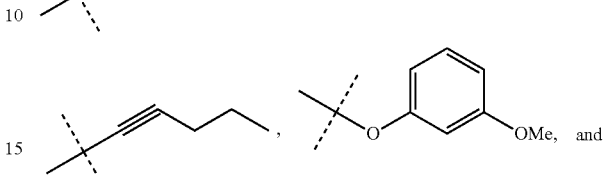
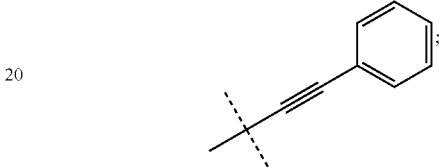
wherein R2 is selected from the group consisting of:
—Br, —COOH, —CHO, —COCH3, 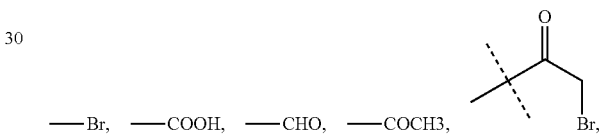Br,
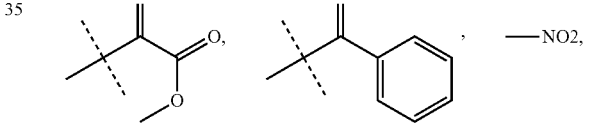, —NO2,
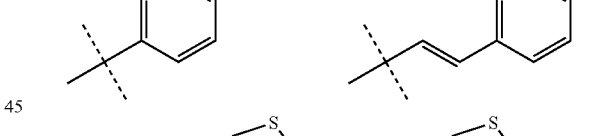
—NH2, 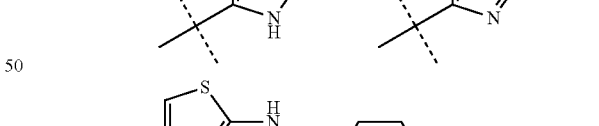
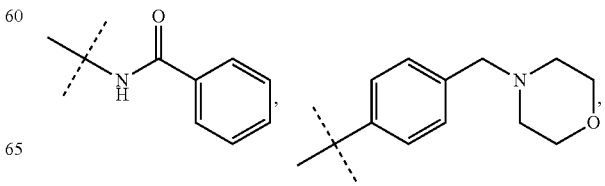

195
-continued
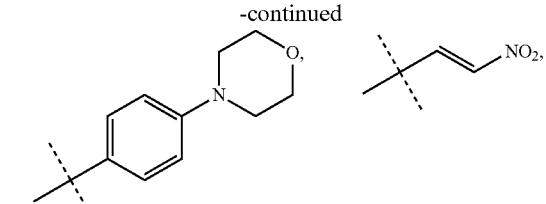
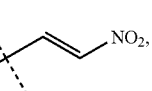
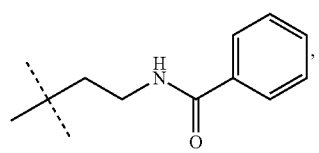
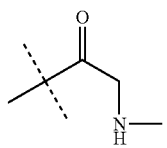
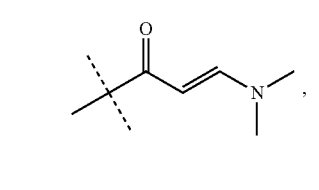
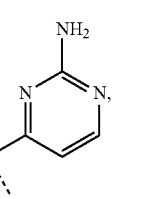
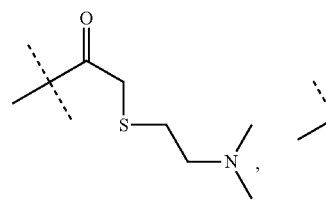
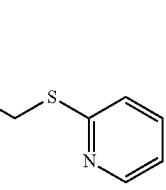
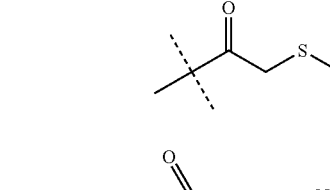
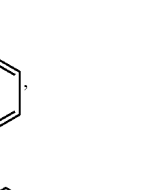
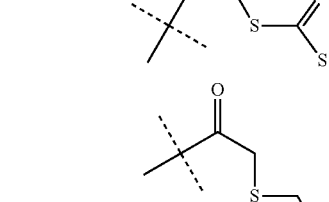
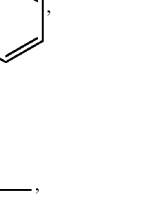
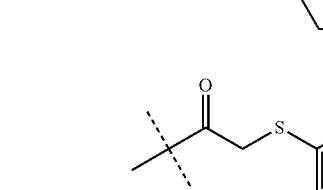
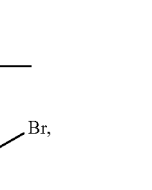
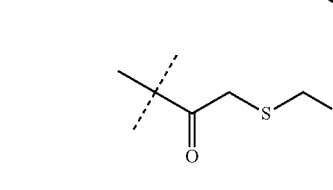
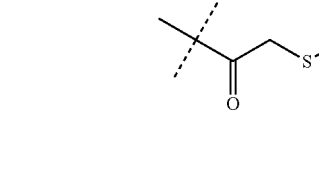
196
-continued
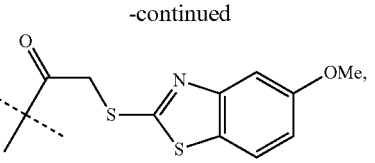
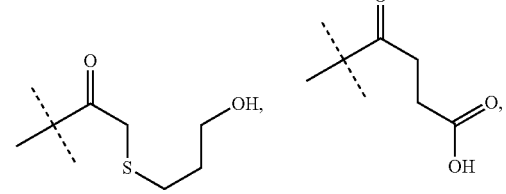
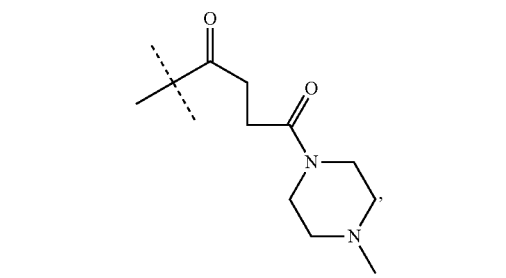
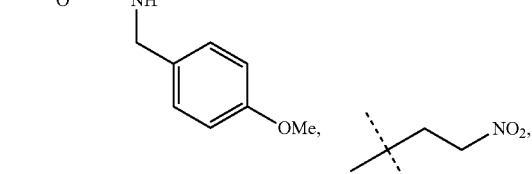
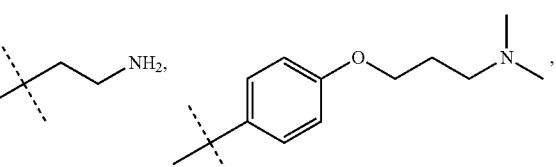
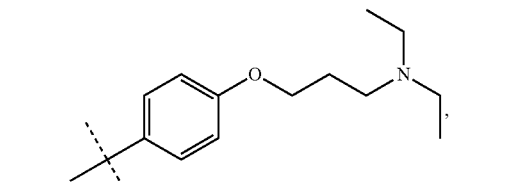
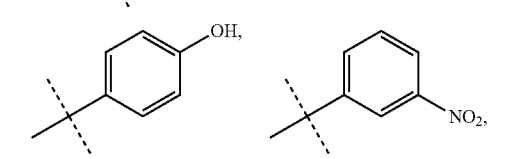
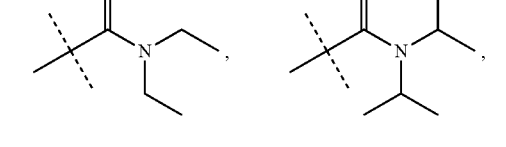

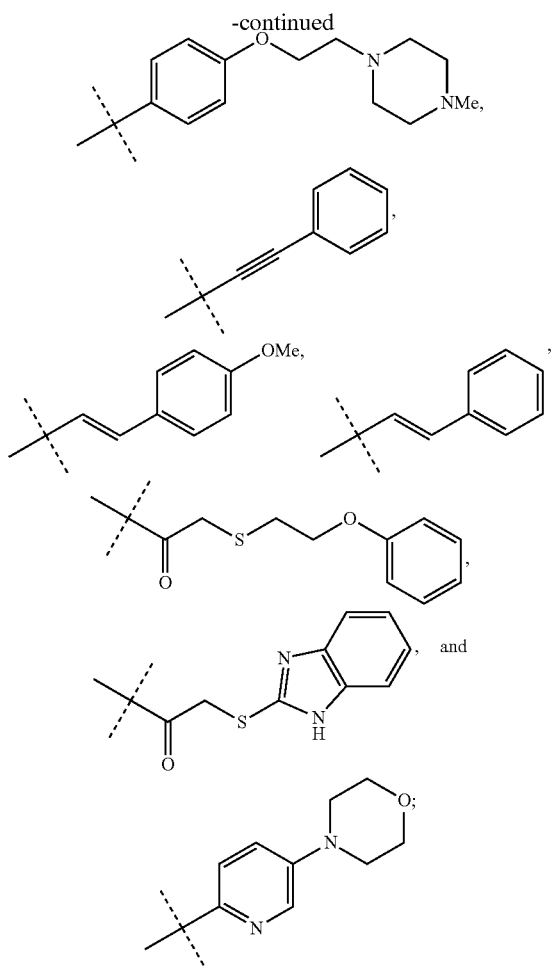

3. The compound according to claim 1, selected from the group consisting of:
6-acetyl-2-methyl-9H-pyrido[2,3-b]indole (R242),
6-acetyl-3-chloro-9H-pyrido[2,3-b]indole (R253),
2-bromo-1-(3-chloro-9H-pyrido[2,3-b]indol-6-yl)etha- none (R251),
2-bromo-1-(2-chloro-9H-pyrido[2,3-b]indol-6-yl)etha- none (1),
6-benzoyl-2-methyl-9H-pyrido[2,3-b]indole (R243),
methyl 2-oxo-2-[2-methyl-9H-pyrido[2,3-b]indol-6-yl] acetate: (R241),
methyl 2-oxo-2-[3-chloro-9H-pyrido[2,3-b]indol-6-yl]ac- etate (2),
3-chloro-9H-pyrido[2,3-b]indole-6-carbaldehyde (R267),
6-formyl-2-methyl-9H-pyrido[2,3-b]indole-9-carboxylic acid tert-butyl ester (3),
2-methyl-9H-pyrido[2,3-b]indole-6-carbaldehyde (4),
3-chloro-9H-pyrido[2,3-b]indol-6-carboxylic acid (5),
2-methyl-9H-pyrido[2,3-b]indol-6-carboxylic acid (6),
N,N-diethyl-9-methyl-9H-pyrido[2,3-b]indole-6-car- boxamide (7),
N,N-diisopropyl-9-methyl-9H-pyrido[2,3-b]indole-6-car- boxamide (8),
6-bromo-2-chloro-9H-pyrido[2,3-b]indole (9),
6-bromo-3-chloro-9H-pyrido[2,3-b]indole (R252),
6-bromo-4-chloro-9H-pyrido[2,3-b]indole (10),
4-(3-chloro-9H-pyrido[2,3-b]indol-6-yl)-4-oxo-butyric acid (11),
4-(2-chloro-9H-pyrido[2,3-b]indol-6-yl)-4-oxo-butyric acid (12),
1-(3-chloro-9H-pyrido[2,3-b]indol-6-yl)-2-phenylsulfa- nylethanone (R275),
1-(3-chloro-9H-pyrido[2,3-b]indol-6-yl)-2-(pyridin-2-yl- sulfanyl)ethanone (R272),
2-(benzothiazol-2-ylsulfanyl)-1-(3-chloro-9H-pyrido[2, 3-b]indol-6-yl)ethanone (R273),
2-(1H-benzoimidazol-2-ylsulfanyl)-1-(3-chloro-9H-py- rido[2,3-b]indol-6-yl)ethanone (R274),
1-(3-chloro-9H-pyrido[2,3-b]indol-6-yl)-2-(2,2-dimethy- laminoethylsulfanyl)ethanone (R284),
1-(3-chloro-9H-pyrido[2,3-b]indol-6-yl)-2-(N,N-diethy- laminoethylsulfanyl)ethanone (R283),
2-(3-bromophenylsulfanyl)-1-(3-chloro-9H-pyrido[2,3-b] indol-6-yl)ethanone (R279),
1-(3-chloro-9H-pyrido[2,3-b]indol-6-yl)-2-(2-phenoxy- ethylsulfanyl)ethanone (R280),
1-(3-chloro-9H-pyrido[2,3-b]indol-6-yl)-2-(4,5-dihy- drothiazol-2-ylsulfanyl)éthanone (R282),
1-(3-chloro-9H-pyrido[2,3-b]indol-6-yl)-2-(5-méthoxy- benzothiazol-2-ylsulfanyl)éthanone (R301),
1-(3-chloro-9H-pyrido[2,3-b]indol-6-yl)-2-(3-hydrox- ypropylsulfanyl)ethan-1-one (R312),
1-(2-chloro-9H-pyrido[2,3-b]indol-6-yl)-2-(N,N-diethy- laminoethylsulfanyl)ethan-1-one (R305),
1-(2-chloro-9H-pyrido[2,3-b]indol-6-yl)-2-phenylsulfa- nylethanone (R306),
1-(3-chloro-9H-pyrido[2,3-b]indol-6-yl)-4-(4-methylpip- erazin-1-yl)butane-1,4-dione (R303),
1-(2-chloro-9H-pyrido[2,3-b]indol-6-yl)-4-(4-methylpip- erazin-1-yl)butane-1,4-dione (R 302),
4-(3-chloro-9H-pyrido[2,3-b]indol-6-yl)-N-(4-methoxy- benzyl)-4-oxobutyramide (R304),
3-chloro-6-(2'-nitrovinyl)-9H-pyrido[2,3-b]indole (R267),
9-benzenesulfonyl-3-chloro-6-(2'-nitrovinyl)-9H-pyrido [2,3-b]indole (14),
9-benzenesulfonyl-3-chloro-6-(2'-nitroethyl)-9H-pyrido [2,3-b]indole (15),
9-benzenesulfonyl-3-chloro-6-(2'-aminoethyl)-9H-pyrido [2,3-b]indole (16),
N-(2-(9-(benzenesulfonyl)-3-chloro-9H-pyrido[2,3-b]in- dol-6-yl)ethyl)benzamide (17),
N-(2-(3-chloro-9H-pyrido[2,3-b]indol-6-yl)ethyl)benza- mide (R265),
9-benzenesulfonyl-6-bromo-2-chloro-9H-pyrido[2,3-b] indole (19),
9-benzenesulfonyl-6-bromo-3-chloro-9H-pyrido[2,3-b] indole (20),
9-benzenesulfonyl-6-bromo-4-chloro-9H-pyrido[2,3-b] indole (21),
9-benzenesulfonyl-3-chloro-6-(4-methoxyphenyl)-9H- pyrido[2,3-b]indole (26),
9-benzenesulfonyl-3-chloro-6-(2'-phenylethenyl)-9H-py- rido[2,3-b]indole (27),
(E)-9-benzenesulfonyl-3-chloro-6-(2'-(4-methoxyphenyl) ethenyl)-9H-pyrido[2,3-b]indole (28),
9-benzenesulfonyl-2-chloro-6-(3-nitrophenyl)-9H-pyrido [2,3-b]indole (29),
9-benzenesulfonyl-3-chloro-6-(4-(morpholin-4-yl)meth- ylphenyl)-9H-pyrido[2,3-b]indole (30),
9-benzenesulphonyl-3-chloro-6-(5-morpholin-4-yl-pyri- din-2-yl)-9H-pyrido[2,3-b]indole (31),
9-benzenesulfonyl-2-chloro-6-(4-methoxyphenyl)-9H- pyrido[2,3-b]indole (32), 9-benzenesulfonyl-2-chloro-6-(2'-phenylethenyl)-9H-pyrido[2,3-b]indole (33),
9-benzenesulfonyl-4-chloro-6-(4-methoxyphenyl)-9H-pyrido[2,3-b]indole (34),
9-benzenesulfonyl-4-chloro-6-(2'-phenylethenyl)-9H-pyrido[2,3-b]indole (35),
9-benzenesulfonyl-2,6-di(4-methoxyphenyl)-9H-pyrido[2,3-b]indole (36),
9-benzenesulfonyl-4,6-di(4-methoxyphenyl)-9H-pyrido[2,3-b]indole (37),
4-(3-chloro-9-(benzenesulfonyl)-9H-pyrido[2,3-b]indol-6-yl)phenol (R353),
3-(4-(9-(benzenesulfonyl)-3-chloro-9H-pyrido[2,3-b]indol-6-yl)phenoxy)-N,N-diethylpropan-1-amine (39),
9-(benzenesulfonyl)-3-chloro-6-(4-(2-(4-methylpiperazin-1-yl)ethoxy)phenyl)-9H-pyrido[2,3-b]indole (40),
3-chloro-6-(4-methoxyphenyl)-9H-pyrido[2,3-b]indole (R277),
3-chloro-6-(5-morpholin-4-yl-pyridin-2-yl)-9H-pyrido[2,3-b]indole (R308),
2-chloro-6-(2'-phenylethenyl)-9H-pyrido[2,3-b]indole (41),
(E)-3-chloro-6-(2'-(4-methoxyphenyl)ethenyl)-9H-pyrido[2,3-b]indole (R350),
3-chloro-6-(4-(morpholin-4-yl)methylphenyl)-9H-pyrido[2,3-b]indole (R313),
2,6-di(4-methoxyphenyl)-9H-pyrido[2,3-b]indole (R311),
3-(4-(3-chloro-9H-pyrido[2,3-b]indol-6-yl)phenoxy)-N,N-diethylpropan-1-amine (R337),
3-chloro-6-(4-(2-(4-methylpiperazin-1-yl)ethoxy)phenyl)-9H-pyrido[2,3-b]indole (R347),
9-benzenesulfonyl-6-(4-methoxyphenyl)-2-(2'-phenylethenyl)-9H-pyrido[2,3-b]indole (43),
9-benzenesulfonyl-2-(furan-2-yl)-6-(3-nitrophenyl)-9H-pyrido[2,3-b]indole (44),
9-benzenesulfonyl-6-(4-methoxyphenyl)-4-(2'-phenylethenyl)-9H-pyrido[2,3-b]indole (45),
6-(4-methoxyphenyl)-3-(2'-phenylethenyl)-9H-pyrido[2,3-b]indole (R315),
6-(5-morpholin-4-yl-pyridin-2-yl)-3-(2'-phenylethenyl)-9H-pyrido[2,3-b]indole (R307),
6-(4-(morpholin-4-yl)methylphenyl)-3-(2'-phenylethenyl)-9H-pyrido[2,3-b]indole (R314),
(E)-3-(2-(3-fluorophenyl)ethenyl)-6-(4-methoxyphenyl)-9H-pyrido[2,3-b]indole (R358),
N,N-diethyl-3-(4-(3-(2'-phenylethenyl)-9H-pyrido[2,3-b]indol-6-yl)phenoxy)propan-1-amine (R338),
N-(phenyl)-6-(2'-phenylethenyl)-9H-pyrido[2,3-b]indol-2-amine (R320),
N-2-nitrophenyl-6-(2'-phenylethenyl)-9H-pyrido[2,3-b]indol-2-amine (R332),
N-(3-methoxyphenyl)-6-(2'-phenylethyl)-9H-pyrido[2,3-b]indol-3-amine (R352),
2-(N,N-(diethylamino)ethylthio)-1-(2-(3-nitrophenylamino)-9H-pyrido[2,3-b]indol-6-yl)ethanone (R321),
9-benzenesulfonyl-3-chloro-6-(2-phenylethynyl)-9H-pyrido[2,3-b]indole (59),
3-chloro-6-(2-phenylethynyl)-9H-pyrido[2,3-b]indole (60),
9-(benzenesulfonyl)-3-chloro-6-(2'-phenylethyl)-9H-pyrido[2,3-b]indole (61),
3-chloro-6-(2'-phenylethyl)-9H-pyrido[2,3-b]indole (R351),
3-(benzo[d][1,3]dioxol-5-yl)-6-phenethyl-9H-pyrido[2,3-b]indole (R354),
(E)-3-(2'-(3-fluorophenyl)ethenyl)-6-(4-hydroxyphenyl)-9H-pyrido[2,3-b]indole (R361),
3-((E)-2'-(3-fluorophenyl)ethenyl)-6-(E)-(2-(phenyl)ethenyl)-9H-pyrido[2,3-b]indole (R359),
6-(4-methoxyphenyl)-3-(3-nitrophenyl)-9H-pyrido[2,3-b]indole (R356),
3-(6-(4-methoxyphenyl)-9H-pyrido[2,3-b]indol-3-yl)benzenamine (R357), and
N-(3-(6-(4-methoxyphenyl)-9H-pyrido[2,3-b]indol-3-yl)phenyl)benzenesulfonamide (R360).

4. A pharmaceutical composition comprising as an active ingredient a compound according to claim 1 in admixture with suitable excipients or vehicles.

5. A method for inhibiting the activity of an oncogenic protein kinase comprising administering a compound according to claim 1; wherein the oncogenic protein kinase is selected from the group consisting of Anaplastic Lymphoma Kinase (ALK), ALK/NPM, RET (Rearranged during Transfection), Bcr-Abl and T315I Bcr-Abl.

6. A method for treating a hyperproliferative disease comprising administering the pharmaceutical composition according to claim 4, wherein the hyperproliferative disease is cancer.

7. The method according to claim 6, wherein the cancer expresses an oncogenic ALK fusion protein and is selected from the group consisting of anaplastic large cell lymphoma (ALCL), diffuse large B cell lymphoma (DLBCL), inflammatory myofibroblastic tumours (IMT) and non-small cell lung cancer (NSCLC).

8. The method according to claim 7, wherein the ALK fusion protein is ALK/NPM.

9. The method according to claim 6, wherein the cancer expresses the Bcr-Abl or the T315I Bcr-Abl protein kinase and is selected from the group consisting of Chronic Myeloid Leukemia (CML) and Ph+ Acute lymphoblastic leukemia (ALL).

10. The method according to claim 6, wherein the cancer is a hereditary or sporadic thyroid cancer linked to RET.

11. The method according to claim 10, wherein the thyroid cancer is papillary thyroid carcinoma (PTC) or multiple endocrine neoplasia type 2 (MEN2).

* * * * *

UNITED STATES PATENT AND TRADEMARK OFFICE
CERTIFICATE OF CORRECTION

PATENT NO. : 8,895,744 B2  
APPLICATION NO. : 13/062665  
DATED : November 25, 2014  
INVENTOR(S) : Carlo Gambacorti Passerini et al.

Page 1 of 1

It is certified that error appears in the above-identified patent and that said Letters Patent is hereby corrected as shown below:

On the Title Page, Item (30) Foreign Application Priority Data reads:

(30) Foreign Application Priority Data

Sep. 8, 2008    (EP) .......................... 08015802 should read:

(30) Foreign Application Priority Data

Sep. 8, 2008    (EP) .......................... 08015802.5

Signed and Sealed this  
Seventeenth Day of March, 2015

Michelle K. Lee  
*Director of the United States Patent and Trademark Office*

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ala Arg Asp Ile Tyr Arg Ala Ser Phe Phe Arg Lys Gly Gly Cys Ala
1               5                   10                  15

Met Leu Pro Val Lys
            20